US010860643B2

(12) United States Patent
Kozuka et al.

(10) Patent No.: US 10,860,643 B2

(45) Date of Patent: Dec. 8, 2020

(54) CONTROL METHOD AND NON-TRANSITORY COMPUTER-READABLE RECORDING MEDIUM FOR COMPARING MEDICAL IMAGES

(71) Applicant: Panasonic Corporation, Osaka (JP)

(72) Inventors: Kazuki Kozuka, Fukui (JP); Kazutoyo Takata, Fukui (JP); Kenji Kondo, Fukui (JP); Hirohiko Kimura, Fukui (JP); Toyohiko Sakai, Fukui (JP)

(73) Assignee: PANASONIC CORPORATION, Osaka (JP)

(*) Notice: Subject to any disclaimer, the term of this patent is extended or adjusted under 35 U.S.C. 154(b) by 2 days.

(21) Appl. No.: 16/239,884

(22) Filed: Jan. 4, 2019

(65) Prior Publication Data

US 2019/0155836 A1 May 23, 2019

Related U.S. Application Data

(63) Continuation of application No. 14/722,189, filed on May 27, 2015, now Pat. No. 10,216,762.

(30) Foreign Application Priority Data

Jun. 4, 2014 (JP) ................................ 2014-116172

(51) Int. Cl.

*G06F 3/0484* (2013.01)
*G06F 16/583* (2019.01)
(Continued)

(52) U.S. Cl.

CPC .......... *G06F 16/5838* (2019.01); *A61B 6/461* (2013.01); *A61B 6/463* (2013.01);
(Continued)

(58) Field of Classification Search

CPC ............ G06F 16/5838; G06F 3/04842; G06F 3/04845; G06F 2203/04806; G16H 30/20;
(Continued)

(56) References Cited

U.S. PATENT DOCUMENTS 5,187,579 A 2/1993 Hiyama
5,954,650 A 9/1999 Saito
(Continued)

FOREIGN PATENT DOCUMENTS

JP 2002-125937 5/2002
JP 2004-215041 7/2004
(Continued)

OTHER PUBLICATIONS

Akira Oosawa et al., "Development of Synapse Case Match", Content-based Image Retrieval System for Supporting Image Diagnosis, Fujifilm Research&Development, No. 58, 2013, pp. 11-14.

*Primary Examiner* — Nicholas Klicos
(74) *Attorney, Agent, or Firm* — Wenderoth, Lind & Ponack, L.L.P.

(57) ABSTRACT

Similar medical images having a predetermined similarity to a region of interest in a medical image to be interpreted are received from a case search system. A display screen on which the received similar medical images are displayed is displayed on a display. The display screen includes display frames within which similar medical images are displayed. In response to an instruction for enlarging the similar medical images, corresponding regions of interest in the similar medical images are enlarged and displayed with the sizes of the display frames maintained unchanged on the display screen. In response to an instruction for causing a selected similar medical image among the enlarged and displayed similar medical images to move within a corresponding display frame, the other unselected similar medical image(s) is caused to move within a corresponding display
(Continued)

frame synchronously with the movement of the selected similar medical image in the same movement direction.

6 Claims, 85 Drawing Sheets

(51) Int. Cl.

| | |
|---|---|
| ***G06F 19/00*** | (2018.01) |
| ***G16H 50/70*** | (2018.01) |
| ***A61B 6/00*** | (2006.01) |
| ***G16H 30/20*** | (2018.01) |
| *G06K 9/32* | (2006.01) |
| *G06T 7/00* | (2017.01) |

(52) U.S. Cl.
CPC .............. *A61B 6/465* (2013.01); *A61B 6/468* (2013.01); *A61B 6/469* (2013.01); *A61B 6/563* (2013.01); *G06F 3/04842* (2013.01); *G06F 3/04845* (2013.01); *G06F 19/00* (2013.01); *G06F 19/321* (2013.01); *G16H 30/20* (2018.01); *G16H 50/70* (2018.01); *G06F 2203/04806* (2013.01); *G06K 9/3233* (2013.01); *G06T 7/0012* (2013.01)

(58) Field of Classification Search
CPC .... G16H 50/70; G06T 7/0012; G06K 9/3233; A61B 6/563; A61B 6/469; A61B 6/468; A61B 6/465; A61B 6/463; A61B 6/461
See application file for complete search history.

(56) References Cited

U.S. PATENT DOCUMENTS

| | | | | |
|---|---|---|---|---|
| 6,388,685 | B1 | 5/2002 | Minoura | |
| 7,676,760 | B1 | 3/2010 | Rosenquist | |
| 7,724,959 | B2 * | 5/2010 | Chiu | G06K 9/3233 382/190 |
| 7,787,672 | B2 | 8/2010 | Reicher | |
| 2001/0043729 | A1 | 11/2001 | Giger | |
| 2002/0065460 | A1 | 5/2002 | Murao | |
| 2003/0018245 | A1 | 1/2003 | Kaufman | |
| 2003/0185426 | A1 | 10/2003 | Ohishi | |
| 2004/0003001 | A1 | 1/2004 | Shimura | |
| 2006/0111634 | A1 * | 5/2006 | Wu | A61B 8/00 600/443 |
| 2007/0027733 | A1 | 2/2007 | Bolle | |
| 2007/0237377 | A1 * | 10/2007 | Oosawa | G06K 9/3233 382/128 |
| 2008/0219530 | A1 | 9/2008 | Levanon | |
| 2008/0243395 | A1 | 10/2008 | Oosawa et al. | |
| 2009/0161927 | A1 | 6/2009 | Mori | |
| 2010/0131873 | A1 | 5/2010 | Meija | |
| 2010/0266170 | A1 | 10/2010 | Khamene | |
| 2012/0245453 | A1 | 9/2012 | Tryggestad | |
| 2013/0253953 | A1 * | 9/2013 | Hisanaga | G16H 50/70 705/3 |
| 2013/0287252 | A1 * | 10/2013 | Bruun | G06K 9/00147 382/103 |
| 2013/0307992 | A1 * | 11/2013 | Erlandsson | G06F 16/58 348/164 |
| 2014/0035914 | A1 | 2/2014 | Noshi | |
| 2014/0334711 | A1 | 11/2014 | Vink | |
| 2015/0154749 | A1 | 6/2015 | Kyusojin | |
| 2015/0310172 | A1 | 10/2015 | Takata | |
| 2015/0335303 | A1 | 11/2015 | Chandelier | |

FOREIGN PATENT DOCUMENTS

| | | |
|---|---|---|
| JP | 2006-305204 | 11/2006 |
| JP | 2008-257292 | 10/2008 |
| JP | 2011-224086 | 11/2011 |

* cited by examiner

FIG. 17

DISEASE LIST 730

| | | |
|---|---|---|
| MYCOSIS | 14 | 731 |
| ASPERGILLOSIS | 8 | 732 |
| CRYPTOCOCCOSIS | 6 | 733 |
| NEOPLASTIC | 13 | 734 |
| LUNG CANCER | 10 | 735 |
| METASTATIC LUNG CANCER | 3 | 736 |
| NONNEOPLASTIC | 6 | 737 |
| LUNG ABSCESS | 4 | 738 |
| SARCOIDOSIS | 1 | 739 |
| SEPTIC EMBOLI | 1 | 740 |
| MYCOBACTERIOSIS | 6 | 741 |
| NONTUBERCULOUS MYCOBACTERIA (NTM) | 4 | 742 |
| TUBERCULOSIS | 2 | 743 |
| OTHER | 2 | 744 |
| BRONCHIECTASIS | 1 | 745 |
| ... | 1 | |

DISTRIBUTIONS OF LESIONS ⟋750
- ☐ DIFFUSE ⟋751
- ▨ SEGMENTAL ⟋752
- ☐ BRONCHIAL ⟋753
- ☐ BILATERAL ⟋754
- ☐ MULTIPLE ⟋755
- ☐ SUBPLEURAL ⟋756
- ☐ HEMATOGENOUS ⟋757

DISTRIBUTIONS OF LESIONS ⟋750
- ☐ DIFFUSE ⟋751
- ▨ SEGMENTAL ⟋752
- ☐ BRONCHIAL ⟋753
- ☑ BILATERAL ⟋754
- ☐ MULTIPLE ⟋755
- ☐ SUBPLEURAL ⟋756
- ☐ HEMATOGENOUS ⟋757

DISTRIBUTIONS OF LESIONS ⎯750
- ☐ DIFFUSE ⎯751
- ▨ SEGMENTAL ⎯752
- ☑ BRONCHIAL ⎯753
- ☐ BILATERAL ⎯754
- ☐ MULTIPLE ⎯755
- ☐ SUBPLEURAL ⎯756
- ☐ HEMATOGENOUS ⎯757

| | | |
|---|---|---|
| 1100 | PATIENT ID | 123456 |
| 1200 | NAME | JOHN DOE |
| 1300 | AGE | 28 |
| 1400 | GENDER | MALE |
| 1500 | PAST MEDICAL HISTORY | NO |
| 1600 | FAMILY HISTORY | NO |
| 1700 | CHIEF COMPLAINT | COUGH |
| 1800 | TEST INFORMATION | (SEE FIG. 30) |
| 1900 | DEFINITE DIAGNOSIS | MYCOPLASMA PNEUMONIAE |

| | |
|---|---|
| TEST ID | 13227895 |
| TEST DATE | 10:00 AM FEBRUARY 5, 20XX |
| TEST TYPE | BLOOD TEST |
| TEST RESULT | YYYY1 |

| | |
|---|---|
| TEST ID | 13227903 |
| TEST DATE | 11:00 AM FEBRUARY 5, 20XX |
| TEST TYPE | SIMPLE X-RAY (CHEST) |
| TEST RESULT | YYYY2 |

| | |
|---|---|
| TEST ID | 13227989 |
| TEST DATE | 9:00 AM FEBRUARY 9, 20XX |
| TEST TYPE | CT (CHEST) |
| TEST RESULT | YYYY3 |

| | | |
|---|---|---|
| 1810 | TEST ID | 13227989 |
| 3100 | FINDINGS | MULTIPLE NODULES OF 0.5 TO 1.0 cm IN THE RIGHT LUNG FIELD WERE ... |
| 3200 | DIAGNOSIS | INFLAMMATORY NODULES OR TUBERCULOSIS IS SUSPECTED. |

| | | |
|---|---|---|
| 4100 | SIMILAR CASE ID | SIM5232 |
| 4200 | SLICE ID | CT149391025 |
| 4300 | REGION-OF-INTEREST INFORMATION | xl, yt, xr, yb |
| 4400 | IMAGE FEATURE DATA | f1, f2, f3, ..., fN |
| 4500 | THUMBNAIL IMAGE DATA | $(I_{0,0}, I_{0,1}, \ldots, I_{w-1,h-1})$ |
| 4600 | DISTRIBUTION-OF-LESION INFORMATION | |
| 4700 | DEFINITE DIAGNOSIS (MAJOR-CATEGORY DISEASE NAME) | NEOPLASTIC |
| 4800 | DEFINITE DIAGNOSIS (SUBCATEGORY DISEASE NAME) | LUNG CANCER |

| | | |
|---|---|---|
| 4610 | DIFFUSE | 1 |
| 4620 | SEGMENTAL | 0 |
| 4630 | BRONCHIAL | 0 |
| 4640 | BILATERAL | 1 |
| 4650 | MULTIPLE | 1 |
| 4660 | SUBPLEURAL | 0 |
| 4670 | HEMATOGENOUS | 1 |

| PATIENT ID | PATIENT NAME | TEST DATE | TEST ID | TEST TYPE |
|---|---|---|---|---|
| 443982 | RICHARD ROE | DEC 1, 20XX | 23982874 | MR (HEAD) |
| 123456 | JOHN DOE | MAY 8, 20XX | 13227989 | CT (CHEST) |
| 345455 | ... | ... | ... | ... |
| 235982 | ... | ... | ... | ... |

810

| SERIES ID | DEFINITION | IMAGE |
|---|---|---|
| | | |
| | | |
| | | |

FIG. 37
800
| PATIENT ID | PATIENT NAME | TEST DATE | TEST ID | TEST TYPE |
|---|---|---|---|---|
| 443982 | RICHARD ROE | DEC 1, 20XX | 23982874 | MR (HEAD) |
| 123456 | JOHN DOE | MAY 8, 20XX | 13227989 | CT (CHEST) |
| 345455 | ··· | ··· | ··· | ··· |
| 235982 | ··· | ··· | ··· | ··· |
810
| SERIES ID | DEFINITION | IMAGE |
|---|---|---|
| CT152729 | PULMONARY CONDITION SLICE THICKNESS: 5 mm | 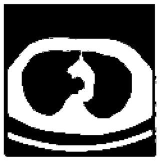 |
| CT152730 | PULMONARY CONDITION SLICE THICKNESS: 1 mm |  |
| CT152731 | MEDIASTINAL CONDITION SLICE THICKNESS: 5 mm | 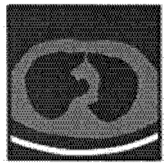 |

| | |
|---|---|
| NUMBER OF ROWS | 2 |
| NUMBER OF COLUMNS | 2 |

4411

| POSITION | SLICE ID |
|---|---|
| FIRST ROW AND FIRST COLUMN | CT12353515 |
| FIRST ROW AND SECOND COLUMN | — |
| SECOND ROW AND FIRST COLUMN | — |
| SECOND ROW AND SECOND COLUMN | — |

| USER ID | TERMINAL ID | NUMBER OF COLUMNS | NUMBER OF ROWS | POSITION OF CASE TO BE DIAGNOSED |
|---|---|---|---|---|
| U01 | T02 | 2 | 2 | (1, 1) |
| | T04 | 3 | 2 | (2, 1) |
| U02 | T02 | 3 | 3 | (2, 2) |
| ... | ... | ... | ... | ... |

| USER ID | NUMBER OF COLUMNS | NUMBER OF ROWS | POSITION OF CASE TO BE DIAGNOSED |
|---|---|---|---|
| U01 | 2 | 2 | (1, 1) |
| U02 | 3 | 2 | (2, 1) |
| U03 | 3 | 3 | (2, 2) |
| ... | ... | ... | ... |

FIG. 46

| DISEASE ID | MAJOR-CATEGORY DISEASE NAME | SUBCATEGORY DISEASE NAME | NUMBER OF RESULTS | SIMILAR CASE ID |
|---|---|---|---|---|
| DIS528 | NEOPLASTIC | LUNG CANCER | 10 | SIM258, SIM551, SIM1209, SIM2341, ... |
| DIS922 | MYCOSIS | ASPERGILLOSIS | 8 | ... |
| ... | MYCOSIS | CRYPTOCOCCOSIS | 6 | ... |
| ... | NONNEOPLASTIC | LUNG ABSCESS | 4 | ... |
| ... | MYCOBACTERIOSIS | NONTUBERCULOUS MYCOBACTERIA (NTM) | 4 | ... |
| ... | ... | ... | ... | ... |

FIG. 47

DISEASE LIST 730

| | |
|---|---|
| LUNG CANCER | 10 |
| ASPERGILLOSIS | 8 |
| CRYPTOCOCCOSIS | 6 |
| LUNG ABSCESS | 4 |
| NONTUBERCULOUS MYCOBACTERIA (NTM) | 4 |
| METASTATIC LUNG CANCER | 3 |
| TUBERCULOSIS | 2 |
| INFLAMMATORY NODULES | 1 |
| SEPTIC EMBOLI | 1 |
| BRONCHIECTASIS | 1 |
| UNKNOWN | 1 |

FIG. 48

DISEASE LIST 730

| | |
|---|---|
| MYCOSIS | 14 |
| NEOPLASTIC | 13 |
| NONNEOPLASTIC | 6 |
| MYCOBACTERIOSIS | 6 |
| OTHER | 2 |

FIG. 49

DISEASE LIST

730

| | | |
|---|---|---|
| MYCOSIS | 14 | |
| ASPERGILLOSIS | | 8 |
| CRYPTOCOCCOSIS | | 6 |
| NEOPLASTIC | 13 | |
| LUNG CANCER | | 10 |
| METASTATIC LUNG CANCER | | 3 |
| NONNEOPLASTIC | 6 | |
| LUNG ABSCESS | | 4 |
| SARCOIDOSIS | | 1 |
| SEPTIC EMBOLI | | 1 |
| MYCOBACTERIOSIS | 6 | |
| NONTUBERCULOUS MYCOBACTERIA (NTM) | | 4 |
| TUBERCULOSIS | | 2 |
| OTHER | 2 | |
| BRONCHIECTASIS | | 1 |
| ... | | 1 |

| NAME OF DISTRIBUTION | NUMBER OF CASES | SIMILAR CASE ID |
|---|---|---|
| DIFFUSE | 3 | SIM2521, SIM4123, SIM5225 |
| SEGMENTAL | 0 | NO CASE |
| BRONCHIAL | 2 | SIM0006, SIM1892, SIM4399 |
| BILATERAL | 12 | ・・・ |
| MULTIPLE | 22 | ・・・ |
| SUBPLEURAL | 0 | NO CASE |
| HEMATOGENOUS | 5 | ・・・ |

FIG. 72 4000

| | | |
|---|---|---|
| 4100 | SIMILAR CASE ID | SIM5232 |
| 4200 | SLICE ID | CT149391025 |
| 4300 | REGION-OF-INTEREST INFORMATION | xl, yt, xr, yb |
| 4400 | IMAGE FEATURE DATA | f1, f2, f3, ..., fN |
| 4500 | THUMBNAIL IMAGE DATA | $(I_{0,0}, I_{0,1}, \ldots, I_{w-1,h-1})$ |
| 4600 | DISTRIBUTION-OF-LESION INFORMATION | |
| 4700 | DEFINITE DIAGNOSIS (MAJOR-CATEGORY DISEASE NAME) | NEOPLASTIC |
| 4800 | DEFINITE DIAGNOSIS (SUBCATEGORY DISEASE NAME) | LUNG CANCER |
| 4900 | PLEURAL AREA INFORMATION | xpl, ypt, xpr, ypb |

| | | |
|---|---|---|
| 4610 | DIFFUSE | 1 |
| 4620 | SEGMENTAL | 0 |
| 4630 | BRONCHIAL | 0 |
| 4640 | BILATERAL | 1 |
| 4650 | MULTIPLE | 1 |
| 4660 | SUBPLEURAL | 0 |
| 4670 | HEMATOGENOUS | 1 |

| | | |
|---|---|---|
| 5100 | SIMILAR CASE ID | SIM32356 |
| 5200 | ENLARGED THUMBNAIL IMAGE DATA (FIRST INSTRUCTION BUTTON) | $I1_{0,0}$, $I1_{0,1}$, $I1_{0,0}$, ..., $I1_{w-1,h-1}$ |
| 5300 | ENLARGED THUMBNAIL IMAGE DATA (SECOND INSTRUCTION BUTTON) | $I2_{0,0}$, $I2_{0,1}$, $I2_{0,0}$, ..., $I2_{w-1,h-1}$ |
| 5400 | ENLARGED THUMBNAIL IMAGE DATA (THIRD INSTRUCTION BUTTON) | $I3_{0,0}$, $I3_{0,1}$, $I3_{0,0}$, ..., $I3_{w-1,h-1}$ |

CONTROL METHOD AND NON-TRANSITORY COMPUTER-READABLE RECORDING MEDIUM FOR COMPARING MEDICAL IMAGES

BACKGROUND

1. Technical Field

The present disclosure relates to a control method for controlling an information terminal for searching for similar medical images that are similar to a medical image to be interpreted, and to a non-transitory computer-readable recording medium.

2. Description of the Related Art

Medical imaging devices such as computed tomography (CT) and magnetic resonance imaging (MRI) devices have been developed and used widely in recent years. The advent of CT, MRI, and the like has enabled acquisition of a large number of high-definition digital medical images. Medical images interpreted by physicians are sequentially accumulated together with interpretation reports in a picture archiving and communication system (PACS). For instance, as disclosed in Japanese Unexamined Patent Application Publication No. 2008-257292, a technique for image retrieval has been being developed. In this technique, previous medical images that are similar to a medical image to be interpreted are searched for in the records of previous clinical cases accumulated in the PACS for the reference of new interpretation.

However, further improvements have been needed.

SUMMARY

One non-limiting and exemplary embodiment provides a further improvement.

In one general aspect, the techniques disclosed here feature a control method for controlling an information terminal for access to a case search system that searches for a medical image with reference to a medical image database having medical images registered therein. The information terminal includes a display and a computer, and a target medical image that is a medical image to be interpreted and that is selected from among candidate medical images to be interpreted is displayed on the display. The control method includes causing the computer of the information terminal to detect designation information indicating a region of interest included in the target medical image; causing the computer of the information terminal to receive from the case search system, in accordance with the region of interest indicated by the designation information, a plurality of similar medical images each having a feature value having a predetermined similarity to a feature value of the region of interest, each of the plurality of similar medical images including a corresponding region of interest which corresponds to the region of interest; causing the computer of the information terminal to display a display screen on the display, the display screen being a screen on which a number of similar medical images that is less than or equal to a predetermined value among the received plurality of similar medical images are displayed, the display screen including a number of display frames that is equal to the predetermined value to display the similar medical images; causing the computer of the information terminal to, in response to detection of an instruction for enlarging the similar medical images being displayed on the display screen, enlarge and display the corresponding regions of interest included in the similar medical images while maintaining sizes of the display frames unchanged on the display screen; and causing the computer of the information terminal to, in response to detection of an instruction for causing a selected similar medical image selected from among the enlarged and displayed similar medical images to move within a corresponding display frame among the display frames, cause an unselected similar medical image other than the selected similar medical image to move synchronously with the movement of the selected similar medical image within a display frame corresponding to the unselected similar medical image among the display frames in a movement direction identical with a movement direction in which the selected similar medical image moves. A ratio of a movement distance by which the selected similar medical image moves to a movement distance by which the unselected similar medical image moves corresponds to a ratio of an area of the corresponding region of interest included in the selected similar medical image to an area of the corresponding region of interest included in the unselected similar medical image.

It should be noted that general or specific embodiments may be implemented as a system, a method, an integrated circuit, a computer program, a computer-readable recording medium, or any selective combination thereof. Examples of the computer-readable recording medium include a non-volatile recording medium such as a compact disc-read only memory (CD-ROM).

In an aspect of the present disclosure, a further improvement may be achievable.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 17 is an enlarged view of a disease list display area;

FIG. 29 is a diagram illustrating the data configuration of patient information;

FIG. 30 is a diagram illustrating the data configuration of test information registered in the patient information illustrated in FIG. 29;

FIG. 32 is a diagram illustrating the data configuration of a diagnostic report;

FIG. 33 is a diagram illustrating the data configuration of similar case data;

FIG. 36 is a view of a test list screen;

FIG. 37 is a view of the test list screen after a test is selected;

FIG. 40 is a diagram illustrating the data configuration of display box management information;

FIG. 42 is a diagram illustrating an example of layout management information;

FIG. 43 is a diagram illustrating an example of the layout management information;

FIG. 46 is a diagram illustrating the data configuration of a disease list generated in S1300 in FIG. 44;

FIG. 47 is a diagram illustrating a first example display of the disease list display area;

FIG. 48 is a diagram illustrating a second example display of the disease list display area;

FIG. 49 is a diagram illustrating a third example display of the disease list display area;

FIG. 72 is a diagram illustrating the data configuration of similar case data that additionally includes pleural area information;

FIG. 85 is a diagram illustrating the data configuration of enlarged thumbnail data;

DETAILED DESCRIPTION

Underlying Knowledge of Present Disclosure

Figure 1:
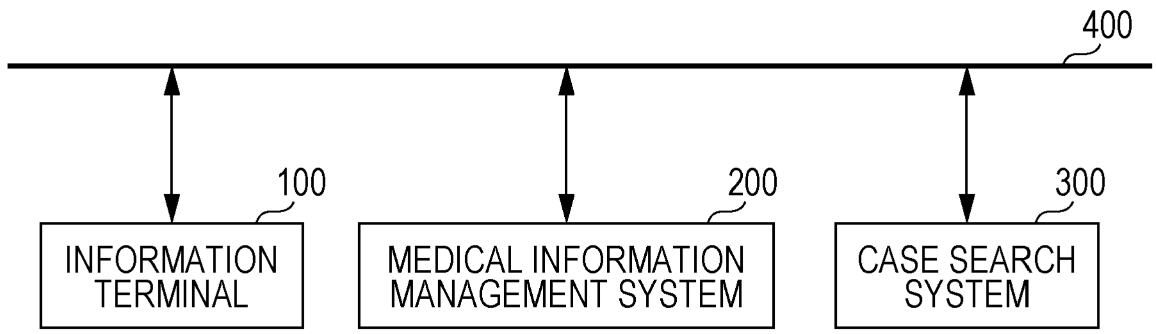
FIG. 1 is an overall configuration diagram of a hospital information system in which an information terminal according to a first embodiment is used.

First, a description will be given of issues pertaining to an aspect of the present disclosure.

Japanese Unexamined Patent Application Publication No. 2008-257292 (hereinafter referred to as "Patent Literature 1") discloses an image-based diagnosis supporting apparatus that presents images of clinical cases which are useful for judging a disease or disorder (hereinafter referred to simply as a "disease") or presents statistical information and the like on the disease for image-based diagnosis which is based on an image to be used for diagnosis (hereinafter referred to as a "diagnostic image"). The image-based diagnosis supporting apparatus displays a search result screen which shows the diagnostic image and information on typical cases of individual diseases. Specifically, the search result screen shows (i) images of typical cases of the top three ranked diseases A, D, and G, (ii) similarities to the diagnostic image, the numbers of registered cases, and the numbers of typical cases for the individual diseases, (iii) the number of search results (or the total number of diseases found as a result of the search), and (iv) a "next page" soft button or the like for accessing information on the other diseases not shown on the current screen (see paragraphs [0062] to [0063] and FIG. 6(E) in Patent Literature 1).

On the other hand, Patent Literature 1 does not describe the enlargement of the images of the typical cases displayed on the search result screen or the movement of the images of the typical cases within individual display frames after enlargement. Since Patent Literature 1 does not disclose even the enlargement of images of typical cases or the movement of the images of the typical cases within individual display frames after enlargement, a devised method such as causing each of the images of the typical cases to move in accordance with the size of a lesion area included in the image of the typical case is also not disclosed.

Japanese Unexamined Patent Application Publication No. 2004-215041 (hereinafter referred to as "Patent Literature 2") discloses an image processing device capable of performing high-usability comparison between a plurality of images. On a screen displayed by the image processing device, two images to be compared are displayed in image display areas 51a and 51b (see FIGS. 7(C) to 7(F), FIGS. 8(C) to 8(F), and FIGS. 9(C) to 9(D) in Patent Literature 2). The image processing device is configured such that, when the image displayed in the image display area 51a is caused to move within the image display area 51a, the image displayed in the image display area 51b is also caused to move within the image display area 51b synchronously (see paragraphs [0060], [0072], [0088], and [0100] in Patent Literature 2).

In Patent Literature 2, however, the plurality of images to be compared are assumed to be images captured by a personal user with their digital camera or the like (paragraphs [0002] to [0005] in Patent Literature 2). Comparison between medical images having lesion areas is not described in Patent Literature 2. Accordingly, it may be difficult to simply apply the method described in Patent Literature 2 to a technique for examining lesion areas in medical images. Accordingly, Patent Literature 2 does not also disclose a devised method such as causing medical images to move synchronously in accordance with the size of lesion areas in the medical images.

OOSAWA et al. discloses, in "Development of 'SYNAPSE Case Match', Content-based Image Retrieval System for Supporting Image Diagnosis", FUJIFILM RESEARCH & DEVELOPMENT, FUJIFILM Corporation, Mar. 27, 2013, No. 58, pp. 11-14 (hereinafter referred to as "Non-Patent Literature 1"), a similar-case search system that uses a function to search for previous similar cases by using the image of a lesion to immediately extract and present exact information based on clinical knowledge accumulated in the PACS described above or the like to assist the physician in image-based diagnosis. Specifically, in the disclosed system, a plurality of clinical case images containing a lesion having a feature similar to that of a lesion in a test image are retrieved and displayed in order of similarity. Then, one reference clinical case image is selected from among the plurality of displayed clinical case images and is displayed along with the test image (Section 2.2, "System Features", on page 12 and FIG. 3 in Non-Patent Literature 1).

However, the system disclosed in Non-Patent Literature 1 does not involve the enlargement of displayed clinical case images or the movement of the clinical case images within individual frames after enlargement. Since Non-Patent Literature 1 does not disclose even the enlargement of clinical case images or the movement of the clinical case images within individual frames after enlargement, a devised method such as causing each of images of typical cases to move in accordance with the size of a lesion area included in the image of the typical case is also not disclosed.

In the examination of a lesion appearing in a medical image to be interpreted for which a disease name has not been specified, it is considered effective to refer to medical images similar to the medical image to be interpreted among other medical images for which disease names have been specified. When such a system is established, however, a large number of medical images are registered in the medical image database described above. In this case, it is still desirable to effectively provide the physician with similar medical images to be referenced for diagnosis using the medical image to be interpreted.

In light of the foregoing discussion, the following aspects are provided.

An aspect of the present disclosure provides a control method for controlling an information terminal for access to a case search system that searches for a medical image with reference to a medical image database having medical images registered therein. The information terminal includes a display and a computer, and a target medical image that is a medical image to be interpreted and that is selected from among candidate medical images to be interpreted is displayed on the display. The control method includes causing the computer of the information terminal to detect designation information indicating a region of interest included in the target medical image; causing the computer of the information terminal to receive from the case search system, in accordance with the region of interest indicated by the designation information, a plurality of similar medical images each having a feature value having a predetermined similarity to a feature value of the region of interest, each of the plurality of similar medical images including a corresponding region of interest which corresponds to the region of interest; causing the computer of the information terminal to display a display screen on the display, the display screen being a screen on which a number of similar medical images that is less than or equal to a predetermined value among the received plurality of similar medical images are displayed, the display screen including a number of display frames that is equal to the predetermined value to display the similar medical images; causing the computer of the information terminal to, in response to detection of an instruction for enlarging the similar medical images being displayed on the display screen, enlarge and display the corresponding regions of interest included in the similar medical images while maintaining sizes of the display frames unchanged on the display screen; and causing the computer of the information terminal to, in response to detection of an instruction for causing a selected similar medical image selected from among the enlarged and displayed similar medical images to move within a corresponding display frame among the display frames, cause an unselected similar medical image other than the selected similar medical image to move synchronously with the movement of the selected similar medical image within a display frame corresponding to the unselected similar medical image among the display frames in a movement direction identical with a movement direction in which the selected similar medical image moves. A ratio of a movement distance by which the selected similar medical image moves to a movement distance by which the unselected similar medical image moves corresponds to a ratio of an area of the corresponding region of interest included in the selected similar medical image to an area of the corresponding region of interest included in the unselected similar medical image.

According to this aspect, first, the corresponding regions of interest included in the similar medical images being displayed on the display screen are enlarged with the sizes of the respective display frames being maintained unchanged. Thus, even if a display area for each of the similar medical images is constrained to fall within the corresponding one of the display frames, the corresponding region of interest included in the similar medical image is enlarged. This may enable a user to efficiently observe a desired portion in each of the similar medical images.

Then, in response to detection of an instruction for causing a selected similar medical image selected from among the enlarged similar medical images to move within a corresponding the display frame among the display frames, an unselected similar medical image other than the selected similar medical image is caused to move synchronously with the movement of the selected similar medical image within a display frame corresponding to the unselected similar medical image in a movement direction identical with the movement direction of the selected similar medical image. That is, in response to detection of an instruction for causing the selected similar medical image to move, not only one selected similar medical image among the similar medical images being displayed on the display screen is caused to move. Rather than this, the unselected similar medical image is caused to move within the display frame within which the unselected similar medical image is being displayed, in a movement direction identical with the movement direction of the selected similar medical image.

Accordingly, the user may be able to efficiently observe, in addition to the corresponding region of interest, surrounding areas of the corresponding region of interest for the similar medical images being displayed on the display screen. For example, a secondary lesion may be present around the corresponding region of interest. According to this aspect, the user may be able to efficiently observe a desired portion in each of the similar medical images being displayed on the display screen.

In this aspect, therefore, in response to a single operation of causing the selected similar medical image to move, the unselected similar medical image is also caused to move synchronously with the movement of the selected similar medical image. This may enable the user to observe desired portions in one batch for not only the corresponding region of interest but also surrounding areas of the corresponding region of interest in each of the similar medical images being displayed on the display screen.

Consequently, it may be possible to eliminate the need for the operation to cause the similar medical images being displayed on the display screen being to separately move, making the physician concentrate their attention on the medical treatment decision. Accordingly, the accuracy of medical treatment decision may be effectively improved.

In addition, the area of the corresponding region of interest included in the selected similar medical image may not necessarily be equal to the area of the corresponding region of interest included in the unselected similar medical image. For example, the area of the corresponding region of interest included in the selected similar medical image may be larger than the area of the corresponding region of interest included in the unselected similar medical image. In this case, if the movement distance by which the selected similar medical image moves (hereinafter also referred to as the movement distance of the selected similar medical image) is equal to the movement distance by which the unselected similar medical image moves (hereinafter also referred to as the movement distance of the unselected similar medical image), as a result of movement of the unselected similar medical image, the corresponding region of interest included in the unselected similar medical image moves a large amount. Consequently, a larger number of surrounding areas away from the corresponding region of interest included in the unselected similar medical image appear. In general, a secondary lesion is more likely to be present in a surrounding area close to the corresponding region of interest included in the unselected similar medical image. For this reason, if, as a result of movement of the unselected similar medical image, a surrounding area away from the corresponding region of interest included in the unselected similar medical image appears, a secondary lesion may fail to be detected.

According to this aspect, the ratio of the movement distance of the selected similar medical image to the movement distance of the unselected similar medical image corresponds to the ratio of the area of the corresponding region of interest included in the selected similar medical image to the area of the corresponding region of interest included in the unselected similar medical image.

Accordingly, for example, even if the area of the corresponding region of interest included in the selected similar medical image is larger than the area of the corresponding region of interest included in the unselected similar medical image, the movement distance of the selected similar medical image is not equal to the movement distance of the unselected similar medical image. This may prevent a surrounding area away from the corresponding region of interest included in the unselected similar medical image from appearing as a result of movement of the unselected similar medical image.

In this aspect, consequently, it may be possible to reduce the risk of secondary lesions failing to be detected without the need for the operation to cause the similar medical images being displayed on the display screen to separately move, making the physician concentrate their attention on the medical treatment decision. Accordingly, the accuracy of medical treatment decision may be effectively improved.

In addition, in the aspect described above, for example, in a case where the area of the corresponding region of interest included in the selected similar medical image is larger than the area of the corresponding region of interest included in the unselected similar medical image, the movement distance by which the unselected similar medical image moves may be made shorter than the movement distance by which the selected similar medical image moves.

In addition, in the aspect described above, for example, the target medical image may have attached information that does not include disease information on a name of a disease of a lesion displayed in the target medical image, and each of the received plurality of similar medical images may have attached information that includes disease information on a name of a disease of a lesion displayed in the image.

According to this aspect, when observing the target medical image and specifying the name of a disease of a lesion displayed in the target medical image, referring to similar medical images indicating lesions for which disease names have been specified may contribute to an improvement in diagnosis accuracy.

In addition, in the aspect described above, for example, the display screen may include a first display area in which the target medical image is displayed, and a second display area that includes the display frames, the number of which is equal to the predetermined value.

According to this aspect, when observing the target medical image and specifying the name of a disease of a lesion displayed in the target medical image, comparing the target medical image and the similar medical images on the same display screen may contribute to an improvement in diagnosis accuracy.

In addition, in the aspect described above, for example, the similar medical images, the number of which is less than or equal to the predetermined value, among the received plurality of similar medical images may be displayed in the display frames in order of decreasing similarity to the target medical image.

According to this aspect, when comparing the target medical image and the similar medical images, displaying the received plurality of similar medical images in order of decreasing similarity to the target medical image may enable a user to compare the similar medical images with the target medical image in order of decreasing similarity. Accordingly, the user may be able to efficiently specify the name of the disease of the lesion displayed in the target medical image, which may contribute to an improvement in diagnosis accuracy.

In addition, in the aspect described above, for example, the control method may further include causing the computer of the information terminal to transmit information indicating a feature value of the region of interest to the case search system; and causing the computer of the information terminal to receive from the case search system a similar medical image having a feature value having the predetermined similarity to the feature value of the region of interest.

In addition, in the aspect described above, for example, the control method may further include causing the computer of the information terminal to transmit the target medical image and the designation information indicating the region of interest to the case search system; and causing the computer of the information terminal to receive from the case search system a similar medical image having a feature value having the predetermined similarity to a feature value of the region of interest, which is obtained from the target medical image and the designation information.

In addition, in the aspect described above, for example, the target medical image may be a medical image of a lung, and each of the similar medical images may be a medical image of a lung. The display screen may include first distribution information for selection of a similar medical image in which the corresponding region of interest belongs to a predetermined first range indicating that a size of the corresponding region of interest is wide relative to the lung area, second distribution information for selection of a similar medical image in which the corresponding region of interest belongs to a predetermined second range lower than first range, the second range indicating that a size of the corresponding region of interest is a portion of a lung area, and third distribution information for selection of a similar medical image in which the corresponding region of interest includes a pleura. The computer of the information terminal may be caused to, in response to detection that distribution information has been selected among the first distribution information, the second distribution information, and the third distribution information, select a similar medical image corresponding to the selected distribution information and to display the selected similar medical image on the display screen.

According to this aspect, it may be possible to further classify a plurality of similar medical images displayed on the display screen according to the distribution type of the corresponding region of interest. This may enable the user to efficiently select, for example, a similar medical image with a similar symptom to the region of interest included in the target medical image from among a large number of displayed similar medical images.

In addition, in the aspect described above, for example, the computer of the information terminal is caused to in response to detection that the first distribution information has been selected, display a similar medical image corresponding to the first distribution information in a corresponding display frame among the display frames with an initial display size; in response to detection that the second distribution information has been selected, display a similar medical image corresponding to the second distribution information in a corresponding display frame among the display frames in such a manner that the similar medical image corresponding to the second distribution information is enlarged and displayed within the corresponding display frame with respect to, as a center of enlargement, the corresponding region of interest included in the similar medical image corresponding to the second distribution information; and in response to detection that the third distribution information has been selected, display a similar medical image corresponding to the third distribution information in a corresponding display frame among the display frames in such a manner that the similar medical image corresponding to the third distribution information is enlarged and displayed within the corresponding display frame with respect to, as a center of enlargement, the corresponding region of interest included in the similar medical image corresponding to the third distribution information and in such a manner that the corresponding region of interest includes the pleura.

According to this aspect, when similar medical images are classified according to the distribution type of the corresponding region of interest, the similar medical images are displayed in accordance with the distribution type. This may enable an operator to classify the similar medical images in accordance with the distribution type of the corresponding region of interest without performing further operations such as enlarging the similar medical images in accordance with the distribution type or centering the corresponding region of interest. Accordingly, a complicated process in which, even after classification according to the distribution type of the corresponding region of interest is completed, similar operations are repeatedly performed on each of a large number of classified similar medical images may be significantly reduced. This may result in a significant reduction in the risk of physician's thoughts or physician's concentration on medical treatment decision being interrupted by such a complicated process, helping the physician maintain their thoughts or concentration on making their medical treatment decision. The accuracy of medical treatment decision may thus be improved.

In addition, in the aspect described above, for example, the first distribution information may be information indicating a distribution that belongs to a bilateral category, a multiple category, a diffuse category, or a hematogenous category. The second distribution information may be information indicating a distribution that belongs to a segmental category or a bronchial category. The third distribution information may be information indicating a distribution that belongs to a subpleural category.

According to this aspect, for a distribution that belongs to the bilateral, multiple, diffuse, or hematogenous category, similar medical images are displayed with the initial display size. For a distribution that belongs to the segmental or bronchial category, similar medical images are enlarged and displayed. For a distribution that belongs to the subpleural category, similar medical images are enlarged and displayed in such a manner that the pleura is included.

For a distribution that belongs to the bilateral, multiple, diffuse, or hematogenous category, a lesion may occupy the entire lung or a lesion may occupy a large area of the lung. Thus, there is a need, based on the medical knowledge, that a similar medical image be displayed with the initial display size or without enlargement of the similar medical image.

For a distribution that belongs to the segmental or bronchial category, in contrast, the above possibility is less likely to occur. Thus, enlarging and displaying similar medical images by selecting a distribution that belongs to the segmental or bronchial category may remove the step of enlarging and displaying similar medical images, preventing the physician's concentration from being interrupted. For a distribution that belongs to the subpleural category, the positional relationship between the pleura and the lesion is an important index for diagnosis. Thus, there is a need, based on the medical knowledge, that a similar medical image be enlarged and displayed in such a manner that a pleura is included.

An aspect of the present disclosure provides a control method including displaying a first resulting image, obtained by enlarging an image included in a first area, in a first display area of a display device instead of displaying a first image in the first display area, the first image including the first area and a third area, the first area including a second area; displaying a second resulting image, obtained by enlarging an image included in a fourth area, in a second display area of the display device instead of displaying a second image in the second display area, the second image including the fourth area and a sixth area, the fourth area including a fifth area; and displaying a fourth resulting image, obtained by enlarging an image included in the sixth area, in the second display area instead of displaying the second resulting image in the second display area, in response to receipt of an instruction for displaying a third resulting image, obtained by enlarging an image included in the third area, in the first display area instead of displaying the first resulting image in the first display area. A ratio of L1/L2 is proportional to a ratio of S2/S1, where L1 represents a distance between a center of the first area and a center of the third area, L2 represents a distance between a center of the fourth area and a center of the sixth area, S1 represents an area of the second area, and S2 represents an area of the fifth area.

First Embodiment

An embodiment of the present disclosure will now be described hereinafter with reference to the drawings. In the drawings, the same or similar components are represented by the same numerals.

FIG. 1 is an overall configuration diagram of a hospital information system in which an information terminal according to this embodiment is used. As illustrated in FIG. 1, the hospital information system includes an information terminal 100, a medical information management system 200, and a case search system 300.

The information terminal 100, the medical information management system 200, and the case search system 300 are connected to one another via a network 400 so as to be capable of communicating with one another.

The medical information management system 200 and the case search system 300 may not necessarily be located in the hospital, and may be implemented by software operating on a data center, a private cloud server, a public cloud server, or the like located outside the hospital. In a case where the medical information management system 200 and the case search system 300 are located in the hospital, the network 400 may be a local area network (LAN). Examples of a LAN include wired LANs specified by the Institute of Electrical and Electronics Engineers (IEEE) 802.3 series standards, wireless LANs specified by the IEEE 802.11 series standards, and networks including both such wired and wireless LANs. In a case where the medical information management system 200 and the case search system 300 are implemented by using a server located outside the hospital, the network 400 may be the Internet.

The information terminal 100 may be a personal computer or an information terminal such as a tablet terminal. The medical information management system 200 may be a picture archiving and communication system (PACS), an electronic medical record system, or the like.

Figure 2:
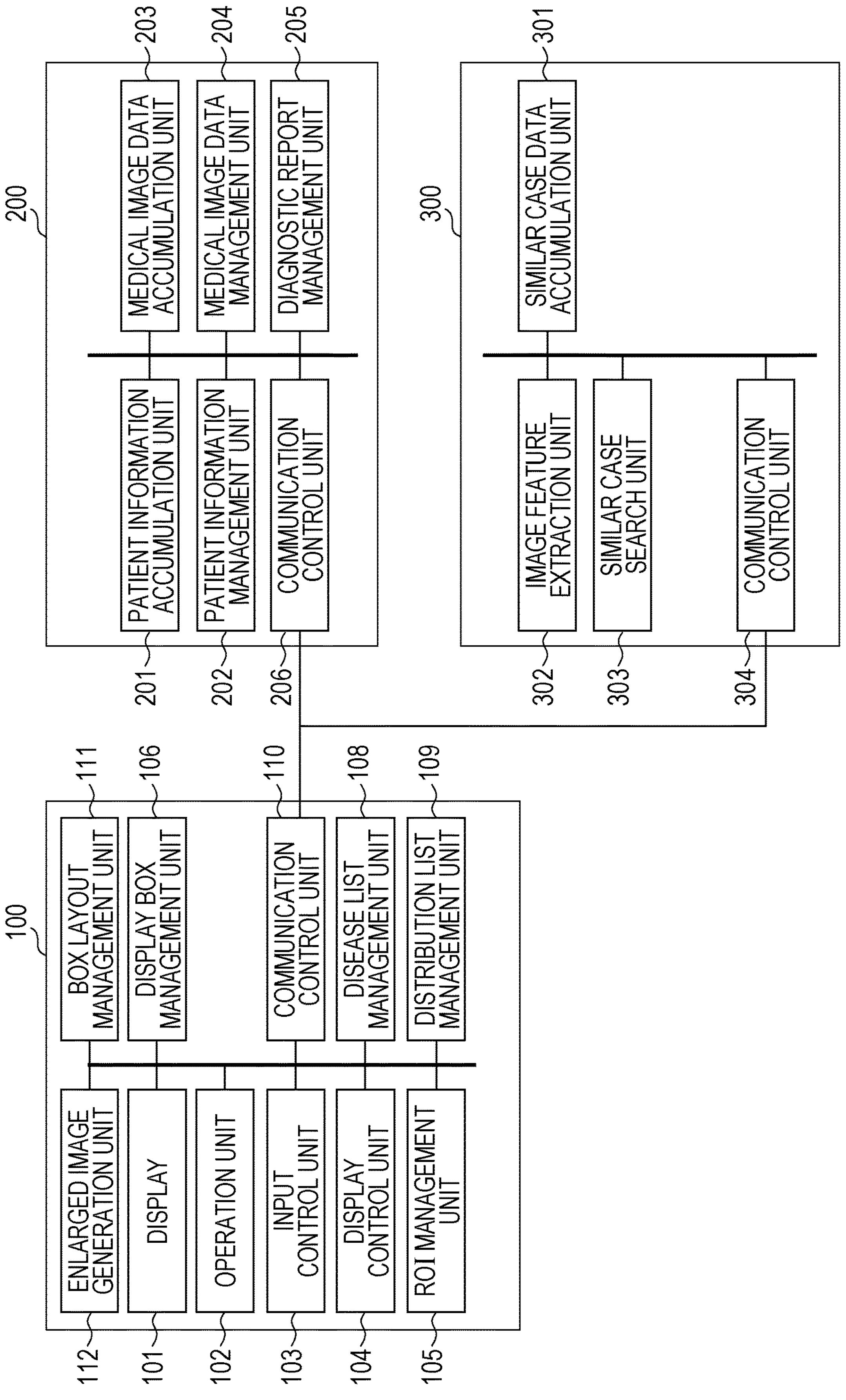
FIG. 2 is a block diagram illustrating the configuration of the information terminal, a medical information management system, and a case search system.

FIG. 2 is a block diagram illustrating the configuration of the information terminal 100, the medical information management system 200, and the case search system 300. As illustrated in FIG. 2, the information terminal 100 includes a display 101, an operation unit 102, an input control unit 103, a display control unit 104, a region of interest (ROI) management unit 105, a display box management unit 106, a disease list management unit 108, a distribution list management unit 109, a communication control unit 110, a box layout management unit 111, and an enlarged image generation unit 112.

The display 101 may be, for example, a liquid crystal monitor. The display 101 displays a medical chart image and a medical image to be used for diagnosis, and also displays a report entry image or the like in which the results of diagnosis are entered. While image-based diagnosis requires at least one display 101, two to three displays 101 are typically used for image-based diagnosis. In this embodiment, two displays 101 are used, one of which is a display 101*a*, and the other of which is a display 101*b* (see FIG. 3).

Figure 3:
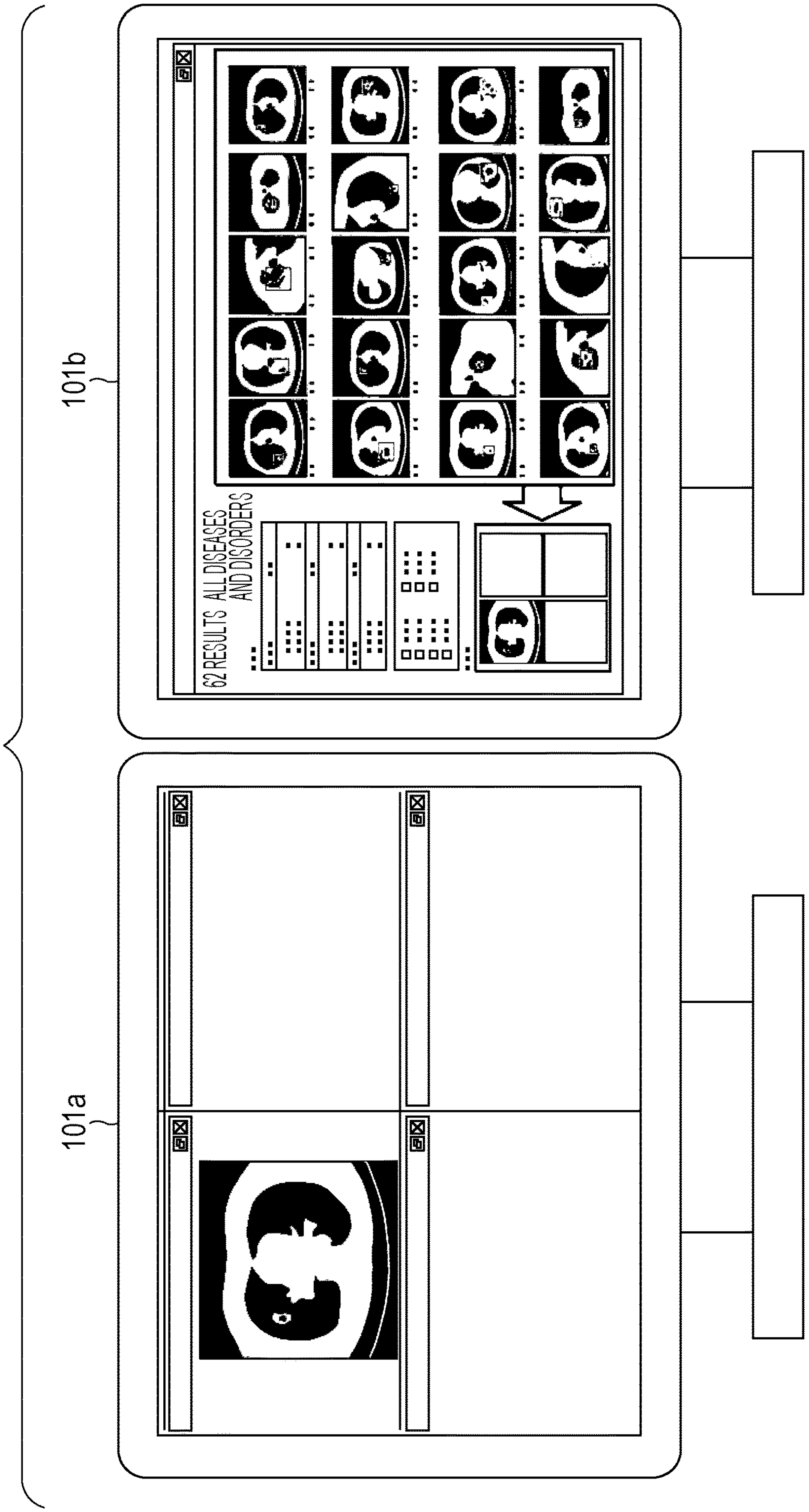
FIG. 3 illustrates external views of two displays.

FIG. 3 illustrates external views of the two displays 101*a* and 101*b*. In FIG. 3, four medical image viewers arranged in two rows and two columns are displayed on the display 101*a*, and a screen for the case search system 300 is displayed on the display 101*b*. In a case where a single display 101 is used, the two display screens are displayed in separate areas on the display screen of the single display 101.

The operation unit 102 includes, for example, a keyboard and a mouse, and accepts a variety of operations input by a user on the information terminal 100. For example, the operation unit 102 accepts operations such as an operation performed by the user on a medical image or medical chart image displayed on the display 101, and an operation for entering the results of diagnosis in a report input screen.

Upon detection of a user's operation on the operation unit 102, the input control unit 103 interprets the operation, and notifies the other components of the content of the operation. For example, the input control unit 103 detects the position of the mouse pointer on the display 101 by using coordinate data output from the mouse serving as the operation unit 102, and causes the mouse pointer to be displayed on the display 101. If a graphical user interface (GUI) component (e.g., a GUI button) generated by the display control unit 104 is displayed at the display position of the mouse pointer when a click of the mouse is detected, the input control unit 103 determines that the user has selected the GUI component, and notifies the other components that the GUI component has been selected by the user.

The display control unit 104 generates a GUI of the information terminal 100, and displays the GUI on the display 101.

The ROI management unit 105 generates region-of-interest information indicating a region of interest (ROI) set on a search query image described below for a similar case search, and stores the region-of-interest information in a memory to manage the region-of-interest information.

The display box management unit 106 stores display box management information 4410 described below (FIG. 40) in the memory to manage the display box management information 4410.

The disease list management unit 108 generates a disease list (FIG. 46) that is a list of diseases corresponding to similar cases displayed in a case display area 710 (FIG. 6), and stores the disease list in the memory to manage the disease list.

The distribution list management unit 109 generates a distribution list (FIG. 51) that is a list of distributions of lesions of the similar cases displayed in the case display area 710, and stores the distribution list in the memory to manage the distribution list.

The communication control unit 110 includes, for example, a communication device for connecting the information terminal 100 to the network 400, and controls communication between the information terminal 100 and the medical information management system 200 and communication between the information terminal 100 and the case search system 300. Further, the communication control unit 110 accepts from other blocks a request for transmitting a variety of types of data, and transmits data to the medical information management system 200 or the case search system 300. In addition, the communication control unit 110 receives data transmitted from the medical information management system 200 or the case search system 300, and passes the data to the corresponding block.

The box layout management unit 111 generates layout management information 4200 described below (FIG. 43), and stores the generated layout management information 4200 in a memory to manage the layout management information 4200.

The enlarged image generation unit 112 generates an enlarged image of a thumbnail image of a similar case. The enlarged image generation unit 112 acquires the amount of operation performed on the operation unit 102 by the user from the input control unit 103. The enlarged image generation unit 112 receives, through the communication control unit 110, similar case data (including similarity and region-of-interest information) transmitted from the case search system 300. The enlarged image generation unit 112 calculates enlargement factors for individual thumbnail images of similar cases displayed in the case display area 710 among a number of similar cases (e.g., NC similar cases) obtained as a result of the similar case search, and generates a number of enlarged images equal to the number of thumbnail images displayed.

As illustrated in FIG. 2, the medical information management system 200 includes a patient information accumulation unit 201, a patient information management unit 202, a medical image data accumulation unit 203, a medical image data management unit 204, a diagnostic report management unit 205, and a communication control unit 206.

The patient information accumulation unit 201 accumulates patient information 1000 (FIG. 29) in which personal information such as the gender and age of a patient, clinical information such as the past medical history that the patient has, and test information on medical tests that the patient has undergone, such as a blood test, are registered.

The patient information management unit 202 performs processes, such as a process for registering data input by a user in the patient information 1000 (FIG. 29) accumulated in the patient information accumulation unit 201 to update the patient information 1000, and a process for outputting the patient information 1000 to the display control unit 104, to manage the patient information 1000. The medical image data accumulation unit 203 accumulates medical image data representing test images of the patient.

The medical image data management unit 204 stores the medical image data in the medical image data accumulation unit 203 to manage the medical image data.

The diagnostic report management unit 205 manages a diagnostic report 3000 (FIG. 32) which shows the results of the diagnosis made by the physician based on the results of tests given to the patient.

The communication control unit 206 includes, for example, a communication device for connecting the medical information management system 200 to the network 400. The communication control unit 206 accepts from other blocks a request for transmitting a variety of types of data, and transmits data to the information terminal 100 or the case search system 300. In addition, the communication control unit 206 receives data transmitted from the information terminal 100 or the case search system 300, and passes the data to the corresponding block.

As illustrated in FIG. 2, the case search system 300 includes a similar case data accumulation unit 301, an image feature extraction unit 302, and a similar case search unit 303, and a communication control unit 304.

The similar case data accumulation unit 301 accumulates, in advance, similar case data 4000 (FIG. 33) in which image features extracted from a large number of similar cases selected as target data for a similar case search from among the similar cases managed in the medical information management system 200, generated thumbnail images, and the like are registered.

The image feature extraction unit 302 extracts an image feature in region-of-interest information on the search query image transmitted from the communication control unit 110 of the information terminal 100. The region-of-interest information is an example of first designation information indicating a region of interest.

The similar case search unit 303 compares the image feature extracted by the image feature extraction unit 302 with each of image features in one or more similar cases accumulated in the similar case data accumulation unit 301, and generates similar case search results.

The communication control unit 304 includes, for example, a communication device for connecting the case search system 300 to the network 400. The communication control unit 304 accepts from other blocks a request for transmitting a variety of types of data, and transmits data to the information terminal 100 or the medical information management system 200. In addition, the communication control unit 304 receives data transmitted from the information terminal 100 or the medical information management system 200, and passes the data to the corresponding block.

Figure 4:
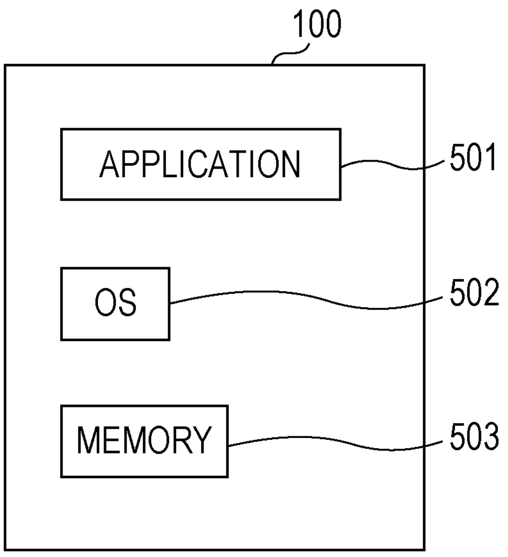
FIG. 4 is a diagram illustrating an example configuration of an implementation of the information terminal.

FIG. 4 is a diagram illustrating an example configuration of an implementation of the information terminal 100. As illustrated in FIG. 4, the information terminal 100 includes an application 501, an operating system (OS) 502, a memory 503, and other hardware (not illustrated).

The application 501 is application software for causing a personal computer or a tablet terminal to function as the information terminal 100, and is executed by a processor of the information terminal 100. The information terminal 100 may implement the application 501 by reading the application 501 from a computer-readable recording medium, or may implement the application 501 by downloading the application 501 from a network.

The application 501 includes a medical information management application and a similar case search application. The medical information management application is an application for allowing the information terminal 100 to operate in coordination with the medical information management system 200, and the similar case search application is an application for allowing the information terminal 100 to operate in coordination with the case search system 300. The medical information management application and the similar case search application transmit and receive data to and from each other so that services provided by the medical information management system 200 and the case search system 300 are integrated in the information terminal 100.

The OS 502 is basic software of the information terminal 100, and is executed by a processor of the information terminal 100. The memory 503 includes storage devices such as a random access memory (RAM) and a read-only memory (ROM), which are included in the information terminal 100, and stores data sets included in the application 501.

The processor of the information terminal 100 executes the application 501 to implement the functions of the input control unit 103, the display control unit 104, the ROI management unit 105, the display box management unit 106, the disease list management unit 108, the distribution list management unit 109, the communication control unit 110, the box layout management unit 111, and the enlarged image generation unit 112, which are illustrated in FIG. 2.

In this embodiment, the information terminal 100 may be implemented solely by the application 501, or may be implemented by the application 501 and the OS 502. Alternatively, the information terminal 100 may be implemented by the application 501, the OS 502, and the memory 503, or may be implemented by the application 501, the OS 502, the memory 503, and any other hardware (not illustrated). The information terminal 100 according to this embodiment is achievable through any of the implementations described above.

Figure 5:
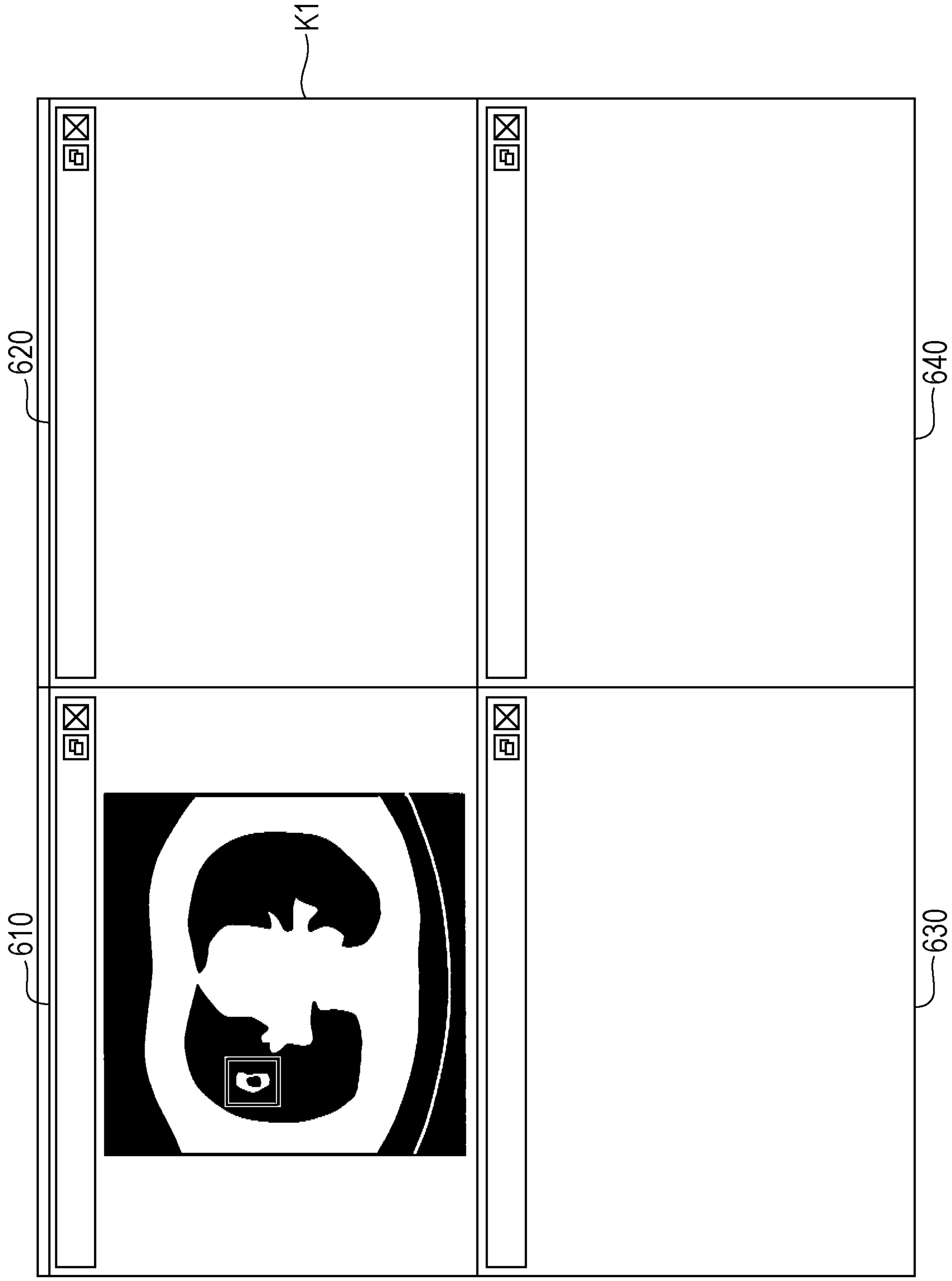
FIG. 5 is a diagram illustrating an example of a basic screen displayed on a display immediately after a similar case search application is started on the information terminal.

FIG. 5 is a diagram illustrating an example of a basic screen K1 displayed on the display 101*a* immediately after the similar case search application is started on the information terminal 100. The basic screen K1 illustrated in FIG. 5 includes four medical image viewers 610 to 640. Typical medical images are recorded in Digital Imaging and Communication in Medicine (DICOM) format, and the medical image viewers 610 to 640 are DICOM-compatible viewers. The medical images as used in this embodiment are chest CT images constituted by a large number of tomographic images (hereinafter referred to as "slice images") in DICOM format. This is merely an example, and CT images of any other body part (e.g., the head, abdomen, legs, or arms) may be used.

Each of the chest CT images displayed in the medical image viewers 610 to 640 is switched from one slice image to another through an operation with the mouse or keyboard. The slice images constituting the chest CT images are arranged in order from, for example, the neck toward the abdomen.

For example, when the input control unit 103 detects a rotation of the mouse wheel while the mouse pointer is on the medical image viewer 610, the display control unit 104 switches the slice image currently displayed in the medical image viewer 610 in accordance with the amount of rotation which is detected. For example, when the mouse wheel is rotated rearward (or toward the user of the mouse) by an amount corresponding to one click while the mouse is in the medical image viewer 610, the display control unit 104 switches the currently displayed slice image to the slice image corresponding to the next slice position. For example, when the mouse wheel is rotated forward (or away from the user of the mouse) by an amount corresponding to one click while the mouse is in the medical image viewer 610, the display control unit 104 switches the currently displayed slice image to the slice image corresponding to the preceding slice position. Accordingly, the user, such as a physician, retrieves the desired slice image while rotating the mouse wheel forward or rearward to appropriately switch between slice images to be displayed in the medical image viewer 610.

In place of chest CT images, magnetic resonance imaging (MRI) images or simple X-ray images may be used as medical images. Furthermore, four medical image viewers are used in the example illustrated in FIG. 5. This is merely an example, and a different number of medical image viewers, such as six or eight medical image viewers, may be used. As the number of medical image viewers used increases, the number of images to be simultaneously compared also increases whilst the display area per image decreases. Accordingly, the number of medical image viewers may be made variable, as desired, in accordance with the display size of the display 101*a*. By way of example, the number of medical image viewers may be changed by the user or an administrator as desired.

Before the similar case search application is started, a slice image of a chest CT image of a certain patient is displayed in the entire area of the display 101*a*. When the similar case search application is started by the user such as a radiologist in this situation, the slice image being displayed in the entire area of the display 101*a* is displayed in the medical image viewer 610.

That is, a search query image being displayed in the entire area of the display 101*a* when the user starts the similar case search application is initially displayed in the medical image viewer 610. The display control unit 104 may superimpose the region of interest (ROI) of the target to be subjected to a similar case search on a search query image for display. The search query image is an example of a target medical image that is a medical image to be interpreted.

In FIG. 5, no images are displayed in the medical image viewers 620 to 640. If there are a plurality of test images of a patient to be diagnosed and a plurality of test images are displayed on the display 101*a* before the similar case search application is started, the display control unit 104 may directly display the plurality of test images in the medical image viewers 620 to 640.

Figure 6:
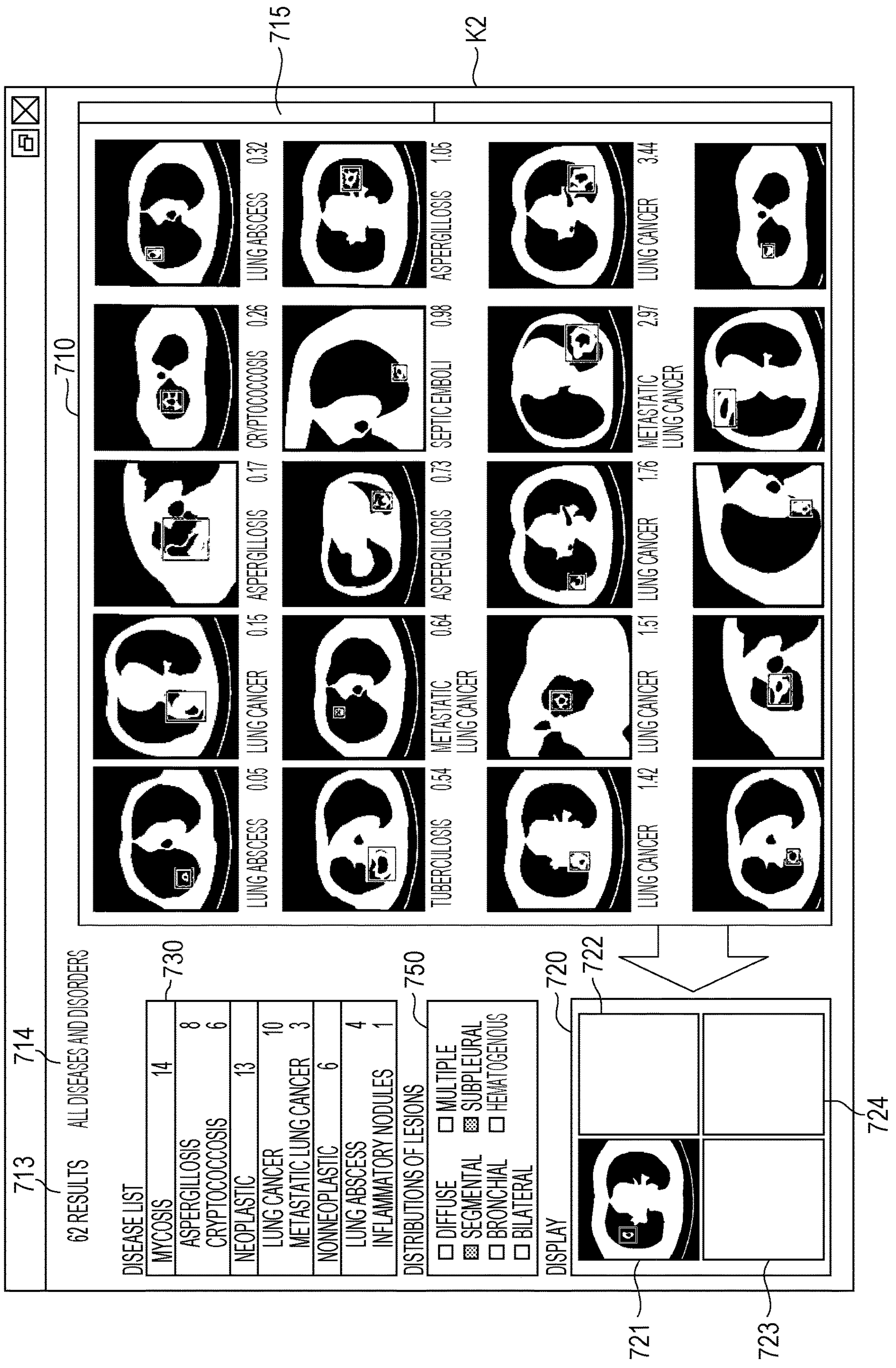
FIG. 6 is a diagram illustrating an example of a basic screen displayed on a display immediately after the similar case search application is started on the information terminal.

FIG. 6 is a diagram illustrating an example of a basic screen K2 displayed on the display 101*b* immediately after the similar case search application is started on the information terminal 100. The basic screen K2 illustrated in FIG. 6 includes a case display area 710, a layout area 720, a disease list display area 730, and a distribution list display area 750. The layout area 720 is an example of a first display area, and the case display area 710 is an example of a second display area.

The case display area 710 is an area where thumbnail images of similar cases that are similar to the search query image are displayed in order of similarity. A thumbnail image of a similar case is an example of a similar medical image.

Since the case display area 710 shows a large number of similar cases, further processing for resolution conversion or pixel-value conversion will take time. To avoid this inconvenience, the thumbnail images are created in advance from the original slice images, and are stored in the case search system 300.

Further description will now be given of resolution conversion and pixel-value conversion. Each original slice image has a resolution of 512 pixels by 512 pixels, whereas each thumbnail image has a lower resolution. Thus, resolution conversion is needed. Each of the thumbnail images is generated through the resolution reduction and grayscale conversion of the corresponding one of the original slice images.

For example, a grayscale conversion process is performed in the following way. The slice images obtained by CT imaging have pixel values (CT values) of 2000 grayscale values from −1000 to +1000 (expressed in Hounsfield units (HU)), and will not be directly displayed on a standard 8-bit grayscale display. Even if such slice images can be displayed, it is difficult for a person to distinguish the areas of pulmonary emphysema (with a CT value of −1000 HU), normal lung tissue (with a CT value of approximately −900 HU), the area of ground-glass opacity (with a CT value of −800 HU), soft tissue (with a CT value of −100 to −50 HU), water (with a CT value of 0 HU), and bone (with a CT value of 1000 HU), in the range of the 2000 grayscale values, from one another with the naked eye.

Thus, slice images are typically reconstructed with 8-bit pixel values for display on a display, where a window level and a window width are set for each pixel value. The window level represents the CT value of the center of the window, and the window width represents the difference between the upper limit and lower limit of a range centered about the center of the window.

For example, in a case where a DICOM image is reconstructed with the pulmonary condition, the window level is set to −550 to −800 and the window width is set to 1000 to 1600. Thus, a thumbnail image is also generated through the processing described above to reduce the pixel values of the original slice image to 8-bit pixel values.

The thumbnail images displayed in the case display area 710 are thumbnail images representing similar cases for which the distance from the feature vector of the case to be diagnosed is less than or equal to a predetermined threshold value. The distance is a Euclidean distance, by way of example. Any other distance measure, such as city block, may be used as the distance. As the distance between the two images to be compared decreases, the similarity between them increases. The feature vectors are not obtained from the thumbnail images but are obtained from the original images, that is, the DICOM images.

Figure 7:
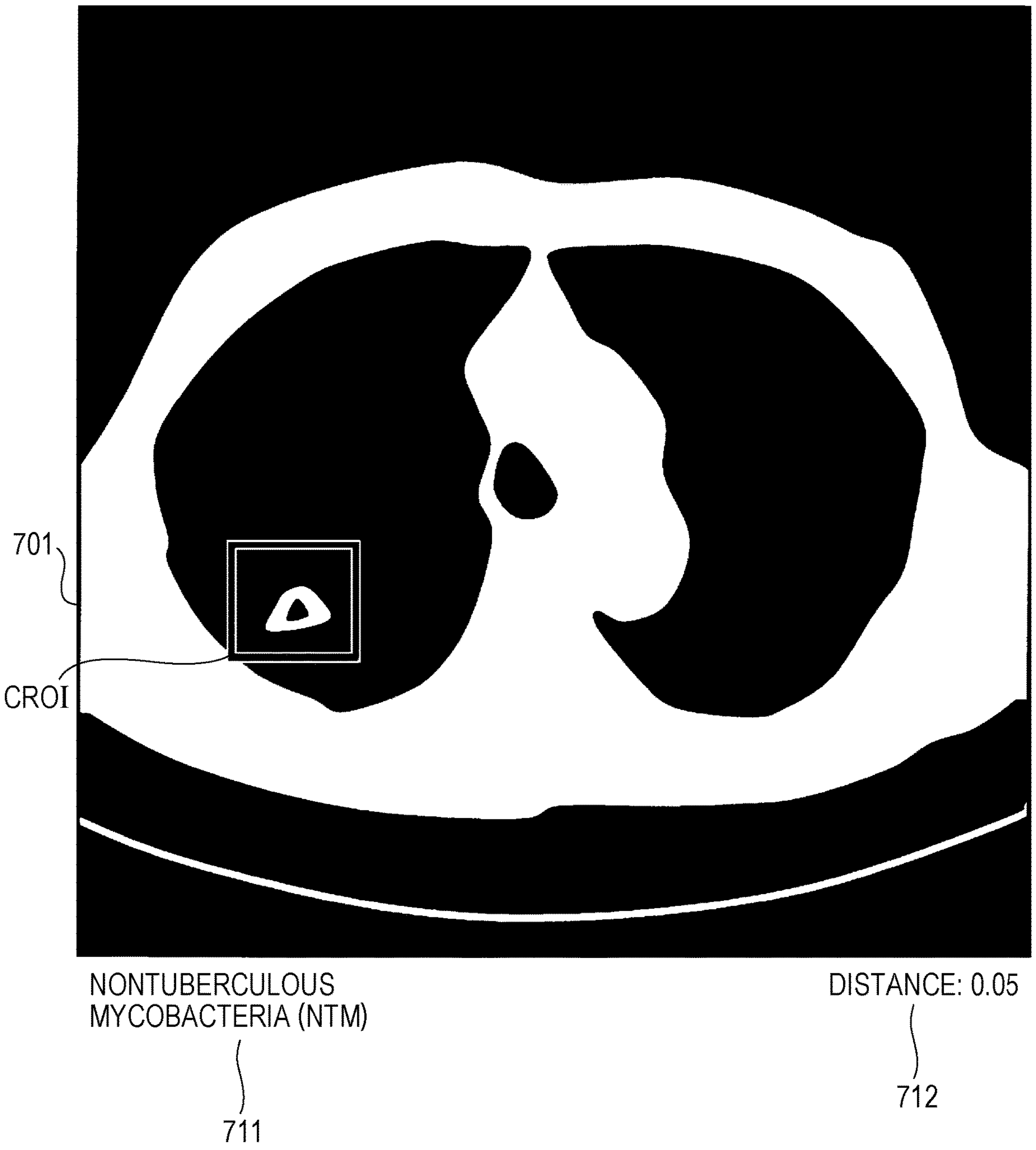
FIG. 7 is a diagram illustrating a display area for a certain similar case extracted from among similar cases displayed in a case display area.

FIG. 7 is a diagram illustrating a display area 701 (an example of a display frame) for a certain similar case extracted from among the similar cases displayed in the case display area 710. A thumbnail image is displayed in the display area 701 for the similar case, and a definitely diagnosed disease display area 711 and a distance display area 712 are placed below the thumbnail image. The definitely diagnosed disease display area 711 shows the name of the definitely diagnosed disease of the target similar case. The name of the definitely diagnosed disease is the name of a disease as which the target similar case has been diagnosed in definite diagnosis. The distance display area 712 shows the distance between the feature vector for the slice image of the target similar case and the feature vector for the search query image. In the example illustrated in FIG. 7, the definitely diagnosed disease display area 711 shows "nontuberculous mycobacteria (NTM)". Thus, the illustrated thumbnail image is a thumbnail image of a similar case diagnosed as "nontuberculous mycobacteria (NTM)" in definite diagnosis. The distance display area 712 shows "0.05", which indicates that the distance between the slice image of the similar case and the search query image is "0.05".

As illustrated in FIG. 7, the thumbnail image of the similar case, which is displayed in the display area 701, includes a corresponding region of interest CROI. The corresponding region of interest CROI is a region corresponding to the region of interest set on the search query image (i.e., the medical image to be interpreted) (that is, the corresponding region of interest CROI is a region similar to the region of interest). In the following, the corresponding region of interest is also referred to simply as the "region of interest".

Referring back to FIG. 6, for example, a number-of-search-result display area 713 is placed in an upper left portion of the basic screen K2. The number-of-search-result display area 713 shows the number of similar cases similar to the case to be diagnosed. The number of similar cases is obtained from the case search system 300 as a result of the search.

If the number of similar cases is very large, it will be difficult to display all the similar cases in the case display area 710 at the same time. Accordingly, the case display area 710 has, in a right portion thereof, for example, a vertical scrollbar 715. The display control unit 104 provides vertical scrolling through the thumbnail images displayed in the case display area 710 in accordance with the amount of movement of the scrollbar 715. This enables the user to display currently invisible similar cases in the case display area 710 so that the user can observe the similar cases.

The scrollbar 715 may be a horizontal scrollbar. In this case, the display control unit 104 may be configured to provide horizontal scrolling through the thumbnail images displayed in the case display area 710 in accordance with the amount of movement of the scrollbar 715.

The information terminal 100 is configured to acquire from the case search system 300 thumbnail images for which the distance from the search query image is less than or equal to a predetermined threshold value. This is merely an example. For example, the information terminal 100 may always acquire a certain number of thumbnail images from the case search system 300 in order of decreasing similarity. Alternatively, the information terminal 100 may acquire thumbnail images from the case search system 300 so that a certain number of thumbnail images of a certain definitely diagnosed disease are always included.

The thumbnail images may be displayed in the case display area 710 in such a manner that, for example, the thumbnail image with the shortest distance from the search query image is displayed at the left end of the top row and the distance sequentially increases from left to right, where, once the right end of the same row is reached, the next, large-distance thumbnail image is displayed at the left end of the second row from the top. That is, the following display technique may be used: The thumbnail images are displayed in the case display area 710, from left to right, top to bottom, in order of increasing distance.

Other display technique may be used in this embodiment. For example, the thumbnail images may be displayed in such a manner that the thumbnail image with the shortest distance is displayed at top end of the first column from the left and the distance sequentially increases from top to bottom, where, once the bottom end of the same column is reached, the next, large-distance thumbnail image is displayed at the top end of the second column from the left. Alternatively, the plurality of display techniques described above may be switched between by the user.

In the example described above, distance is used as similarity measure. Any index indicating the similarity between images, such as cosine similarity, may be used. In a case where cosine similarity is used, as the value approaches 1, the similarity between two images to be compared increases.

The similar cases to be displayed in the case display area 710 can be refined by a disease name, e.g., a disease name displayed in the disease list display area 730, or by a distribution of lesions, e.g., a distribution of lesions displayed in the distribution list display area 750, which will be described in detail below. A condition under which the similar cases are refined in the current setting is displayed in a display condition display area 714. The example illustrated in FIG. 6 illustrates the state immediately after a similar case search has been performed, and no refinement is performed. Thus, "all diseases and disorders" is displayed in the display condition display area 714.

The thumbnail images of the similar cases, which are displayed in the case display area 710, are designed to be able to be enlarged by a user operation. The enlarged display of the thumbnail images of the similar cases will be described hereinbelow.

Figure 8:
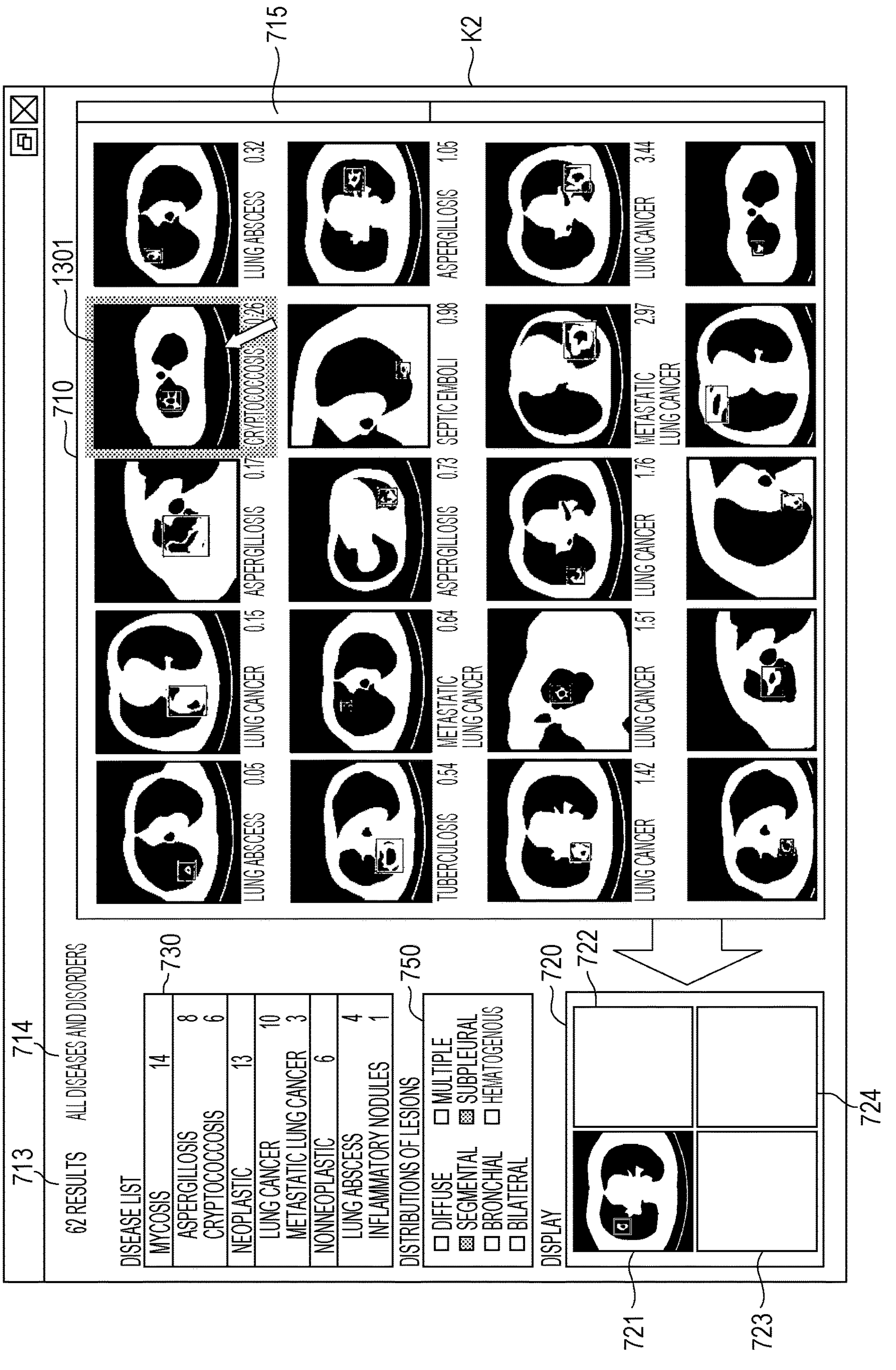
FIG. 8 is a diagram illustrating a basic screen obtained when one of the thumbnail images displayed in the case display area is selected.

FIG. 8 is a diagram illustrating the basic screen K2, which is obtained when one of the thumbnail images displayed in the case display area 710 is selected. As illustrated in FIG. 8, in each display area, a thumbnail image is displayed in its entirety in the state where the basic screen K2, which is obtained immediately after the similar case search is made, is being displayed. The case display area 710 includes a predetermined number ND (in this embodiment, ND=20) of display areas each showing a thumbnail image.

The input control unit 103 of the information terminal 100 constantly monitors the input through the operation unit 102 such as the mouse. The input control unit 103 detects that the operation of clicking the mouse has been input by the user and that one of the thumbnail images of the similar cases displayed in the case display area 710 has been selected in accordance with the operation. Then, the display control unit 104 changes the color of the background of the selected thumbnail image.

In the example illustrated in FIG. 8, a thumbnail image of a similar case displayed in a display area 1301 in the first row and the fourth column is selected in the case display area 710. Accordingly, the color of the background against which the thumbnail image is displayed in the display area 1301 is changed. Specifically, the color of a frame area surrounding the selected thumbnail image is changed. This enables the user to be notified that the associated thumbnail image has been selected.

The color of the background is, for example, a color that is clearly distinguishable from the color of the background of the case display area 710. In the example illustrated in FIG. 8, yellow is used by way of example. The example illustrated in FIG. 8 provides an embodiment in which the color of the frame area of the thumbnail image is changed. In an alternative embodiment, the method of blinking or illuminating the frame area may be used.

Figure 9:
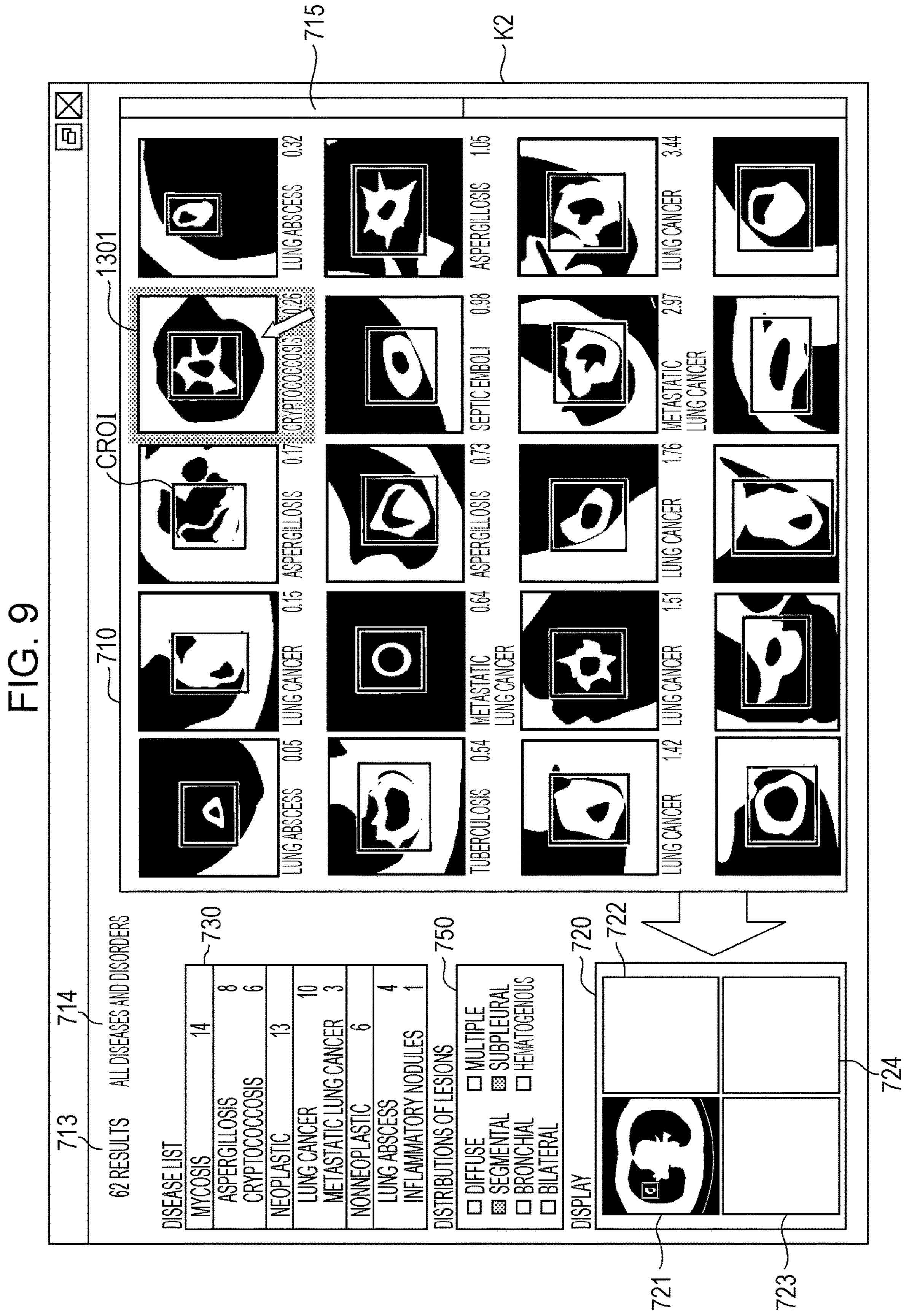
FIG. 9 is a diagram illustrating a basic screen obtained when a thumbnail image different from that illustrated in FIG. 8 is selected among the thumbnail images displayed in the case display area.
Figure 10:
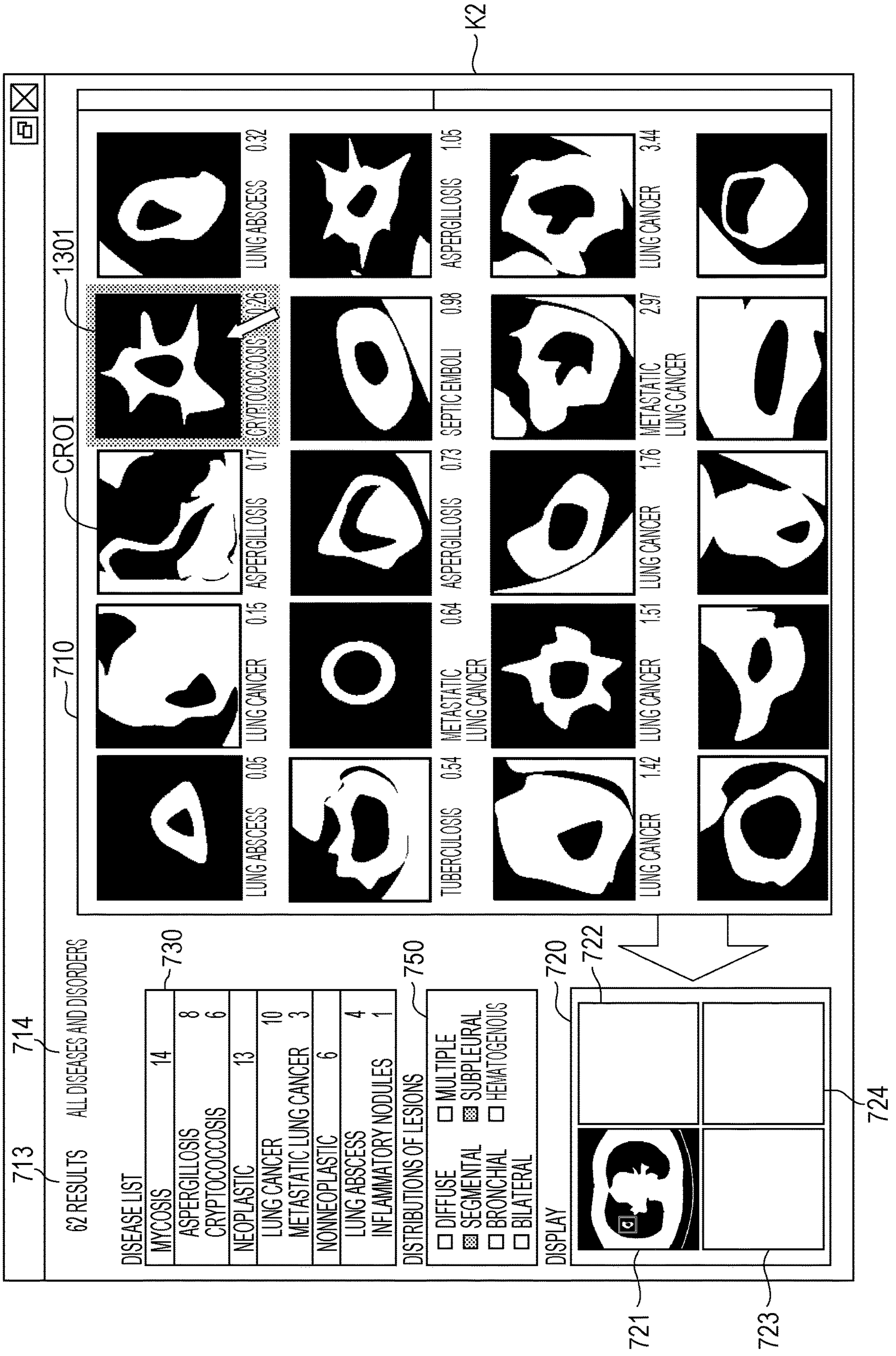
FIG. 10 is a diagram illustrating a basic screen obtained when all the thumbnail images displayed in the case display area are enlarged.

As illustrated in FIG. 8, when the user performs an enlargement operation by, for example, rotating the mouse wheel while one thumbnail image is selected, the input control unit 103 detects the amount of rotation of the mouse wheel, and notifies the enlarged image generation unit 112 of the detected amount of rotation. Then, the enlarged image generation unit 112 individually determines enlargement factors for the respective thumbnail images by, for example, using the notified amount of rotation, and enlarges all the thumbnail images with the determined enlargement factors. As illustrated in FIG. 9 or FIG. 10, for example, the display control unit 104 displays the thumbnail images enlarged by the enlarged image generation unit 112 in the case display area 710.

FIG. 9 is a diagram illustrating the basic screen K2, which is obtained when all the thumbnail images displayed in the case display area 710 are enlarged. As illustrated in FIG. 9, the 20 thumbnail images displayed in the case display area 710 have been enlarged. This may significantly reduce the processing load on the information terminal 100, compared to the case where the thumbnail images of all the 62 pieces of similar case data received from the case search system 300 are enlarged.

FIG. 10 is a diagram illustrating the basic screen K2, which is obtained when all the thumbnail images displayed in the case display area 710 are enlarged and which is different from that illustrated in FIG. 9. In FIG. 10, the enlarged image generation unit 112 generates enlarged thumbnail images so that the size of the corresponding region of interest CROI in each of the enlarged thumbnail images is the same as the size of the corresponding one of the display areas.

When enlarging a currently displayed thumbnail image, the enlarged image generation unit 112 generates an enlarged image so that, as illustrated in FIG. 9 or FIG. 10, the position of the center of the corresponding region of interest CROI matches the position of the center of the display area 1301. When enlarging a thumbnail image, furthermore, as illustrated in FIG. 9 or FIG. 10, the display control unit 104 maintains the size of the display area 1301 as is without increasing the size of the display area 1301.

Further, the enlarged image generation unit 112 may set an enlargement factor for each thumbnail image to a different value. This enables the thumbnail images to be enlarged so that, as illustrated in FIG. 9 or FIG. 10, the corresponding regions of interest CROI of the thumbnail images, when enlarged, have the same size.

In the way described above, a physician who makes image-based diagnosis merely performs an enlargement operation on one thumbnail image of a similar case on which they focus their attention, thus allowing the thumbnail images of all the other similar cases being displayed, as well as the thumbnail image of the similar case, to be enlarged and displayed. Thus, the physician is able to compare a plurality of similar cases in detail by issuing instructions once. Accordingly, the number of operations may be significantly reduced.

In FIG. 8, the thumbnail image of the similar case displayed in the display area 1301 in the first row and the fourth column is selected. The user can select any thumbnail image. The user may only be required to select any one of the 20 thumbnail images being displayed.

Figure 11:
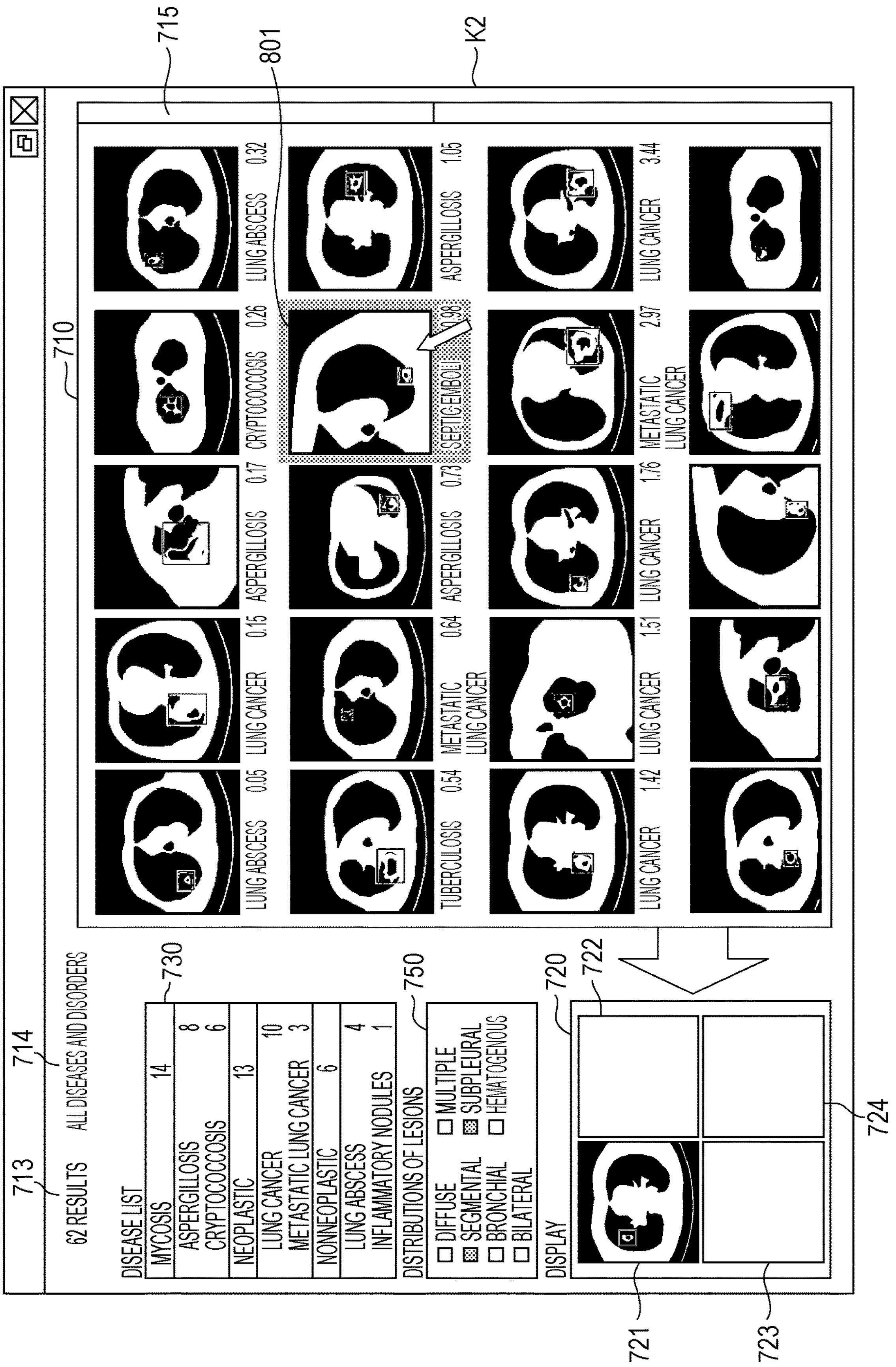
FIG. 11 is a diagram illustrating a basic screen, different from that illustrated in FIG. 10, which is obtained when all the thumbnail images displayed in the case display area are enlarged.

FIG. 11 is a diagram illustrating the basic screen K2, which is obtained when a thumbnail image different from that illustrated in FIG. 8 is selected from among the thumbnail images displayed in the case display area 710. In FIG. 11, the thumbnail image displayed in a display area 801 in the second row and the fourth column is selected by a user. Also in FIG. 11, when the user performs an enlargement operation by, for example, rotating the mouse wheel while the thumbnail image in the second row and the fourth column is selected, the input control unit 103 detects the amount of rotation of the mouse wheel, and notifies the enlarged image generation unit 112 of the detected amount of rotation. Then, the enlarged image generation unit 112 individually determines enlargement factors for the respective thumbnail images by, for example, using the notified amount of rotation, and enlarges all the thumbnail images with the determined enlargement factors. The display control unit 104 displays the thumbnail images enlarged by the enlarged image generation unit 112 in the case display area 710.

In the foregoing description, a user performs an enlargement operation by rotating the mouse wheel. However, the present disclosure is not limited to this. The user may perform an enlargement operation by, for example, placing the mouse pointer on one of the thumbnail images displayed in the case display area 710 and pressing, for example, the up arrow key or down arrow key on the keyboard while pressing the mouse button. In this case, the input control unit 103 may count the length of time during which the up arrow key or down arrow key is pressed. The enlarged image generation unit 112 may determine an enlargement factor by using, for example, the length of time during which the up arrow key or down arrow key is pressed.

The details of a specific processing procedure for enlarging a thumbnail image will be described below.

The thumbnail images displayed in the case display area 710 are designed so that the display areas in the thumbnail images can be changed by a user operation. In the following, a change of a display area of a thumbnail image of a similar case will be described.

Figure 12:
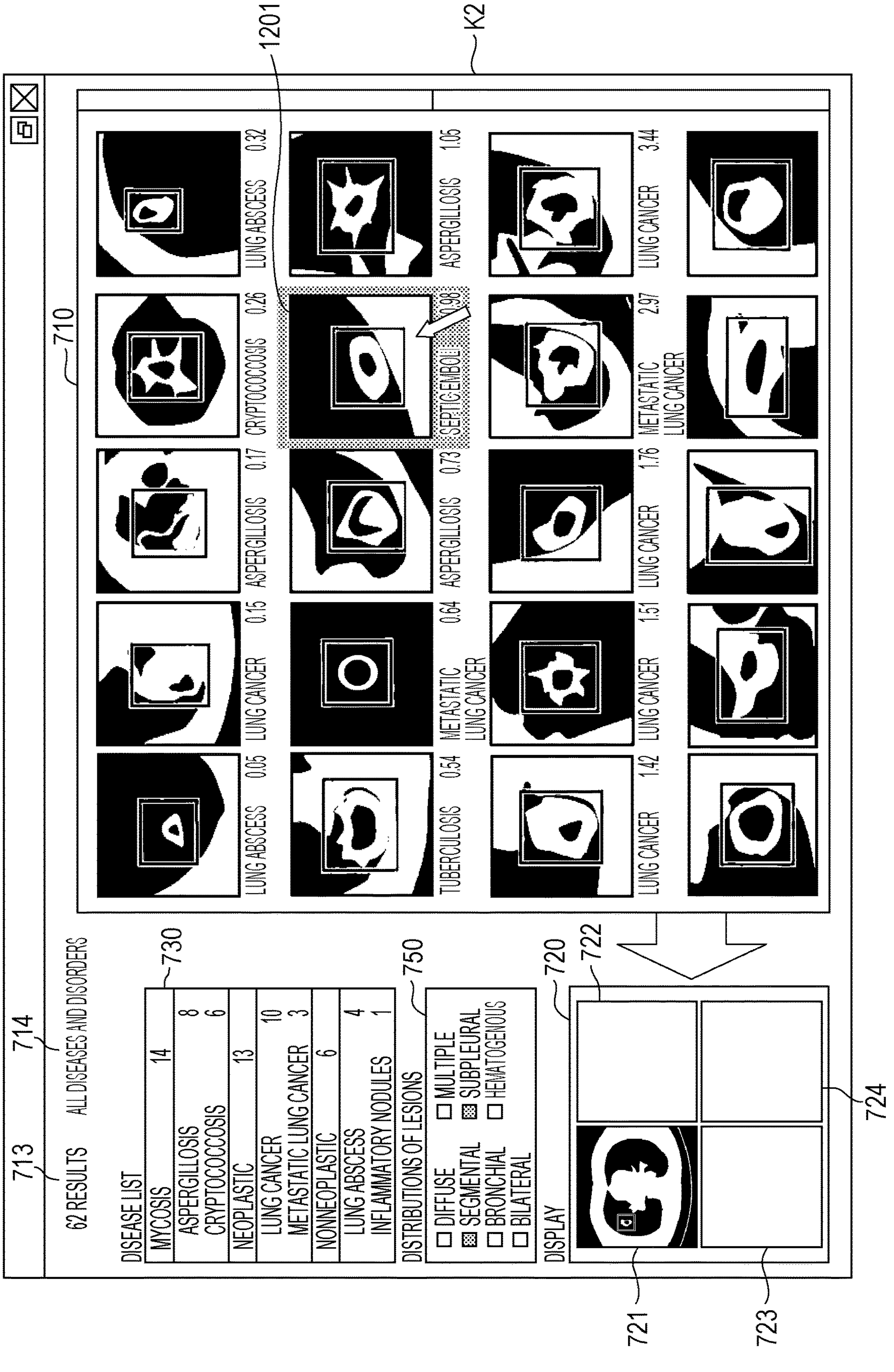
FIG. 12 is a diagram illustrating a basic screen obtained when one of the thumbnail images displayed in the case display area is selected after the thumbnail images are enlarged and displayed.

FIG. 12 is a diagram illustrating the basic screen K2, which is obtained when one of the thumbnail images displayed in the case display area 710 is selected after the thumbnail images are enlarged and displayed. As illustrated in FIG. 12, while the basic screen K2, which is obtained after the thumbnail images are enlarged and displayed, is being displayed, the thumbnail images are enlarged and displayed in the respective display areas.

The input control unit 103 of the information terminal 100 constantly monitors the input through the operation unit 102 such as the mouse. The input control unit 103 detects that the operation of clicking the mouse has been input by the user and that one of the thumbnail images of the similar cases displayed in the case display area 710 has been selected in accordance with the operation. Then, the display control unit 104 changes the color of the background of the selected thumbnail image.

In the example illustrated in FIG. 12, the thumbnail image of the similar case displayed in a display area 1201 in the second row and the fourth column is selected in the case display area 710. Accordingly, the color of the background against which the thumbnail image is displayed in the display area 1201 is changed. Specifically, the color of a frame area surrounding the selected thumbnail image is changed. This enables the user to be notified that the associated thumbnail image has been selected.

The color of the background is, for example, a color that is clearly distinguishable from the color of the background of the case display area 710. In the example illustrated in FIG. 12, yellow is used by way of example. The example illustrated in FIG. 12 provides an embodiment in which the color of the frame area of the thumbnail image is changed. In an alternative embodiment, the method of blinking or illuminating the frame area may be used.

As illustrated in FIG. 12, the user performs a (drag) operation of changing the mouse position while, for example, pressing the left button of the mouse while one of the thumbnail images is selected.

Figure 13:
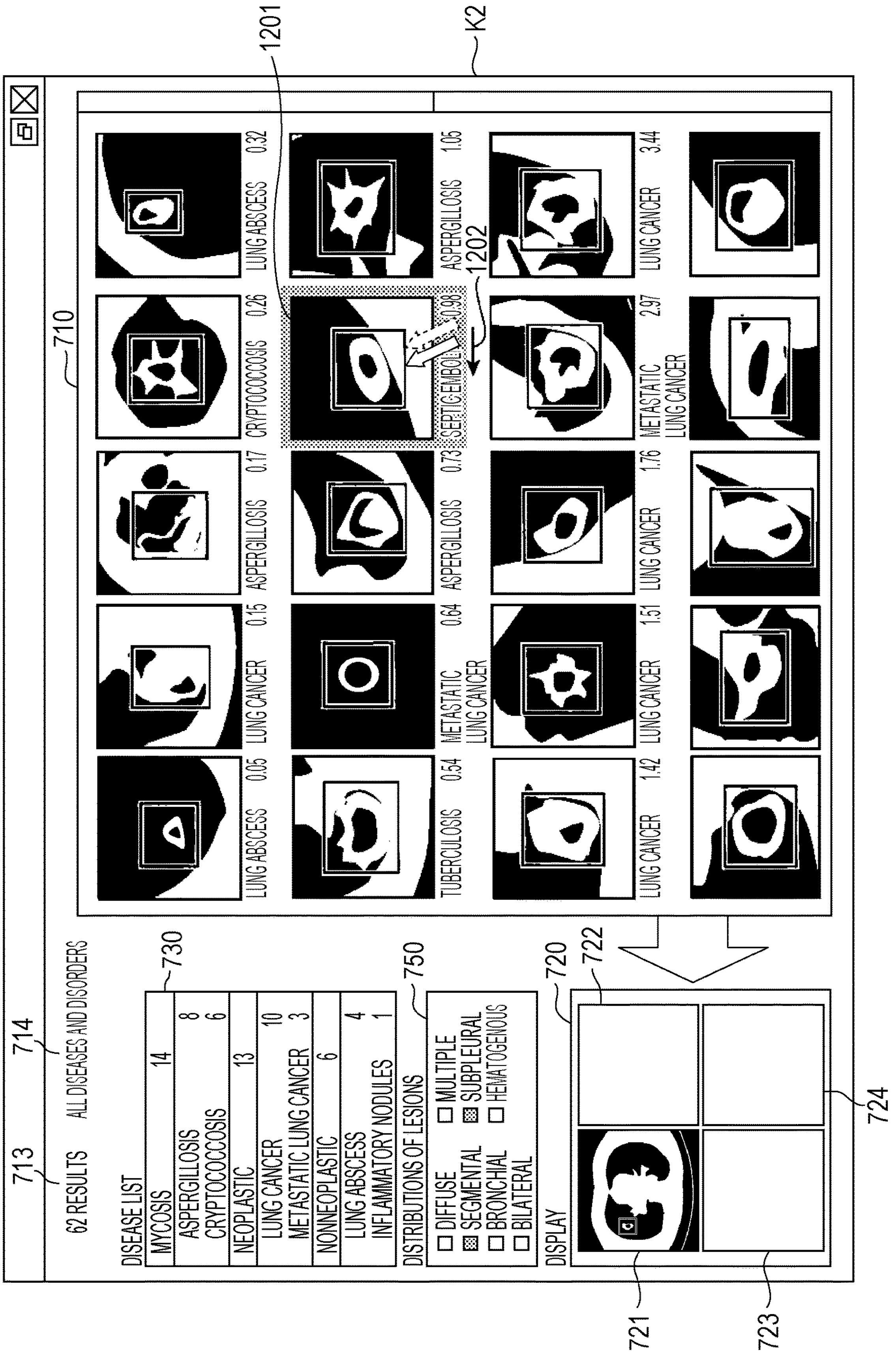
FIG. 13 is a diagram schematically illustrating a drag operation performed by a user while a basic screen is being displayed.

FIG. 13 is a diagram schematically illustrating a drag operation 1202 performed by a user while the basic screen K2 is being displayed. When the user performs the drag operation 1202, the input control unit 103 detects the amount of movement of the mouse, and notifies the enlarged image generation unit 112 of the detected amount of movement. Then, the enlarged image generation unit 112 determines an amount of movement of a display area in a thumbnail image by using the detected amount of movement of the mouse, and generates a thumbnail image in which the display area has moved by the determined amount. The display control unit 104 displays, in the case display area 710, thumbnail images that have been caused to move by the enlarged image generation unit 112.

Figure 14:
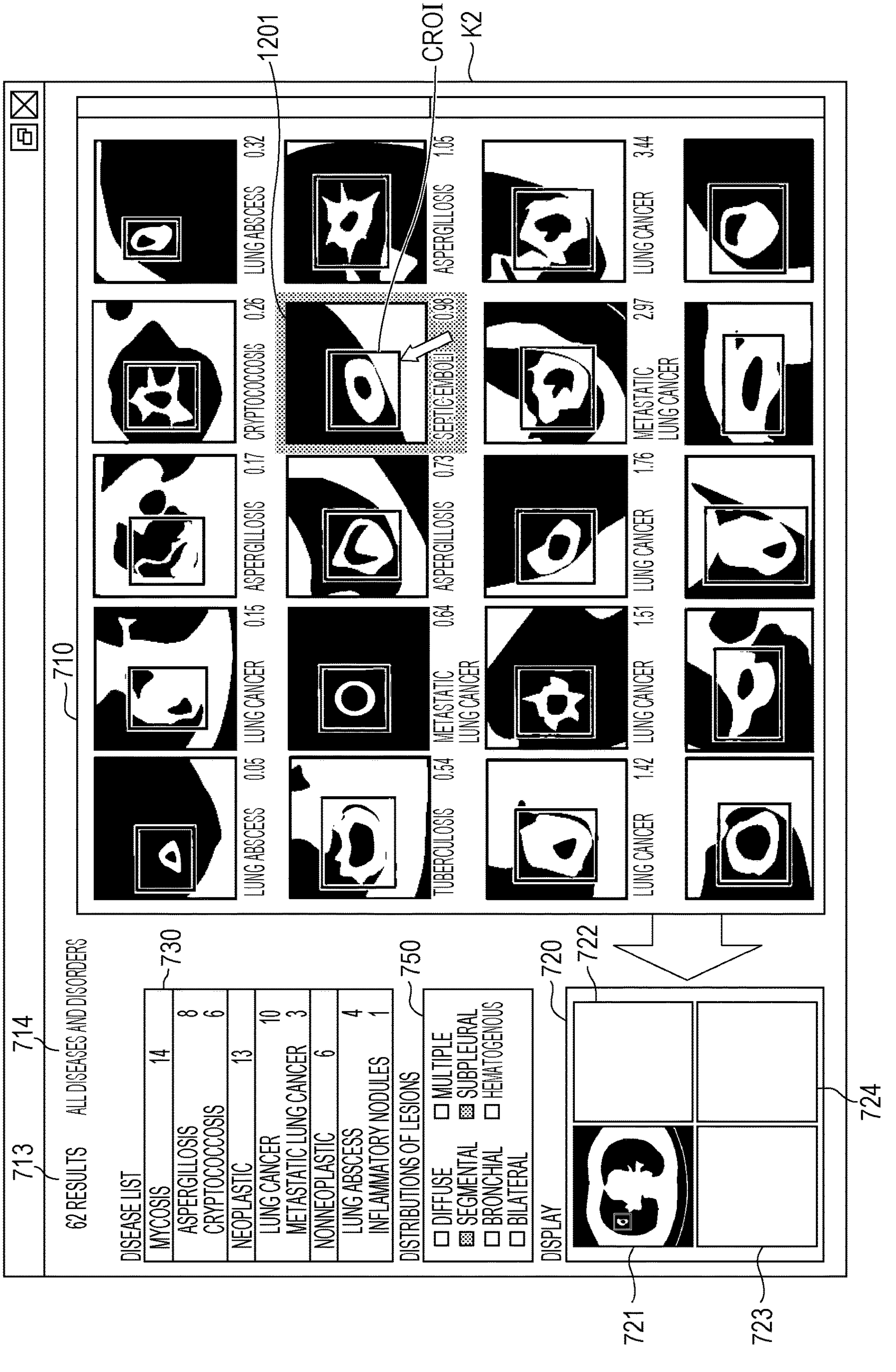
FIG. 14 is a diagram illustrating a basic screen obtained when display areas in thumbnail images displayed in the case display area are caused to move.

FIG. 14 is a diagram illustrating the basic screen K2, which is obtained when a display area of a thumbnail image displayed in the case display area 710 is caused to move. Specifically, in FIG. 14, not only the display area of the selected thumbnail image but also the display areas of the 20 thumbnail images in total which are displayed in the case display area 710 are caused to move.

When causing the display areas of the currently displayed thumbnail images to move, the enlarged image generation unit 112 generates thumbnail images after movement so that, as illustrated in FIG. 14, the positions of the corresponding regions of interest CROI in all the thumbnail images displayed in the case display area 710 are moved in the respective display areas 1201 by the same amount. Specifically, for example, the user drags the mouse to the left, causing the display areas of the 20 thumbnail images in total, which are displayed in enlarged form, to move so that the portion to the right of the corresponding region of interest CROI in each of the 20 thumbnail images appears.

Figure 15:
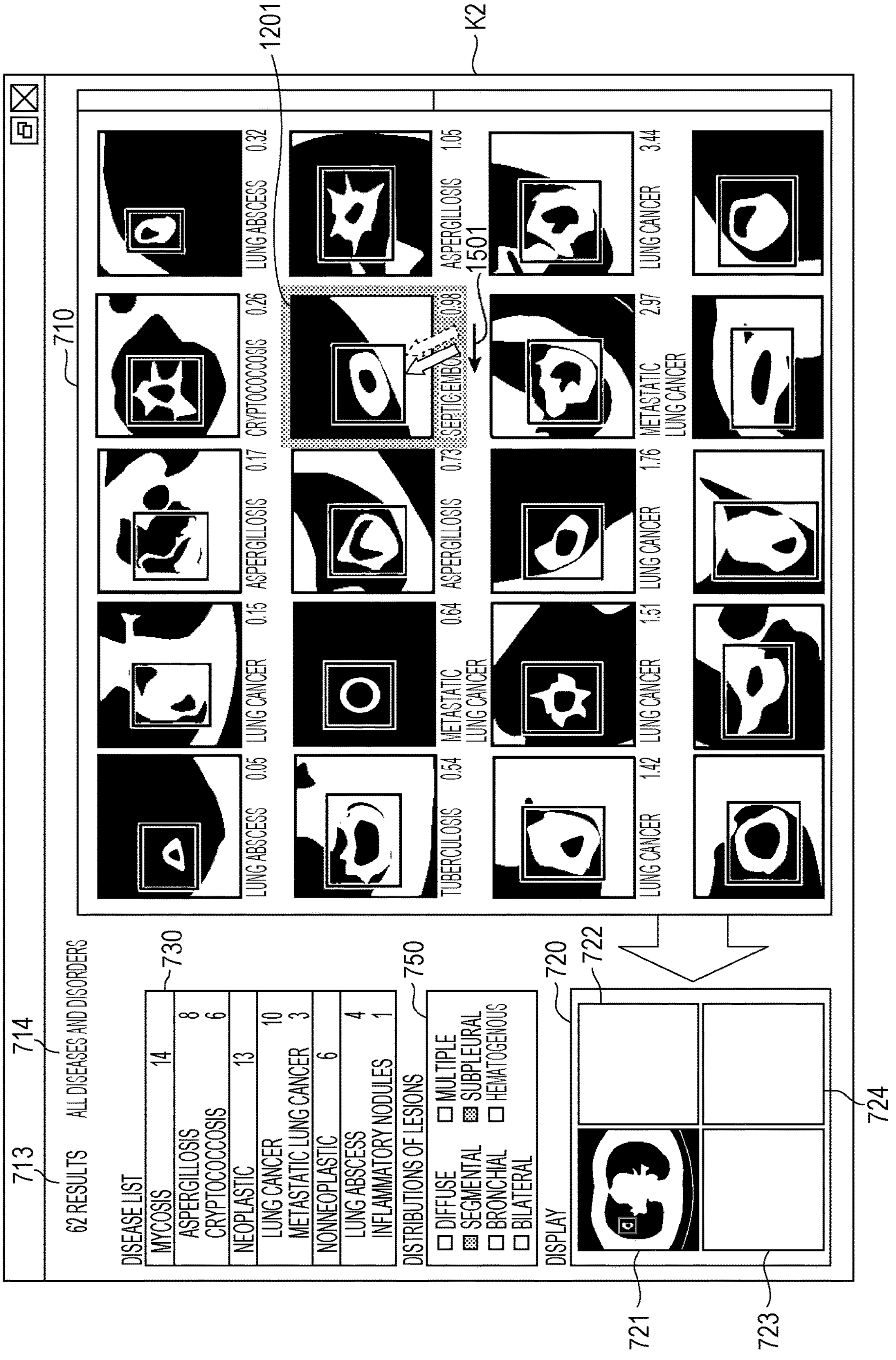
FIG. 15 is a diagram schematically illustrating a drag operation further performed by the user while the basic screen illustrated in FIG. 14 is being displayed.

FIG. 15 is a diagram schematically illustrating a drag operation 1501 performed by a user while the basic screen K2 is being displayed in the manner illustrated in FIG. 14. As illustrated in FIG. 15, when the user performs an operation of changing the mouse position while further pressing the left button of the mouse from the state illustrated in FIG. 14, the input control unit 103 detects the amount of movement of the mouse, and notifies the enlarged image generation unit 112 of the detected amount of movement. Then, the enlarged image generation unit 112 determines an amount of movement of a display area in a thumbnail image by using the detected amount of movement of the mouse, and generates a thumbnail image in which the display area has moved the determined amount. The display control unit 104 displays, in the case display area 710, thumbnail images that have been caused to move by the enlarged image generation unit 112.

Figure 16:
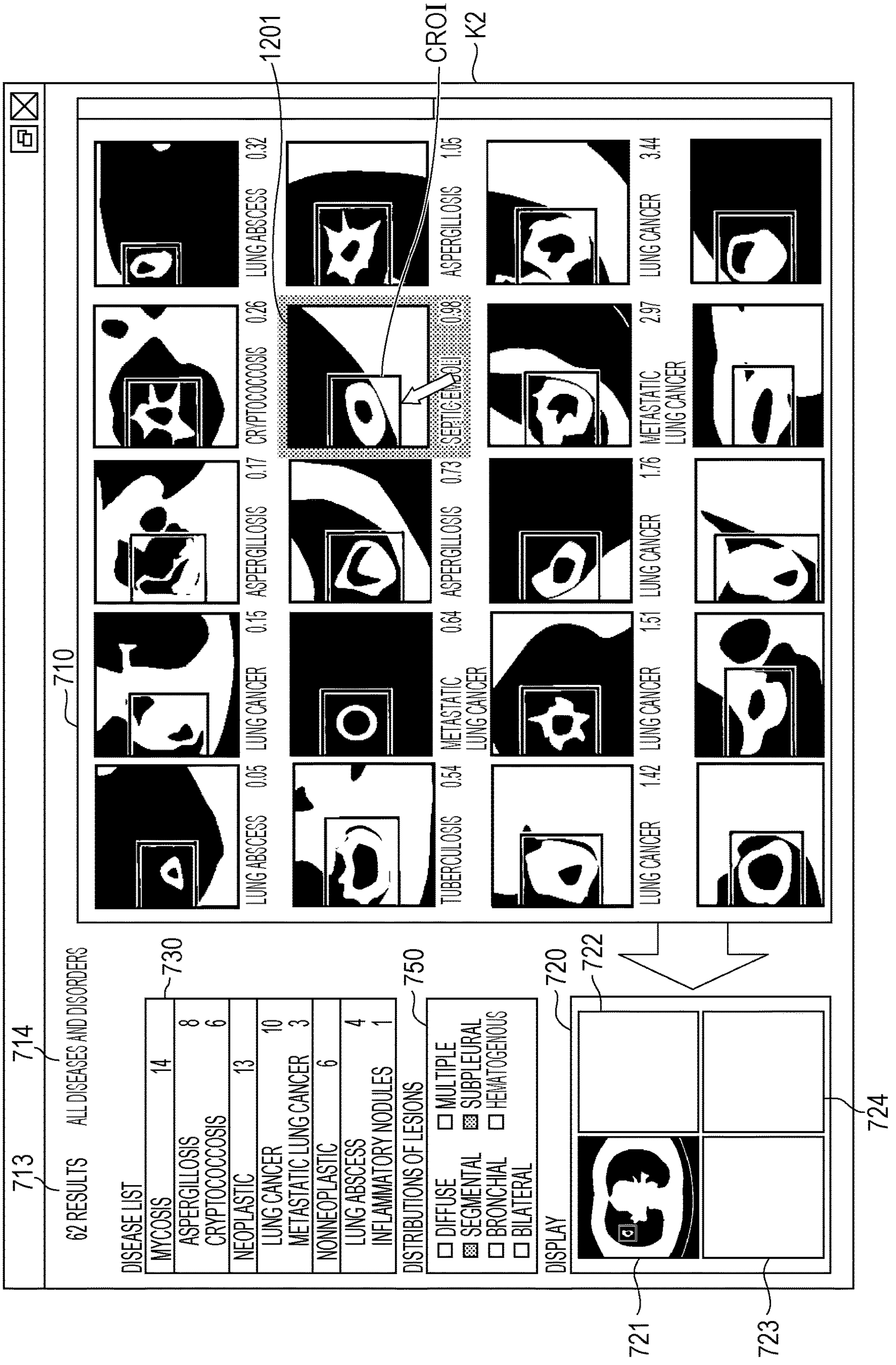
FIG. 16 is a diagram illustrating a basic screen obtained when the display area in the thumbnail image displayed in the case display area is moved by the drag operation illustrated in FIG. 15.

FIG. 16 is a diagram illustrating the basic screen K2, which is obtained when a display area in a thumbnail image displayed in the case display area 710 moves with the drag operation 1501 illustrated in FIG. 15. Specifically, as in FIG. 14, in FIG. 16, not only the display area in the selected thumbnail image but also the display areas in the 20 thumbnail images in total which are displayed in the case display area 710 have moved. Also in FIG. 16, when causing the display areas of the currently displayed thumbnail images to move, the enlarged image generation unit 112 generates thumbnail images after movement so that the positions of the corresponding regions of interest CROI in all the thumbnail images displayed in the case display area 710 are moved in the respective display areas by the same amount. Specifically, the user drags the mouse to the left, causing the display areas in the 20 thumbnail images in total, which are displayed in enlarged form, to move so that the portion to the right of the corresponding regions of interest CROI in each of the 20 thumbnail images appears. The details of the process for causing a display area in a thumbnail image to move will be described below.

For example, in pulmonary adenocarcinoma, pulmonary tuberculosis, and the like, in the process of separating a cancer cell or bacteria from the primary lesion, such a cancer cell or bacteria may be inhaled into other parts, and disseminated lesions in the bronchiole may be observed. Thus, a physician observes not only a primary lesion but also secondary lesions around the primary lesion in image-based diagnosis.

In a similar case search, there is a need fora physician to, after determining that the primary lesion in the similar case under diagnosis is similar to the case to be used for image interpretation, determine whether or not secondary lesions around the primary lesion are also similar to refine similar cases obtained as a result of the search to narrow down the selection of disease names. To meet the need, a function of enabling a user to observe not only the primary lesion to which the corresponding region of interest is assigned in a thumbnail image of a similar case but also a region surrounding the primary lesion by causing the display area to move in response to an operation performed by the user may be effective for image-based diagnosis. In particular, in order to distinguish a plurality of diseases having similar primary lesions, the user compares secondary lesions around the primary lesions. It is thus preferable that the user be able to compare surrounding regions in a plurality of similar cases at the same time.

With the function described above, a physician who makes image-based diagnosis merely operates a display area of a thumbnail image of a similar case on which they focus their attention, thus allowing the display areas for the similar cases other than the similar case on which they focus their attention to move synchronously with the display area for the focused similar case. Thus, the physician is able to compare similar cases in detail by issuing instructions once. Accordingly, the number of operations may be significantly reduced.

As illustrated in FIG. 14 and FIG. 16, the enlarged image generation unit 112 generates thumbnail images after movement so that the positions of the corresponding regions of interest CROI in all the thumbnail images displayed in the case display area 710 are moved in the respective display areas 1201 by the same amount. Note that the area of the corresponding region of interest CROI included in the similar medical image selected by the user (in the examples illustrated in FIG. 12 to FIG. 16, the thumbnail image displayed in the display area 1201 in the second row and the fourth column) may not necessarily be the same as the area of the corresponding regions of interest CROI included in the other similar medical images.

Accordingly, a value obtained by multiplying the amount of operation input by the user by the enlargement factor for each thumbnail image is used as the amount of movement of the associated display area. For example, it is assumed that the area of the corresponding region of interest CROI included in the similar medical image selected by the user (an example of a selected similar medical image) is larger than the area of the corresponding region of interest CROI included in another similar medical image (an example of an unselected similar medical image). In this case, if the movement distance of the similar medical image selected by the user is the same as the movement distance of the other similar medical image, as a result of movement of the other similar medical image, the corresponding region of interest CROI included in the other similar medical image moves a large amount. Consequently, a larger number of surrounding areas away from the corresponding region of interest CROI in the other similar medical image appear. In general, secondary lesions are more likely to be present in surrounding areas close to the corresponding region of interest CROI in the other similar medical image.

For this reason, if, as a result of movement of another similar medical image other than a selected similar medical image, a surrounding area away from the corresponding region of interest CROI in the other similar medical image appears, secondary lesions may fail to be detected. To avoid such a risk, as illustrated in FIG. 14 and FIG. 16, the display areas of the thumbnail images are caused to move so that enlarged thumbnail images which are displayed in the case display area 710 seem to move the same amount in the respective display areas 1201. Accordingly, for example, even if the area of the corresponding region of interest CROI included in a similar medical image selected by the user is larger than the area of the corresponding region of interest CROI included in another similar medical image, the movement distance of the similar medical image selected by the user is not equal to the movement distance of the other similar medical image. This may prevent a surrounding area away from the corresponding region of interest CROI included in the other similar medical image from appearing as a result of movement of the other similar medical image.

Consequently, it may be possible to reduce the risk of secondary lesions failing to be detected without the need for the operation to cause a plurality of similar medical images to separately move, making the physician concentrate their attention on the medical treatment decision. Accordingly, the accuracy of medical treatment decision may be effectively improved.

Referring back to FIG. 6, the layout area 720 is displayed in, for example, a lower left portion of the basic screen K2 illustrated in FIG. 6. The layout area 720 is used so that an image that the user wishes to observe in more detail among the thumbnail images of the similar cases displayed in the case display area 710 is displayed in a medical image viewer on the display 101*a*. As illustrated in FIG. 5, the four medical image viewers 610 to 640 arranged in two rows and two columns are displayed on the display 101*a*. Further, the layout area 720 has four display boxes 721 to 724 arranged in two rows and two columns. In the manner described above, the number and layout of the medical image viewers 610 to 640 displayed on the display 101*a* is consistent with the number and layout of the display boxes 721 to 724 in the layout area 720. In accordance with the display of the search query image in the medical image viewer 610 illustrated in FIG. 5, the thumbnail image of the search query image is initially displayed in the display box 721.

Each of the other display boxes 722 to 724 shows a thumbnail image of a similar case in accordance with an image displayed in the corresponding one of the medical image viewers 620 to 640. That is, when the input control unit 103 detects that one of the thumbnail images displayed in the case display area 710 has been dragged and dropped onto one of the display boxes 722 to 724, the display control unit 104 causes the thumbnail image to be displayed in the display box, and also causes the slice image corresponding to the thumbnail image to be displayed in the medical image viewer corresponding to the display box. Accordingly, the medical image viewers 610 to 640 are associated with the display boxes 721 to 724 in a one-to-one correspondence.

In the example illustrated in FIG. 6, the display boxes 722 to 724 are blank, and the medical image viewers 620 to 640 illustrated in FIG. 5 are also blank accordingly.

The user performs a drag-and-drop operation using the mouse to move the thumbnail image that the user wishes to observe in more detail from the case display area 710 to the layout area 720. For example, when the user moves a thumbnail image to the display box 722, the slice image corresponding to the thumbnail image is displayed in the medical image viewer 620 corresponding to the display box 722. Also, when the user moves a thumbnail image to the display box 723, the slice image corresponding to the thumbnail image is displayed in the medical image viewer 630 corresponding to the display box 723. That is, a thumbnail image is moved to any display box among the display boxes 721 to 724, resulting in a thumbnail image of a similar case being displayed adjacent to the thumbnail image of the search query image. This enables the user to compare the case to be diagnosed and the similar case on the level of thumbnail images and to quickly determine the similarity between the two cases. Since thumbnail images have a smaller amount of information than slice images, the user is able to roughly estimate how much the case to be diagnosed and the similar case which is adjacent in the layout area 720 are similar. This enables the user to efficiently narrow a large number of similar cases displayed in the case display area 710 down to a final set of candidates of similar cases to be compared with the target case to be diagnosed in more detail on the level of slice images.

The search query image and the slice image of the similar case are also displayed on the display 101*a* in the same position and layout as those in the layout area 720. After the completion of narrowing down to a final set of candidates of similar cases in the layout area 720, the case to be diagnosed and similar cases obtained as the final set of candidates are displayed on the display 101*a* on the level of slice images without inputting any operation. This guides the user smoothly to the next operation step of detailed image interpretation of the case to be diagnosed and the similar cases obtained as the final set of candidates.

The disease list display area 730 with the heading "disease list" is displayed in an upper left portion of the basic screen illustrated in FIG. 6. The disease list display area 730 shows the names of the definitely diagnosed diseases of all the similar cases obtained as a result of the similar case search. The case to be diagnosed is labeled the name of a definitely diagnosed disease after diagnosis, and is then accumulated in the case search system 300 as a similar case. Thus, each similar case is labeled in advance the name of a definitely diagnosed disease which is obtained through diagnosis.

FIG. 17 is an enlarged view of the disease list display area 730. In FIG. 17, the names of definitely diagnosed diseases are displayed separately as the names of major-category diseases (731, 734, 737, 741, and 744) and the names of subcategory diseases (732, 733, 735, 736, 738, 739, 740, 742, 743, and 745). In the example illustrated in FIG. 17, "mycosis" 731, "neoplastic" 734, "nonneoplastic" 737, "mycobacteriosis" 741, and "other" 744 are displayed as the names of major-category diseases.

In the example illustrated in FIG. 17, furthermore, "aspergillosis" 732 and "cryptococcosis" 733 are displayed as the names of subcategory diseases of the "mycosis" 731. Further, "lung cancer" 735 and "metastatic lung cancer" 736 are displayed as the names of subcategory diseases of the "neoplastic" 734. Further, "lung abscess" 738, "sarcoidosis" 739, and "septic emboli" 740 are displayed as the names of subcategory diseases of the "nonneoplastic" 737. Further, "nontuberculous mycobacteria (NTM)" 742 and "tuberculosis" 743 are displayed as the names of subcategory diseases of the "mycobacteriosis" 741. Further, "bronchiectasis" 745 is displayed as the name of a subcategory disease of the "other" 744.

Figure 18:
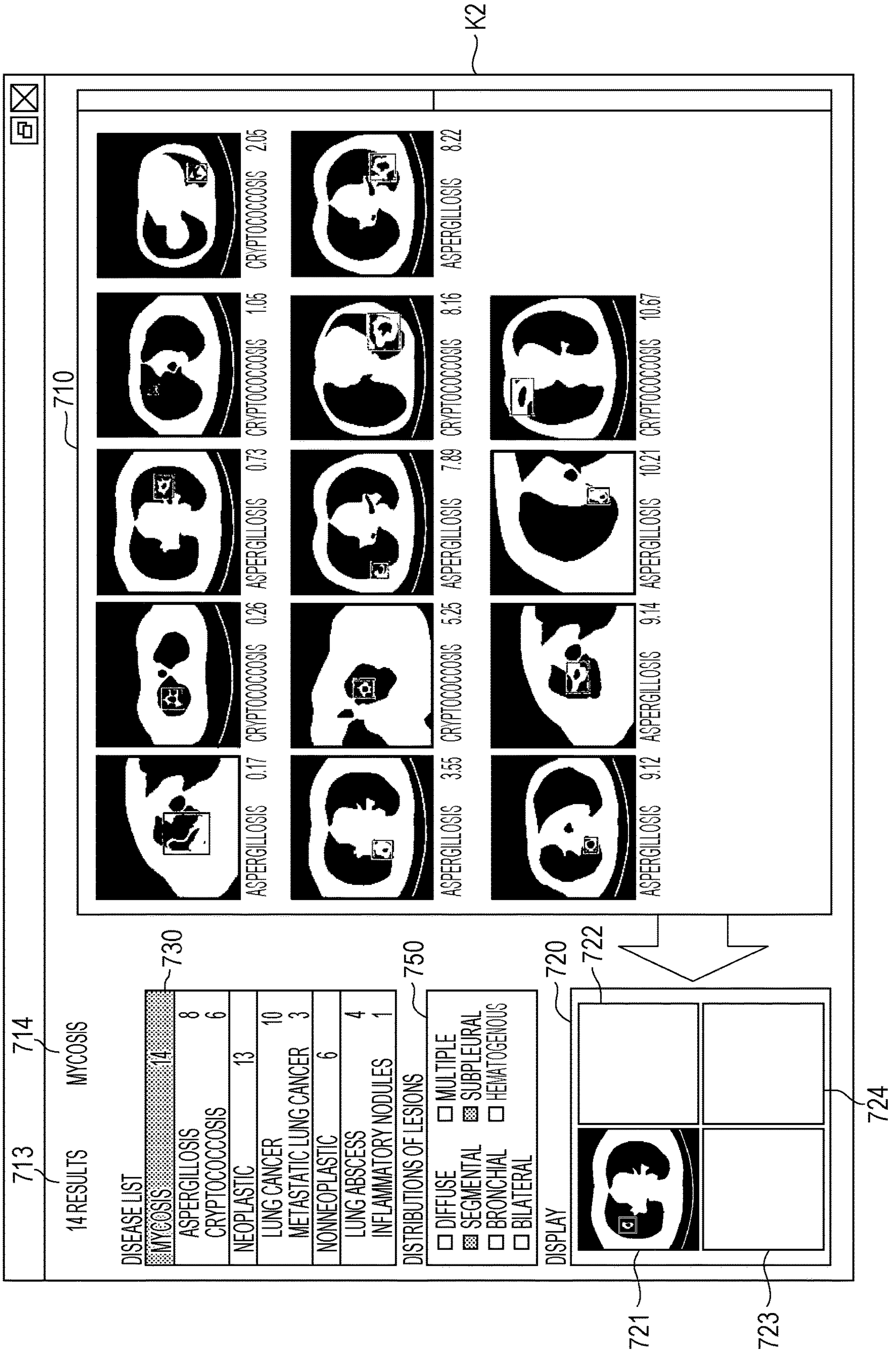
FIG. 18 is a diagram illustrating a basic screen on which similar cases are refined according to "mycosis"
Figure 19:
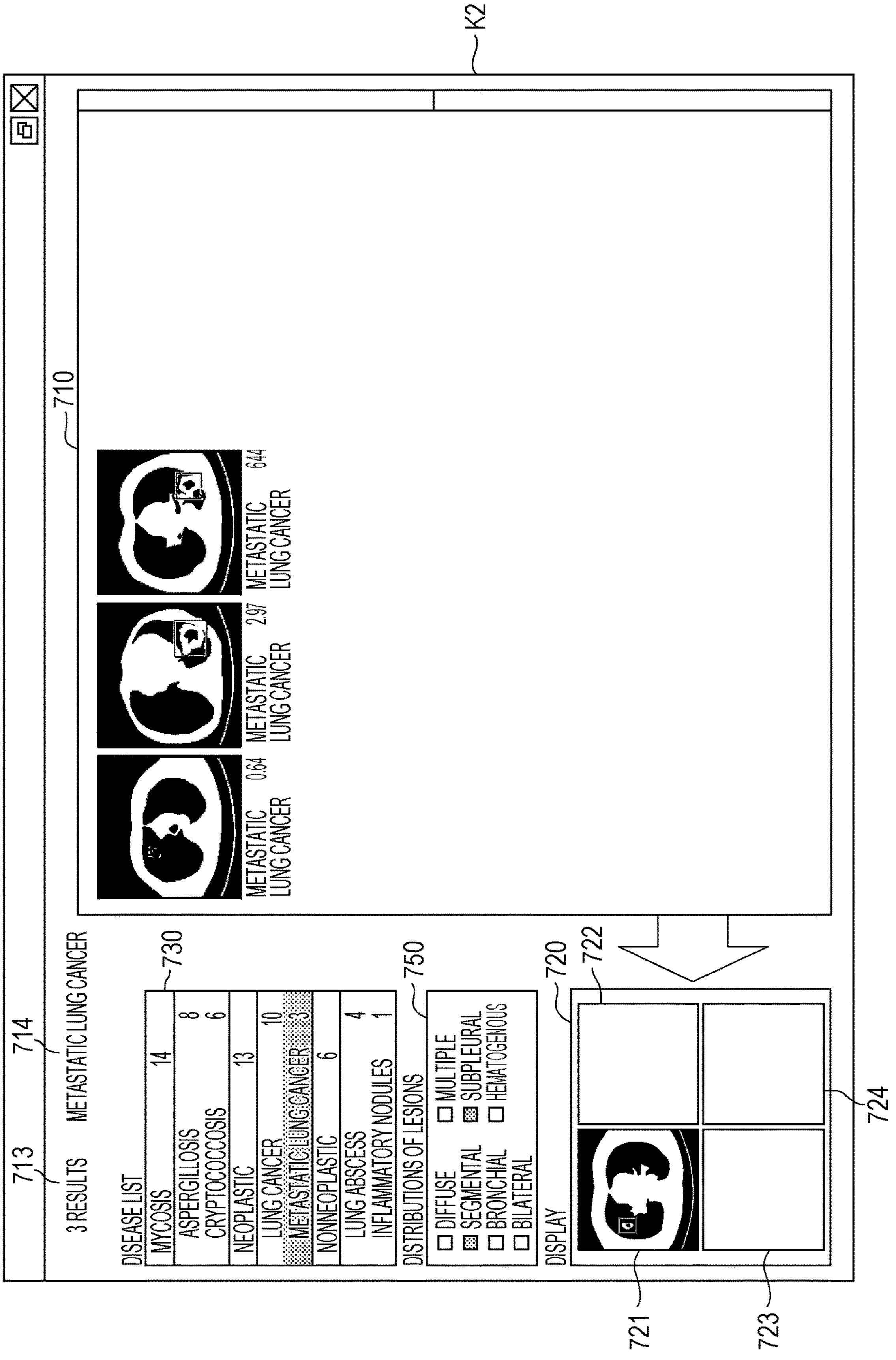
FIG. 19 is a diagram illustrating a basic screen on which similar cases are refined according to "metastatic lung cancer"

Further, next to the names of the major-category diseases and the subcategory diseases are the numbers of cases of the respective diseases. By selecting a row corresponding to any of the names of the major-category diseases or subcategory diseases in the disease list display area 730, the user can refine the similar cases to be displayed in the case display area 710. As illustrated in FIG. 6, immediately after a similar case search is made, 62 similar cases including diverse diseases and disorders are set as targets to be displayed. As a result of clicking on the row corresponding to the "mycosis" 731 in FIG. 17 with the mouse, as illustrated in FIG. 18, the display control unit 104 displays similar cases of mycosis in the case display area 710. As a result of clicking on the row corresponding to the "metastatic lung cancer" 736 in FIG. 17 with the mouse, as illustrated in FIG. 19, the display control unit 104 displays similar cases of metastatic lung cancer in the case display area 710.

In this case, the display control unit 104 displays the name of the disease used for refinement in the display condition display area 714 so that the user can identify how the similar cases currently being displayed in the case display area 710 have been refined. FIG. 18 is a diagram illustrating the basic screen K2 on which similar cases are refined according to "mycosis". FIG. 19 is a diagram illustrating the basic screen K2 on which similar cases are refined according to "metastatic lung cancer".

In the example illustrated in FIG. 18, "mycosis" is displayed in the display condition display area 714 since refinement is performed in accordance with "mycosis". In the example illustrated in FIG. 19, "metastatic lung cancer" is displayed in the display condition display area 714 since refinement is performed in accordance with "metastatic lung cancer".

In this case, furthermore, the display control unit 104 displays the number of similar cases in the number-of-search-result display area 713 so that the user can identify the number of similar cases currently being displayed in the case display area 710. Since there are 14 similar cases of "mycosis", "14 results" is displayed in the number-of-search-result display area 713 in the example illustrated in FIG. 18. Since there are three similar cases of "metastatic lung cancer", "3 results" is displayed in the number-of-search-result display area 713 in the example illustrated in FIG. 19.

With the function described above, similar cases of a disease suspected by a physician as a target of image-based diagnosis are displayed in the case display area 710, enabling the physician to easily make sure that the case to be diagnosed is consistent with the suspected disease.

In FIG. 18, thumbnail images of M (in FIG. 18, M=14) similar cases are displayed in the case display area 710 with the maximum number ND of results allowed to be displayed (in this embodiment, ND=20).

The distribution list display area 750 with the heading "distributions of lesions" is displayed in a left middle portion of the basic screen K2 illustrated in FIG. 6. The distribution list display area 750 shows types of distributions of lesions seen in all the similar cases obtained from the case search system 300 as a result of the similar case search.

Figure 20:
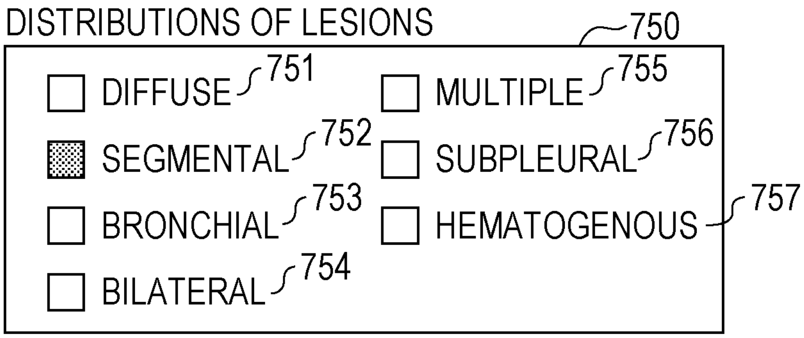
FIG. 20 is an enlarged view of a distribution list display area.

FIG. 20 is an enlarged view of the distribution list display area 750. In the example illustrated in FIG. 20, the names of seven distributions of lesions are displayed, and checkboxes are displayed to the left of the respective names of the distributions of lesions. In the example illustrated in FIG. 20, "diffuse" 751, "segmental" 752, "bronchial" 753, "bilateral" 754, "multiple" 755, "subpleural" 756, and "hematogenous" 757 are displayed as distributions of lesions.

The distributions of lesions described above are defined in advance, and each similar case is given in advance a distribution flag value ("1" for Applicable or "0" for Not Applicable) indicating the applicability of the similar case to each of the "diffuse" 751 to the "hematogenous" 757. In some similar cases, the distribution flag values for all the distributions of lesions may be set to Not Applicable ("0"), and, in other similar cases, the distribution flag values for a plurality of distributions of lesions may be set to Applicable ("1").

The case search system 300 according to this embodiment searches for a similar case that has a region of interest similar to a region of interest set by a user in a slice image of the case to be diagnosed. A lesion may be present in a slice image other than the slice image in which the region of interest has been set by the user. Further, the user may wish to, after searching for a similar case on the basis of the slice image in which the region of interest has been set, compare a slice image other than the slice image in which the region of interest has been set with the similar case found as a result of the search. In this case, the user inputs a slice-based forwarding operation on the medical image viewer 610 to display a different slice image, and compares the displayed slice image with the found similar case. If a similar case related to the lesion of interest among all the similar cases found as a result of the search is displayed in the case display area 710, the operation of extracting a slice image having the desired lesion from among slice images other than the slice image in which the region of interest has been set can be smoothly performed. Accordingly, this embodiment provides a function of refining the found similar cases according to the desired distribution of lesions to make the operation described above smoother.

In this embodiment, the "diffuse" 751 to the "hematogenous" 757 illustrated in FIG. 20 are used as distributions of lesions in the pulmonary field. In addition, as illustrated in FIG. 20, the display control unit 104 displays the checkboxes and the names of the distributions of lesions in such a manner that the distributions of lesions available for refinement are active and the distributions of lesions not available for refinement are inactive. Here, being "active" refers to having higher luminance than the state of being "inactive", and being "inactive" refers to having lower luminance than the state of being "active".

In the example illustrated in FIG. 20, the "diffuse" 751 and the "bronchial" 753 to the "hematogenous" 757 are displayed as active, whereas the "segmental" 752 is inactive, because of the following reasons: The distribution flag values for the "diffuse" 751 and the "bronchial" 753 to the "hematogenous" 757 are currently set to "1" (Applicable) in at least one similar case among all the similar cases obtained through the similar case search, whereas the distribution flag value for the "segmental" 752 is currently set to "0" (Not Applicable) in all the obtained similar cases.

When the input control unit 103 detects that one or more of the active checkboxes have been checked, the display control unit 104 causes similar cases that meet the lesion condition(s) for which the checkbox has been checked to be displayed in the case display area 710.

Note that the distribution flag value for the "segmental" 752 is set to "0" (Not Applicable) in any of the similar cases obtained as a result of the search. Thus, if the checkbox for the "segmental" 752 is allowed to be checked, even though the checkbox for such a distribution of lesions is checked, no similar case will be displayed in the case display area 710. In this case, it is meaningless to check the checkbox. To avoid this situation, in this embodiment, a distribution of lesions for which the distribution flag value is set to "0" (Not Applicable) in any of the similar cases obtained as a result of the search is displayed as inactive.

Figure 21:
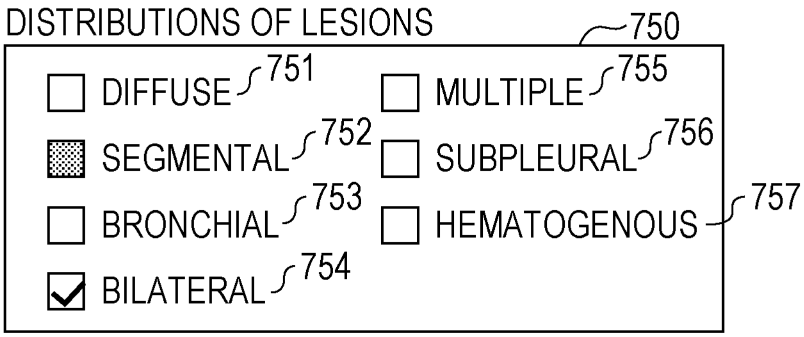
FIG. 21 is a diagram illustrating the distribution list display area in which the checkbox for "bilateral" is checked.
Figure 22:
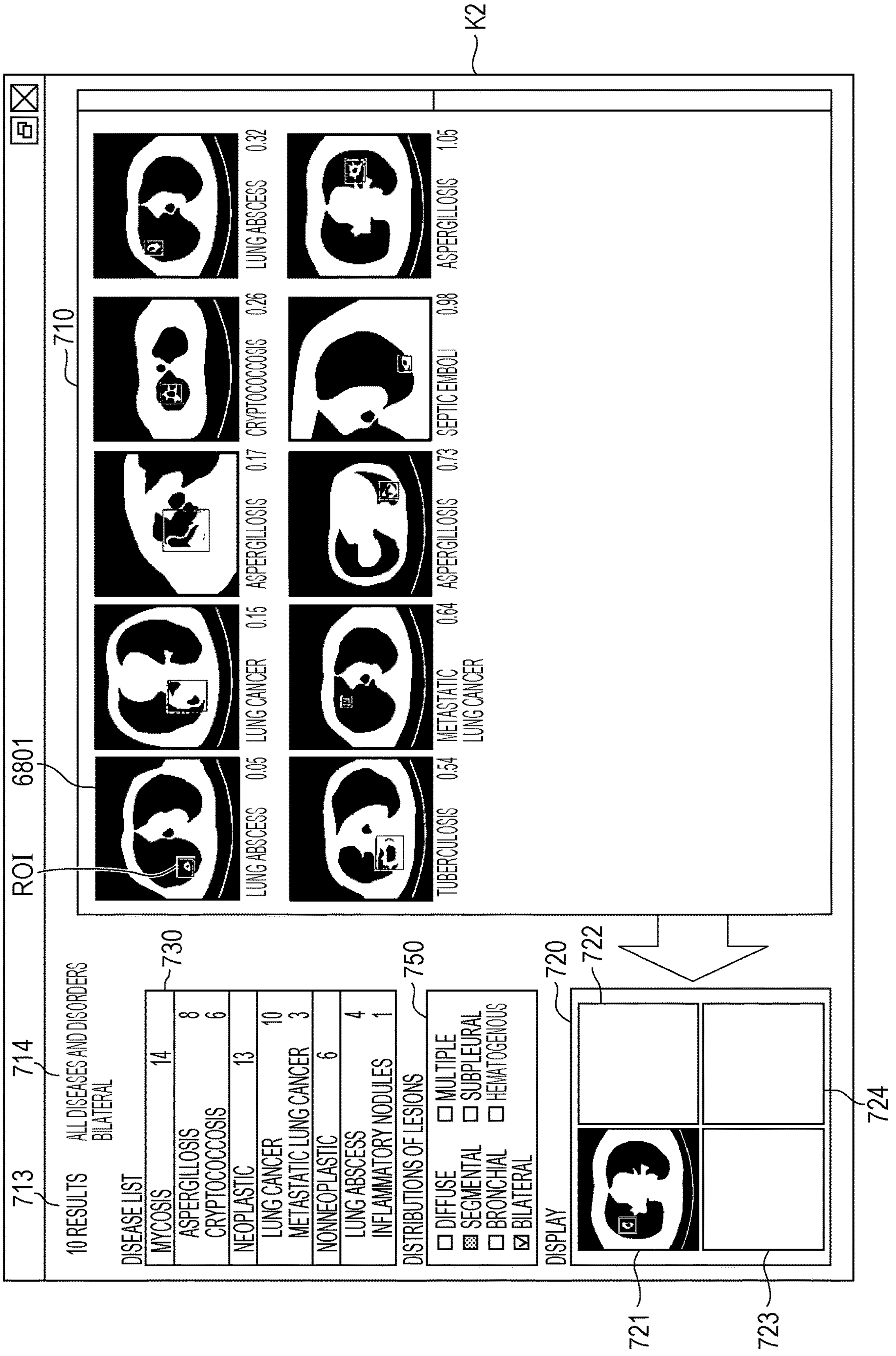
FIG. 22 is a diagram illustrating a basic screen on which refinement is performed in accordance with bilateral lesion distribution.

FIG. 21 is a diagram illustrating the distribution list display area 750 in which the checkbox for the "bilateral" 754 is checked. FIG. 22 is a diagram illustrating the basic screen K2 on which refinement is performed in accordance with the distribution of lesions identified by the "bilateral" 754. As illustrated in FIG. 21, when the checkbox for the "bilateral" 754 is checked, as illustrated in FIG. 22, the display control unit 104 displays similar cases exhibiting bilateral lesion distribution in the case display area 710. In the illustrated example, ten similar cases exhibiting bilateral lesion distribution. Thus, the display control unit 104 displays "10 results" in the number-of-search-result display area 713. The display control unit 104 further displays the name of the disease being displayed and the name of the distribution of lesions, i.e., "bilateral", in the display condition display area 714. In the example illustrated in FIG. 22, there is no refinement according to a disease name in the disease list display area 730, "all diseases and disorders" is displayed in the display condition display area 714.

As illustrated in FIG. 21, if the checkbox for the "bilateral" 754 is checked, as illustrated in FIG. 22, the display control unit 104 displays a thumbnail image enlarged by the enlarged image generation unit 112 with the enlargement factor corresponding to the distribution of lesions selected by the case display area 710. If the name of the distribution of lesions "bilateral" is selected, it is desirable that the user be able to observe both sides of the lungs. Accordingly, the enlarged image generation unit 112 sets the enlargement factor to 1.0. The display control unit 104 displays thumbnail images with an enlargement factor of 1.0.

Similarly, if the checkbox for the "multiple" 755 is checked, the display control unit 104 displays similar cases exhibiting multiple lesion distribution in the case display area 710. When the name of the distribution of lesions "multiple" is selected, it is desirable that the user be able to observe a distribution of multiple lesions. Accordingly, the enlarged image generation unit 112 sets the enlargement factor to 1.0. The display control unit 104 displays thumbnail images with an enlargement factor of 1.0.

Similarly, if the checkbox for the "diffuse" 751 is checked, the display control unit 104 displays similar cases exhibiting diffuse lesion distribution in the case display area 710. If the name of the distribution of lesions "diffuse" is selected, it is desirable that the user be able to observe distributions of diffuse lesions extending over a large area. Accordingly, the enlarged image generation unit 112 sets the enlargement factor to 1.0. The display control unit 104 displays thumbnail images with an enlargement factor of 1.0.

Similarly, if the checkbox for the "hematogenous" 757 is checked, the display control unit 104 displays similar cases exhibiting hematogenous lesion distribution in the case display area 710. If "hematogenous" is selected, there is a possibility that a metastasis of a lesion other than the lesion of interests may occur. Thus, it is desirable to observe the entire image. Accordingly, the enlarged image generation unit 112 sets the enlargement factor to 1.0. The display control unit 104 displays thumbnail images with an enlargement factor of 1.0.

Figure 23:
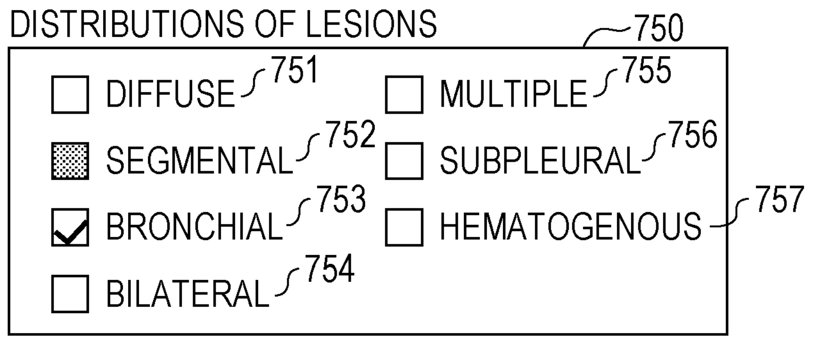
FIG. 23 is a diagram illustrating the distribution list display area in which the checkbox for "bronchial" is checked.
Figure 24:
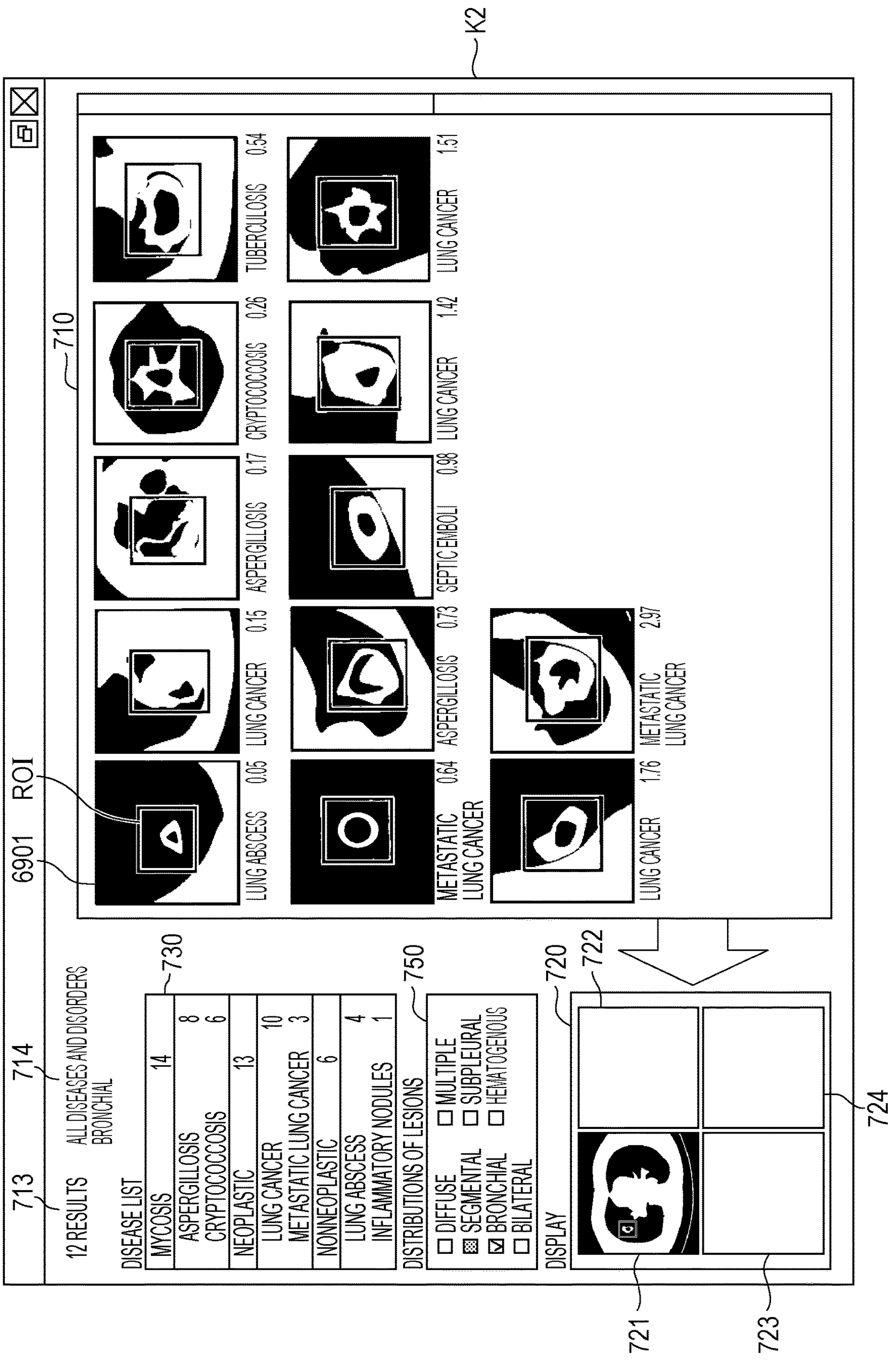
FIG. 24 is a diagram illustrating a basic screen on which refinement is performed in accordance with bronchial lesion distribution.

FIG. 23 is a diagram illustrating the distribution list display area 750 in which the checkbox for the "bronchial" 753 is checked. FIG. 24 is a diagram illustrating the basic screen K2 on which refinement is performed in accordance with the distribution of lesions identified by the "bronchial"

753. As illustrated in FIG. 23, if the checkbox for the "bronchial" 753 is checked, as illustrated in FIG. 24, the display control unit 104 displays similar cases exhibiting bronchial lesion distribution in the case display area 710. In the illustrated example, 12 similar cases exhibit bronchial lesion distribution. Thus, the display control unit 104 displays "12 results" in the number-of-search-result display area 713. The display control unit 104 further displays, in the display condition display area 714, the name of the disease being displayed and the name of the distribution of lesions, i.e., "bronchial". In the example illustrated in FIG. 24, there is no refinement according to any of the disease names listed in the disease list display area 730, and "all diseases and disorders" is displayed in the display condition display area 714.

As illustrated in FIG. 23, if the checkbox for the "bronchial" 753 is checked, as illustrated in FIG. 24, the display control unit 104 displays, in the case display area 710, thumbnail images enlarged by the enlarged image generation unit 112 with the enlargement factor corresponding to the selected distribution of lesions. If the name of the distribution of lesions "bronchial" is selected, it is desirable that the user be able to determine whether or not each result is bronchial. Accordingly, the enlarged image generation unit 112 determines an enlargement factor so that the area of each region of interest is equal to approximately one half of the area of the display area. The display control unit 104 displays thumbnail images enlarged by the enlarged image generation unit 112.

Similarly, if the checkbox for the "segmental" 752 is checked, the display control unit 104 displays similar cases exhibiting having segmental lesion distribution in the case display area 710. If the name of the distribution of lesions "segmental" is selected, it is desirable that the user be able to observe the details of segmental lesions. Accordingly, the enlarged image generation unit 112 determines an enlargement factor so that the area of each region of interest is equal to approximately one half of the area of the display area. The display control unit 104 displays thumbnail images enlarged by the enlarged image generation unit 112.

Figure 25:
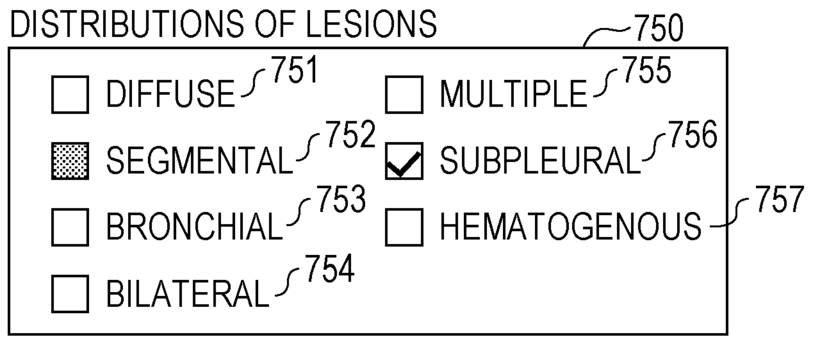
FIG. 25 is a diagram illustrating the distribution list display area in which the checkbox for "subpleural" is checked.
Figure 26:
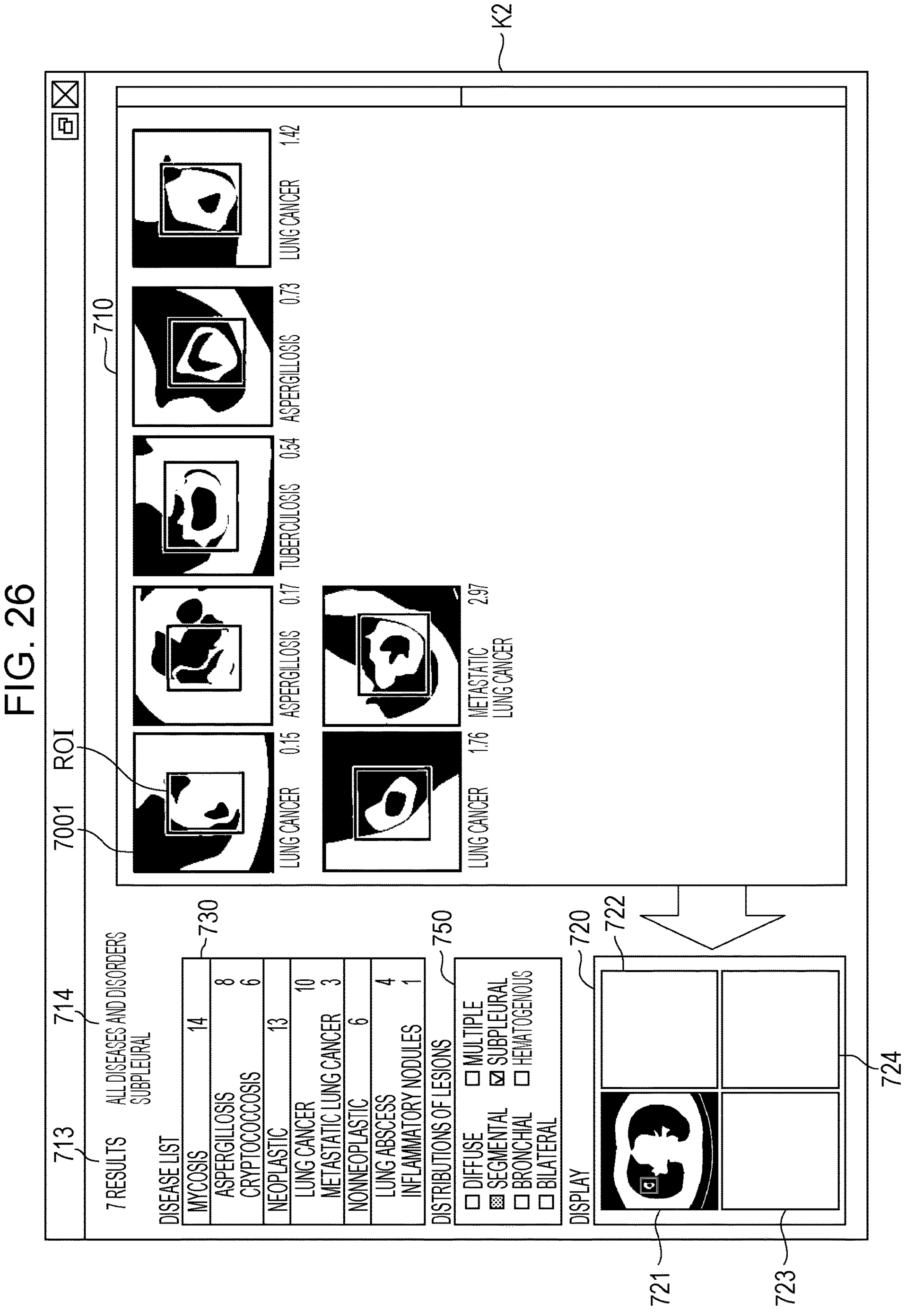
FIG. 26 is a diagram illustrating a basic screen on which refinement is performed in accordance with subpleural lesion distribution.

FIG. 25 is a diagram illustrating the distribution list display area 750 in which the checkbox for the subpleural 756 is checked. FIG. 26 is a diagram illustrating the basic screen K2 on which refinement is performed in accordance with the distribution of lesions identified by the subpleural 756. As illustrated in FIG. 25, if the checkbox for the subpleural 756 is checked, as illustrated in FIG. 25, the display control unit 104 displays similar cases exhibiting subpleural lesion distribution in the case display area 710. In the illustrated example, seven similar cases exhibit subpleural lesion distribution. Thus, the display control unit 104 displays "7 results" in the number-of-search-result display area 713. The display control unit 104 further displays the name of the disease being displayed and the name of the distribution of lesions, i.e., "subpleural", in the display condition display area 714. In the example illustrated in FIG. 26, no refinement is performed in accordance with any of the disease names listed in the disease list display area 730. Thus, "all diseases and disorders" is displayed in the display condition display area 714.

As illustrated in FIG. 25, if the checkbox for the subpleural 756 is checked, as illustrated in FIG. 26, the display control unit 104 displays, in the case display area 710, thumbnail images enlarged by the enlarged image generation unit 112 with the enlargement factor corresponding to the selected distribution of lesions. If the name of the distribution of lesions "subpleural" is selected, it is desirable that the user be able to observe a positional relationship with the pleura. Accordingly, the enlarged image generation unit 112 determines an enlargement factor so that the pleura is included. The display control unit 104 displays thumbnail images enlarged by the enlarged image generation unit 112.

The thumbnail images displayed in the case display area 710 are designed so that the display areas thereof can be changed by a user operation even when the thumbnail images are refined according to a predetermine distribution of lesions.

Note that, as illustrated in FIG. 21, if the checkbox for the "bilateral" 754 is checked, as described above, the display control unit 104 displays thumbnail images enlarged by the enlarged image generation unit 112 with a factor of 1.0. Accordingly, as illustrated in FIG. 22, the original thumbnail images are displayed in their entirety. In this case, the display area is not changed.

In contrast, as illustrated in FIG. 23, if the checkbox for the "bronchial" 753 is checked, as illustrated in FIG. 24, each of the thumbnail images is enlarged and displayed. Accordingly, in response to instructions given by the user for causing a display area to move, the display areas of the thumbnail images are caused to move.

Figure 27:
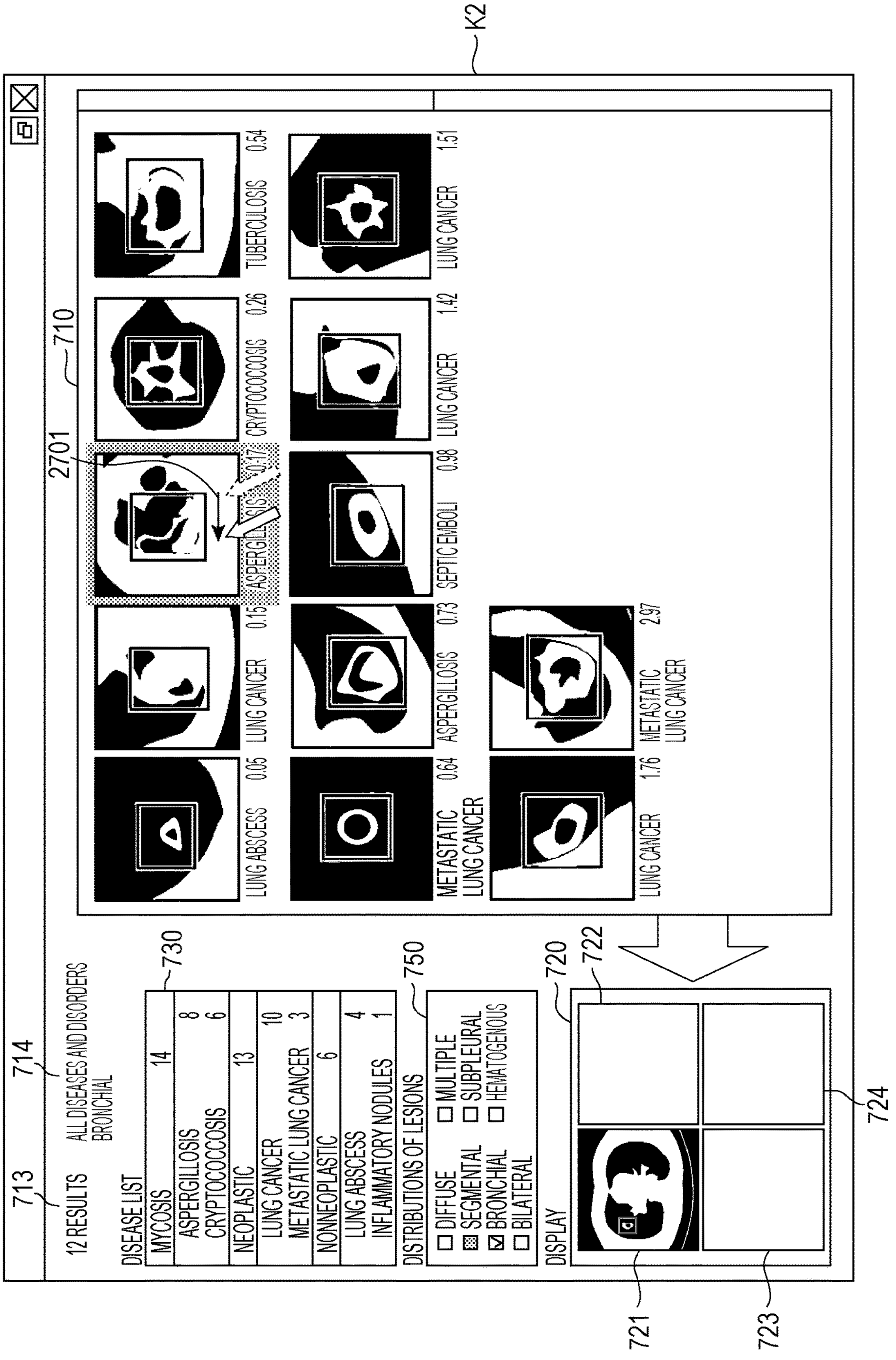
FIG. 27 is diagram schematically illustrating a drag operation performed by a user while the basic screen illustrated in FIG. 24 is being displayed.

FIG. 27 is a diagram schematically illustrating a drag operation 2701 performed by a user while the basic screen K2 illustrated in FIG. 24 is being displayed. When the user performs the drag operation 2701, the input control unit 103 detects the amount of movement of the mouse, and notifies the enlarged image generation unit 112 of the detected amount of movement. Then, the enlarged image generation unit 112 determines an amount of movement of a display area in a thumbnail image by using the detected amount of movement of the mouse, and generates a thumbnail image in which the display area has moved the determined amount. The display control unit 104 displays, in the case display area 710, thumbnail images that have been caused to move by the enlarged image generation unit 112.

As illustrated in FIG. 25, if the checkbox for the subpleural 756 is checked, as illustrated in FIG. 26, the individual thumbnail images are enlarged and displayed. Accordingly, in response to instructions given by the user for causing a display area to move, the display areas of the thumbnail images are caused to move.

Figure 28:
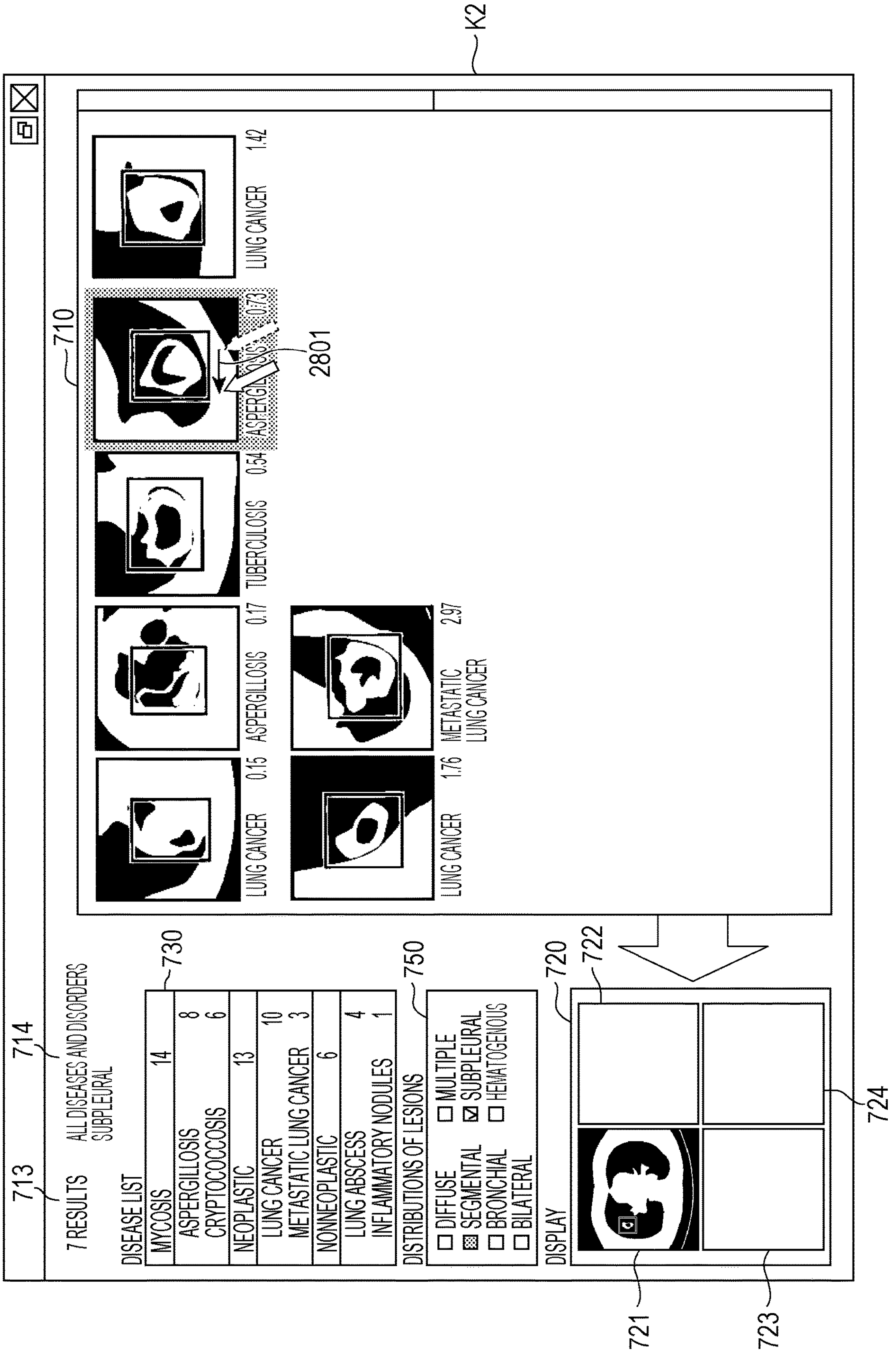
FIG. 28 is a diagram schematically illustrating a drag operation performed by a user while the basic screen illustrated in FIG. 26 is being displayed.

FIG. 28 is a diagram schematically illustrating a drag operation 2801 performed by a user while the basic screen K2 illustrated in FIG. 26 is being displayed. When the user performs the drag operation 2801, the input control unit 103 detects the amount of movement of the mouse, and notifies the enlarged image generation unit 112 of the detected amount of movement. Then, the enlarged image generation unit 112 determines an amount of movement of a display area in a thumbnail image by using the detected amount of movement of the mouse, and generates a thumbnail image in which the display area has moved the determined amount. The display control unit 104 displays, in the case display area 710, thumbnail images that have been caused to move by the enlarged image generation unit 112.

The process for enlarging each thumbnail image and the display area movement process when a distribution of lesions is selected in FIG. 22, FIG. 24, and FIG. 26 will be described in detail below.

FIG. 29 is a diagram illustrating the data configuration of the patient information 1000. The patient information 1000 is accumulated in the patient information accumulation unit 201 on a patient-by-patient basis, and is managed by the patient information management unit 202 of the medical information management system 200. The patient information 1000 has personal information on each patient, such as the gender and age, clinical information such as the past medical history, and test information on medical tests such as a blood test. As illustrated in FIG. 29, the patient information 1000 includes a patient ID 1100, a name 1200, an age 1300, a gender 1400, a past medical history 1500, a family history 1600, a chief complaint 1700, test information 1800, and a definite diagnosis 1900.

The patient ID 1100 is an identifier specific to the patient. The name 1200, the age 1300, the gender 1400, the past medical history 1500, the family history 1600, and the chief complaint 1700 are the name, age, gender, past medical history, family history, and chief complaint of the patient identified by the patient ID 1100, respectively. The test information 1800 indicates information concerning one or more medical tests that the patient has already undergone, as illustrated in FIG. 30.

FIG. 30 is a diagram illustrating the data configuration of the test information 1800 illustrated in FIG. 29. The test information 1800 is information concerning tests performed on the patient, and a piece of test information is created for each test. The test information 1800 includes a test ID 1810, a test date 1820, a test type 1830, and a test result 1840. The test ID 1810 is an identifier specific to each test. The test date 1820 is the date on which the test was performed. The test type 1830 is the type of the test. Examples of the type of the test include blood tests, respiratory tests, endoscopic examinations, simple X-ray imaging tests, and CT imaging tests.

The test result 1840 includes the values of various indices, such as white blood cell count (or leukocyte count), lactate dehydrogenase (LDH), and glutamic-pyruvic transaminase (GPT) for a blood test. The test result 1840 also includes, for example, a decision made by a physician based on various indices. For an imaging test such as a simple X-ray imaging test or a CT imaging test, the test result 1840 includes pointer information on a pointer to a captured image and pointer information on a pointer to a report obtained as a result of image-based diagnosis. Images captured during tests are accumulated in DICOM format in the medical image data accumulation unit 203 of the medical information management system 200.

In a case where the test type 1830 is an imaging test such as simple X-ray, CT, MRI, or positron emission tomography (PET), medical image data obtained with such imaging tests is accumulated in a medical image database 2000 stored in the medical image data accumulation unit 203 of the medical information management system 200.

Figure 31:
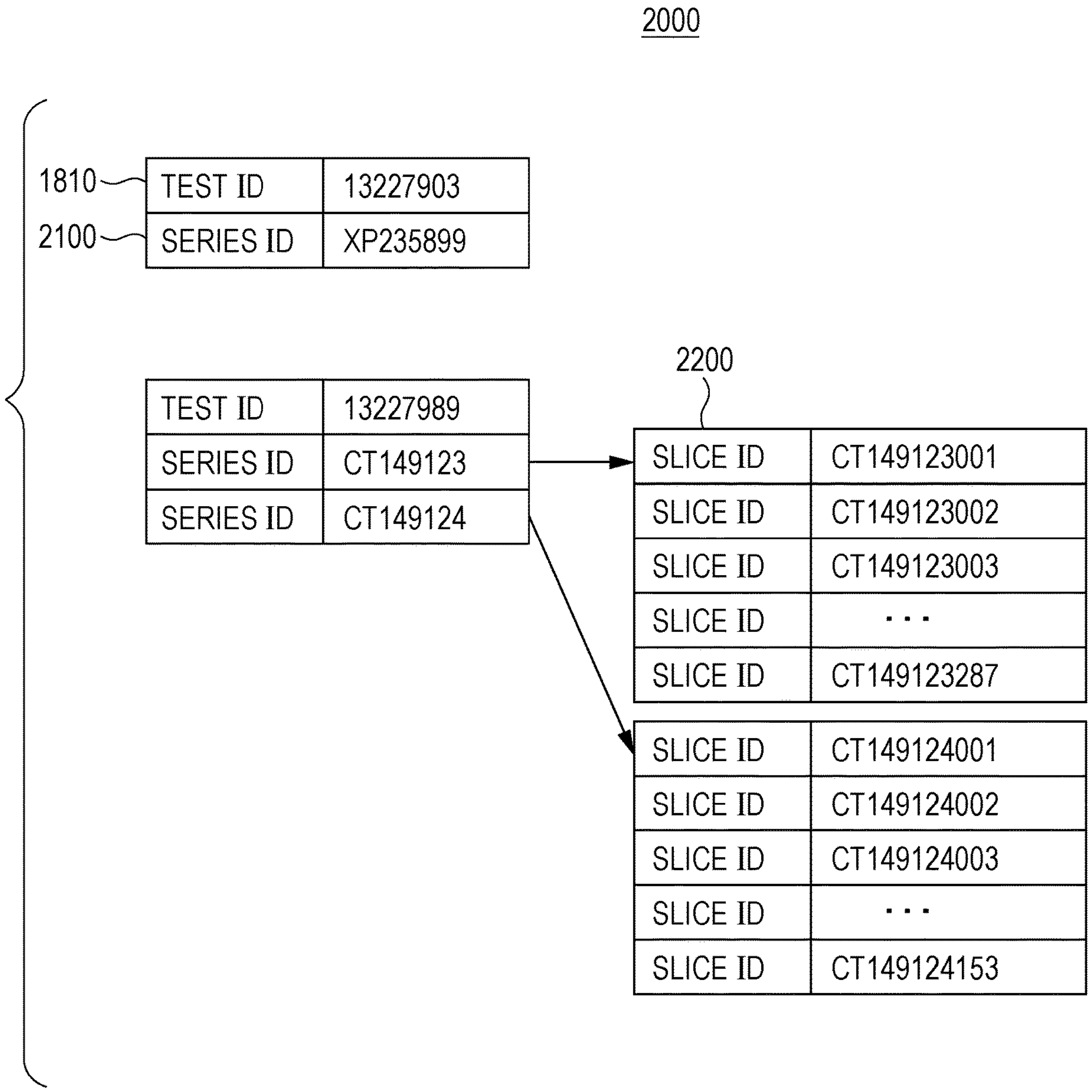
FIG. 31 is a diagram illustrating the data configuration of a medical image database.

FIG. 31 is a diagram illustrating the data configuration of the medical image database 2000. The medical image database 2000 includes a test ID 1810 and a series ID 2100. A plurality of series IDs 2100 may be associated with a single test ID 1810 since a plurality of types of imaging sessions (e.g., simple CT, contrast CT, etc.) may be performed in a single test. That is, a number of series corresponding to the number of types of imaging sessions are obtained.

A series is also obtained for each condition of the reconstruction of captured images, as well as for each type of imaging session. For example, when captured images are reconstructed under the pulmonary condition and the mediastinal condition, one series is obtained for each of these conditions. In images reconstructed under the pulmonary condition, blood vessels in the lungs, bronchi, alveoli, and the like are displayed highlighted. In images reconstructed under the mediastinal condition, the mediastinal structures, such as blood vessels and lymph nodes, are displayed highlighted. The pulmonary condition and the mediastinal condition are obtained by the reconstruction of images obtained in single imaging sessions. Thus, two imaging sessions, or simple CT and contrast CT, are performed, and images are reconstructed under the pulmonary condition and the mediastinal condition in each of the two imaging sessions, thereby obtaining two series for the pulmonary condition and two series for the mediastinal condition.

For imaging tests such as CT and MRI, a plurality of slice images are obtained in a single imaging session. Thus, a plurality of slice IDs 2200 are associated with one series ID 2100. In FIG. 31, two series IDs "CT149123" and "CT149124" are associated with the test ID "13227989". Thus, it is found that CT images of two series have been obtained with the test. It is also found that a plurality of slice IDs 2200 are associated with each of the series IDs "CT149123" and "CT149124".

In a case where the test type 1830 is an imaging test such as simple X-ray, CT, MRI, or PET, a diagnostic report 3000 as illustrated in FIG. 32 is accumulated in the diagnostic report management unit 205 of the medical information management system 200. The diagnostic report 3000 includes a diagnosis from a physician for each test.

FIG. 32 is a diagram illustrating the data configuration of the diagnostic report 3000. The diagnostic report 3000 includes a test ID 1810, findings 3100, and a diagnosis 3200. The test ID 1810 is the same as the test ID 1810 illustrated in FIG. 30. Accordingly, the diagnostic report 3000 and the test information 1800 are associated with each other. The findings 3100 include a note indicating the physician's findings of the test. The diagnosis 3200 includes a note indicating the physician's diagnosis for the test.

FIG. 33 is a diagram illustrating the data configuration of the similar case data 4000. The similar case data 4000 is data to be referred to in order to search for a similar case that is similar to the case to be diagnosed, and a piece of similar case data is created for each similar case. The similar case data 4000 is an example of attached information attached to a similar case. The similar case data 4000 is accumulated for each similar case in the similar case data accumulation unit 301 of the case search system 300. As illustrated in FIG. 33, the similar case data 4000 includes a similar case ID 4100, a slice ID 4200, region-of-interest information 4300, image feature data 4400, thumbnail image data 4500, distribution-of-lesion information 4600, a definite diagnosis (major-category disease name) 4700, and a definite diagnosis (sub-category disease name) 4800.

The similar case ID 4100 is an identifier of the similar case data 4000. Since a piece of similar case data is generated for each region of interest set on a slice image of a similar case, the similar case ID 4100 can also be referred to as an identifier of the region of interest. In the example illustrated in FIG. 33, the similar case ID 4100 is constituted by a symbol sequence including "SIM" and a number which follows it.

Figure 34:
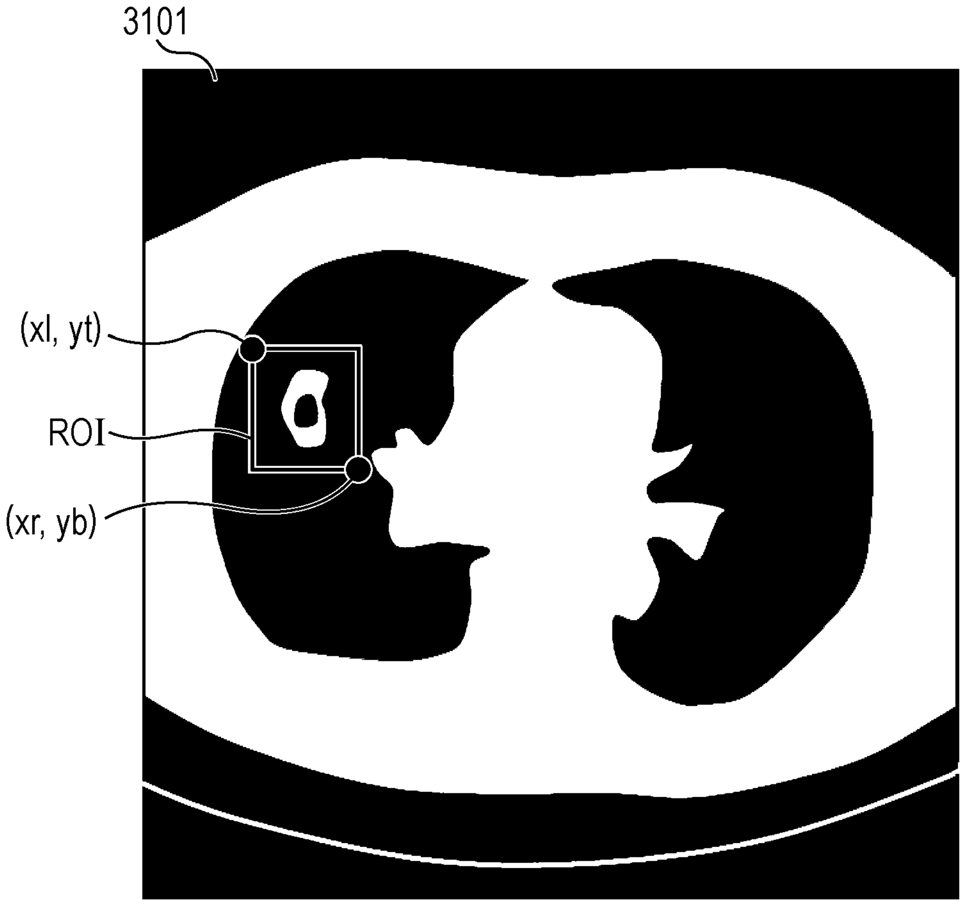
FIG. 34 is a diagram schematically illustrating a region of interest set on a slice image.

The slice ID 4200 is an identifier of a slice image in which a region of interest is set, and is the same as the slice ID 2200 illustrated in FIG. 31. The region-of-interest information 4300 is information indicating the position of the region of interest set on the slice image. FIG. 34 is a diagram schematically illustrating a region of interest ROI set on a slice image 3101. In the example illustrated in FIG. 34, the region of interest ROI has a rectangular shape. Thus, the region-of-interest information 4300 includes four values, namely, the coordinates (xl, yt) of the upper left corner of the region of interest ROI and the coordinates (xr, yb) of the lower right corner of the region of interest ROI. The region of interest ROI may also be of any other shape than rectangular, in which case a parameter capable of uniquely identifying the region is used as the region-of-interest information 4300. For example, the region of interest ROI may be circular. In this case, the coordinates of the center of the circular region and the radius of the circular region may be used as the region-of-interest information 4300.

The image feature data 4400 is certain-number dimensional (here, N-dimensional) feature values extracted from the region of interest defined in the region-of-interest information 4300. The thumbnail image data 4500 is image data of a thumbnail image generated based on a DICOM slice image identified by the slice ID 4200 for display in the case display area 710. In the thumbnail image data 4500, for example, pixel values of the thumbnail image are arranged in raster scan order from the upper left corner to the lower right corner of the thumbnail image. As described previously, a DICOM image obtained with a CT test is an 11-bit image having a size of 512 pixels×512 pixels (with a pixel value of −1000 to +1000). In this embodiment, accordingly, to increase the speed of display of a thumbnail image, a DICOM image on which the thumbnail image is based is subjected to resolution reduction and grayscale conversion to create a thumbnail image with 8-bit pixel values in advance, and the resulting thumbnail image is registered in the similar case data 4000. Thumbnail images may be created by, for example, the medical information management system 200, and transmitted to the case search system 300. Alternatively, thumbnail images may be created by the case search system 300 by obtaining DICOM images from the medical information management system 200.

The distribution-of-lesion information 4600 is a distribution flag value ("1" for Applicable or "0" for Not Applicable) indicating the applicability of the target similar case to each of the predetermined distributions of lesions identified by "diffuse" 4610, "segmental" 4620, "bronchial" 4630, "bilateral" 4640, "multiple" 4650, "subpleural" 4660, and "hematogenous" 4670.

The definite diagnosis (major-category disease name) 4700 indicates the name of a disease that is definitely diagnosed in the target similar case and that is classified as a major category (hereinafter referred to as a "major-category disease"). The definite diagnosis (major-category disease name) 4700 is used to refine similar cases according to a major-category disease name.

The definite diagnosis (subcategory disease name) 4800 indicates the name of a disease that is definitely diagnosed in the target similar case and that is classified as a subcategory (hereinafter referred to as a "subcategory disease"). The definite diagnosis (subcategory disease name) 4800 is used to refine similar cases according to a subcategory disease name.

In the definite diagnosis (major-category disease name) 4700, the name of a major-category disease that is uniquely associated with the definite diagnosis (subcategory disease name) 4800 is defined in advance. The definite diagnosis (major-category disease name) 4700 is stored in the similar case data 4000 using the association relationship between them.

In the definite diagnosis (subcategory disease name) 4800, a series ID 2100 is identified in the medical image data accumulation unit 203 by a slice ID 2200 illustrated in FIG. 31. Further, a test ID 1810 is identified in the patient information accumulation unit 201 by the identified series ID 2100, and associated patient information 1000 (FIG. 29) is identified by the test ID 1810. Accordingly, the definite diagnosis 1900 of the patient is identified by the identified patient information 1000.

Next, a process from the start of image interpretation to the start of a similar case search by using the information terminal 100 in coordination with the medical information management system 200 and the case search system 300 will be described.

Figure 35:
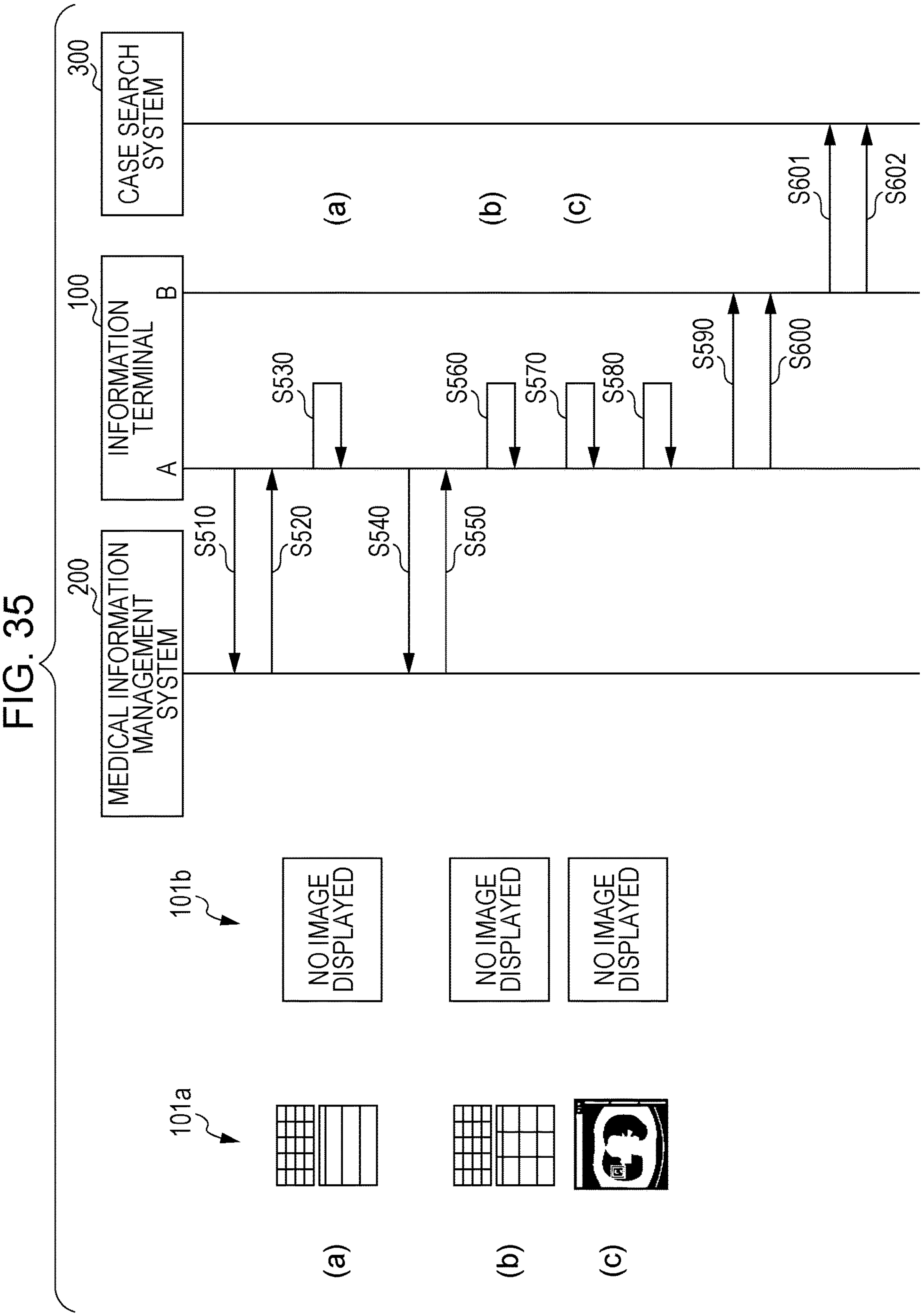
FIG. 35 is a sequence diagram illustrating a process performed during a period in which the information terminal obtains a case to be diagnosed from the medical information management system and then sends a similar case search request to the case search system and the case search system receives the similar case search request.

FIG. 35 is a sequence diagram illustrating a process performed during a period in which the information terminal 100 obtains a case to be diagnosed from the medical information management system 200 and then sends a similar case search request to the case search system 300 and the case search system 300 receives the similar case search request. In FIG. 35, rectangular objects to the left of the sequence diagram, which are arranged side-by-side in two lines, represent screens displayed on the displays 101*a* and 101*b* through the processing of the respective steps. In FIG. 35, furthermore, in the information terminal 100, "A" represents the medical information management application, and "B" represents the similar case search application. It is assumed that the medical information management application is started in advance before the commencement of the above-described sequence.

First, the information terminal 100 accepts a request for displaying a test list in which image interpretation is to be performed by a user (a specialist who provides image interpretation) through the operation unit 102, and transmits the request for displaying the test list to the communication control unit 206 of the medical information management system 200 via the input control unit 103 and the communication control unit 110 (S510).

The patient information management unit 202 of the medical information management system 200 lists tests in which image interpretation has yet to be performed after the completion of an imaging test to generate a test list in which image interpretation is to be performed. Then, the patient information management unit 202 transmits the generated test list to the communication control unit 110 of the information terminal 100 via the communication control unit 206 (S520). The test list includes the patient information 1000 on the patient, and the test information 1800.

The display control unit 104 of the information terminal 100 displays the test list received by the communication control unit 110 on the display 101 (S530).

In this case, the test list is displayed on the display 101*a*, whereas no image is displayed on the display 101*b*.

FIG. 36 is a view of a test list screen. The test list includes an area 800 where tests with image interpretation yet to be performed are displayed, and an area 810 where information concerning series included in the tests is displayed. The area 800 has the following fields: "patient ID", "patient name", "test date", "test ID", and "test type". The "patient ID" and "patient name" fields show the patient ID 1100 and the name 1200 registered in the patient information 1000, respectively. The "test date", "test ID", and "test type" fields show the test date 1820, the test ID 1810, and the test type 1830 registered in the test information 1800, respectively. The area 810 is an area for displaying the details of a test selected by the user in the area 800, and has the following fields: "series ID", "definition", and "image". In FIG. 36, no test (corresponding to each row) is selected by the user in the area 800, and thus no image is displayed in the area 810.

The user selects a test in which image interpretation is about to be performed from among the tests displayed in the area 800. When the selection of the test is detected by the input control unit 103, as illustrated in FIG. 35, the communication control unit 110 transmits a request for displaying all the series included in the test ID of the selected test to the medical information management system 200 (S540).

When the communication control unit 206 of the medical information management system 200 receives the request, the patient information management unit 202 refers to the medical image database 2000 illustrated in FIG. 31 to obtain all the slice images in all the series included in the test ID designated in the request, and transmits the slice images to the information terminal 100 via the communication control unit 206 (S550). For example, in the example illustrated in FIG. 31, when the test with the test ID "13227989" is selected by the user, all the slice images included in the series with the series IDs "CT149123" and "CT149124" are transmitted in S550.

When the communication control unit 110 of the information terminal 100 obtains the images in all the series, the display control unit 104 displays a series list in the area 810 to display information concerning all the series included in the designated test ID in list form (S560).

In this case, the area 810 for a test list, which is displayed on the display 101*a*, shows a list of series corresponding to the test selected in the area 800, whereas no image is displayed on the display 101*b*.

FIG. 37 is a view of a test list screen obtained after a test is selected. In the area 800 illustrated in FIG. 37, a selected row is highlighted. In the example illustrated in FIG. 37, the test for "John Doe" in the second row is selected in the area 800. Accordingly, the "series IDs", "definitions", and "images" for the selected test are displayed in the area 810. The series IDs associated with the test ID of the selected test in the medical image database 2000 are displayed in the "series ID" field, and thumbnail images of single typical slice images of the displayed series IDs are displayed in the "image" field. Each of the single typical slice images of the series IDs is an image corresponding to a predetermined slice position. The predetermined slice position may be the initial slice position or the center slice position. The "definition" indicates an imaging condition or a reconstruction condition for the associated series. The "definition" is registered in association with, for example, a series ID 2100 in the medical image database 2000 in FIG. 31, although not illustrated in the drawings.

Figure 38:
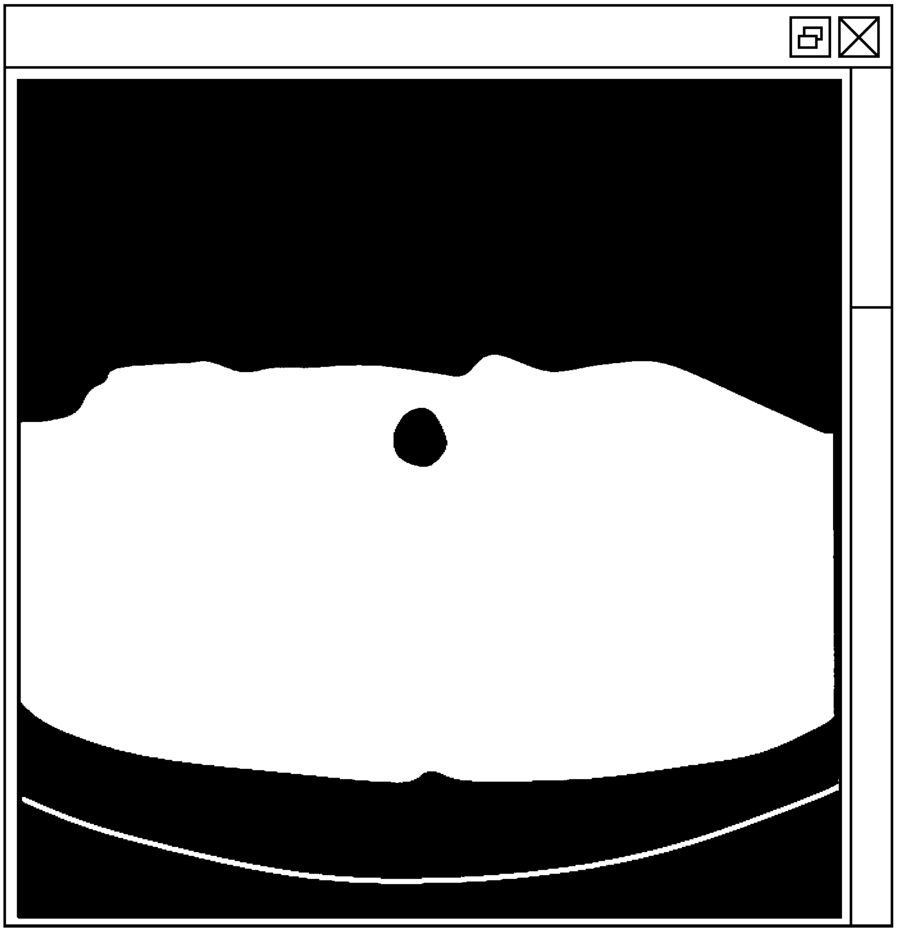
FIG. 38 is a diagram illustrating a slice image displayed in a medical image viewer when a user selects a series.

When the user selects a series to be interpreted in the area 810 and the selection of the series is detected by the input control unit 103, as illustrated in FIG. 38, the display control unit 104 displays the initial slice image in the selected series on the display 101*a* (S570). FIG. 38 is a diagram illustrating a slice image displayed on the display 101*a* when a user selects a series. FIG. 38 is a diagram illustrating the first slice in chest CT imaging, and illustrates a slice image of a shoulder part which is nearer the head than the apex of the lung. The display control unit 104 displays all the slice images in the selected series on the display 101*a* so that a slice-based forwarding operation can be performed. No image is displayed on the display 101*b*. For example, the user inputs a slice-based forwarding operation which involves rotating the mouse wheel while the mouse pointer is on the display 101*a*, and the input operation is detected by the input control unit 103. Then, the display control unit 104 switches the slice image displayed on the display 101*a* to a slice image corresponding to another slice position in accordance with the amount of rotation of the mouse wheel. The user performs image-based diagnosis while inputting a slice-based forwarding operation. When confused about image-based diagnosis, the user starts the similar case search application.

The similar case search application may be started in response to the input of a predetermined shortcut key on the keyboard of the operation unit 102, or may be started by specifying a similar case search menu from a medical image viewer menu which is displayed in response to the right click of the mouse. When an instruction is given to start the similar case search application, the management of the information terminal 100 is passed to the ROI management unit 105, and the information terminal 100 waits for a region of interest (ROI) to be received.

The user sets a region of interest (ROI) on a lesion in the slice image displayed on the display 101*a* through the operation unit 102 (S580). As illustrated in FIG. 34, the user may enter the coordinates of the upper left corner of the region of interest ROI in the slice image 3101 by, for example, left-clicking on the mouse. Then, the user may drag the mouse diagonally down from left to right while left-clicking on the mouse and then release the left click to enter the coordinates of the lower right corner of the region of interest ROI.

When the input control unit 103 detects the operation of setting a region of interest, the ROI management unit 105 receives coordinate data of the upper left and lower right corners of the region of interest from the input control unit 103, and generates region-of-interest information by using the received coordinate data. Then, the ROI management unit 105 transmits the generated region-of-interest information to the communication control unit 110 (S590).

Also, the ROI management unit 105 transmits the slice image of the case to be diagnosed to the communication control unit 110 (S600). In this case, one slice image (i.e., a search query image) in which the user has set a region of interest in the series selected by the user among the slice images in all the series received by the information terminal 100 from the medical information management system 200 in S550 is transmitted.

Then, the communication control unit 110 receives the region-of-interest information transmitted from the ROI management unit 105, and transmits the region-of-interest information to the communication control unit 304 of the case search system 300 (S601).

Also, the communication control unit 110 receives the slice image transmitted from the ROI management unit 105, and transmits the slice image to the communication control unit 304 of the case search system 300 (S602).

In S600 and S601, a slice image itself is transmitted. The slice ID of a slice image may be transmitted instead. In this case, upon receipt of the slice ID, the case search system 300 may acquire a slice image from the medical information management system 200 by specifying the slice ID.

Next, a process performed during a period in which the case search system 300 performs a similar case search and the information terminal 100 initially displays similar case search results will be described.

Figure 39:
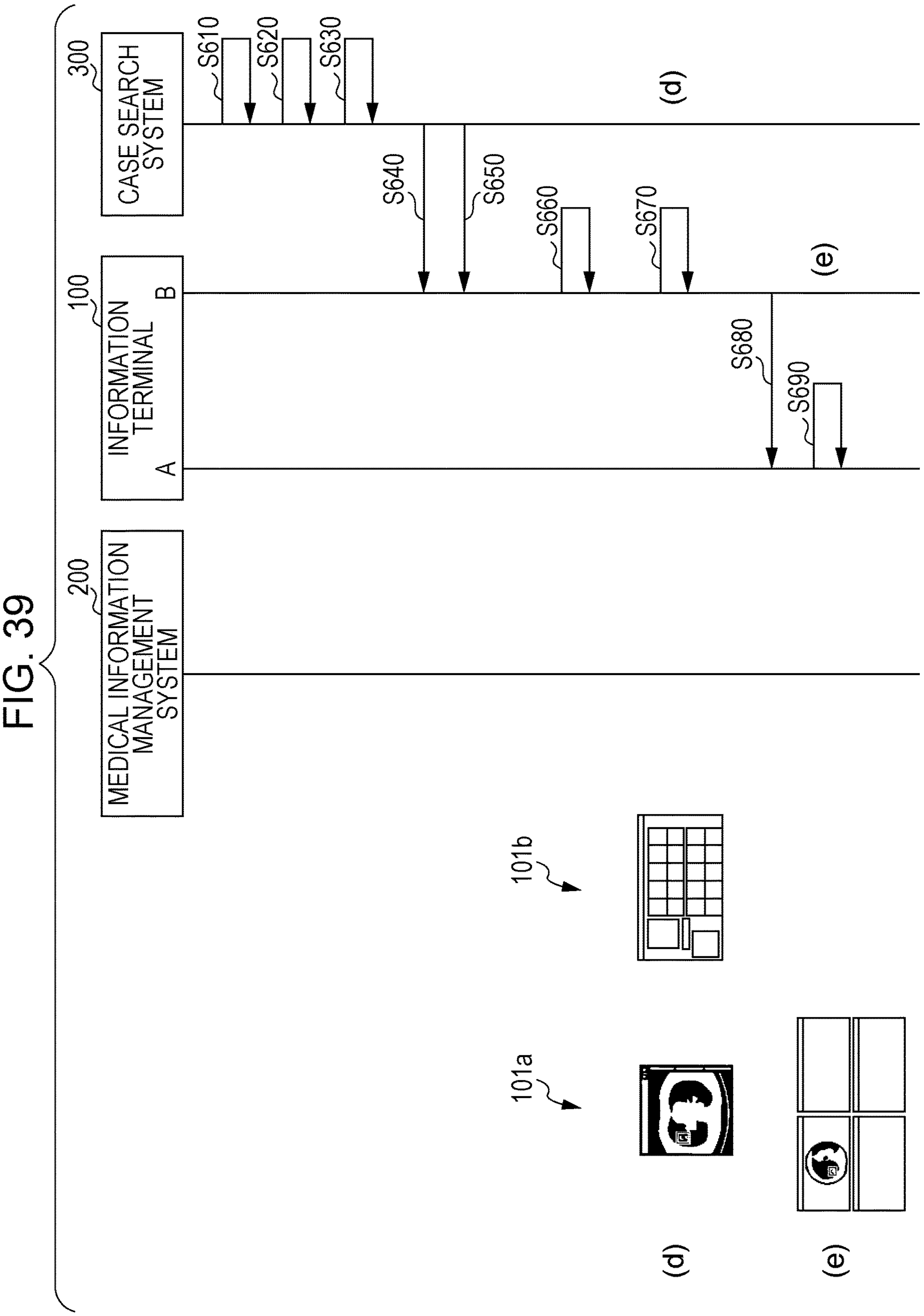
FIG. 39 is a sequence diagram illustrating a process performed during a period in which, after receiving a similar case search request, the case search system returns similar case search results to the information terminal.

FIG. 39 is a sequence diagram illustrating a process performed during a period in which, after receiving a similar case search request, the case search system 300 returns similar case search results to the information terminal 100.

The image feature extraction unit 302 of the case search system 300 extracts predetermined multi-dimensional image features from the region of interest set on the search query image (S610).

Examples of the "image features" include image features for the shape of organs or lesions in medical images, and image features for a luminance distribution. For example, NEMOTO et al. describes, in "Improvement of Tumor Detection Performance in Mammograms by Feature Selection from a Large Number of Features and Proposal of Fast Feature Selection Method", the transactions of the Institute of Electronics, Information and Communication Engineers D-II, Vol. J88-D-II, No. 2, pp. 416-426, February 2005, the use of 490-dimensional image features. In this embodiment, for example, the image features described in this non-patent literature are used. However, this is merely an example, and other image features may be used.

The similar case search unit 303 compares the image feature extracted by the image feature extraction unit 302 with an image feature in each of the similar cases accumulated in the similar case data accumulation unit 301 (S620). The similar case search unit 303 compares the two image features by calculating a distance between image feature data extracted from the search query image and the image feature data 4400 registered in the similar case data 4000 (FIG. 33) accumulated for each similar case in the similar case data accumulation unit 301.

Then, the similar case search unit 303 sorts similar cases for which the distance is less than or equal to a predetermined threshold value in order of increasing distance, and determines the resulting similar cases as similar cases to be transmitted (S630). Then, the communication control unit 304 transmits, within the similar case data 4000 accumulated in the similar case data accumulation unit 301, the similar case ID 4100 of the similar cases determined to be transmitted, the slice ID 4200, the region-of-interest information 4300, the thumbnail image data 4500, the distribution-of-lesion information 4600, the definite diagnosis (major-category disease name) 4700, and the definite diagnosis (subcategory disease name) 4800, and further the distance calculated by the similar case search unit 303 to the information terminal 100 (S640).

Subsequently, a process for generating the initial basic screen K2 (FIG. 6) on which similar case search results are displayed is executed. First, management information used to generate the layout area 720 on the initial basic screen K2 will be described.

First, the communication control unit 304 of the case search system 300 transmits layout information to the information terminal 100 (S650). The layout information is information for specifying the number of rows and columns of display boxes in the layout area 720.

Then, when the communication control unit 110 of the information terminal 100 receives the layout information, the display box management unit 106 registers the number of rows and columns of display boxes, which is specified in the transmitted layout information, in the display box management information 4410 (FIG. 40), and also registers the slice ID of the search query image in the display box management information 4410 (FIG. 40) (S660).

FIG. 40 is a diagram illustrating the data configuration of the display box management information 4410. The display box management information 4410 includes a table 4411 in which the number of rows and the number of columns are registered, and a table 4412 in which the slice ID of a slice image to be displayed in each display box is registered. Accordingly, the display box management unit 106 registers the number of rows and the number of columns, which are specified in the layout information transmitted from the case search system 300, in a number-of-row field and a number-of-column field of the table 4411. In this embodiment, the thumbnail image of the search query image is displayed in the upper left display box 721 among the four display boxes 721 to 724. The display box management unit 106 registers the slice ID of the search query image transmitted from the medical information management system 200 in the "first row and first column" item of the table 4412.

The default value of the number of rows and columns of display boxes in the layout area 720 is set in advance by the case search system 300. For example, the default values of the number of rows and the number of columns are two and two, respectively. Thus, "two rows and two columns" is registered in the display box management information 4410 illustrated in FIG. 40.

In the example illustrated in FIG. 6, the display boxes 721 to 724 are displayed in two rows and two columns in the layout area 720. The number of rows and the number of columns in the layout area 720 is set by the user as desired.

Figure 41:
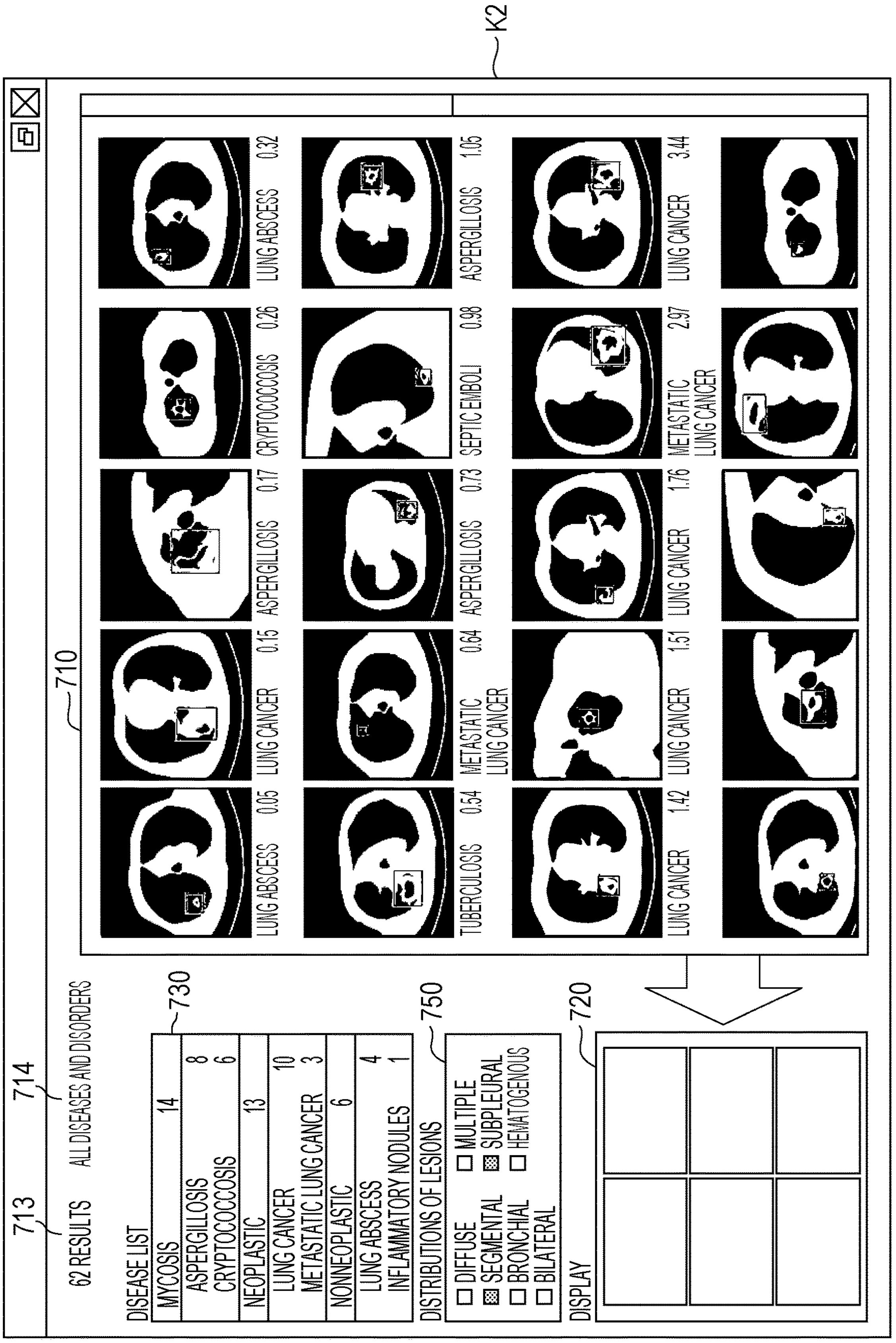
FIG. 41 is a diagram illustrating a basic screen having a layout area in which display boxes are set in three rows and two columns.

FIG. 41 is a diagram illustrating the basic screen K2, which includes the layout area 720 in which display boxes are set in three rows and two columns. Given that the display boxes included in the layout area 720 are generalized for a set of display boxes in M rows and N columns, if M≠N, M>N is preferable when the display 101 is a portrait-oriented display, and M<N is preferable when the display 101 is a landscape-oriented display.

One important feature of this embodiment is to display a thumbnail image of a target case to be diagnosed in one of the display boxes included in the layout area 720. That is, allowing the case to be diagnosed and a similar case to be displayed adjacent to each other helps the user determine the similarity between the two cases. Thus, display boxes are preferably arranged in up to three rows and up to three columns in the layout area 720.

In a case where display boxes are arranged in three rows and two columns, the thumbnail image of the search query image is preferably displayed in the display box in the second row and the first column or in the display box in the second row and the second column. In a case where display boxes are arranged in two rows and three columns, the thumbnail image of the search query image is preferably displayed in the display box in the first row and the second column or in the display box in the second row and the second column. In a case where display boxes are arranged in three rows and three columns, the thumbnail image of the search query image is preferably displayed in the display box in the second row and the second column. With the configuration described above, a similar case is always displayed adjacent to the target case to be diagnosed in the layout area 720.

The layout information on the layout area 720, which is set by the user, is registered in the layout management information 4200 illustrated in FIG. 42 or FIG. 43.

The box layout management unit 111 that stores the layout management information 4200 may be included in the case search system 300.

Even the same user may change the layout of the layout area 720 so as to fit the size of the display 101 of the information terminal 100 or the type of the screen (portrait-oriented or landscape-oriented). Accordingly, as illustrated in FIG. 42, layout information set by the user may be registered in the layout management information 4200 in association with the user ID and the terminal ID. FIG. 42 is a diagram illustrating an example of the layout management information 4200. In the layout management information 4200, the "user ID", the "terminal ID", the "number of columns", the "number of rows", and the "position of case to be diagnosed" are associated with each other. The "user ID" represents a user identifier assigned in advance to a user who uses the information terminal 100. The "terminal ID" represents an identifier of an information terminal 100 that the user is expected to use.

In the example illustrated in FIG. 42, the user with the user ID "U01" is expected to use the information terminals with the terminal IDs "T02" and "T04". Thus, the user ID "U01" is associated with the terminal IDs "T02" and "T04".

The "number of rows" and the "number of columns" contain the number of rows and the number of columns in the layout area 720 set by the user. The "position of case to be diagnosed" represents the position of a display box in which the case to be diagnosed is displayed. For example, the layout area 720 with two rows and three columns is set for the information terminal 100 with the terminal ID "T04", and (2, 1) which indicates the second row and the first column is registered as the "position of case to be diagnosed" in order to allow the case to be diagnosed and all the similar cases to be displayed adjacent to each other.

In FIG. 42, an embodiment is given in which layout information is managed in association with a user ID and a terminal ID. Alternatively, layout information may be managed in association with a user ID. FIG. 43 is a diagram illustrating an example of the layout management information 4200. The layout management information 4200 illustrated in FIG. 43 does not include the "terminal ID" field, which is included in the layout management information 4200 illustrated in FIG. 42. Except for that, the layout management information 4200 of FIG. 43 and the layout management information 4200 of FIG. 42 are the same. In the embodiment illustrated in FIG. 43, the "terminal ID" field is not included because one user is expected to use one information terminal 100.

In a case where layout information is managed by the case search system 300, in S650 in FIG. 39, layout information on the associated user is transmitted to the information terminal 100.

Then, the display control unit 104 generates the initial basic screen K2 on which similar case search results are displayed, by using the similar case data transmitted in S640 and the display box management information 4410 stored in S660 (S670).

In this case, the basic screen K2 illustrated in FIG. 6 is displayed on the display 101*b*. Further, the search query image is displayed on the display 101*a*.

Figure 44:
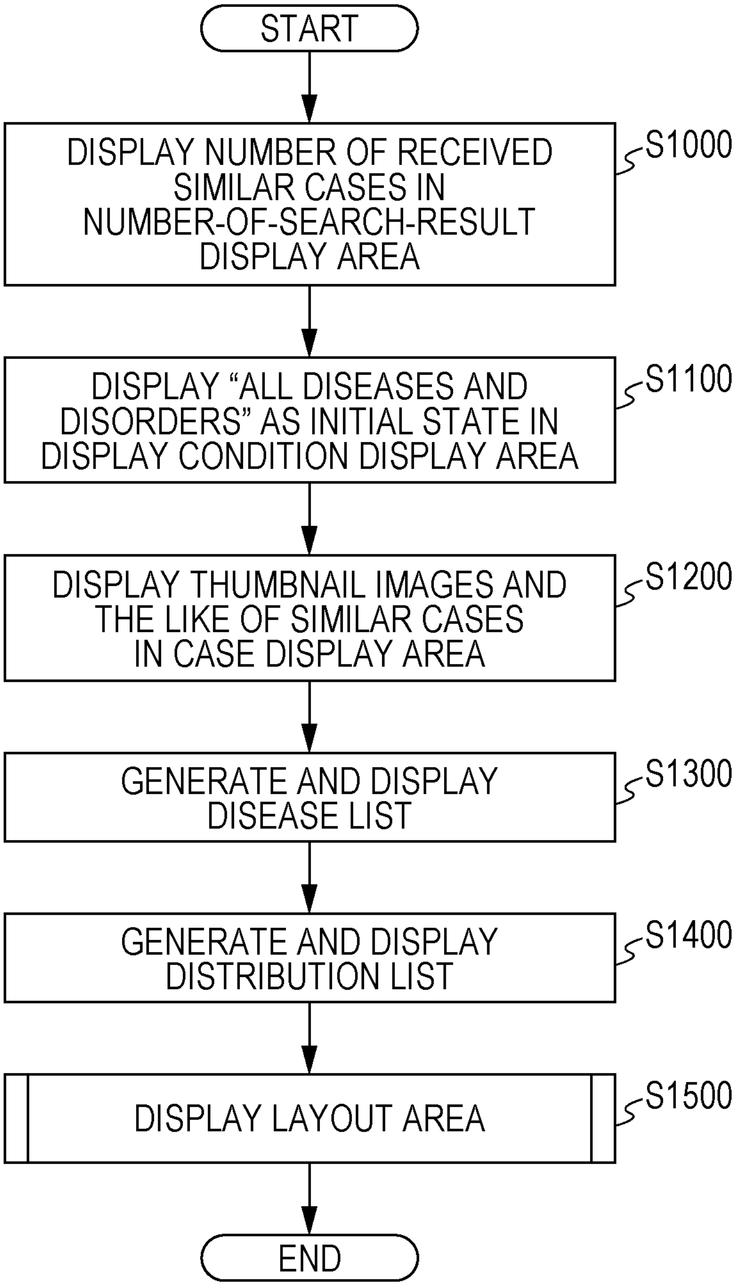
FIG. 44 a flowchart illustrating the details of an initial basic screen generation process illustrated in S670 in FIG. 39.

FIG. 44 is a flowchart illustrating the details of the process for generating the initial basic screen K2 illustrated in S670 in FIG. 39.

First, in S1000, the display control unit 104 counts the number of similar cases received in S640 in FIG. 39, and displays the count value in the number-of-search-result display area 713.

Then, in S1100, the display control unit 104 displays "all diseases and disorders" in the display condition display area 714. Here, "all diseases and disorders" is displayed because no refinement is performed in accordance with a disease name or a distribution of lesions by the user on the initial basic screen K2.

Then, in S1200, the display control unit 104 displays in the case display area 710 thumbnail images of similar cases, the number of which is equal to the number of similar cases whose thumbnail images can be displayed in the case display area 710 among the similar cases received in S640 in FIG. 39, and also displays definite diagnoses and similarities in association with the respective thumbnail images.

In the example illustrated in FIG. 6, the maximum number of similar cases that can be displayed in the case display area 710 is 20. The maximum number of similar cases that can be displayed is determined in advance. The maximum number of similar cases that can be displayed may also be changed by the user as desired. If the number of similar cases received in S640 in FIG. 39 is larger than the maximum number of similar cases that can be displayed, the display control unit 104 displays the vertical scrollbar 715 at the right end of the case display area 710. By moving the scrollbar 715, the user is able to view the thumbnail images of similar cases that are not currently visible on the initial basic screen K2.

Then, in S1300, a disease list is generated and displayed. First, a disease list is generated based on the similar cases received in S640 in FIG. 39. The disease list is a list in which the similar cases received in S640 are classified according to each definitely diagnosed disease name.

It is assumed here that the number of similar cases received in S640 is represented by NC. The disease list management unit 108 generates a disease list by using the definite diagnosis (major-category disease name) 4700 and the definite diagnosis (subcategory disease name) 4800 registered in each of the NC pieces of similar case data 4000. The generated disease list is managed by the disease list management unit 108 as data in table format, as illustrated in FIG. 46.

FIG. 46 is a diagram illustrating the data configuration of the disease list generated in S1300 in FIG. 44. The disease list includes the following fields: "disease ID", "major-category disease name", "subcategory disease name", "number of results", and "similar case ID". The "disease ID" field represents an identifier assigned to each definitely diagnosed disease name. Here, a disease ID is assigned to a combination of major-category and subcategory disease names.

The "major-category disease name" field represents a definitely diagnosed disease name indicated by the definite diagnosis (major-category disease name) 4700 registered in the similar case data 4000. The "subcategory disease name" field represents a name definitely diagnosed disease indicated by the definite diagnosis (subcategory disease name) 4800 registered in the similar case data 4000. The "number of results" field represents the number of similar cases of the definitely diagnosed disease name identified by the "disease ID". The "similar case ID" field represents a similar case ID that identifies a similar case of the disease name identified by the "disease ID".

The disease list management unit 108 extracts the definite diagnosis (major-category disease name) 4700 and the definite diagnosis (subcategory disease name) 4800 in each of the pieces of similar case data 4000 received in S640, and classifies pieces of similar case data 4000 having the same definite diagnosis (major-category disease name) 4700 and the same definite diagnosis (subcategory disease name) 4800 as pieces of similar case data indicating similar cases of the same definitely diagnosed disease name. Further, the disease list management unit 108 counts the number of similar cases of the same definitely diagnosed disease name, and registers the number of similar cases in the "number of results" field of the record of the corresponding definitely diagnosed disease name. The disease list management unit 108 also registers the similar case IDs of the similar cases classified as the same definitely diagnosed disease name in the "similar case ID" field of the record of the corresponding definitely diagnosed disease name.

In the example illustrated in FIG. 46, the disease ID "DIS528" is assigned to the definitely diagnosed disease name categorized as the major-category disease name "neoplastic" and the subcategory disease name "lung cancer". The number of similar cases of this definitely diagnosed disease name is 10. Thus, "10" is registered in the "number of results" field of the corresponding record, and the similar case IDs "SIM258", "SIM551", "SIM1209", "SIM2341", and so forth of the similar cases of the definitely diagnosed disease name are registered in the "similar case ID" field of the corresponding record.

The display control unit 104 generates the disease list display area 730 by using the disease list generated in the way described above, and displays the disease list display area 730 on the display 101.

FIG. 47, FIG. 48, and FIG. 49 are diagrams illustrating a first example display, a second example display, and a third example display of the disease list display area 730, respectively. As illustrated in FIG. 47, in the first example display, subcategory disease names are displayed in list form in association with the numbers of similar cases thereof, which are obtained as a result of the similar case search, according to the decreasing number of similar cases.

As illustrated in FIG. 48, in the second example display, major-category disease names are displayed in list form in association with the numbers of similar cases thereof, which are obtained as a result of the similar case search, according to the decreasing number of similar cases.

As illustrated in FIG. 49, in the third example display, major-category disease names are displayed in list form in association with the numbers of similar cases thereof, which are obtained as a result of the similar case search, according to the decreasing number of similar cases, and subcategory disease names included in each of the major-category disease names are further displayed in list form in association with the numbers of similar cases thereof according to the decreasing number of similar cases. In this case, each definitely diagnosed disease name is expressed using a hierarchical structure of a major-category disease name and a subcategory disease name.

Figure 50:
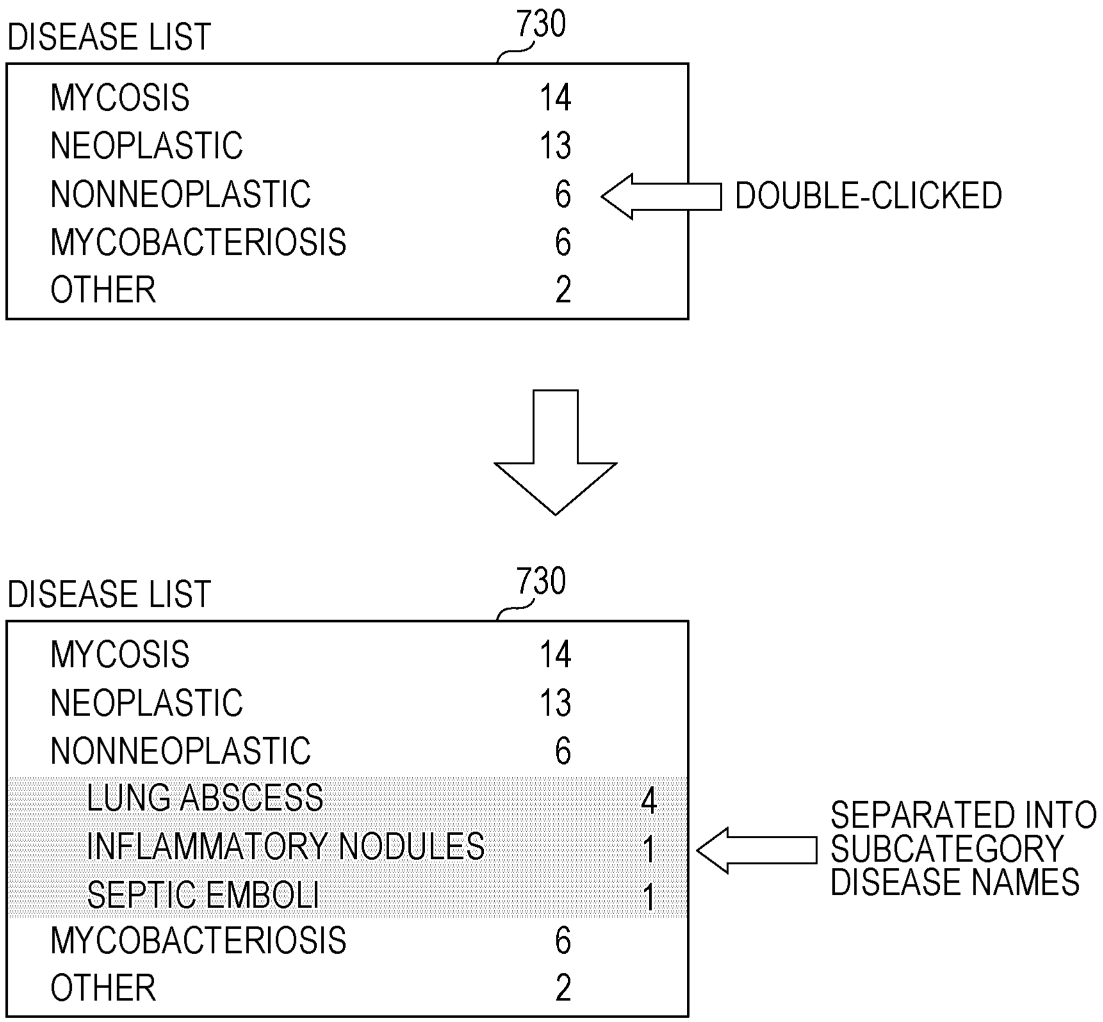
FIG. 50 is a diagram illustrating a screen transition that occurs in the disease list display area illustrated in FIG. 48.

FIG. 50 is a diagram illustrating a screen transition that occurs in the disease list display area 730 illustrated in FIG. 48. As illustrated in the upper part of FIG. 50, when the input control unit 103 detects the selection of a major-category disease name by the user among the major-category disease names displayed in list form, as illustrated in the lower part of FIG. 50, the display control unit 104 displays the subcategory disease names that belong to the selected major-category disease name in association with the numbers of similar cases thereof according to the decreasing number of similar cases. In this case, the user may select a desired major-category disease name from among, for example, the major-category disease names displayed in list form in the disease list display area 730 by, for example, double clicking or single clicking. In the example illustrated in FIG. 50, "nonneoplastic" is double-clicked. Thus, subcategory disease names that belong to "nonneoplastic" are displayed in list form.

In the lower part of FIG. 50, when an area showing a list of subcategory disease names is double-clicked or single-clicked by the user, the display control unit 104 may hide the subcategory disease names displayed in the area.

The display control unit 104 may determine subcategory disease names that belong to a major-category disease name by referring to the disease list (FIG. 46). For example, in the example illustrated in FIG. 46, aspergillosis and cryptococcosis are associated with mycosis. Thus, the display control unit 104 may determine that aspergillosis and cryptococcosis belong to mycosis.

Referring back to FIG. 44, in S1400, a distribution list is generated and displayed. First, a distribution list is generated based on the similar cases received in S640. The distribution list is a list in which the similar cases received in S640 are classified according to each distribution of lesions.

The disease list management unit 108 generates a distribution list by using the distribution-of-lesion information 4600 registered in each of the NC pieces of similar case data 4000. The generated distribution list is managed by the distribution list management unit 109 as data in table format, as illustrated in FIG. 51.

Figures 51, 52:
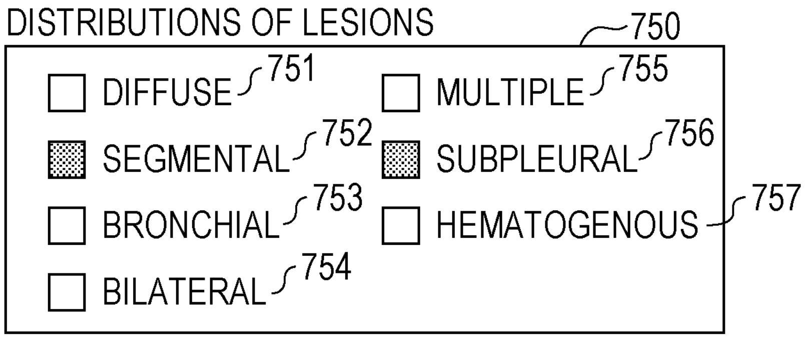
FIG. 51 is a diagram illustrating the data configuration of a distribution list generated in S1400 in FIG. 44.
FIG. 52 is a diagram illustrating a distribution list display area generated using the distribution list illustrated in FIG. 51.

FIG. 51 is a diagram illustrating the data configuration of the distribution list generated in S1400 in FIG. 44. The distribution list includes the following fields: "name of distribution", "number of cases", and "similar case ID". The "name of distribution" field represents the names of a plurality of predetermined distributions of lesions such as diffuse and segmental distributions. The "number of cases" field represents the number of similar cases corresponding to each distribution of lesions. The "similar case ID" field represents a similar case ID that identifies a similar case corresponding to each distribution of lesions.

The distribution list management unit 109 extracts the distribution-of-lesion information 4600 in each of the pieces of similar case data 4000 received in S640, counts the number of distributions of lesions with the distribution flag value set to "1" (Applicable) in the extracted distribution-of-lesion information 4600, and registers the count value in the "number of cases" field of the record of the corresponding distribution of lesions. The distribution list management unit 109 also registers the similar case IDs of the similar cases with the distribution flag value set to "1" in the "similar case ID" field of the record of the corresponding distribution of lesions.

In the example illustrated in FIG. 51, the number of similar cases corresponding to the diffuse distribution is three. Thus, "3" is registered in the "number of cases" field of the record of the diffuse distribution. Further, the similar case IDs "SIM2521", "SIM4123", and "SIM5225" of the similar cases corresponding to the diffuse distribution are registered in the "similar case ID" field of the record of the diffuse distribution.

The display control unit 104 generates the distribution list display area 750 by using the distribution list generated in the way described above, and displays the distribution list display area 750 on the display 101.

FIG. 52 is a diagram illustrating the distribution list display area 750 generated using the distribution list illustrated in FIG. 51. In FIG. 51, the number of cases corresponding to the segmental and subpleural distributions is 0. Accordingly, the "segmental" 752 and the "subpleural" 756 are displayed as inactive in FIG. 52. The number of cases corresponding to the other distributions of lesions is greater than or equal to one, and such distributions of lesions are displayed as active accordingly.

Referring back to FIG. 44, in S1500, the layout area 720 is displayed. This process is performed by the display control unit 104.

Figure 45:
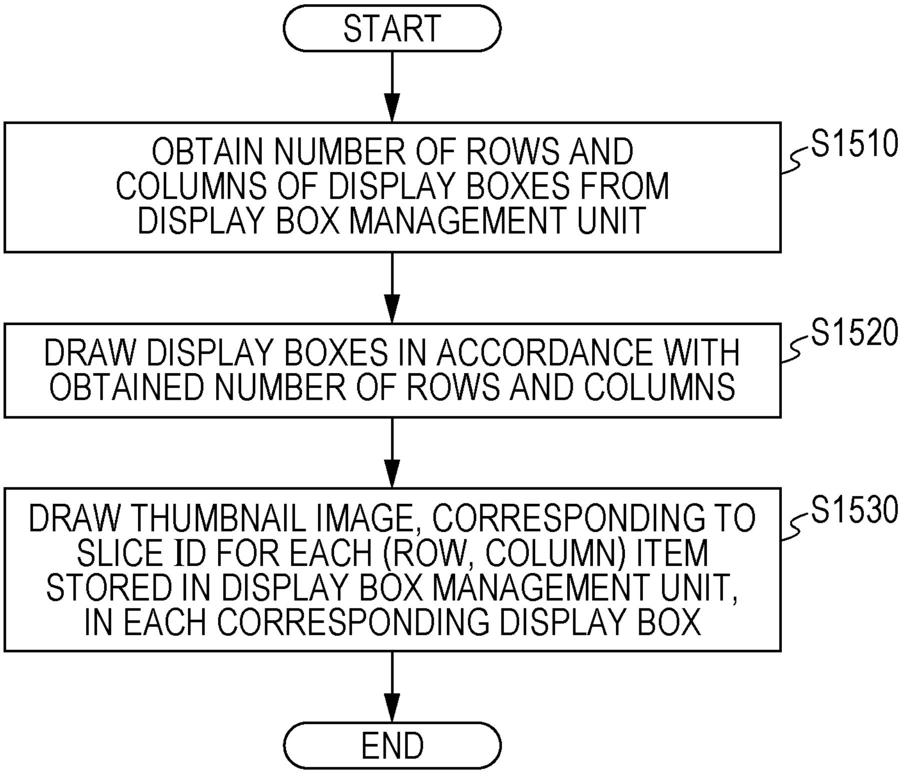
FIG. 45 is a flowchart illustrating the processing of S1500 illustrated in FIG. 44.

FIG. 45 is a flowchart illustrating the processing of S1500 illustrated in FIG. 44. In S1510, the display control unit 104 obtains the number of rows and columns of display boxes in the layout area 720 from the display box management information 4410 set in S660. In the example of the display box management information 4410 illustrated in FIG. 40, the number of rows and the number of columns are set to two and two, respectively, and information indicating "two rows and two columns" is obtained. If a user changes the number of rows and columns of display boxes, the number of rows and columns of display boxes in the layout area 720 is obtained from the layout management information 4200 illustrated in FIG. 42 or FIG. 43.

Then, in S1520, the display control unit 104 draws display boxes in accordance with the number of rows and columns obtained in S1510.

Finally, in S1530, the display control unit 104 identifies a slice ID for each display box from the display box management information 4410, and draws a thumbnail image corresponding to the identified slice ID in the corresponding one of the display boxes.

In the example illustrated in FIG. 40, the slice ID of the case to be diagnosed is stored in the display box in the first row and the first column. Accordingly, the display control unit 104 generates a thumbnail image from the slice image of the case to be diagnosed, which is transmitted in S600 in FIG. 35, and draws the generated thumbnail image in the display box 721.

In this stage, no slice IDs are stored in the other display boxes (i.e., the display boxes 722, 723, and 724 in the first row and the second column, the second row and the first column, the second row and the second column, respectively). Thus, the display control unit 104 displays no images in these display boxes. A thumbnail image of a similar case is displayed in these display boxes through a process described below.

Referring back to FIG. 39, the communication control unit 110 transmits the display box management information 4410 stored in the display box management unit 106 to the display control unit 104 (S680).

Then, the display control unit 104 starts a medical image viewer in the same display state and layout as the display state and layout of the layout area 720 (S690).

Figure 53:
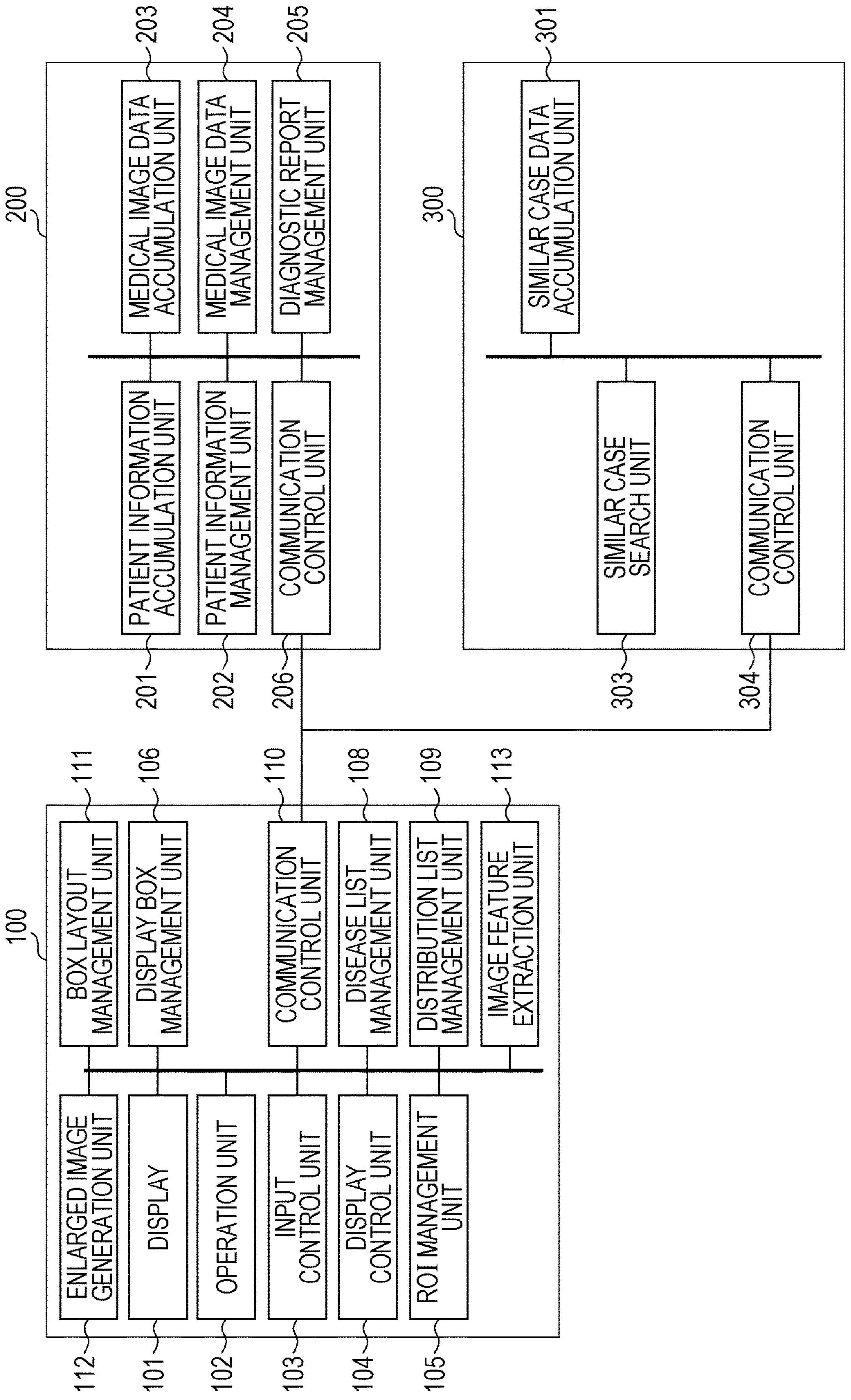
FIG. 53 is a block diagram of an information terminal, a medical information management system, and a case search system according to an embodiment in which the case search system extracts an image feature.

In the illustrated example, the case search system 300 extracts an image feature. Alternatively, the information terminal 100 may extract an image feature. FIG. 53 is a block diagram of the information terminal 100, the medical information management system 200, and the case search system 300 according to an embodiment in which the case search system 300 extracts an image feature.

The configuration illustrated in FIG. 53 is different from that illustrated in FIG. 2 in that the information terminal 100 further includes an image feature extraction unit 113 and the case search system 300 does not include the image feature extraction unit 302.

Figure 54:
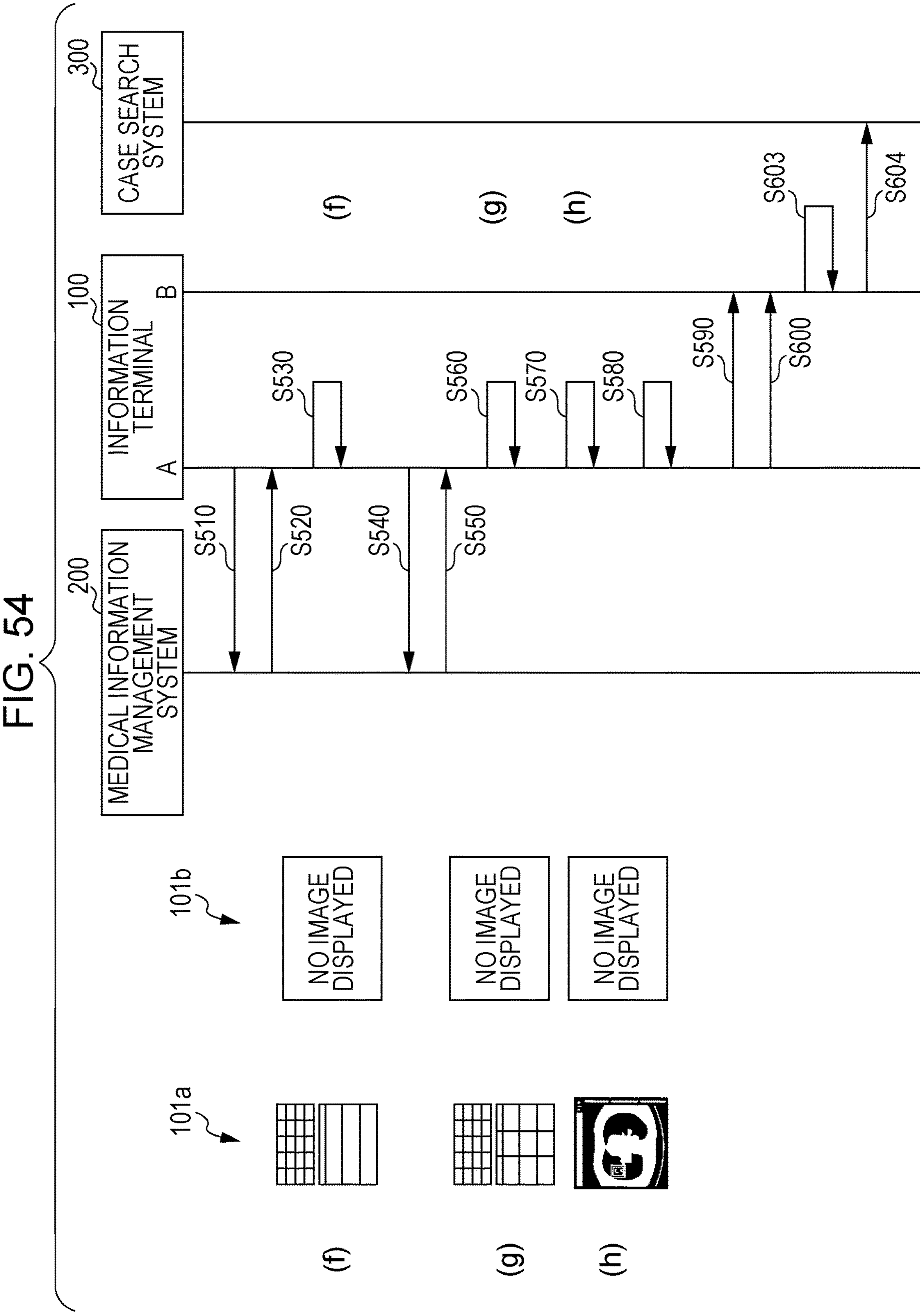
FIG. 54 is a sequence diagram illustrating a process performed during a period in which, after the information terminal obtains a case to be diagnosed from the medical information management system, the case search system receives a similar case search request.

FIG. 54 is a sequence diagram illustrating a process performed during a period in which, after the information terminal 100 obtains a case to be diagnosed from the medical information management system 200, the case search system 300 receives a similar case search request.

The operation illustrated in FIG. 54 is different from that illustrated in FIG. 35 in that, after the ROI management unit 105 transmits a slice image of the case to be diagnosed to the communication control unit 110 (S600), the information terminal 100 extracts an image feature (S603) and transmits the extracted image feature to the case search system 300 (S604). The process for extracting an image feature (S603) is similar to that in the case where the case search system 300 extracts an image feature.

Figure 55:
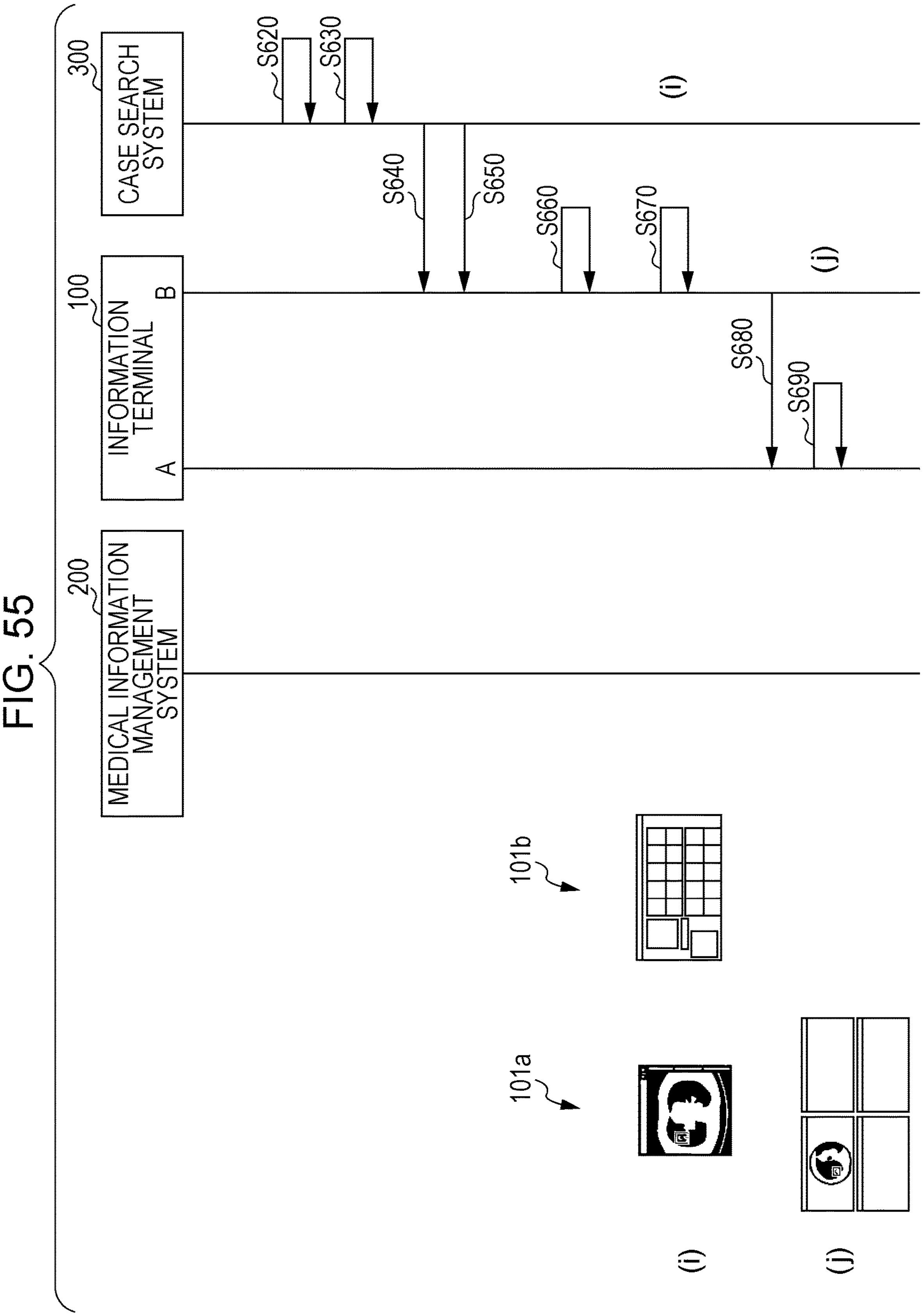
FIG. 55 is a sequence diagram illustrating a process performed during a period in which, after receiving the similar case search request, the case search system returns similar case search results to the information terminal.

FIG. 55 is a sequence diagram illustrating a process performed during a period in which, after receiving the similar case search request, the case search system 300 returns similar case search results to the information terminal 100. The operation illustrated in FIG. 55 is different from that illustrated in FIG. 39 in that, since an image feature is extracted by the information terminal 100, the extraction of an image feature (S610) in FIG. 39 is omitted in FIG. 55.

Next, the process for enlarging the thumbnail images displayed in the case display area 710, which has been described with reference to FIG. 8 to FIG. 11, will be described.

Figure 56:
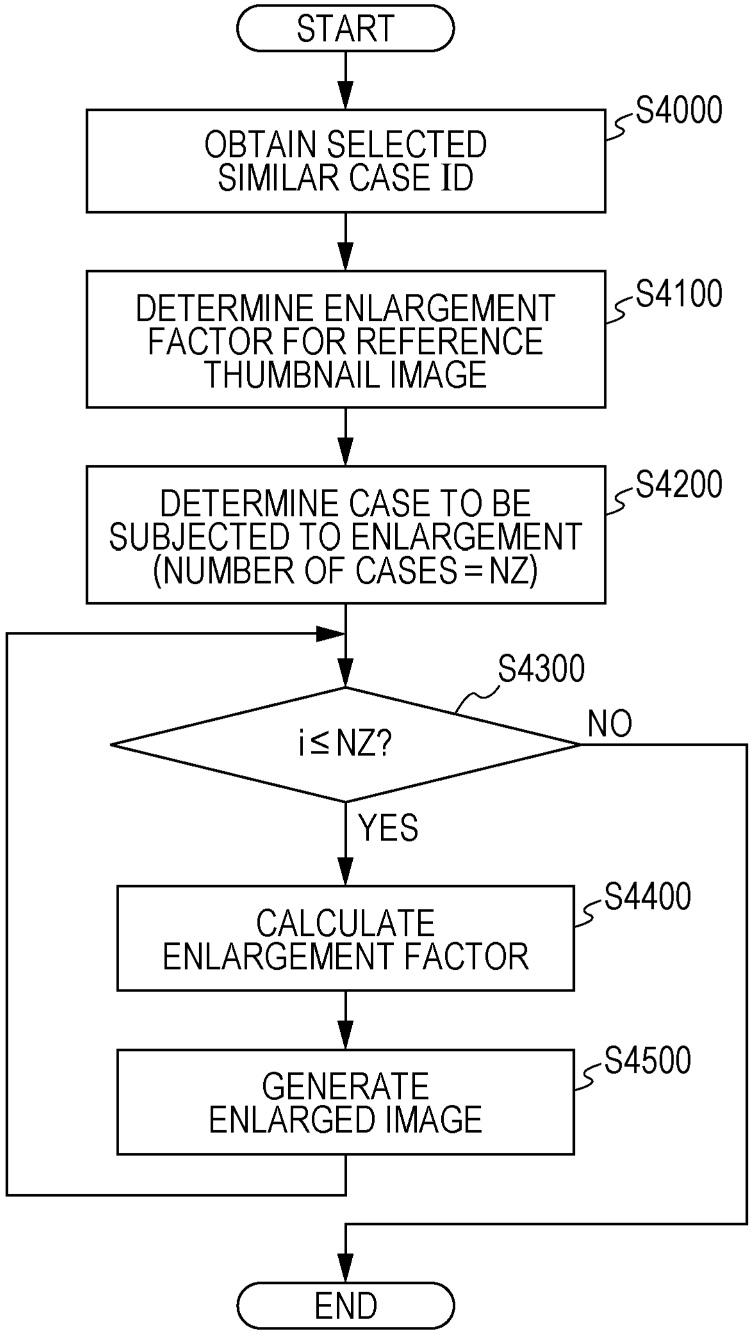
FIG. 56 is a flowchart illustrating a process for enlarging thumbnail images displayed in the case display area.

FIG. 56 is a flowchart illustrating a process for enlarging the thumbnail images displayed in the case display area 710.

In S4000, the enlarged image generation unit 112 obtains the similar case ID 4100 (FIG. 33) of the thumbnail image selected by the user (in FIG. 8, the thumbnail image in the first row and the fourth column). In the following, the thumbnail image selected by the user is referred to as the "reference thumbnail image". The enlarged image generation unit 112 determines enlargement factors for the other thumbnail images displayed in the case display area 710, in association with an enlargement operation performed on the reference thumbnail image by the user.

In S4100, the enlarged image generation unit 112 obtains, from the input control unit 103, the amount of enlargement operation performed on the reference thumbnail image, which is input to the operation unit 102 by the user. Then, the enlarged image generation unit 112 determines an enlargement factor for the reference thumbnail image on the basis of the obtained amount of operation.

Specifically, the input control unit 103 detects the amount of rotation of the mouse wheel, which is input to the operation unit 102 as an enlargement operation. The input control unit 103 notifies the enlarged image generation unit 112 of the detected amount of rotation. The enlarged image generation unit 112 multiplies the amount of rotation by a predetermined coefficient to calculate an enlargement factor for the reference thumbnail image.

As described above, the user may perform an enlargement operation by using the up arrow key or the down arrow key on the keyboard. In this case, the input control unit 103 may detect the length of time during which the key is pressed. The enlarged image generation unit 112 may multiply the length of time during which the key is pressed by a predetermined coefficient to calculate an enlargement factor for the reference thumbnail image.

In S4200, the enlarged image generation unit 112 determines a target similar case to be subjected to an enlargement process among a large number of similar cases obtained from the case search system 300. As illustrated in FIG. 6, the display control unit 104 displays, in the case display area 710, thumbnail images of similar cases, the number of which is equal to the predetermined maximum number ND (in this embodiment, ND=20) of results allowed to be displayed in the case display area 710, among NC (in FIG. 6, NC=62) pieces of similar case data found as a result of the search by the similar case search unit 303 of the case search system 300.

In this step, the enlarged image generation unit 112 determines a target similar case to be subjected to an enlargement process within a range less than or equal to ND so that thumbnail image selected by the user is included. In this embodiment, the enlarged image generation unit 112 determines NZ target similar cases to be subjected to an enlargement process, where NZ≤ND. This step may reduce the processing load on the information terminal 100, compared to the case where the thumbnail image of all the NC similar cases are enlarged.

In S4300, the enlarged image generation unit 112 determines a thumbnail image of a similar case i (where i is an index identifying a target similar case to be processed, and is an integer greater than or equal to 1) as a thumbnail image to be processed. Then, the enlarged image generation unit 112 repeatedly performs the processing of S4400 and S4500 until the index i has reached NZ (YES in S4300). The enlarged image generation unit 112 increments the index i by 1 each time the processing of S4400 and S4500 is executed. If the index i exceeds NZ (NO in S4300), the process illustrated in FIG. 56 ends.

In S4400, the enlarged image generation unit 112 calculates an enlargement factor for the thumbnail image of the similar case i to be subjected to enlargement. The enlarged image generation unit 112 calculates an enlargement factor for the similar case i to be subjected to enlargement, on the basis of the enlargement factor for the reference thumbnail image, which is determined in S4100, the region-of-interest information 4300 (FIG. 33) on the similar case corresponding to the reference thumbnail image, and the region-of-interest information 4300 (FIG. 33) on the similar case i to be subjected to enlargement.

Figure 57:
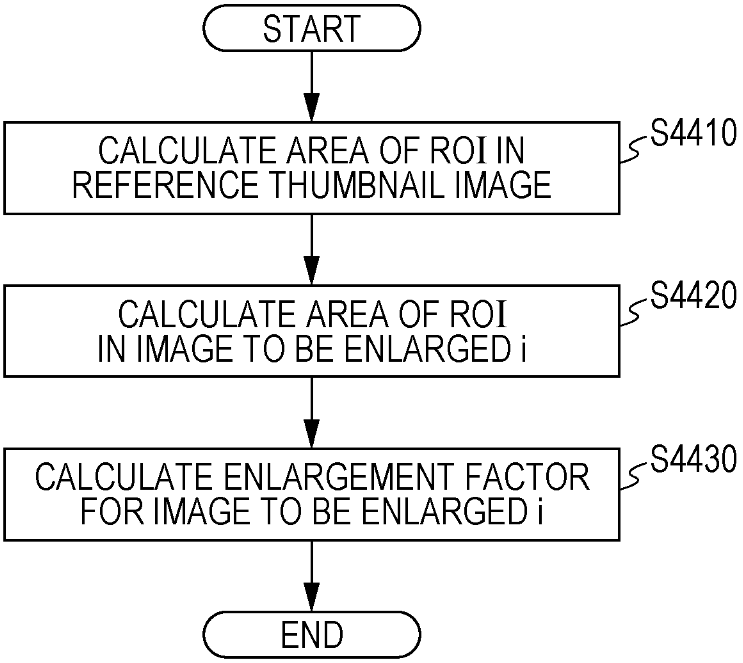
FIG. 57 is a flowchart illustrating a process in a subroutine of S4400 in FIG. 56.

FIG. 57 is a flowchart illustrating a process in a subroutine of S4400 in FIG. 56.

In S4410, the enlarged image generation unit 112 calculates the area of the region of interest in the reference thumbnail image on the basis of the region-of-interest information 4300 on the similar case corresponding to the reference thumbnail image. Given that the area of the region of interest in the reference thumbnail image is represented by Sr, the coordinates of the upper left corner of the region of interest are represented by (xl, yt), and the coordinates of the lower right corner of the region of interest are represented by (xr, yb), the area Sr of the region of interest can be calculated in accordance with the following equation:

$$Sr=|xL-xr|\times|yt-yb|.$$

In S4420, the enlarged image generation unit 112 calculates the area of the region of interest in the thumbnail image of the similar case i to be subjected to enlargement, on the basis of the region-of-interest information 4300 on the similar case i to be subjected to enlargement. Given that the area of the region of interest in the thumbnail image of the similar case i to be subjected to enlargement is represented by Si, the coordinates of the upper left corner of the region of interest are represented by (xli, yti), and the coordinates of the lower right corner of the region of interest are represented by (xri, ybi), the area Si of the region of interest can be calculated in accordance with the following equation:

$$Si=|xli-xri|\times|yti-ybi|.$$

In S4430, the enlarged image generation unit 112 calculates an enlargement factor for the similar case i to be subjected to enlargement, on the basis of the area Sr of the region of interest in the reference thumbnail image, which is calculated in S4410, the area Si of the region of interest in the thumbnail image of the similar case i to be subjected to enlargement, which is calculated in S4420, and the enlargement factor for the reference thumbnail image, which is determined in S4100. Given that the enlargement factor for the reference thumbnail image is represented by kr, the enlargement factor ki for the similar case i to be subjected to enlargement can be calculated in accordance with the following equation:

$$ki=kr(Sr/Si).$$

Figure 58:
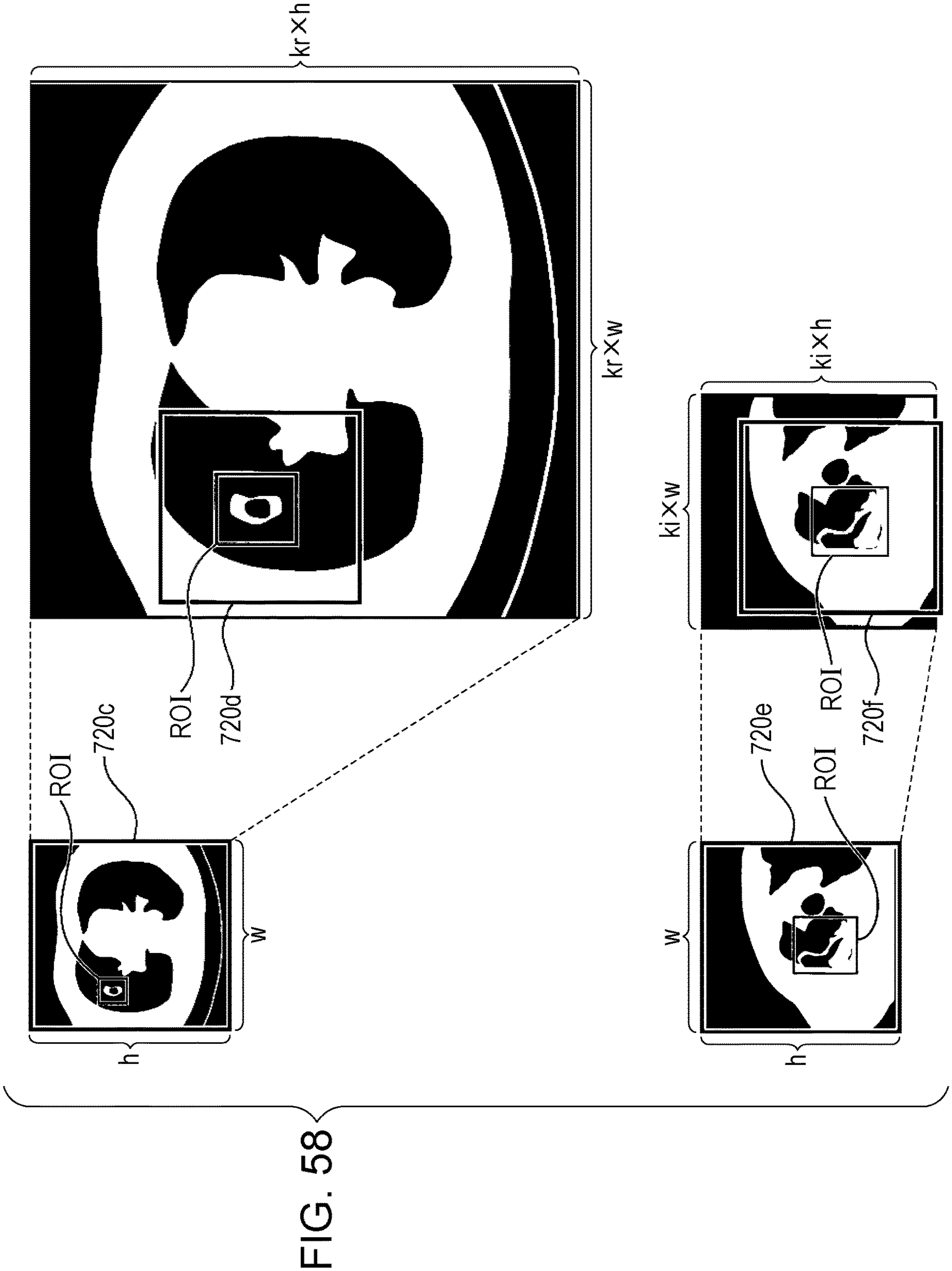
FIG. 58 is a diagram schematically illustrating reference thumbnail images obtained before and after an enlargement process is performed and enlargement-intended thumbnail images obtained before and after an enlargement process is performed.

FIG. 58 is a diagram schematically illustrating reference thumbnail images obtained before and after an enlargement process is performed and enlargement-intended thumbnail images obtained before and after an enlargement process is performed. The upper left part of FIG. 58 illustrates the reference thumbnail image obtained before the enlargement process is performed. The upper right part of FIG. 58 illustrates the reference thumbnail image obtained after the enlargement process is performed. The lower left part of FIG. 58 illustrates the enlargement-intended thumbnail image obtained before the enlargement process is performed. The lower right part of FIG. 58 illustrates the enlargement-intended thumbnail image obtained after the enlargement process is performed.

As a result of enlarging the reference thumbnail image illustrated in the upper left part of FIG. 58 with the enlargement factor kr, the thumbnail image illustrated in the upper right part of FIG. 58 is obtained. The enlarged image generation unit 112 determines a display area 720*d* so that, in the upper right part of FIG. 58, the position of the center of the region of interest ROI matches the position of the center of the display area 720*d*. The enlarged image generation unit 112 performs enlargement so that the size of the display area 720*d* is maintained to be equal to the size of a display area 720*c* before the enlargement process is performed.

As a result of enlarging the enlargement-intended thumbnail image illustrated in the lower left part of FIG. 58 with the enlargement factor ki, the thumbnail image illustrated in the lower right part of FIG. 58 is obtained. The enlarged image generation unit 112 determines a display area 720*f* so that, in the lower right part of FIG. 58, the position of the center of the region of interest ROI matches the position of the center of the display area 720*f*. The enlarged image generation unit 112 performs enlargement so that the size of the display area 720*f* is maintained to be equal to the size of a display area 720*e* before the enlargement process is performed.

In FIG. 58, the enlargement factor ki for the enlargement-intended thumbnail image i with respect to the enlargement factor kr for the reference thumbnail image is determined in accordance with the area ratio of the regions of interest. Accordingly, as illustrated in FIG. 58, the sizes of the regions of interest ROI after enlargement match.

Referring back to FIG. 56, in S4500, the enlarged image generation unit 112 generates an enlarged thumbnail image of the similar case i to be subjected to enlargement, on the basis of the enlargement factor calculated in S4400 and the region-of-interest information 4300 and the thumbnail image data 4500 in the similar case data 4000 (FIG. 33). The display control unit 104 displays the thumbnail image generated by the enlarged image generation unit 112.

Figure 59:
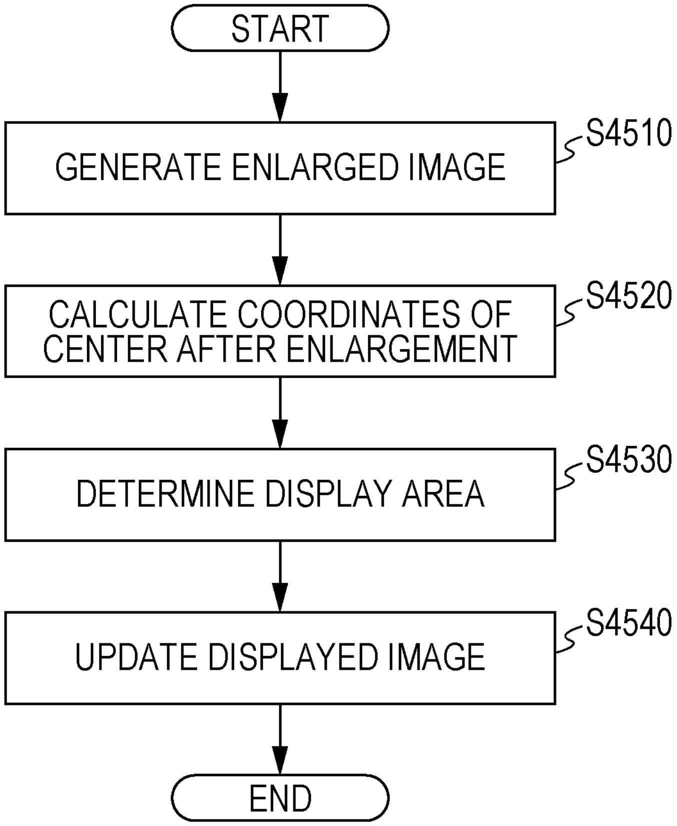
FIG. 59 is a flowchart illustrating a process in a subroutine of S4500 in FIG. 56.
Figure 60:
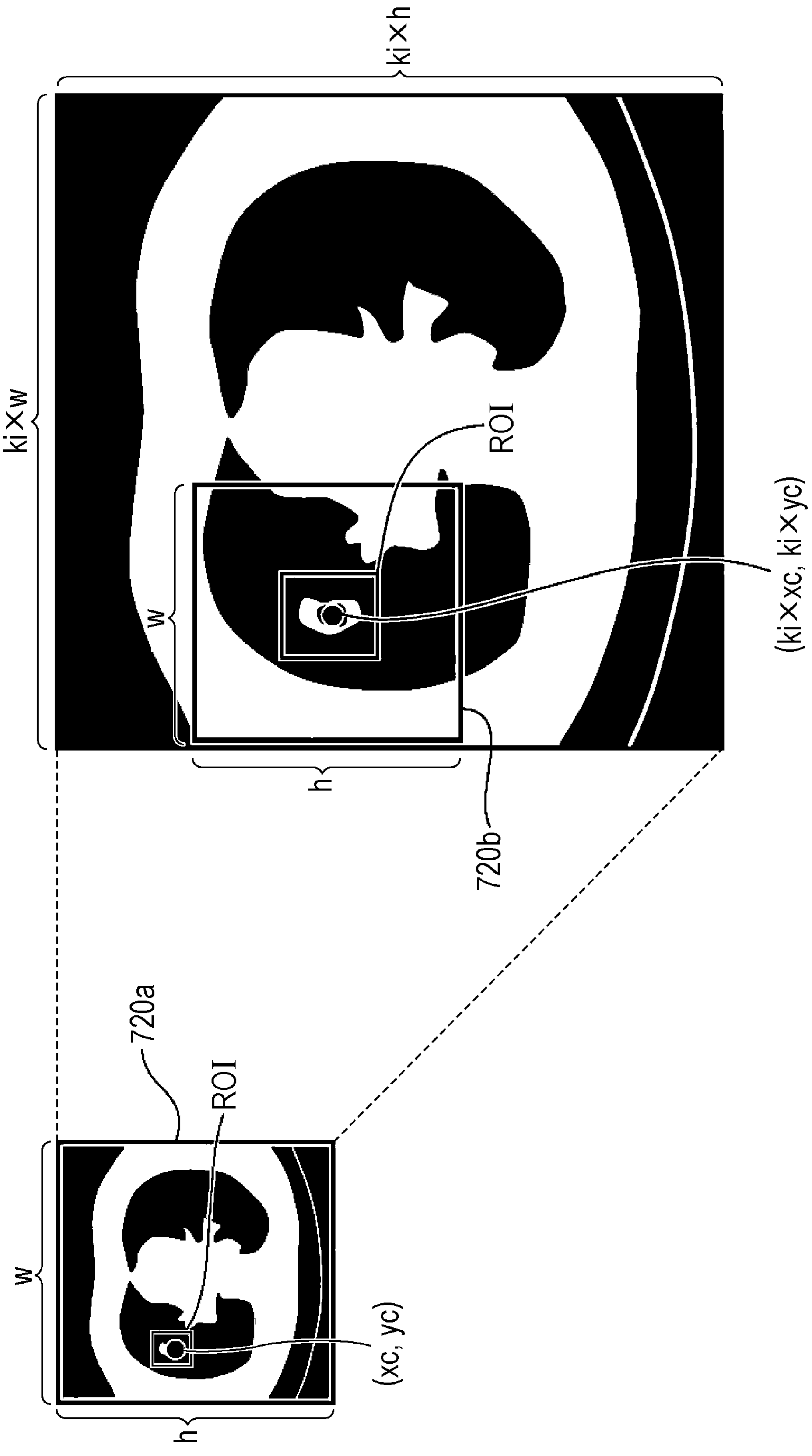
FIG. 60 is a diagram schematically illustrating the relationship between an enlargement factor and a display area.

FIG. 59 is a flowchart illustrating a process in a subroutine of S4500 in FIG. 56. FIG. 60 is a diagram schematically illustrating the relationship between an enlargement factor and a display area. The process for generating an enlarged image so that the position of the center of the region of interest matches the position of the center of an enlarged thumbnail image will now be described in detail with reference to FIG. 59 and FIG. 60.

In S4510, the enlarged image generation unit 112 generates an enlarged image on the basis of the enlargement factor calculated in S4400 and the thumbnail image data 4500 in the similar case data 4000 (FIG. 33). If the enlargement factor is ki, an enlarged thumbnail image illustrated in the right part of FIG. 60 is generated from a thumbnail image illustrated in the left part of FIG. 60.

In S4520, the enlarged image generation unit 112 calculates the coordinates of the center of the region of interest in the enlarged thumbnail image, on the basis of the region-of-interest information 4300 in the similar case data 4000 (FIG. 33) and the enlargement factor calculated in S4400. Given that the coordinates of the center of the region of interest before enlargement is represented by (xc, yc), as illustrated in FIG. 60, coordinates (ki×xc, ki×yc), which are obtained by multiplying the coordinates of the center of the region of interest before enlargement by the enlargement factor, are the coordinates of the center of the region of interest after enlargement.

In S4530, the enlarged image generation unit 112 determines a display area in the enlarged thumbnail image i by using the coordinates (ki×xc, ki×yc) of the center of the region of interest after enlargement, which are calculated in S4520, and a predetermined size of the display area. As illustrated in the left part of FIG. 60, a display area 720*a* is set to have a width dimension w and a height dimension h. In this case, a rectangular area illustrated in the right part of FIG. 60 corresponds to a display area 720*b*. The display area 720*b* has upper left coordinates given by (ki×xc−w/2, ki×yc−h/2), and lower right coordinates given by (ki×xc+w/2, ki×yc+h/2).

In S4540, the display control unit 104 displays, in the display area of the similar case i within the case display area 710, an image of the display area 720*b* calculated in S4530 within the enlarged image generated in S4510 by the enlarged image generation unit 112. Through the process illustrated in FIG. 59, an enlarged thumbnail image i can be generated in such a manner that the position of the center of the region of interest coincides with the position of the center of the center of the display area.

Through the process described above, thumbnail images are displayed in the case display area 710 with an arbitrary enlargement factor specified by the user. In response to an enlargement operation performed on a single thumbnail image by the user, the enlargement factors for all the thumbnail images in the case display area 710 can be changed. This may reduce the operation load on the user. In addition, the thumbnail images are displayed in the case display area 710 in such a manner that the sizes of the regions of interest are uniform. This may prevent the occurrence of oversight caused by the way in which the region of interest in some similar medical images has been enlarged but is small, and may improve diagnosis accuracy. In addition, not all the similar cases obtained as a result of the similar case search but similar cases displayed in the case display area 710 are subjected to an enlargement process, resulting in a significantly reduced load on a system.

Next, a process performed during a period in which, after thumbnail images obtained as a result of the similar case search are enlarged and displayed on the information terminal 100, a display area of a thumbnail image is changed in response to a user operation will be described.

Figure 61:
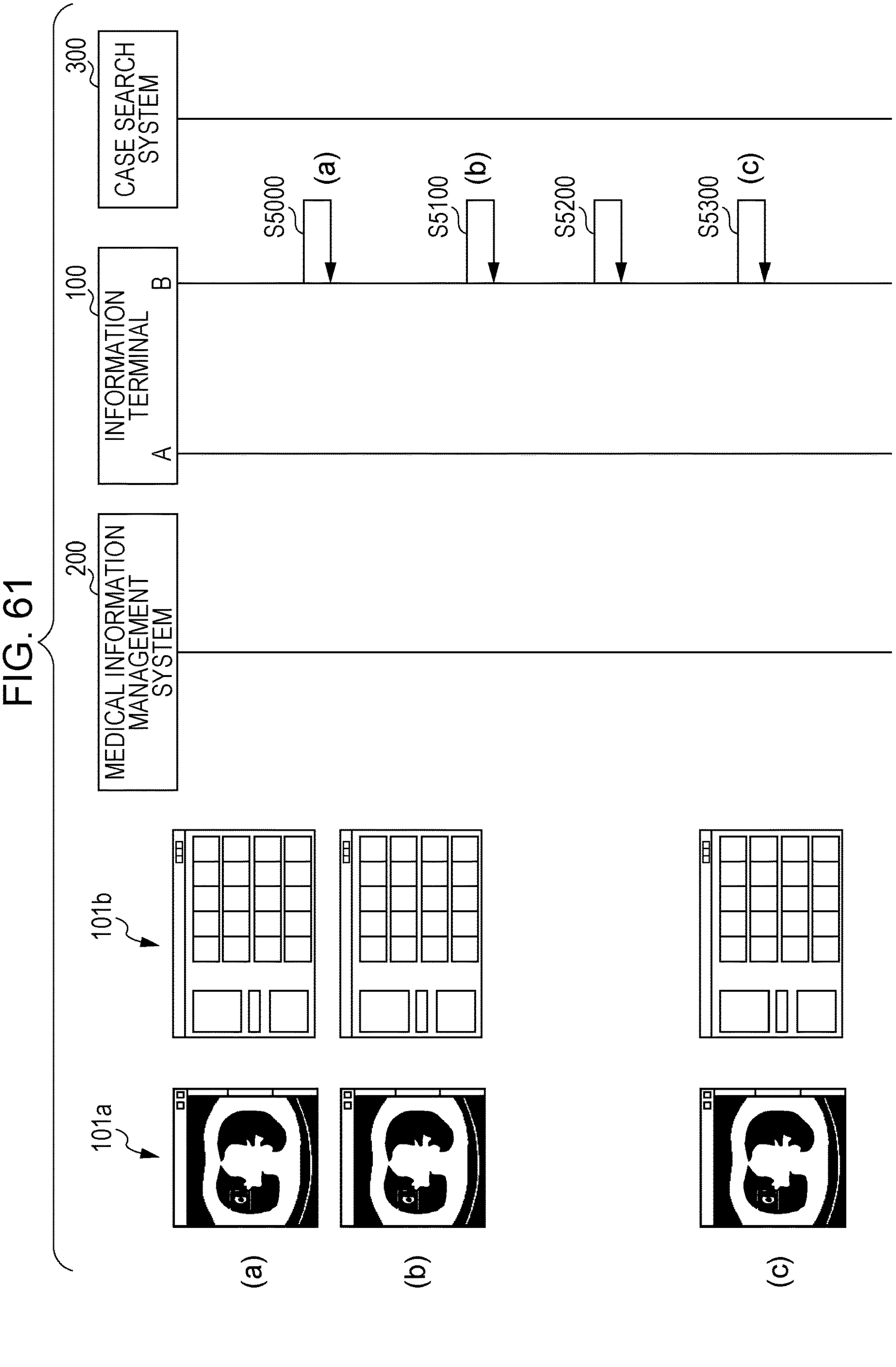
FIG. 61 is a sequence diagram illustrating a process performed during a period in which, after thumbnail images obtained as a result of the similar case search are enlarged and displayed on a display of the information terminal, a display area is changed.

FIG. 61 is a sequence diagram illustrating a process performed during a period in which, after thumbnail images obtained as a result of the similar case search are enlarged and displayed on the display 101*b* of the information terminal 100, a display area is changed.

First, the input control unit 103 of the information terminal 100 detects that the user has selected a thumbnail image by operating the operation unit 102 (e.g., by operating the left button of the mouse) (S5000).

Then, when the user performs a (drag) operation of changing the mouse position, the input control unit 103 detects the amount of movement of the mouse, and notifies the enlarged image generation unit 112 of the detected amount of movement of the mouse (S5100).

Then, the enlarged image generation unit 112 determines an amount of movement of a display area in a thumbnail image by using the detected amount of movement of the mouse, and generates a thumbnail image in which the display area has moved the determined amount (S5200).

Then, the display control unit 104 displays the thumbnail image generated by the enlarged image generation unit 112 in the case display area 710 (S5300).

The details of the processing of S5200 described above will now be described. The processing of S5200 is performed by the enlarged image generation unit 112. In the following, first, the details of the processing blocks of the enlarged image generation unit 112 will be described, and then the flow of the display area changing process will be described.

Figure 62:
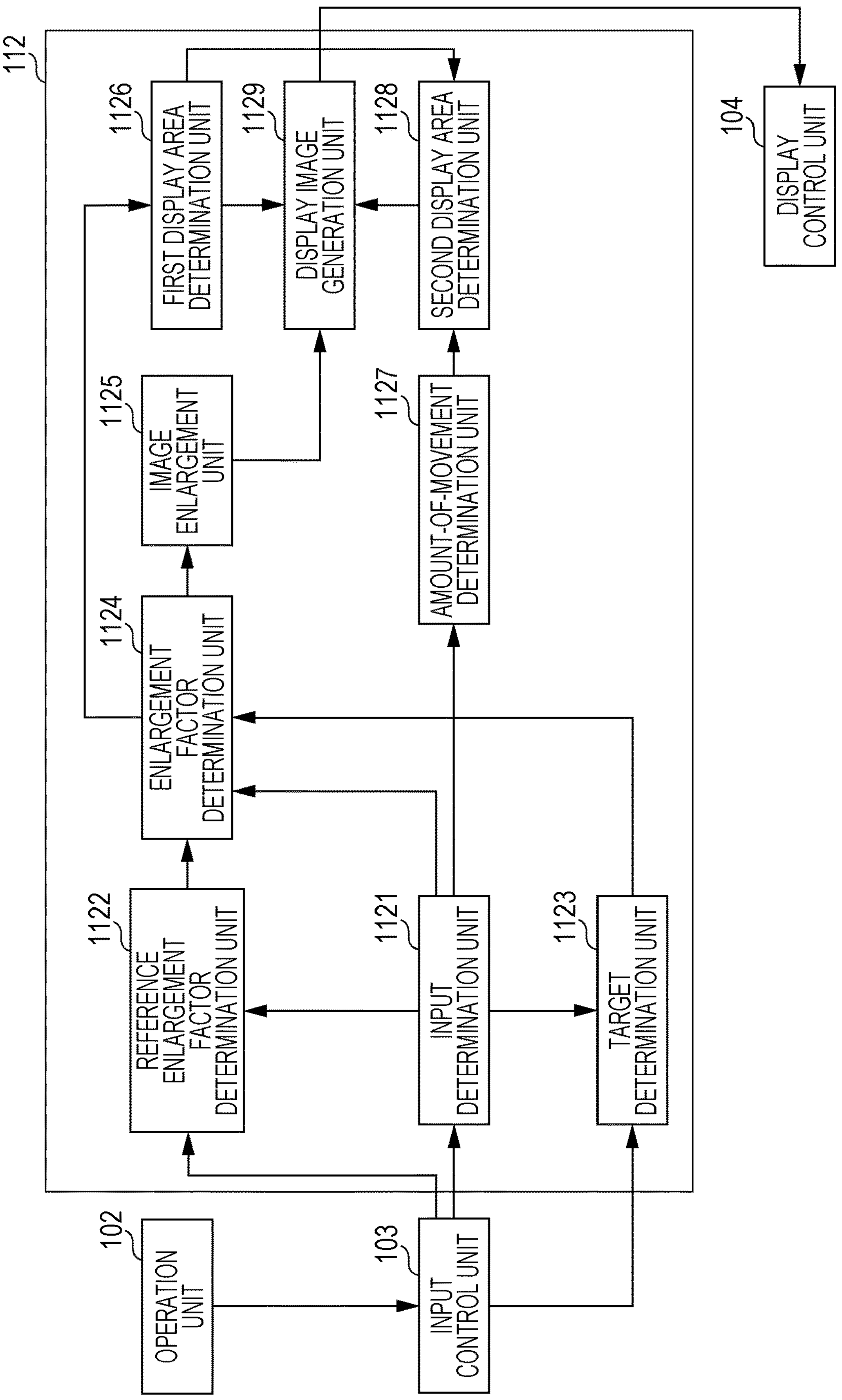
FIG. 62 is a block diagram illustrating a detailed configuration of an enlarged image generation unit.

FIG. 62 is a block diagram illustrating the detailed configuration of the enlarged image generation unit 112. The enlarged image generation unit 112 includes an input determination unit 1121, a reference enlargement factor determination unit 1122, a target determination unit 1123, an enlargement factor determination unit 1124, an image enlargement unit 1125, a first display area determination unit 1126, an amount-of-movement determination unit 1127, a display image generation unit 1129, and a second display area determination unit 1128. The enlarged image generation unit 112 performs an enlargement factor changing process and a display area changing process. In the following, the individual units of the enlarged image generation unit 112 will be described.

The input determination unit 1121 determines the content of the operation performed on the operation unit 102 by a user, of which the enlarged image generation unit 112 is notified by the input control unit 103. If the determined content of the operation indicates an enlargement factor changing operation (e.g., the rotation of the mouse wheel), the input determination unit 1121 outputs the amount of operation (the amount of rotation of the wheel) and the type of the operation (the rotation of the mouse wheel) to the reference enlargement factor determination unit 1122. The input determination unit 1121 further outputs operation content information to the target determination unit 1123 and the enlargement factor determination unit 1124. The operation content information to be output is information indicating a change of the enlargement factor. For example, the value "1" preset as a value corresponding to information indicating a change of the enlargement factor is output from the input determination unit 1121 to the target determination unit 1123 and the enlargement factor determination unit 1124.

Note that the content of the operation of which the enlarged image generation unit 112 is notified by the input control unit 103 as the enlargement factor changing operation is not limited to the operation of rotating the mouse wheel. For example, as described above, the up arrow key or down arrow key on the keyboard may be operated. In this case, the input control unit 103 may count the length of time during which the up arrow key or the down arrow key is pressed. The input determination unit 1121 may use the length of time during which the up arrow key or the down arrow key is pressed as the amount of operation.

If the determined content of the operation indicates a display area changing operation (e.g., mouse dragging), the input determination unit 1121 outputs the amount of operation (e.g., the start position and end position of mouse dragging) to the amount-of-movement determination unit 1127. The input determination unit 1121 further outputs operation content information to the target determination unit 1123. The operation content information to be output is information indicating a change of a display area. For example, the value "2" preset as a value corresponding to information indicating a change of a display area is output from the input determination unit 1121 to the target determination unit 1123.

Note that the content of the operation of which the enlarged image generation unit 112 is notified by the input control unit 103 as the display area changing operation is not limited to mouse dragging. For example, a control button and an arrow key on the keyboard may be concurrently operated. In this case, the input control unit 103 may count the length of time during which the control button and the arrow key are pressed. The input determination unit 1121 may use the length of time during which the control button and the arrow key are pressed as the amount of operation. The input determination unit 1121 may further determine the direction corresponding to the operated arrow key as a movement direction.

If the determined content of the operation indicates the selection of a distribution of lesions (checking the checkbox for the distribution list display area 750), the input determination unit 1121 outputs the information indicating the selected distribution of lesions to the enlargement factor determination unit 1124. The input determination unit 1121 further outputs operation content information to the target determination unit 1123. The operation content information to be output is information indicating a change of the enlargement factor in response to the selection of a distribution of lesions. For example, the value "3" preset as a value corresponding to information indicating a change of the enlargement factor in response to the selection of a distribution of lesions is output from the input determination unit 1121 to the target determination unit 1123.

Note that the information output from the input determination unit 1121 to the enlargement factor determination unit 1124 is not limited to the information indicating the selected distribution of lesions. As described below, the distributions of lesions are separated into first distribution information, second distribution information, and third distribution information. Thus, the input determination unit 1121 may output distribution information (the first distribution information, the second distribution information, or the third distribution information) to which the selected distribution of lesions belongs to the enlargement factor determination unit 1124.

The reference enlargement factor determination unit 1122 determines an enlargement factor for the thumbnail image selected by the user. As described above, the amount and type of operation performed by the user using the operation unit 102 are output to the reference enlargement factor determination unit 1122 from the input determination unit 1121. The reference enlargement factor determination unit 1122 obtains, from the input control unit 103, information indicating the area selected by the user (e.g., in FIG. 12, the thumbnail image in the second row and the fourth column). The reference enlargement factor determination unit 1122 obtains the similar case ID 4100 with reference to the similar case data 4000 (FIG. 33) of the thumbnail image selected by the user.

If the operation type is the rotation of the mouse wheel, the reference enlargement factor determination unit 1122 obtains the amount of rotation of the wheel as the amount of operation. If the type of operation is an arrow key on the keyboard, the reference enlargement factor determination unit 1122 obtains the length of time during which the arrow key is pressed as the amount of operation. The reference enlargement factor determination unit 1122 calculates a value by multiplying the amount of operation by a predetermined coefficient, and determines the calculated value as an enlargement factor for the reference thumbnail image. The reference enlargement factor determination unit 1122 outputs the similar case ID 4100 and the determined enlargement factor to the enlargement factor determination unit 1124.

The target determination unit 1123 determines a similar case to be subjected to a thumbnail image enlargement process or a display area changing process, on the basis of the operation content information input from the input determination unit 1121.

If the operation content information is information indicating a change of the enlargement factor, the target determination unit 1123 obtains, from the input control unit 103, information indicating the area selected by the user (e.g., in FIG. 12, the thumbnail image in the second row and the fourth column). The target determination unit 1123 obtains the similar case ID 4100 with reference to the similar case data 4000 (FIG. 33) of the thumbnail image selected by the user. The target determination unit 1123 determines similar cases, the number of which is less than or equal to ND, as targets to be subjected to enlargement so that the thumbnail image selected by the user is included. The target determination unit 1123 outputs the number of similar cases and the similar case IDs 4100 of the similar cases to the enlargement factor determination unit 1124.

If the operation content information is information indicating a change of a display area, the target determination unit 1123 uses the similar case to be subjected to enlargement, which is determined in the enlargement factor changing process, directly as a target to be subjected to the display area changing process.

If the operation content information is information indicating a change of the enlargement factor in response to the selection of a distribution of lesions, the target determination unit 1123 outputs the similar case IDs 4100 obtained as a result of refinement in accordance with a selected distribution of lesions and the number of similar case IDs 4100 to the enlargement factor determination unit 1124.

The enlargement factor determination unit 1124 determines an enlargement factor for the similar cases that are targets of enlargement, which are determined by the target determination unit 1123. If information indicating the selected distribution of lesions is input from the input determination unit 1121 as operation content information, the enlargement factor determination unit 1124 calculates a predetermined enlargement factor corresponding to the selected distribution of lesions. The enlargement factor determination unit 1124 outputs the determined enlargement factor, and the similar case IDs 4100 of the targets of enlargement and the number of similar case IDs, which are input from the target determination unit 1123, to the image enlargement unit 1125. Predetermined enlargement factors corresponding to the respective distributions of lesions are as described above with reference to FIG. 21 to FIG. 26.

If information indicating a change of the enlargement factor is input from the input determination unit 1121 as operation content information, the enlargement factor determination unit 1124 extracts the region-of-interest information 4300 corresponding to the similar case IDs 4100 (FIG. 33) of the targets of enlargement, which are input from the target determination unit 1123. The enlargement factor determination unit 1124 calculates enlargement factors for the respective similar cases by using the extracted region-of-interest information 4300 and the enlargement factor for the reference thumbnail image, which is input from the reference enlargement factor determination unit 1122, through the procedure described above with reference to FIG. 57. The enlargement factor determination unit 1124 outputs the calculated enlargement factors, the similar case IDs 4100 of the targets of enlargement, and the number of similar case IDs to the image enlargement unit 1125.

The image enlargement unit 1125 generates thumbnail images, which are obtained by enlarging the thumbnail images of the input similar case IDs 4100, by using the enlargement factors input from the enlargement factor determination unit 1124, the similar case IDs 4100 of the targets of enlargement, and the number of similar case IDs. The image enlargement unit 1125 outputs the generated enlarged thumbnail images to the display image generation unit 1129.

The first display area determination unit 1126 determines a display area in an enlarged thumbnail image of a similar case that is a target of enlargement. The first display area determination unit 1126 extracts the region-of-interest information 4300 corresponding to the similar case ID 4100 (FIG. 33) of the target of enlargement, which is input from the enlargement factor determination unit 1124. The first display area determination unit 1126 calculates the coordinates of the display area in the enlarged thumbnail image by using the enlargement factor input from the enlargement factor determination unit 1124 and the extracted region-of-interest information 4300 through the process described above in S4520 and S4530 in FIG. 59. The first display area determination unit 1126 outputs the similar case ID 4100 of the target of enlargement and the coordinates of the corresponding display area to the display image generation unit 1129 and the second display area determination unit 1128.

The amount-of-movement determination unit 1127 determines the amount of movement of the display area in the enlarged thumbnail image. The amount-of-movement determination unit 1127 calculates a value by multiplying the amount of operation input from the input determination unit 1121 (e.g., the start position and end position of mouse dragging) by a predetermined coefficient, and determines the calculated value as the amount of movement of display area in the enlarged thumbnail image.

For example, it is assumed that the operation performed on the operation unit 102 by the user is mouse dragging. In addition, the x-direction coefficient is defined as "a", the y-direction coefficient is defined as "b", the drag start position is defined as "ps(xs, ys)", and the drag end position is defined as "pe(xe, ye)". In this case, the amount of movement d is given by the following expression:

$$d(a(xe-xs),b(ye-ys)).$$

The amount-of-movement determination unit 1127 outputs the calculated amount of movement to the second display area determination unit 1128.

Figure 63:
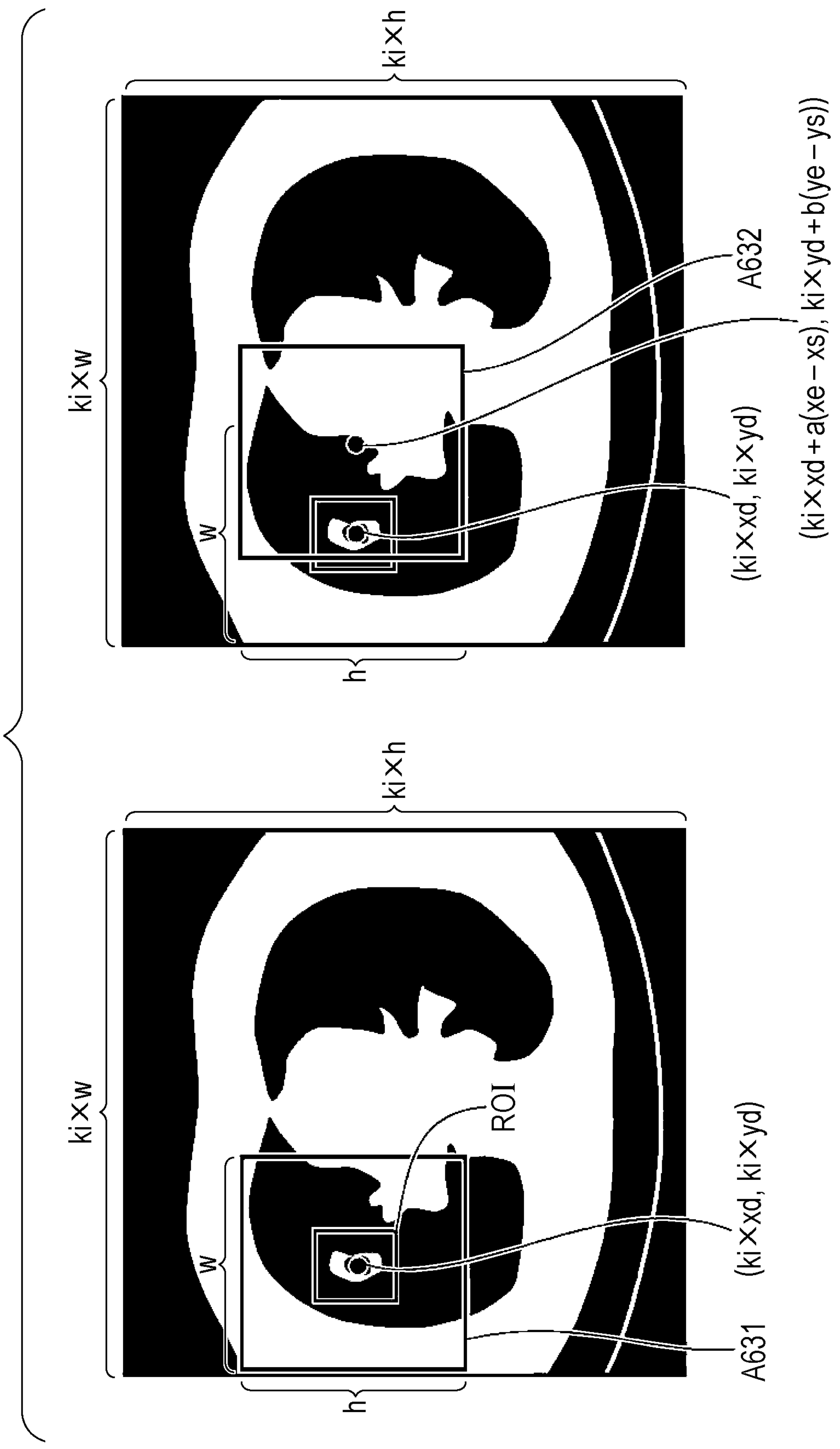
FIG. 63 is a diagram schematically illustrating the movement of a display area across an enlarged thumbnail image.

FIG. 63 is a diagram schematically illustrating the movement of a display area across an enlarged thumbnail image. The left part of FIG. 63 corresponds to the right part of FIG. 60, and illustrates an enlarged thumbnail image. The right part of FIG. 63 illustrates the display area that has moved from the state illustrated in the left part of FIG. 63.

In the left part of FIG. 63, the coordinates of the center of a display area A631 in the enlarged thumbnail image is given by the following expression:

$$(ki\times xd,ki\times yd).$$

In a case where the display area in the enlarged thumbnail image moves the amount of movement d from the state illustrated in the left part of FIG. 63, the coordinates of the center of a display area A632 that has moved, which is illustrated in the right part of FIG. 63, is given by the following expression:

$$(ki\times xd+a(xe-xs),\text{kixyd}+b(ye-ys)).$$

In this case, the display areas A631 and A632 have the same size, and the position of the display area has been changed in the enlarged thumbnail image.

Referring back to FIG. 62, the second display area determination unit 1128 determines a display area in a thumbnail image of a similar case when the display area moves. The second display area determination unit 1128 determines the coordinates of a display area that has moved, by using the amount of movement input from the amount-of-movement determination unit 1127 and the display area corresponding to the similar case ID 4100 of the target of enlargement, which is input from the first display area determination unit 1126. The second display area determination unit 1128 outputs the determined coordinates of the display area to the display image generation unit 1129.

If the information input from the image enlargement unit 1125, the first display area determination unit 1126, and the second display area determination unit 1128 includes a change in a display image, the display image generation unit 1129 updates the display image.

Specifically, the display image generation unit 1129 generates, as an enlarged thumbnail image, an area defined by the coordinates of the display area, which are input from the first display area determination unit 1126 or the second display area determination unit 1128, within an enlarged thumbnail image of the similar case to be subjected to enlargement, which is input from the image enlargement unit 1125. The display image generation unit 1129 outputs the generated thumbnail image to the display control unit 104.

As described above, in a case where the enlargement factor is changed in response to the selection of a distribution of lesions, if the "bilateral" 754 is selected (FIG. 21), the entire thumbnail images are displayed with an enlargement factor of 1.0 (FIG. 22). Thus, the display areas are not changed. The same applies when the "diffuse" 751, the "multiple" 755, or the "hematogenous" 757 is selected in FIG. 20. The "diffuse", "bilateral", "multiple", and "hematogenous" lesion distributions belong to the first distribution information (described below). That is, when a distribution of lesions that belongs to the first distribution information is selected, the entire thumbnail images are displayed with an enlargement factor of 1.0, and the display areas are not changed.

Accordingly, in a case where the enlargement factor is changed in response to the selection of a distribution of lesions that belongs to the first distribution information, the input determination unit 1121 may not necessarily output the amount of operation to the amount-of-movement determination unit 1127 even if the determined content of the operation indicates a display area changing operation. Alternatively, the target determination unit 1123 may determine that none of the similar cases is set as a target to be subjected to a display area changing process.

Next, the flow of a process for changing a display area for an enlarged thumbnail image will be described.

Figure 64:
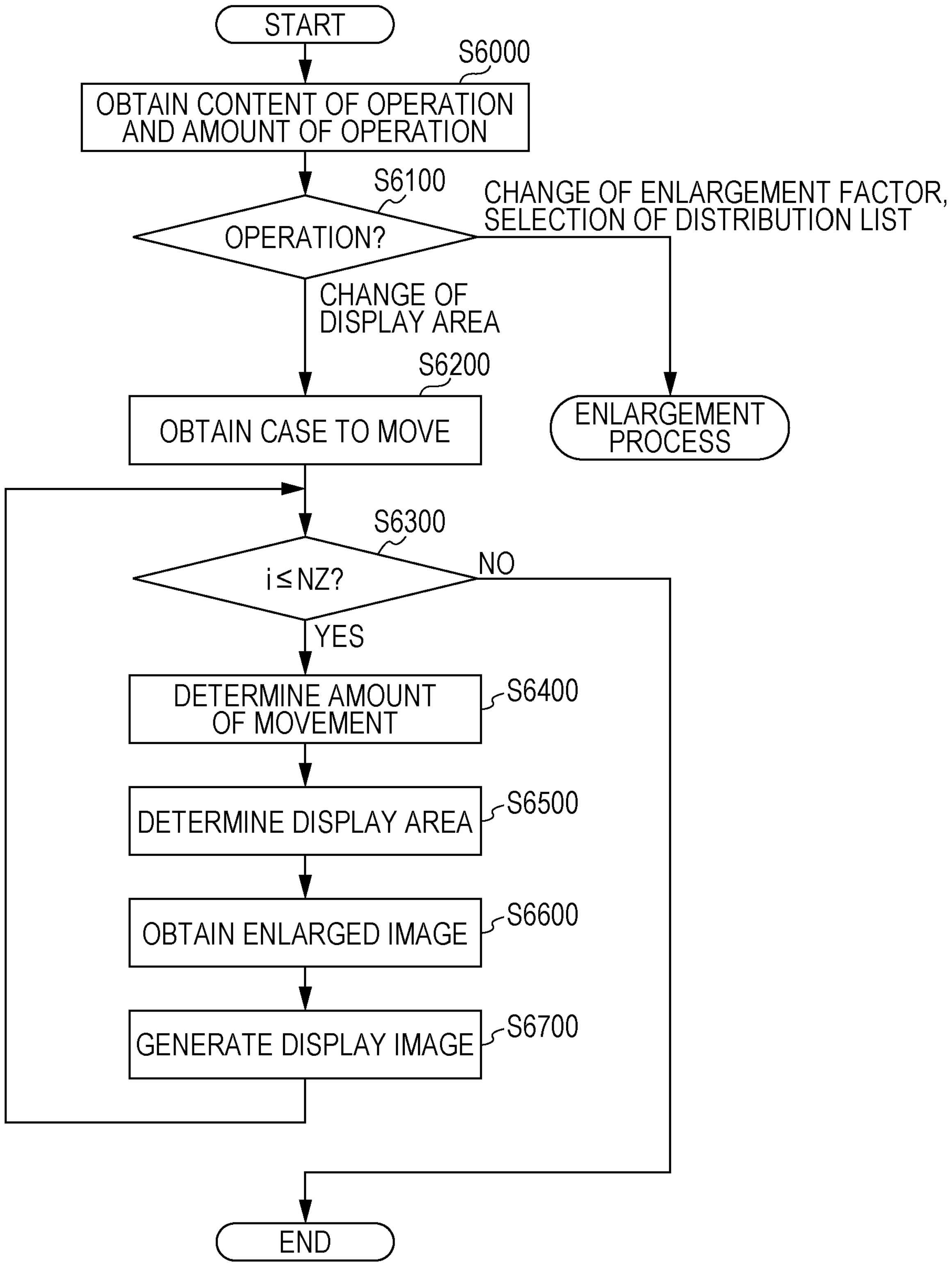
FIG. 64 is a flowchart illustrating a process for changing the display area for an enlarged thumbnail image.

FIG. 64 is a flowchart illustrating a process for changing a display area for an enlarged thumbnail image. In S6000, the input determination unit 1121 obtains, from the input control unit 103, the content of the operation performed on the operation unit 102 by the user and the amount of the operation.

In S6100, the input determination unit 1121 determines the content of the operation obtained in S6000. If the determined content of the operation indicates an enlargement factor changing operation, the process proceeds to, for example, the enlargement process illustrated in FIG. 56. If the determined content of the operation indicates the selection of a distribution of lesions, the process proceeds to, for example, a process illustrated in FIG. 71 (described below). If the determined content of the operation indicates a display area changing operation, the process proceeds to S6200.

In S6200, the target determination unit 1123 obtains a similar case to move on which a display area changing process is to be performed. In this embodiment, the target determination unit 1123 uses, as a similar case to move, a similar case for which the enlargement factor has been changed in the enlargement factor changing process in S6200. When the display area changing process is performed, thumbnail images of similar cases, the number of which is equal to NZ less than or equal to the maximum number ND of similar cases allowed to be displayed in the case display area 710 (in this embodiment, ND=20), among the NC similar cases received from the similar case search unit 303 are enlarged and displayed in the case display area 710. In the example illustrated in FIG. 12, 20 thumbnail images are enlarged and displayed.

In S6300, the enlarged image generation unit 112 determines a thumbnail image of a similar case i (where i is an index identifying a target similar case to be processed, and is an integer greater than or equal to 1) as a thumbnail image to be processed. Then, the enlarged image generation unit 112 repeatedly performs the processing of S6400 to S6700 until the index i has reached NZ (YES in S6300). The enlarged image generation unit 112 increments the index i by 1 each time the processing of S6400 to S6700 is executed. If the index i exceeds NZ (NO in S6300), the process illustrated in FIG. 64 ends.

In S6400, the amount-of-movement determination unit 1127 calculates the amount of movement of the thumbnail image of the similar case i to be processed. The amount-of-movement determination unit 1127 calculates a value by multiplying the amount of operation input from the input determination unit 1121 by a predetermined coefficient, and determines the calculated value as the amount of movement of the display area.

In S6500, the second display area determination unit 1128 determines a display area that has been changed in the thumbnail image, by using the display area determined in S4530 (FIG. 59) and the amount of movement determined in S6400. In S6600, the display image generation unit 1129 obtains the enlarged image generated in S4510 (FIG. 59). In S6700, the display image generation unit 1129 generates a display image by using the display area determined in S6500 and the enlarged image obtained in S6600.

As described above, if a distribution of lesions that belongs to the first distribution information is selected, the display area is not changed. Accordingly, in a case where the enlargement factor has been changed in response to the selection of a distribution of lesions that belongs to the first distribution information, then in S6200, the target determination unit 1123 may determine that none of the similar cases is set as a target to be subjected to a display area changing process, and the process may end. Alternatively, in S6200, the target determination unit 1123 may set the index i to a value exceeding NZ, and may obtain a negative determination in S6300.

The configuration of the enlarged image generation unit 112 that performs a display area changing process is not limited to the configuration illustrated in FIG. 62. Next, a modification of the display area changing process will be described. In the following, first, the details of the processing blocks of the enlarged image generation unit 112 will be described, and then the flow of the display area changing process will be described.

Figure 65:
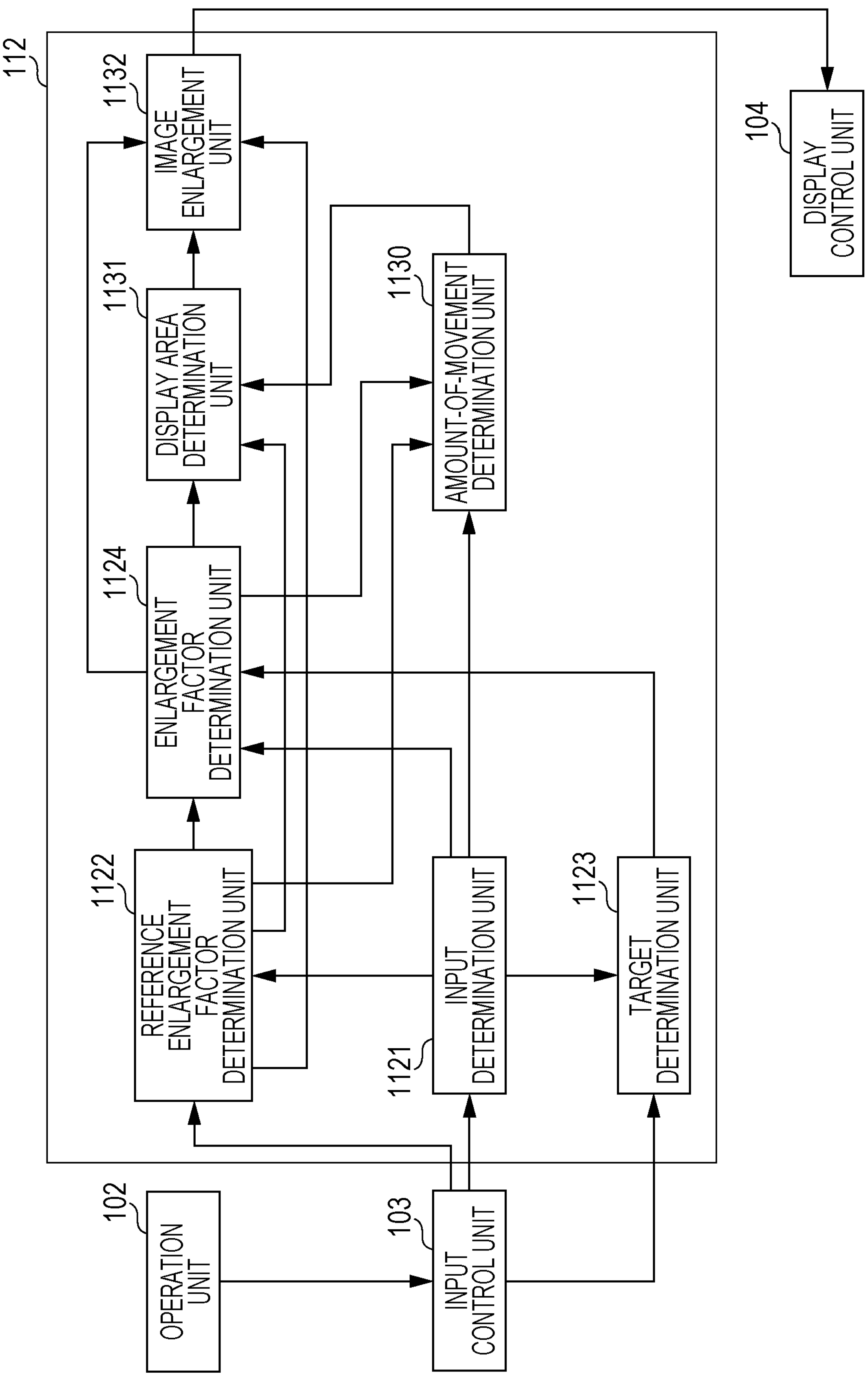
FIG. 65 is a block diagram illustrating another detailed configuration of the enlarged image generation unit, which is different from that illustrated in FIG. 62.

FIG. 65 is a block diagram illustrating a detailed configuration of the enlarged image generation unit 112, which is different from that illustrated in FIG. 62. The enlarged image generation unit 112 includes the input determination unit 1121, the reference enlargement factor determination unit 1122, the target determination unit 1123, the enlargement factor determination unit 1124, an amount-of-movement determination unit 1130, a display area determination unit 1131, and an image enlargement unit 1132. In FIG. 65, substantially the same blocks as those in FIG. 62 are assigned the same numerals, and are not described in detail herein.

The amount-of-movement determination unit 1130 obtains the enlargement factor for the reference thumbnail image from the reference enlargement factor determination unit 1122. The amount-of-movement determination unit 1130 obtains the determined enlargement factors for the respective thumbnail images from the enlargement factor determination unit 1124. The amount-of-movement determination unit 1130 obtains the amount of operation from the input determination unit 1121. The amount-of-movement determination unit 1130 calculates the amount of movement in the thumbnail image before enlargement, by using the enlargement factors for the respective thumbnail images and the amount of operation. The amount-of-movement determination unit 1130 outputs the calculated amount of movement and the enlargement factors for the respective thumbnail images to the display area determination unit 1131.

Similarly to the first display area determination unit 1126, the display area determination unit 1131 determines a display area in the enlarged thumbnail image of the similar case that is a target of enlargement. That is, the display area determination unit 1131 obtains the similar case ID 4100 (FIG. 33) of the target of enlargement from the enlargement factor determination unit 1124. The display area determination unit 1131 extracts the region-of-interest information 4300 corresponding to the obtained similar case ID 4100 (FIG. 33) of the target of enlargement. The display area determination unit 1131 calculates the coordinates of the display area in the enlarged thumbnail image by using the enlargement factor input from the enlargement factor determination unit 1124 and the extracted region-of-interest information 4300 through the procedure described above with reference to S4520 and S4530 in FIG. 59.

The display area determination unit 1131 obtains the enlargement factor for the reference thumbnail image from the reference enlargement factor determination unit 1122. The display area determination unit 1131 obtains the enlargement factors for the respective thumbnail images from the enlargement factor determination unit 1124. The display area determination unit 1131 obtains the amount of movement in the thumbnail image before enlargement from the amount-of-movement determination unit 1130. The display area determination unit 1131 calculates the coordinates of the display area in the thumbnail image before enlargement before the display area has moved, by using the calculated coordinates of the display area in the enlarged thumbnail image and the acquired enlargement factors.

The display area determination unit 1131 adds the obtained amount of movement in the thumbnail image before enlargement to the calculated coordinates of the display area in the thumbnail image before enlargement before the display area has moved to calculate the coordinates of the display area in the thumbnail image before enlargement after display area has moved. The display area determination unit 1131 outputs the calculated coordinates of the display area in the thumbnail image before enlargement after display area has moved to the image enlargement unit 1132.

The image enlargement unit 1132 obtains the enlargement factor for the reference thumbnail image from the reference enlargement factor determination unit 1122. The image enlargement unit 1132 obtains the enlargement factors for the respective thumbnail images from the enlargement factor determination unit 1124. The image enlargement unit 1132 enlarges thumbnail images in the display area, by using the coordinates of the display area in the thumbnail image before enlargement after display area has moved, which are input from the display area determination unit 1131, and the obtained enlargement factors for the respective thumbnail images. The image enlargement unit 1132 outputs the generated enlarged thumbnail images to the display control unit 104.

Figure 66:
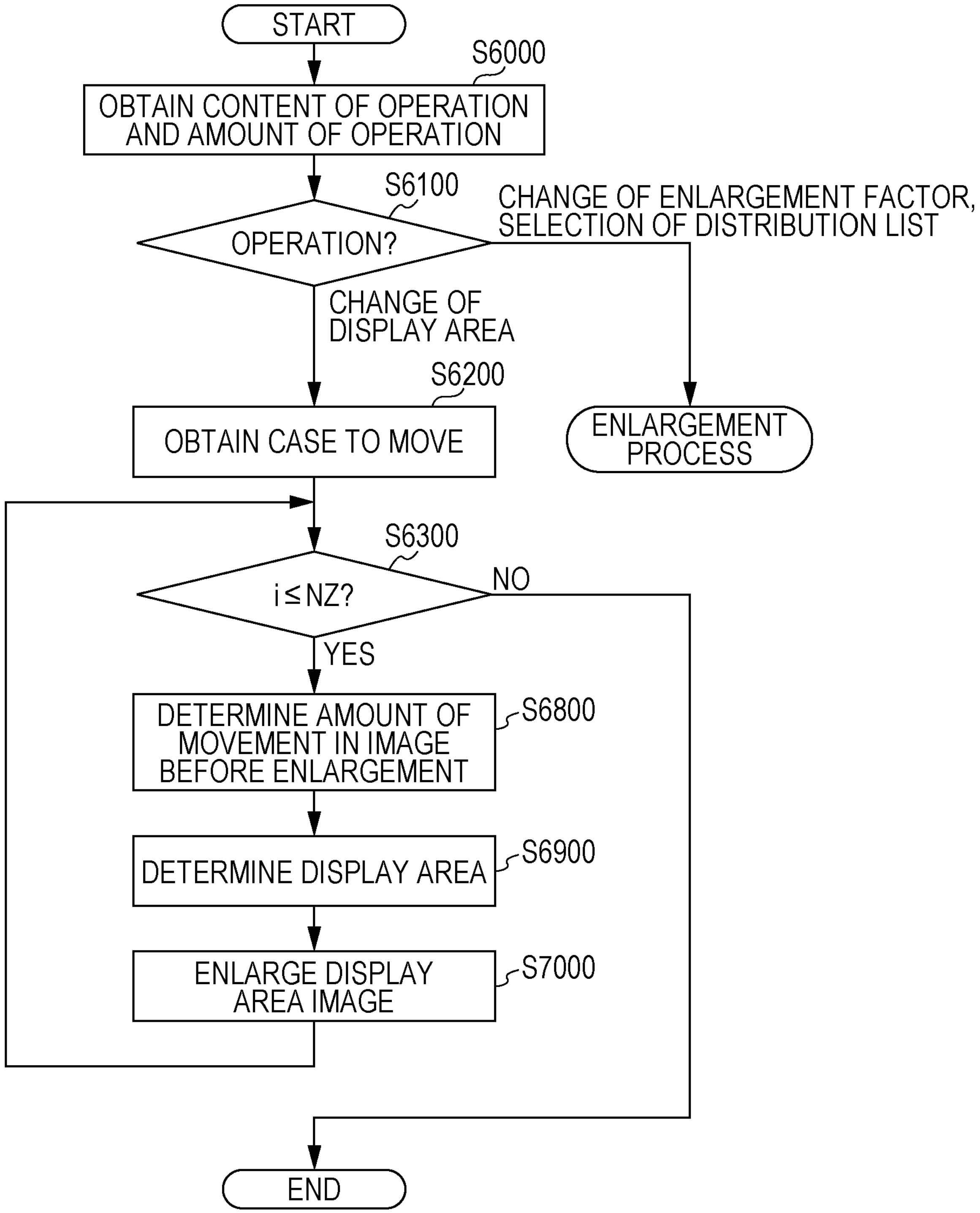
FIG. 66 is a flowchart illustrating a display area changing process performed using the configuration illustrated in FIG. 65.
Figure 67A:
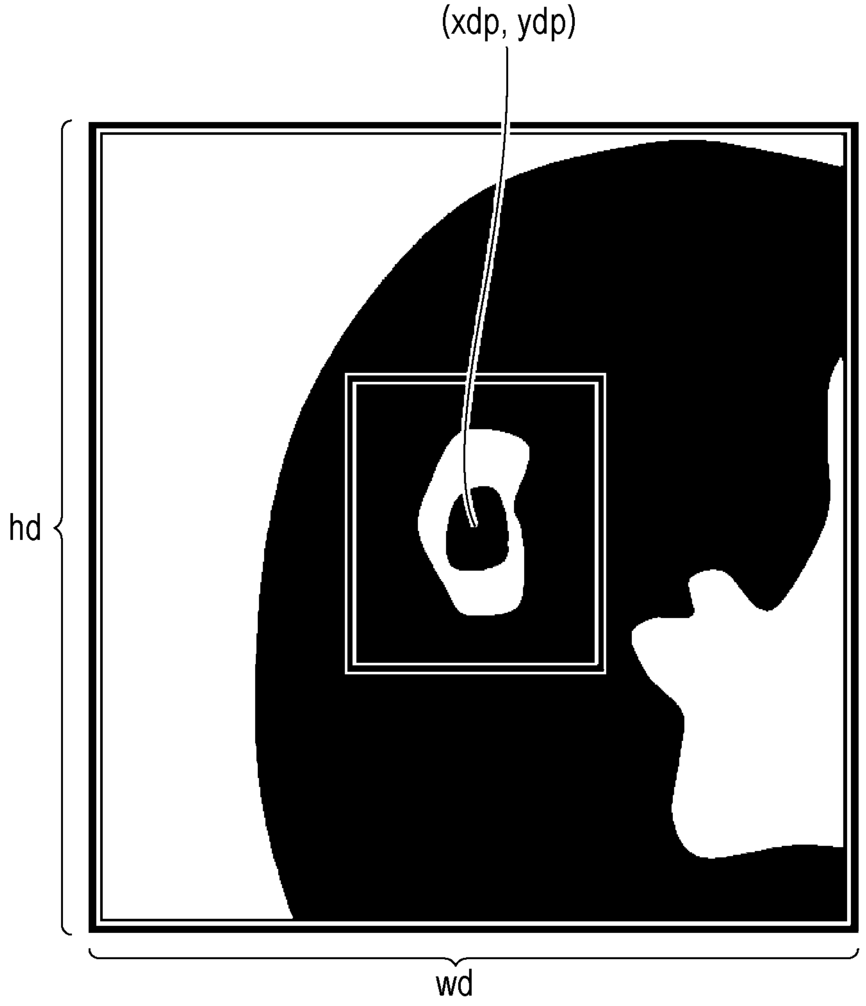
FIG. 67A is a diagram illustrating an example of an enlarged thumbnail image.
Figure 67B:
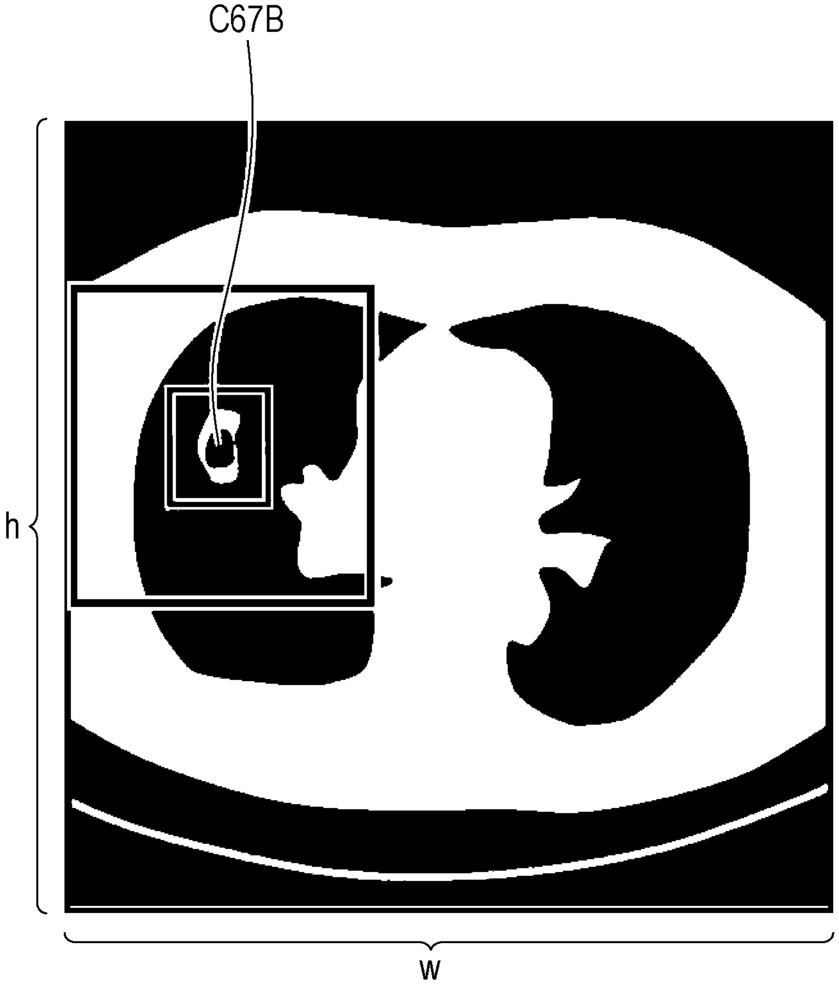
FIG. 67B is a diagram illustrating an entire thumbnail image before the thumbnail image illustrated in FIG. 67A is enlarged.
Figure 67C:
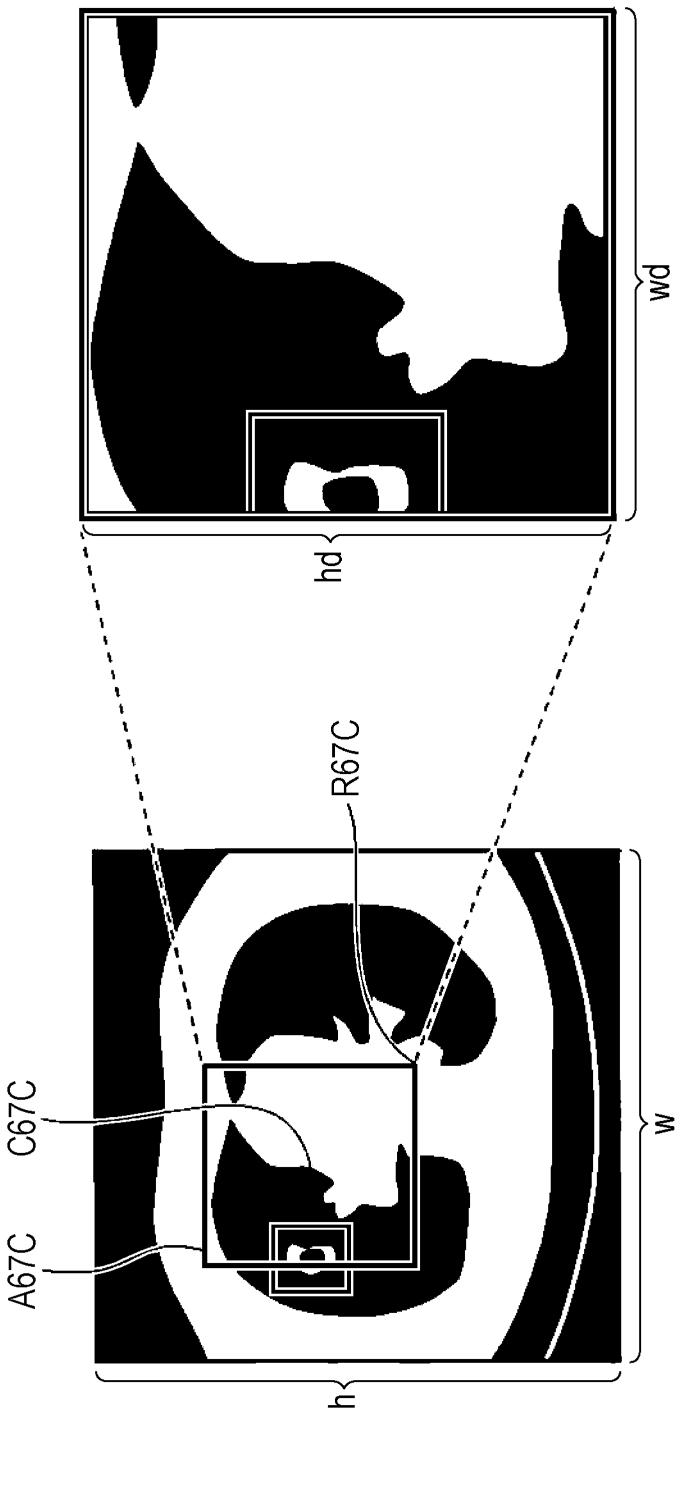
FIG. 67C is a diagram schematically illustrating the movement of a display area across a thumbnail image before enlargement.

FIG. 66 is a flowchart illustrating a display area changing process performed using the configuration illustrated in FIG. 65. FIG. 67A is a diagram illustrating an example of an enlarged thumbnail image. FIG. 67B is a diagram illustrating an entire thumbnail image before the thumbnail image illustrated in FIG. 67A is enlarged. FIG. 67C is a diagram schematically illustrating the movement of a display area across the thumbnail image before enlargement. In FIG. 66, substantially the same steps as those illustrated in FIG. 64 are assigned the same numerals, and are not described in detail herein.

In S6800, the amount-of-movement determination unit 1130 calculates the amount of movement in the thumbnail image before enlargement, by using the obtained amount of operation and the enlargement factors for the respective thumbnail images.

For example, it is assumed that the operation performed on the operation unit 102 by the user is mouse dragging. In addition, the x-direction coefficient is defined as "a", the y-direction coefficient is defined as "b", the drag start position is defined as "ps(xs, ys)", and the drag end position is defined as "pe(xe, ye)". In this case, when the position of the display area is moved, the amount of movement da in an enlarged thumbnail image in the x-direction and y-direction is given by the following equation:

$$da=(a(xe-xs),b(ye-ys)).$$

The amount of movement db in a thumbnail image before enlargement in the x-direction and y-direction is given by the following equation:

$$db=(a(xe-xs)/ki,b(ye-ys)/ki).$$

In S6900, the display area determination unit 1131 adds the amount of movement in the thumbnail image before enlargement, which is input from the amount-of-movement determination unit 1130, to the calculated coordinates of the display area in the thumbnail image before enlargement before the display area has moved to calculate the coordinates of the display area in the thumbnail image before enlargement after display area has moved.

As illustrated in FIG. 67A, the center of the display area in the enlarged thumbnail image is defined as (xdp, ydp), and the enlargement factor for the thumbnail image is defined as ki. In this case, the coordinates of the center C67B in the thumbnail image before enlargement, which is illustrated in FIG. 67B, is given by the following expression:

$$(xdp/ki,ydp/ki).$$

The coordinates of the center C67C of the display area in the thumbnail image before enlargement after the user has performed a movement operation, which is illustrated in the left part of FIG. 67C, is given by the following expression by using the amount of movement db described above:

$$(xdp/ki+a(xe-xs)/ki,ydp/ki+b(ye-ys)/ki).$$

Accordingly, the display area that has moved in the thumbnail image before enlargement is a rectangular area A67C in the thumbnail image illustrated in the left part of FIG. 67C. The lower right coordinates R67C of the rectangular area A67C are given by the following expression:

$$(xdp/ki+a(xe-xs)+wd/2ki,ydp/ki+b(ye-ys)/ki+hd/2ki).$$

Referring back to FIG. 66, in S7000, the image enlargement unit 1132 generates an enlarged thumbnail images in the display area, by using the coordinates of the display area in the thumbnail image before enlargement after display area has moved, which is input from the display area determination unit 1131, and the obtained enlargement factors for the respective thumbnail images. That is, the image enlargement unit 1132 uses pixel values in the rectangular area A67C illustrated in the left part of FIG. 67C as targets of enlargement, and enlarges the thumbnail image to generate an enlarged thumbnail image illustrated in the right part of FIG. 67C.

Next, the flow of a thumbnail image enlargement process performed when the user operates the scrollbar 715 after enlarged thumbnail images are displayed in the case display area 710 will be described. In this embodiment, as illustrated in FIG. 10 or FIG. 11, all the thumbnail images displayed in the case display area 710 have been enlarged.

Figure 68:
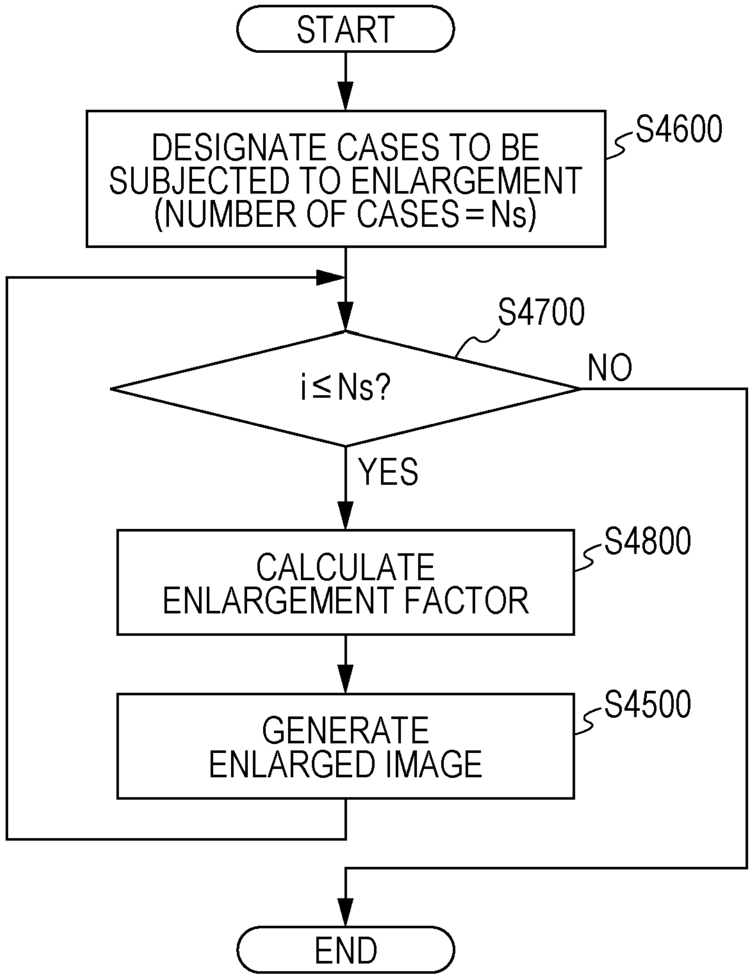
FIG. 68 is a flowchart illustrating a thumbnail image enlargement process performed when a user operates a scrollbar after an enlarged thumbnail image is displayed in the case display area.
Figure 69:
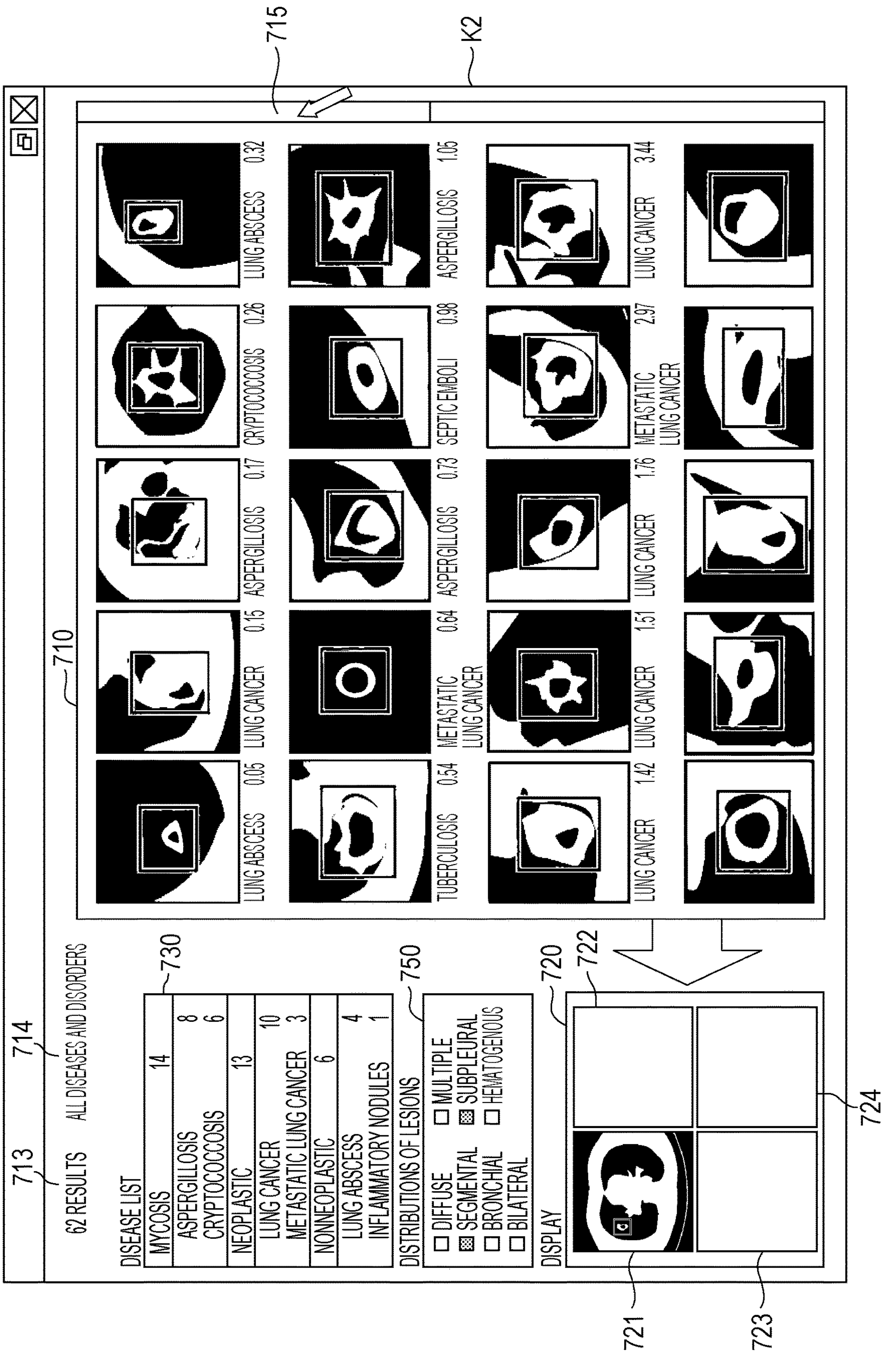
FIG. 69 is a diagram illustrating a basic screen on which enlarged thumbnail images are being displayed in the case display area.

FIG. 68 is a flowchart illustrating a thumbnail image enlargement process performed when the user operates the scrollbar 715 after enlarged thumbnail images are displayed in the case display area 710. FIG. 69 is a diagram illustrating the basic screen K2 on which enlarged thumbnail images are being displayed in the case display area 710.

In the state illustrated in FIG. 69, the user scrolls the scrollbar 715 down. Then, the input control unit 103 detects the amount of operation performed on the scrollbar 715, and notifies the enlarged image generation unit 112 of the detected amount of operation. Then, the enlarged image generation unit 112 starts the process illustrated in FIG. 68.

In S4600, the enlarged image generation unit 112 obtains the number of cases Ns to be additionally displayed in the case display area 710 in response to the operation performed on the scrollbar 715 by the user. Specifically, the enlarged image generation unit 112 obtains, from the display control unit 104, the predetermined maximum number ND of results allowed to be displayed in the case display area 710. In this embodiment, as illustrated in FIG. 6, the maximum number ND of results allowed to be displayed is four rows and five columns, or 20. Accordingly, five additional thumbnail images are to be displayed. Thus, the enlarged image generation unit 112 obtains Ns=5.

In S4600, furthermore, the enlarged image generation unit 112 identifies the similar case IDs of the thumbnail images to be additionally displayed in the case display area 710. In this case, the enlarged image generation unit 112 refers to the similarities of the similar cases, which are received from the similar case search unit 303 of the case search system 300. The display control unit 104 currently displays the thumbnail images of the ND similar cases in order from highest similarity to lowest similarity. Thus, the enlarged image generation unit 112 sets the similar cases having the (ND+1)-th highest similarity to the (ND+Ns)-th highest similarity as cases that are target of enlargement. The enlarged image generation unit 112 identifies the similar case IDs of the targets of enlargement.

In S4700, the enlarged image generation unit 112 determines a thumbnail image of a similar case i (where i is an index identifying a target similar case to be processed, and is an integer greater than or equal to 1) as a thumbnail image to be processed. Then, the enlarged image generation unit 112 repeatedly performs the processing of S4800 and S4500 until the index i has reached Ns. The enlarged image generation unit 112 increments the index i by 1 each time the processing of S4800 and S4500 is executed. If the index i exceeds Ns (NO in S4700), the process illustrated in FIG. 68 ends.

In S4800, the enlarged image generation unit 112 calculates an enlargement factor ki for the similar case i to be subjected to enlargement. Enlarged thumbnail images have been displayed in the case display area 710. Thus, the enlarged image generation unit 112 uses the enlargement factor kr for the reference thumbnail image, which is determined in S4100 in FIG. 56. Then, similarly to S4400 in FIG. 56, the enlarged image generation unit 112 calculates the enlargement factor ki for the similar case i to be subjected to enlargement. The processing of S4500 is substantially the same as that of S4500 in FIG. 56, and is not described in detail herein. Through the process illustrated in FIG. 68, a screen illustrated in FIG. 70 is obtained.

Figure 70:
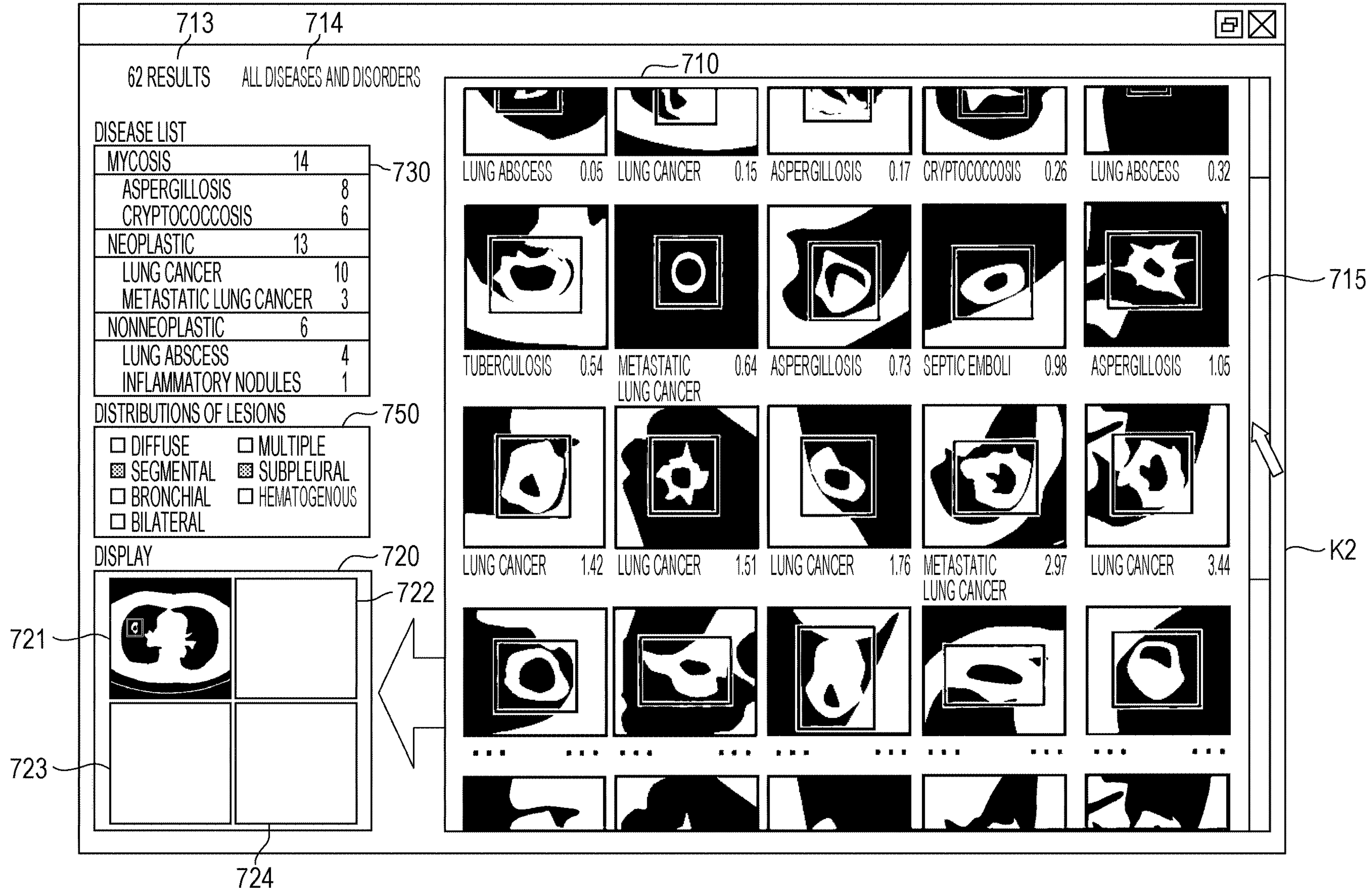
FIG. 70 is a diagram illustrating a basic screen on which enlarged thumbnail images have moved from the state illustrated in FIG. 69.

FIG. 70 is a diagram illustrating the basic screen K2 on which enlarged thumbnail images have moved from the state illustrated in FIG. 69. As illustrated in FIG. 70, the thumbnail images of the similar cases being displayed in the case display area 710 have moved upward in response to the operation of the scrollbar 715.

In a case where the user continues to operate the scrollbar 715, the enlarged image generation unit 112 further executes the process illustrated in FIG. 68.

Through the process described above, even if a large number of similar cases exist, it may be sufficient that the enlarged image generation unit 112 performs an enlargement process on thumbnail images which are newly displayed in the case display area 710 through the operation of the scrollbar 715. This results in a significantly reduced load on a system.

Figure 71:
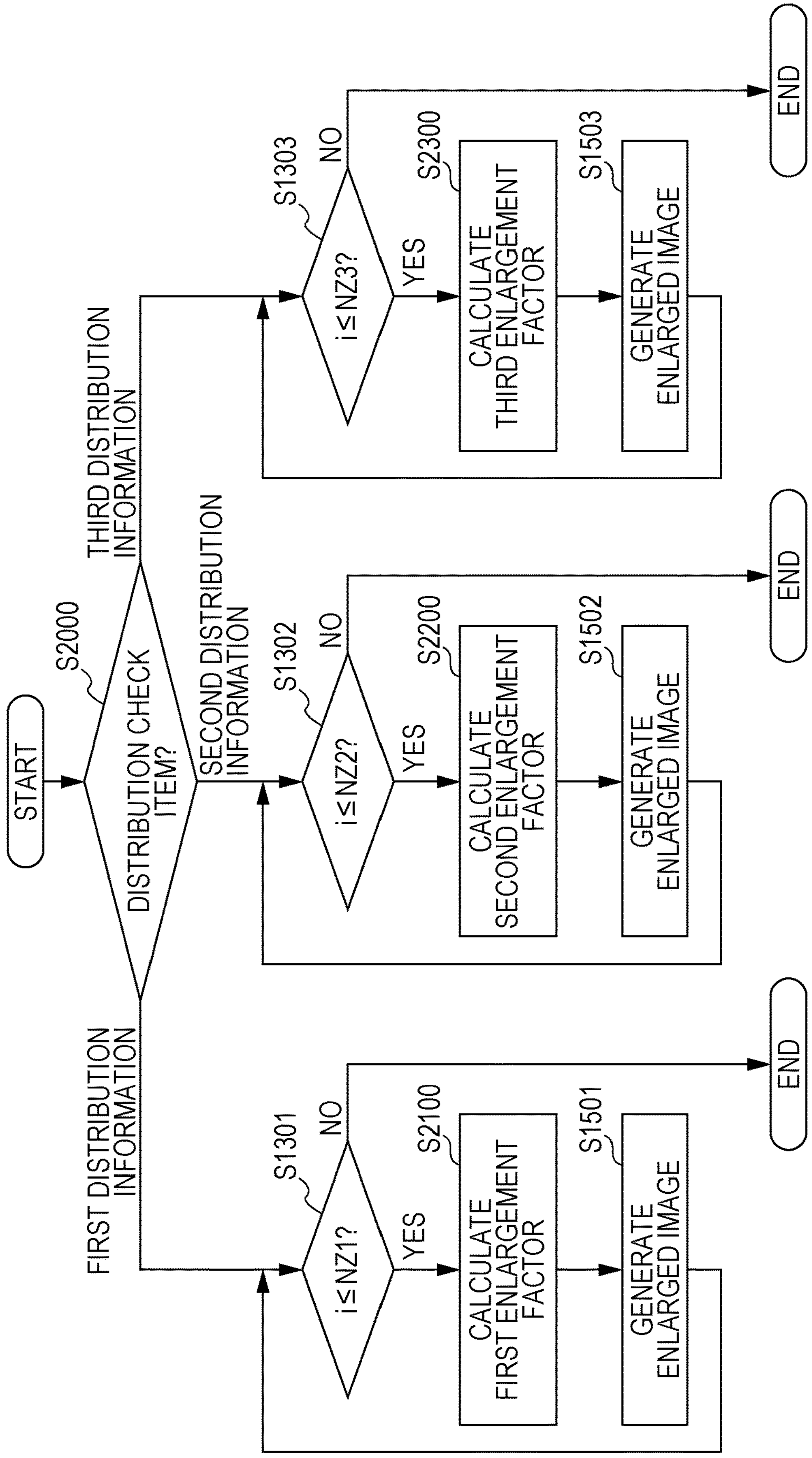
FIG. 71 is a flowchart illustrating a process performed when a distribution of lesions displayed in the distribution list display area is selected.

Next, an enlargement process performed when a distribution of lesions displayed in the distribution list display area 750 illustrated in FIG. 21, FIG. 23, and FIG. 25 is selected will be described. FIG. 71 is a flowchart illustrating a process performed when a distribution of lesions displayed in the distribution list display area 750 is selected.

In S2000, when the input control unit 103 detects an operation of selecting any one distribution check item among the distributions of lesions (or distribution check items) displayed in the distribution list display area 750, the enlarged image generation unit 112 determines which of the first distribution information, the second distribution information, and the third distribution information the detected distribution check item corresponds to. If the detected distribution check item corresponds to the first distribution information, the process proceeds to S1301. If the detected distribution check item corresponds to the second distribution information, the process proceeds to S1302. If the detected distribution check item corresponds to the third distribution information, the process proceeds to S1303.

The first distribution information is information for selecting a thumbnail image in which the region of interest belongs to a predetermined first range indicating that the size of the region of interest is wide relative to the lung area among the thumbnail images of the similar cases displayed in list form in the case display area 710. By way of example, the first distribution information includes "bilateral", "multiple", "diffuse", and "hematogenous". Accordingly, the first range is a range of values to which the size of the region of interest set for the diagnosis of such distributions of lesions belongs.

The second distribution information is information for selecting a thumbnail image in which the region of interest belongs to a predetermined second range (lower than first range; the upper limit of the second range is less than or equal to the lower limit of the first range) indicating that the size of the region of interest is part of the lung area among the thumbnail images of the similar cases displayed in list form in the case display area 710. By way of example, the second distribution information includes "bronchial" and "segmental". Accordingly, the second range is a range of values to which the size of the region of interest set for the diagnosis of such distributions of lesions belongs.

The third distribution information is information for selecting a thumbnail image in which the region of interest has a size so as to exist in an edge of the pleura among the thumbnail images of the similar cases displayed in list form in the case display area 710. By way of example, the third distribution information includes "subpleural".

In S1301, the enlarged image generation unit 112 extracts similar cases, which are obtained as a result of the similar case search and the number of which is less than or equal to the maximum number of (in this embodiment, 20) thumbnail images that can be displayed in the case display area 710, among the similar cases of the distributions of lesions selected as the first distribution information by the user, in order of decreasing similarity, and determines the number of extracted similar cases as the number of similar cases NZ1 to be subjected to enlargement. Further, the enlarged image generation unit 112 determines a thumbnail image of an extracted similar case i (where i is an index identifying an extracted similar case, and is an integer greater than or equal to 1) as a thumbnail image to be processed. The enlarged image generation unit 112 repeatedly performs the processing of S2100 and S1501 until the index i has reached NZ1. The enlarged image generation unit 112 increments the index i by 1 each time the processing of S2100 and S1501 is executed. If the index i exceeds NZ1 (NO in S1301), the process illustrated in FIG. 71 ends.

In S2100, the enlarged image generation unit 112 calculates a first enlargement factor for the first distribution information on the similar case i. The first enlargement factor is, for example, 1.0. This is an example, and any value other than 1.0 may be used as the first enlargement factor as long as the entire region of interest set for the diagnosis of a distribution of lesions indicated by the first distribution information falls within the display area.

In S1501, a process similar to S4500 in FIG. 56 is performed. As a result, the display control unit 104 displays in the case display area 710 an image obtained by enlarging the thumbnail image of the similar case i with the first enlargement factor for the similar case i.

In FIG. 22 described above, "bilateral" is selected. In this case, thumbnail images of similar cases exhibiting bilateral lesion distribution among the similar cases are displayed in the case display area 710. In addition, since the enlargement factor is 1.0, the thumbnail images are displayed in the same display style as the thumbnail images displayed in the case display area 710 immediately after similar case search results are obtained. That is, the thumbnail images are displayed without adjusting the display positions of the thumbnail images so that the center of the region of interest ROI in each thumbnail image matches the center of a display area 6801 or without enlarging the thumbnail images.

In S1302, the enlarged image generation unit 112 extracts similar cases, which are obtained as a result of the similar case search and the number of which is less than or equal to the maximum number of thumbnail images that can be displayed in the case display area 710, among the similar cases of the distributions of lesions selected as the second distribution information by the user, in order of decreasing similarity, and determines the number of extracted similar cases as the number of similar cases NZ2 to be subjected to enlargement. Further, the enlarged image generation unit 112 determines a thumbnail image of an extracted similar case i as a thumbnail image to be processed. The enlarged image generation unit 112 repeatedly performs the processing of S2200 and S1502 until the index i has reached NZ2. The enlarged image generation unit 112 increments the index i by 1 each time the processing of S2200 and S1502 is executed. If the index i exceeds NZ2 (NO in S1302), the process illustrated in FIG. 71 ends.

In S2200, the enlarged image generation unit 112 calculates a second enlargement factor corresponding to the second distribution information on the similar case i by using a display area size determined in advance for each thumbnail image in the case display area 710 and the region-of-interest information on the similar case i.

If the second distribution information is selected, the enlarged image generation unit 112 enlarges the similar case i so that the size of the region of interest is equal to approximately one half of the size of the display area. Accordingly, for example, the enlarged image generation unit 112 computes a second enlargement factor ki for the similar case i in accordance with the following equation:

$$ki=\frac{1}{2}(Sd/Si),$$

where Sd denotes the area of the display area and Si denotes the area of the region of interest in the thumbnail image of the similar case i to be subjected to enlargement.

In S1502, a process similar to S4500 in FIG. 56 is performed. As a result, the enlarged image generation unit 112 enlarges the thumbnail image of the similar case i with the second enlargement factor ki. The display control unit 104 displays the thumbnail image enlarged by the enlarged image generation unit 112 in the case display area 710 so that the center of the region of interest in the thumbnail image matches the center of the display area.

In FIG. 24 described above, "bronchial" is selected. In this case, thumbnail images of similar cases exhibiting bronchial lesion distribution among the similar cases are displayed in the case display area 710. In addition, all the thumbnail images in the case display area 710 have been enlarged with the second enlargement factor so that the center of the region of interest ROI in each thumbnail image matches the center of a display area 6901.

In S1303, the enlarged image generation unit 112 extracts similar cases, which are obtained as a result of the similar case search and the number of which is less than or equal to the maximum number of thumbnail images that can be displayed in the case display area 710, among the similar cases of the distributions of lesions selected as the third distribution information by the user, in order of decreasing similarity, and determines the number of extracted similar cases as the number of similar cases NZ3 to be subjected to enlargement. Further, the enlarged image generation unit 112 determines a thumbnail image of an extracted similar case i as a thumbnail image to be processed. The enlarged image generation unit 112 repeatedly performs the processing of S2300 and S1503 until the index i has reached NZ3. The enlarged image generation unit 112 increments the index i by 1 each time the processing of S2300 and S1503 is executed. If the index i exceeds NZ3 (NO in S1303), the process illustrated in FIG. 71 ends.

In S2300, the enlarged image generation unit 112 calculates a third enlargement factor for the third distribution information on the similar case i by using a display area size determined in advance for each thumbnail image in the case display area 710, the region-of-interest information on the similar case i, and pleural area information 4900.

FIG. 72 is a diagram illustrating the data configuration of similar case data 4000 that additionally includes the pleural area information 4900. If the similar case data 4000 does not have registered therein the pleural area information 4900, the pleural area information 4900 is not obtained. In this case, it may be sufficient that the enlarged image generation unit 112 sets the third enlargement factor to 1.0, which is equal to the first enlargement factor. The pleural area information 4900 is information indicating the pleural area in a similar case.

In S1503, a process similar to S4500 in FIG. 56 is performed. As a result, the enlarged image generation unit 112 enlarges the thumbnail image of the similar case i with the third enlargement factor ki. The display control unit 104 displays the thumbnail image enlarged by the enlarged image generation unit 112 in the case display area 710 so that the center of the region of interest in the thumbnail image matches the center of the display area.

Figure 73:
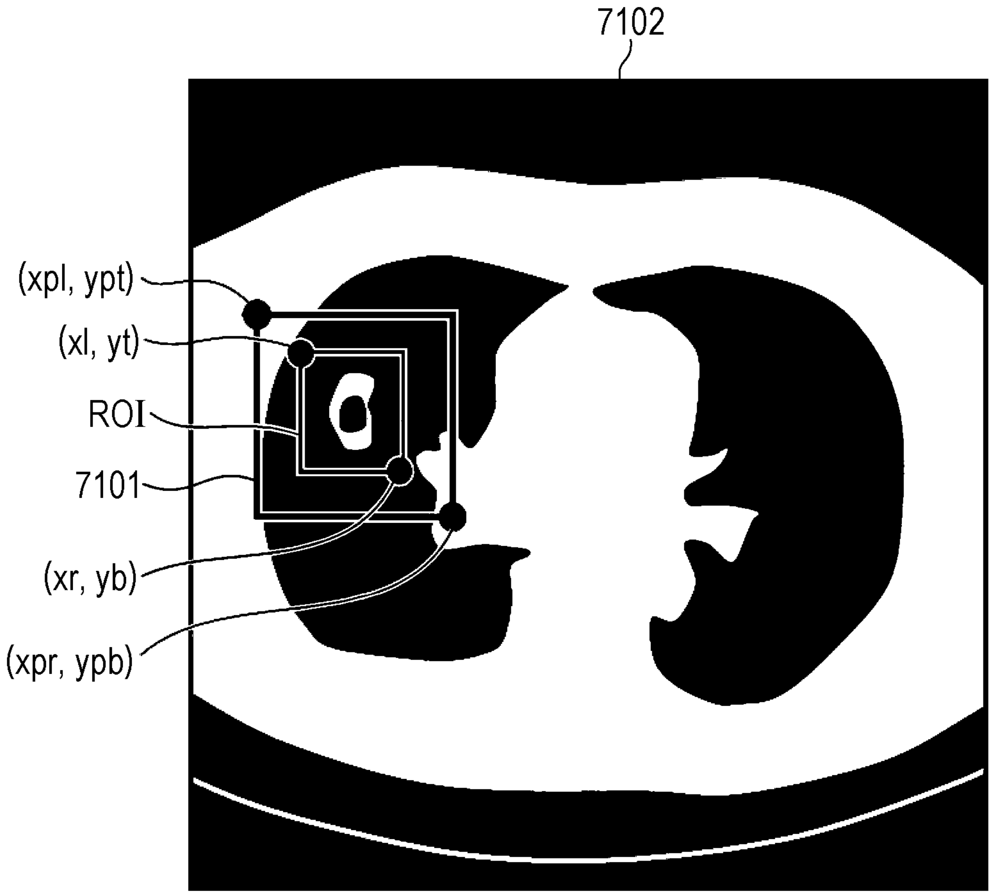
FIG. 73 is a diagram depicting a pleural area.

FIG. 73 is a diagram depicting a pleural area 7101. As illustrated in FIG. 73, the pleural area 7101 includes the pleura and is a rectangular area that is centered on the center of the region of interest ROI and that has a slightly larger size than the region of interest ROI. The pleural area information 4900 includes four values, namely, the coordinates (xpl, ypt) of the upper left corner of the pleural area 7101 and the coordinates (xpr, ypb) of the lower right corner of the pleural area 7101. If the third distribution information is selected, the pleural area is enlarged and displayed. Thus, the enlarged image generation unit 112 computes the third enlargement factor ki in accordance with the following equation:

$$ki=Sd/Sp,$$

where Sd denotes the area of a display area 7102 and Sp denotes the area of the pleural area 7101.

The user may input the pleural area information 4900 together with region-of-interest information when creating the similar case data 4000. Alternatively, the pleural area information 4900 may be automatically created by automatically extracting the lung area from a slice image and determining the pleural position using an image processing device.

In FIG. 26 described above, "subpleural" is selected. In this case, only thumbnail images of similar cases exhibiting subpleural lesion distribution among the similar cases are displayed in the case display area 710. In addition, all the thumbnail images in the case display area 710 have been enlarged with the third enlargement factor so that the center of the region of interest ROI in each thumbnail image matches the center of a display area 7001.

Through the process described above, thumbnail images are displayed in the case display area 710 with an enlargement factor that reflects the content of the diagnosis regarding a distribution of lesions. In addition, the thumbnail images are displayed in the case display area 710 with uniformity in size across the regions of interest in the individual thumbnail images. This may prevent the occurrence of oversight caused by the way in which the region of interest in some similar medical images has been enlarged but is small, and may improve diagnosis accuracy. In addition, not all the similar cases obtained as a result of the similar case search but similar cases displayed in the case display area 710 are subjected to an enlargement process, resulting in a significantly reduced load on a system.

Second Embodiment

In the first embodiment, an enlargement factor for a thumbnail image of a similar case is controlled in accordance with the amount of operation performed on the operation unit 102 by the user. In a second embodiment, the enlargement factor is controlled on the basis of a user operation on an enlargement factor change button on a basic screen.

Figure 74:
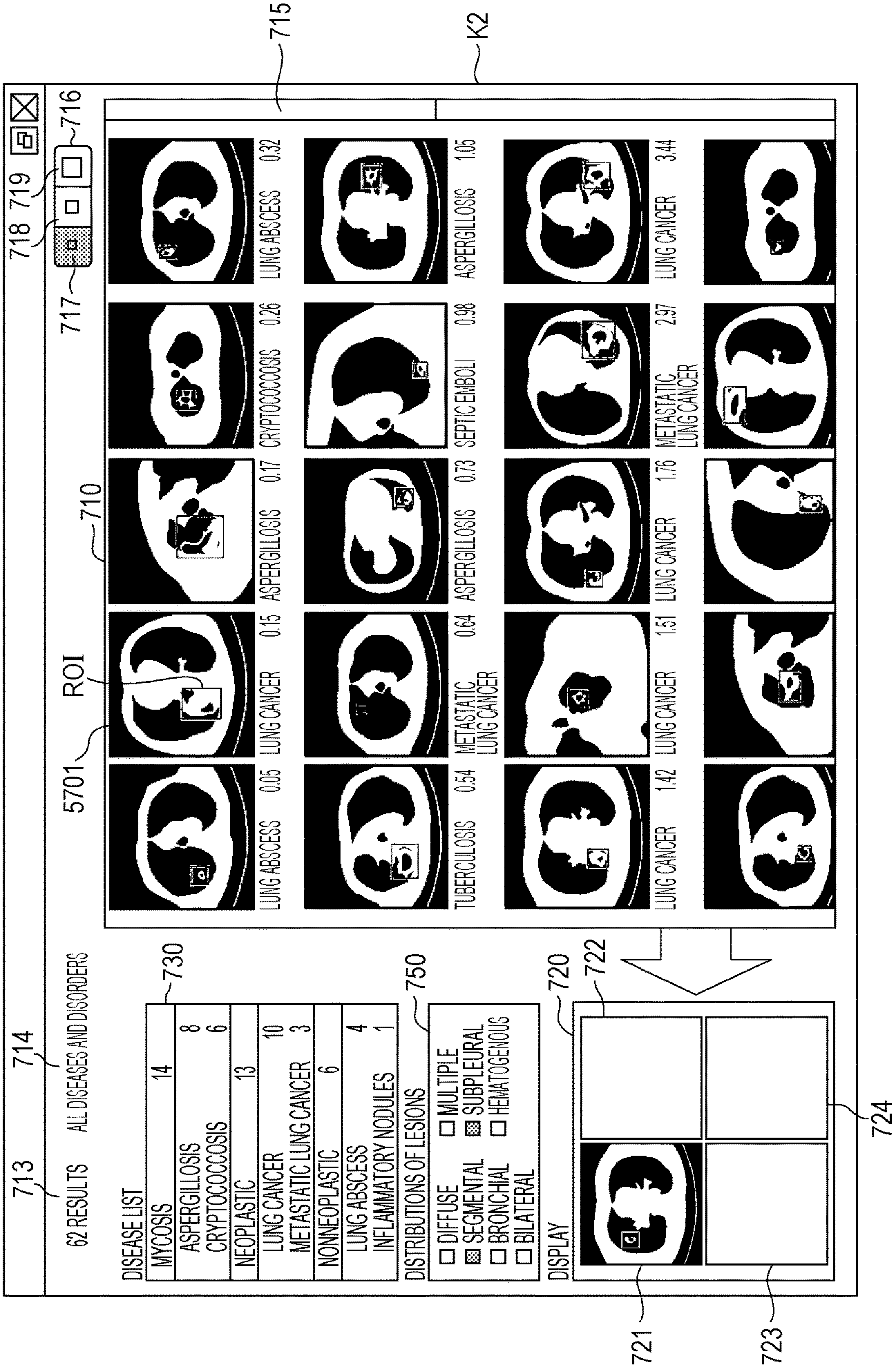
FIG. 74 is a diagram illustrating a basic screen on which thumbnail images of similar cases retrieved as a result of the similar case search are being displayed in the case display area according to a second embodiment.

FIG. 74 is a diagram illustrating a basic screen K2 on which thumbnail images of similar cases retrieved as a result of the similar case search are being displayed in the case display area 710 according to a second embodiment. The following description will focus mainly on the portions different from those in the first embodiment described above.

In the second embodiment, the basic screen K2 includes an enlargement factor change button 716 (an example of an instruction button). As illustrated in FIG. 74, the basic screen K2 includes, as the enlargement factor change button 716, a first instruction button 717, a second instruction button 718, and a third instruction button 719.

In the second embodiment, when the user selects any one of the first instruction button 717, the second instruction button 718, and the third instruction button 719 included in the enlargement factor change button 716, the input control unit 103 detects the selection of the instruction button. Then, the input control unit 103 notifies the enlarged image generation unit 112 of information on the button selected by the user. The enlarged image generation unit 112 changes the enlargement factor for all the thumbnail images displayed in the case display area 710 in accordance with the notified information on the selected button.

If the first instruction button 717 is selected by the user, the enlarged image generation unit 112 calculates the enlargement factor to be 1.0. The first instruction button 717 is selected on the initial basic screen K2 after the similar case search is made. Accordingly, the enlargement factor for the thumbnail images on the basic screen K2 illustrated in FIG. 74 is 1.0. In FIG. 74, furthermore, the display control unit 104 changes the color of the first instruction button 717.

Figure 75:
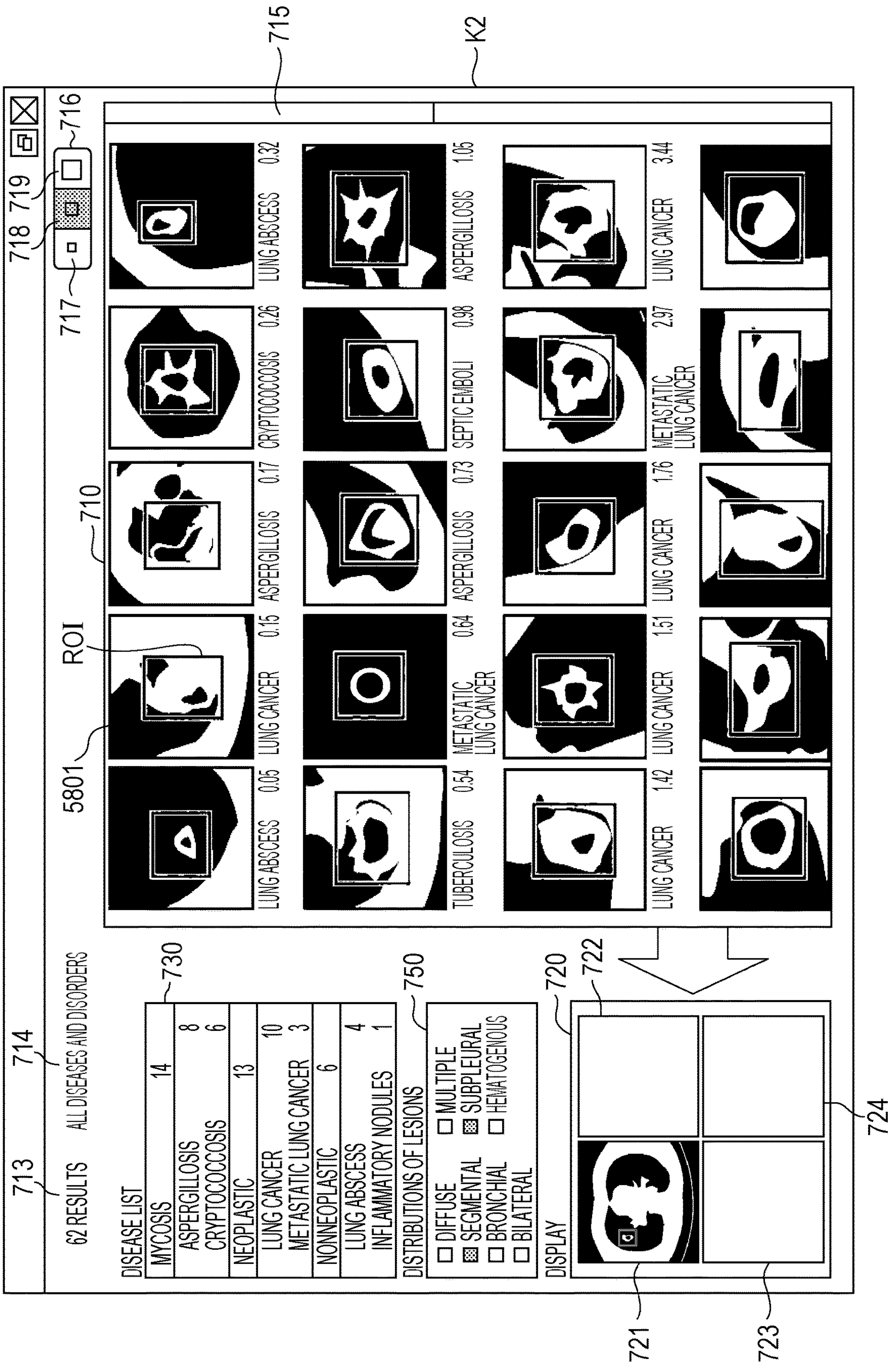
FIG. 75 is a diagram illustrating a basic screen obtained when a second instruction button is selected by a user.
Figure 76:
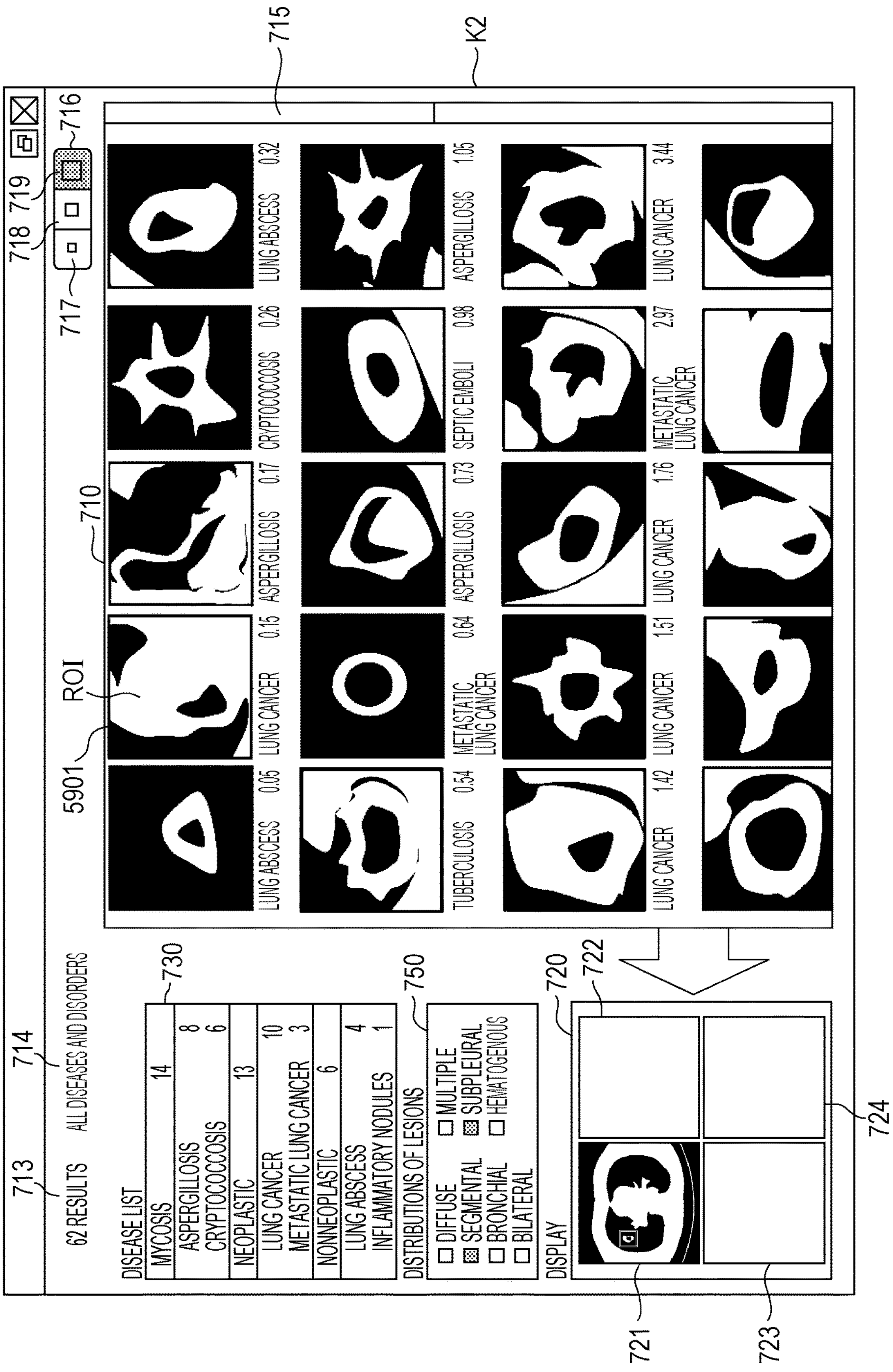
FIG. 76 is a diagram illustrating a basic screen obtained when a third instruction button is selected by a user.

FIG. 75 is a diagram illustrating the basic screen K2, which is obtained when the second instruction button 718 is selected by the user. FIG. 76 is a diagram illustrating the basic screen K2, which is obtained when the third instruction button 719 is selected by the user.

In FIG. 75, the display control unit 104 changes the color of the second instruction button 718. In FIG. 76, the display control unit 104 changes the color of the third instruction button 719.

If the second instruction button 718 is selected by the user on the basic screen K2 illustrated in FIG. 74 or FIG. 76, as illustrated in FIG. 75, the enlarged image generation unit 112 calculates the enlargement factors for the respective thumbnail images so that the region of interest ROI is enlarged in such a manner that the size of the region of interest ROI is equal to approximately one half of the size of a display area 5801.

If the third instruction button 719 is selected by the user on the basic screen K2 illustrated in FIG. 74 or FIG. 75, as illustrated in FIG. 76, the enlarged image generation unit 112 calculates the enlargement factors for the respective thumbnail images so that the region of interest ROI is enlarged in such a manner that the size of the region of interest ROI is approximately equal to the size of a display area 5901.

In FIG. 75 and FIG. 76, thumbnail images of similar cases, the number of which is equal to M (in FIG. 75 and FIG. 76, M=20), are displayed in the case display area 710 in which the maximum number of results allowed to be displayed is equal to ND (in this embodiment, ND=20), and M (in FIG. 75 and FIG. 76, M=20) thumbnail images are enlarged. In the manner described above, in the second embodiment, all the thumbnail images displayed in the case display area 710 are enlarged. For example, as illustrated in FIG. 18, if M=14, all the 14 thumbnail images are enlarged.

Figure 77:
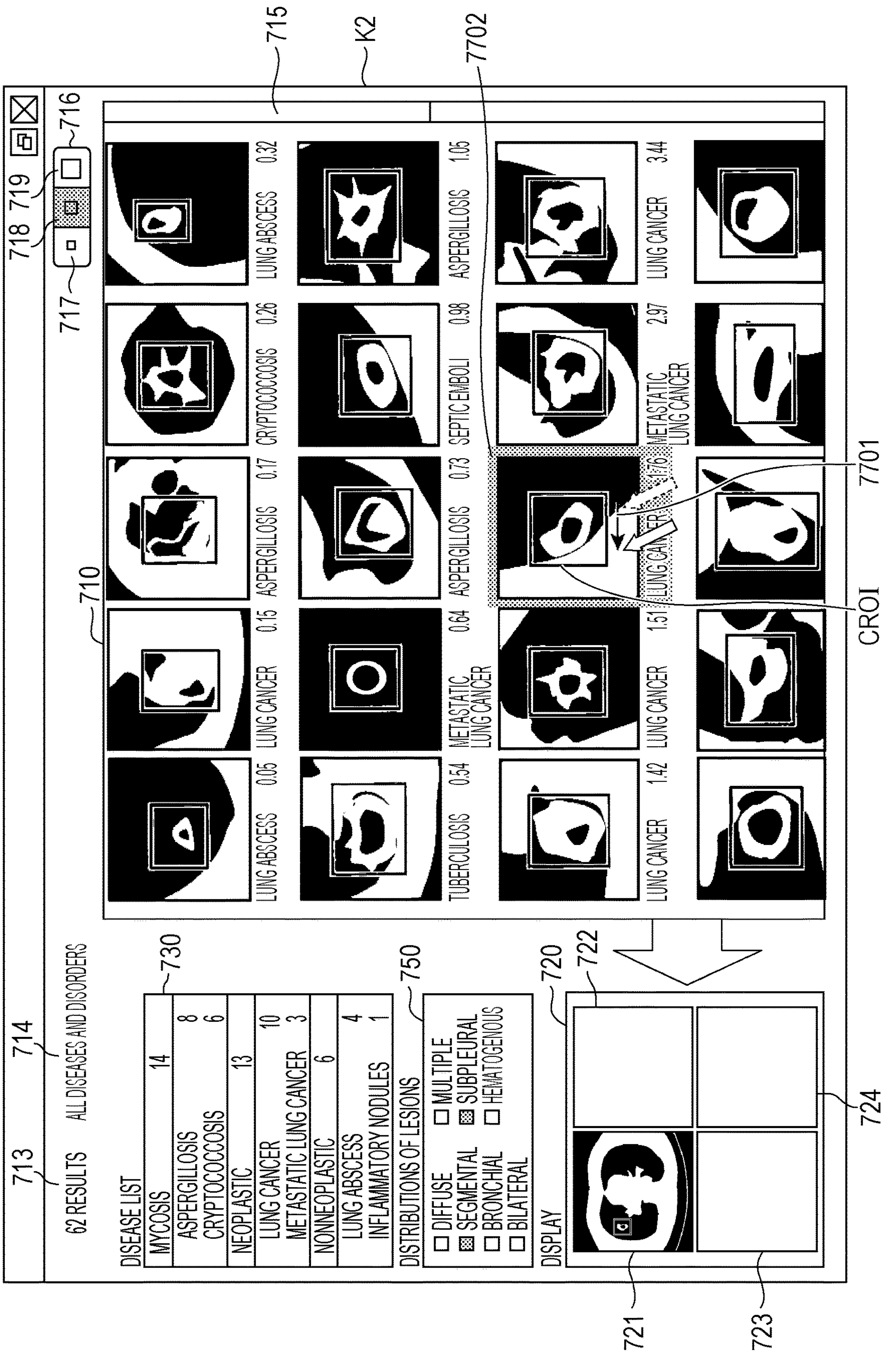
FIG. 77 is a diagram schematically illustrating a drag operation performed by a user while the basic screen (FIG. 75) obtained when the second instruction button is selected by the user is being displayed.
Figure 78:
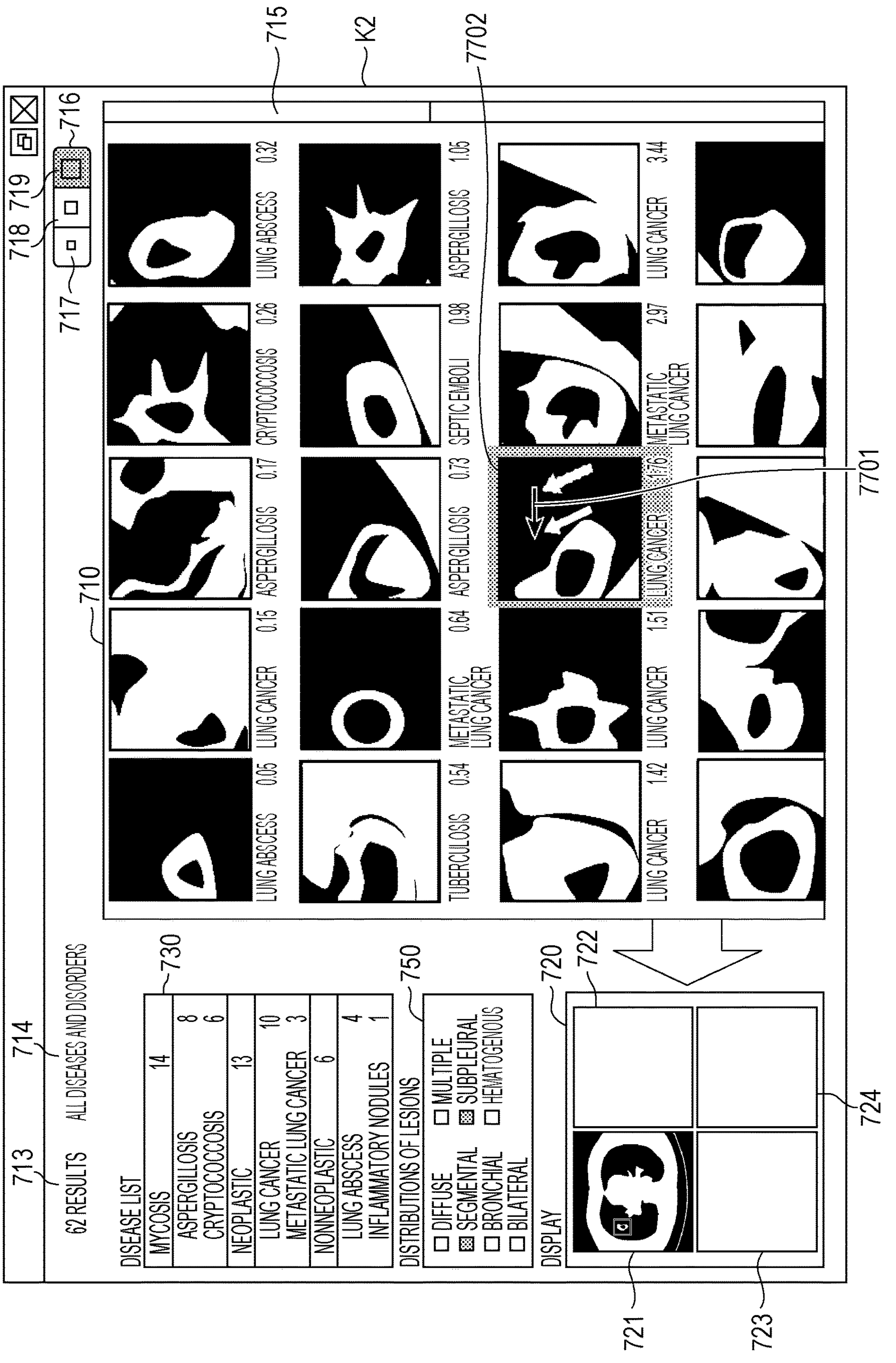
FIG. 78 is a diagram schematically illustrating a drag operation performed by a user while the basic screen (FIG. 76) obtained when the third instruction button is selected by the user is being displayed.

FIG. 77 is a diagram schematically illustrating a drag operation 7701 performed by a user while the basic screen K2 (FIG. 75) on which the second instruction button 718 is selected by the user is being displayed. FIG. 78 is a diagram schematically illustrating a drag operation 7701 performed by a user while the basic screen K2 (FIG. 76) on which the third instruction button 719 is selected by the user is being displayed.

As illustrated in FIG. 77 and FIG. 78, the user selects one of the enlarged thumbnail images in the case display area 710. In FIG. 77 and FIG. 78, a thumbnail image of a display area 7702 in the third row and the third column is selected. When the user performs the drag operation 7701 in this state, the input control unit 103 detects the amount of movement of the mouse, and notifies the enlarged image generation unit 112 of the detected amount of movement. Then, the enlarged image generation unit 112 determines an amount of movement of a display area in a thumbnail image by using the detected amount of movement of the mouse, and generates a thumbnail image in which the display area has moved the determined amount. The display control unit 104 displays, in the case display area 710, thumbnail images that have been caused to move by the enlarged image generation unit 112.

Specifically, as illustrated in FIG. 77 and FIG. 78, the user performs the drag operation 7701 to drag the mouse to the left, causing the display areas of the 20 thumbnail images displayed in the case display area 710 in enlarged form to move so that the portion to the right of the corresponding region of interest CROI in each of the 20 thumbnail images appears. This eliminates the need for the user to individually perform a movement operation on the 20 similar cases displayed in the case display area 710 in enlarged form, and may significantly reduce the number of operations.

Next, an enlargement process performed when the user selects the enlargement factor change button 716 will be described.

Figure 79:
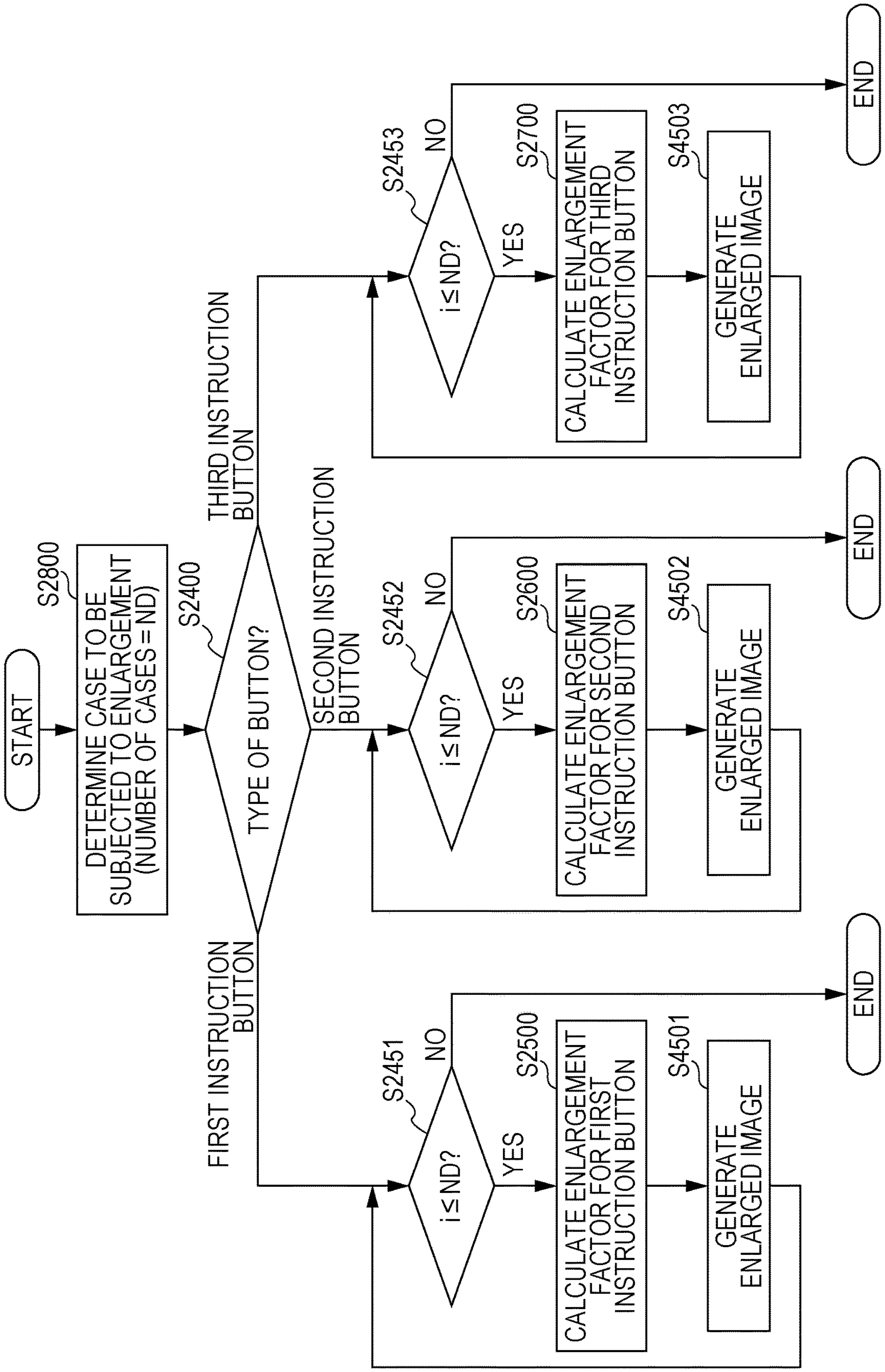
FIG. 79 is a flowchart illustrating an enlargement process performed when a user selects an enlargement factor change button.

FIG. 79 is a flowchart illustrating an enlargement process performed when a user selects the enlargement factor change button 716.

In S2800, the enlarged image generation unit 112 determines a target to be subjected to an enlargement process among a large number of similar cases obtained as a result of the similar case search.

In the second embodiment, unlike the first embodiment (S4100 in FIG. 56), instead of the user selecting a thumbnail image of a reference similar case, the user selects the enlargement factor change button 716. Thus, the enlarged image generation unit 112 regards all the similar cases displayed in the case display area 710 when the user selects the enlargement factor change button 716, as targets to be subjected to an enlargement process. Accordingly, the enlarged image generation unit 112 obtains, from the similar case data 4000 (FIG. 33), the similar case IDs of all the thumbnail images displayed in the case display area 710.

In S2400, the enlarged image generation unit 112 determines the type of the button selected by the user on the basis of the button information of which the enlarged image generation unit 112 is notified by the input control unit 103. If the button selected by the user is the first instruction button 717, the process proceeds to S2451. If the selected button is the second instruction button 718, the process proceeds to S2452. If the selected button is the third instruction button 719, the process proceeds to S2543.

In S2451, the enlarged image generation unit 112 determines a thumbnail image of a similar case i (where i is an index identifying a target similar case to be processed, and is an integer greater than or equal to 1) as a thumbnail image to be processed. The enlarged image generation unit 112 repeatedly performs the processing of S2500 and S4501 until the index i has reached ND. The enlarged image generation unit 112 increments the index i by 1 each time the processing of S2500 and S4501 is executed. If the index i exceeds ND (NO in S2451), the process illustrated in FIG. 79 ends.

In S2500, the first instruction button 717 has been selected by the user. Thus, in S2500, the enlarged image generation unit 112 calculates the enlargement factor to be 1.0.

In S4501, a process similarly to S4500 in FIG. 56 is performed. As a result, since the enlargement factor is 1.0, as illustrated in FIG. 74, the display control unit 104 displays the thumbnail image in the same display style as the thumbnail image displayed in the case display area 710 immediately after similar case search results are obtained.

In S2452, the enlarged image generation unit 112 determines a thumbnail image of a similar case i (where i is an index identifying a target similar case to be processed, and is an integer greater than or equal to 1) as a thumbnail image to be processed. The enlarged image generation unit 112 repeatedly performs the processing of S2600 and S4502 until the index i has reached ND. The enlarged image generation unit 112 increments the index i by 1 each time the processing of S2600 and S4502 is executed. If the index i exceeds ND (NO in S2452), the process illustrated in FIG. 79 ends.

In S2600, the second instruction button 718 has been selected by the user. Thus, in S2600, as described above, the enlarged image generation unit 112 calculates an enlargement factor for the enlargement-intended thumbnail image i so that the size of the region of interest is equal to approximately one half of the size of the display area. The enlarged image generation unit 112 calculates the enlargement factor on the basis of the size of the display area and the region-of-interest information 4300 in the similar case data 4000 (FIG. 33) of the enlargement-intended thumbnail image i. The enlarged image generation unit 112 computes an enlargement factor ki in accordance with an equation below. Given that the area of a display area 5701 (FIG. 74) is represented by Sd and the area of the region of interest ROI (FIG. 74) in the enlargement-intended thumbnail image i is represented by Si, the enlargement factor ki for the thumbnail image of the similar case i to be subjected to enlargement can be calculated in accordance with the following equation:

$$ki=\frac{1}{2}(Sd/Si).$$

In S4502, a process similar to S4500 in FIG. 56 is performed. As a result, the enlarged image generation unit 112 enlarges the thumbnail image of the similar case i so that the center of the region of interest in the thumbnail image matches the center of the display area. The display control unit 104 displays the enlarged thumbnail image generated by the enlarged image generation unit 112 in the case display area 710.

In the second embodiment, when the second instruction button 718 is selected, the enlarged image generation unit 112 calculates an enlargement factor so that the ratio of the size of the region of interest to the size of the display area is equal to approximately ½. In the present disclosure, however, the ratio is not limited to ½. The ratio may be any other value such as ⅓ or ⅔.

In S2453, the enlarged image generation unit 112 determines a thumbnail image of a similar case i (where i is an index identifying a target similar case to be processed, and is an integer greater than or equal to 1) as a thumbnail image to be processed. The enlarged image generation unit 112 repeatedly performs the processing of S2700 and S4503 until the index i has reached ND. The enlarged image generation unit 112 increments the index i by 1 each time the processing of S2700 and S4503 is executed. If the index i exceeds ND (NO in S2453), the process illustrated in FIG. 79 ends.

In S2700, the third instruction button 719 has been selected by the user. Thus, in S2700, as described above, the enlarged image generation unit 112 calculates an enlargement factor for the enlargement-intended thumbnail image i so that the size of the region of interest is approximately equal to the size of the display area. The enlarged image generation unit 112 calculates the enlargement factor on the basis of the size of the display area and the region-of-interest information 4300 in the similar case data 4000 (FIG. 33) of the similar case i to be subjected to enlargement. The enlarged image generation unit 112 computes an enlargement factor ki in accordance with an equation below. Given that the area of a display area 5701 (FIG. 74) is represented by Sd and the area of the region of interest ROI (FIG. 74) in the thumbnail image of the similar case i to be subjected to enlargement is represented by Si, the enlargement factor ki for the thumbnail image of the similar case i to be subjected to enlargement can be calculated in accordance with the following equation:

$$ki=Sd/Si.$$

In S4503, a process similar to S4500 in FIG. 56 is performed. As a result, the enlarged image generation unit 112 enlarges the thumbnail image of the similar case i so that the center of the region of interest in the thumbnail image matches the center of the display area. The display control unit 104 displays the enlarged thumbnail image generated by the enlarged image generation unit 112 in the case display area 710.

In the second embodiment, when the third instruction button 719 is selected, the enlarged image generation unit 112 calculates an enlargement factor so that the ratio of the size of the region of interest to the size of the display area is equal to approximately 1.0. In the present disclosure, however, the ratio is not limited to 1.0. The ratio may be any other value such as 1.1 or 0.9.

Through the process described above, the sizes of the regions of interest ROI in the individual display areas within the case display area 710 can be made uniform. This may prevent the occurrence of oversight caused by the way in which the region of interest in some similar medical images has been enlarged but is small, and may improve diagnosis accuracy. In this case, not all the similar cases obtained as a result of the similar case search but similar cases displayed in the case display area 710 are subjected to an enlargement process. This results in a significantly reduced load on a system.

Next, a process performed during a period in which, after thumbnail images obtained as a result of the similar case search are enlarged and displayed on the information terminal 100, a display area of a thumbnail image is changed in response to a user operation will be described. In the following, first, the details of the processing blocks of the enlarged image generation unit 112 will be described, and then the flow of the display area changing process will be described.

Figure 80:
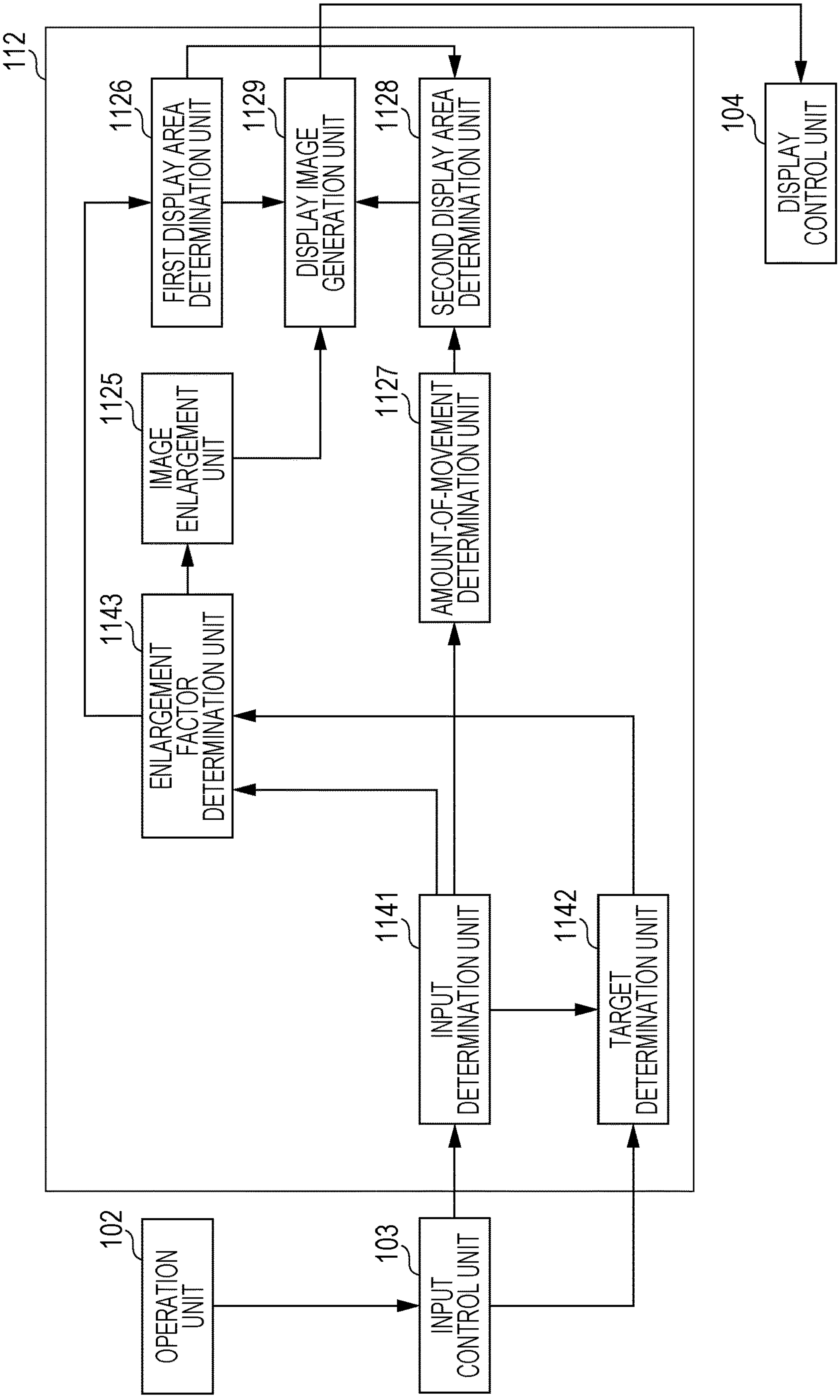
FIG. 80 is a block diagram illustrating a detailed configuration of an enlarged image generation unit according to the second embodiment.

FIG. 80 is a block diagram illustrating the detailed configuration of the enlarged image generation unit 112 according to the second embodiment. The enlarged image generation unit 112 includes an input determination unit 1141, a target determination unit 1142, an enlargement factor determination unit 1143, an image enlargement unit 1125, a first display area determination unit 1126, an amount-of-movement determination unit 1127, a display image generation unit 1129, and a second display area determination unit 1128. The enlarged image generation unit 112 performs an enlargement factor changing process and a display area changing process. In the second embodiment, substantially the same processing blocks as those in the first embodiment are assigned the same numerals, and are not described in detail herein.

The input determination unit 1141 determines the content of the operation performed on the operation unit 102 by a user, of which the enlarged image generation unit 112 is notified by the input control unit 103. If the determined content of the operation indicates an enlargement factor changing operation (in the second embodiment, the selection of a button), the input determination unit 1141 outputs the type of the selected button (that is, the first instruction button 717, the second instruction button 718, or the third instruction button 719) to the enlargement factor determination unit 1143. The input determination unit 1141 outputs operation content information (information indicating a change of the enlargement factor, for example, the value "1" preset as a value corresponding to information indicating a change of the enlargement factor) to the target determination unit 1142.

If the determined content of the operation indicates a display area changing operation (e.g., mouse dragging), the input determination unit 1141 outputs the amount of operation (e.g., the start position and end position of mouse dragging) to the amount-of-movement determination unit 1127. The input determination unit 1141 further outputs operation content information (information indicating a change of a display area, for example, the value "2" preset as a value corresponding to information indicating a change of a display area) to the target determination unit 1142.

If the determined content of the operation indicates the selection of a distribution of lesions (checking the checkbox for the distribution list display area 750), the input determination unit 1141 outputs distribution information to which the selected distribution of lesions belongs, that is, the first distribution information, the second distribution information, or the third distribution information, to the enlargement factor determination unit 1143. The input determination unit 1141 outputs operation content information (information indicating a change of the enlargement factor in response to the selection of a distribution of lesions, for example, the value "3" preset as a value corresponding to information indicating a change of the enlargement factor in response to the selection of a distribution of lesions) to the target determination unit 1142.

The target determination unit 1142 determines a similar case to be subjected to a thumbnail image enlargement process or a display area changing process, on the basis of the operation content information input from the input determination unit 1141.

In the second embodiment, the enlargement factor changing operation is an operation on the first instruction button 717, the second instruction button 718, or the third instruction button 719. In a case where the operation content information is information indicating a change of the enlargement factor, the target determination unit 1142 determines all the (in the examples illustrated in FIG. 74 to FIG. 76, 20) similar cases displayed on the display 101 as targets to be subjected to an enlargement process. The target determination unit 1142 outputs the number of similar cases and the similar case IDs 4100 of the similar cases to the enlargement factor determination unit 1143.

If the operation content information is information indicating a change of a display area, the target determination unit 1142 uses the similar cases to be subjected to enlargement, which are determined in the enlargement factor changing process, directly as targets to be subjected to the display area changing process.

If the operation content information is information indicating a change of the enlargement factor in response to the selection of a distribution of lesions, the target determination unit 1142 outputs the similar case IDs 4100 obtained as a result of refinement in accordance with a selected distribution of lesions, and the number of similar case IDs 4100 to the enlargement factor determination unit 1143.

The enlargement factor determination unit 1143 determines an enlargement factor for the similar cases that are targets of enlargement, which are determined by the target determination unit 1142. If information indicating the selected distribution of lesions is input from the input determination unit 1141 as operation content information, the enlargement factor determination unit 1143 calculates a predetermined enlargement factor corresponding to the selected distribution of lesions. The enlargement factor determination unit 1143 outputs the determined enlargement factor, and the similar case IDs 4100 of the targets of enlargement and the number of similar case IDs, which are input from the target determination unit 1142, to the image enlargement unit 1125. Predetermined enlargement factors corresponding to the respective distributions of lesions are as described above with reference to FIG. 21 to FIG. 26.

If information indicating a change of the enlargement factor is input from the input determination unit 1141 as operation content information, the enlargement factor determination unit 1143 extracts the region-of-interest information 4300 corresponding to the similar case IDs 4100 (FIG. 33) of the targets of enlargement, which are input from the target determination unit 1142. The enlargement factor determination unit 1143 calculates enlargement factors for the respective similar cases by using the extracted region-of-interest information 4300 and the type of the button (that is, the first instruction button 717, the second instruction button 718, or the third instruction button 719) input from the input determination unit 1141 through the procedure described above with reference to FIG. 79. The enlargement factor determination unit 1143 outputs the calculated enlargement factors, the similar case IDs 4100 of the targets of enlargement, and the number of similar case IDs to the image enlargement unit 1125.

Also in the second embodiment, similarly to the first embodiment, when a distribution of lesions that belongs to the first distribution information is selected, display areas are not changed. In the second embodiment, furthermore, in a case where the enlargement factor is changed in response to the operation on the first instruction button 717, as illustrated in FIG. 74, entire thumbnail images are displayed with an enlargement factor of 1.0. Thus, also when the enlargement factor is changed in response to the operation on the first instruction button 717, the display areas are not changed.

In the second embodiment, accordingly, in a case where a distribution of lesions that belongs to the first distribution information is selected and the enlargement factor is changed in response to the operation on the first instruction button 717, the input determination unit 1141 may not necessarily output the amount of operation to the amount-of-movement determination unit 1127 even if the determined content of the operation indicates a display area changing operation. Alternatively, the target determination unit 1142 may determine that none of the similar cases is set as a target to be subjected to a display area changing process.

Next, the flow of a process for changing a display area in an enlarged thumbnail image will be described.

Figure 81:
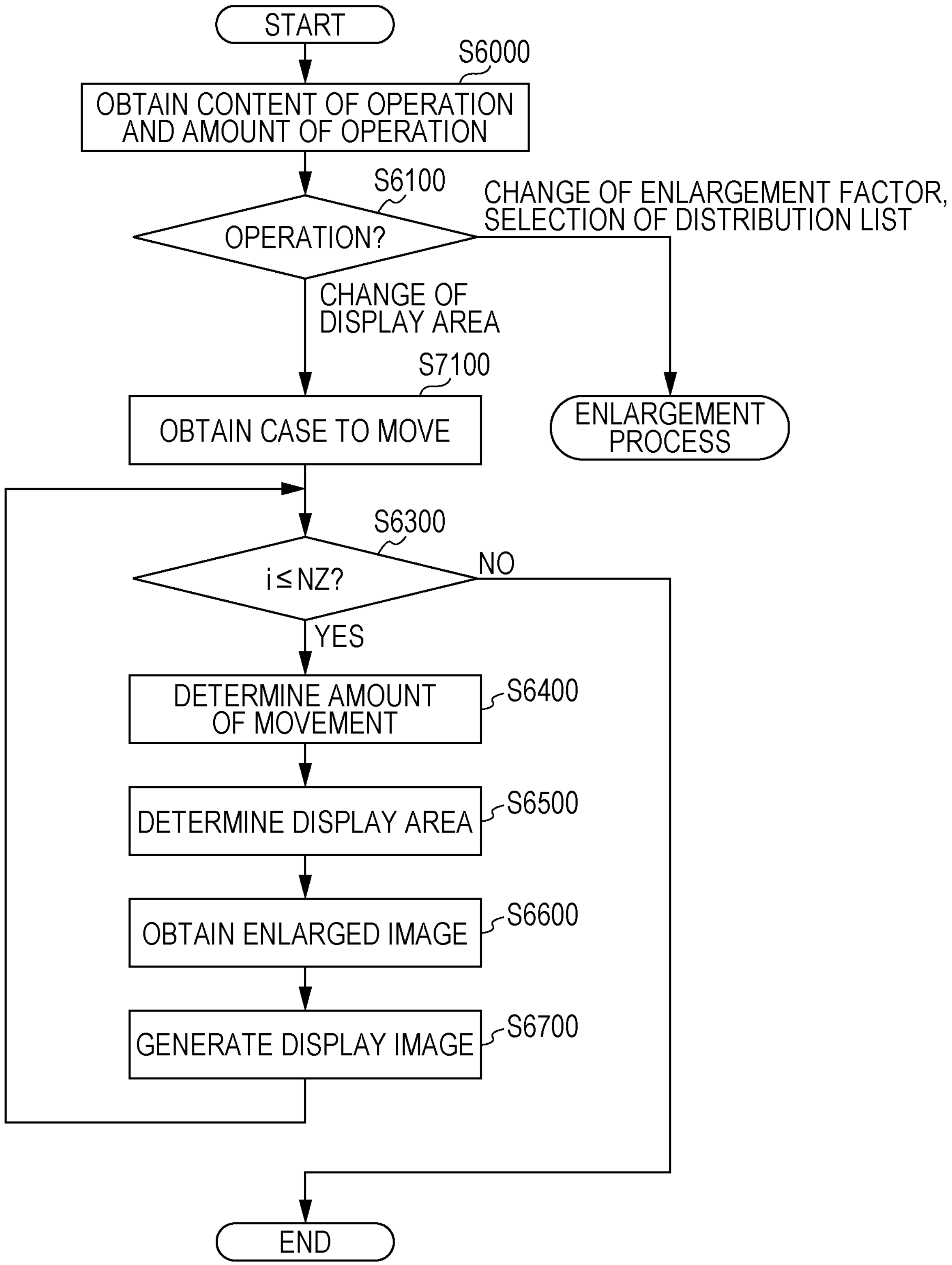
FIG. 81 is a flowchart illustrating a process for changing the display area for an enlarged thumbnail image.

FIG. 81 is a flowchart illustrating a process for changing the display area for an enlarged thumbnail image. In FIG. 81, substantially the same steps as those illustrated in FIG. 64 are assigned the same numerals, and are not described in detail herein.

In S7100, the target determination unit 1142 obtains a similar case to move on which a display area changing process is to be performed. In the second embodiment, similarly to the first embodiment, in S7100, the target determination unit 1142 uses, as a similar case to move, a similar case for which the enlargement factor has been changed in the enlargement factor changing process. This step may reduce the processing load on the information terminal 100, compared to the case where display areas for all the NC similar cases received from the similar case search unit 303 move.

As described above, in the second embodiment, in a case where a distribution of lesions that belongs to the first distribution information is selected and the enlargement factor is changed in response to the operation on the first instruction button 717, display areas are not changed.

Accordingly, in a case where a distribution of lesions that belongs to the first distribution information has been selected and the enlargement factor has been changed in response to the operation on the first instruction button 717, then in S7100, the target determination unit 1142 may determine that none of the similar cases is set as a target to be subjected to a display area changing process, and the process may end. Alternatively, in S7100, the target determination unit 1142 may set the index i to a value exceeding NZ, and may obtain a negative determination in S6300.

The configuration of the enlarged image generation unit 112 that performs a display area changing process is not limited to that illustrated in FIG. 80. Next, a modification of the display area changing process will be described.

Figure 82:
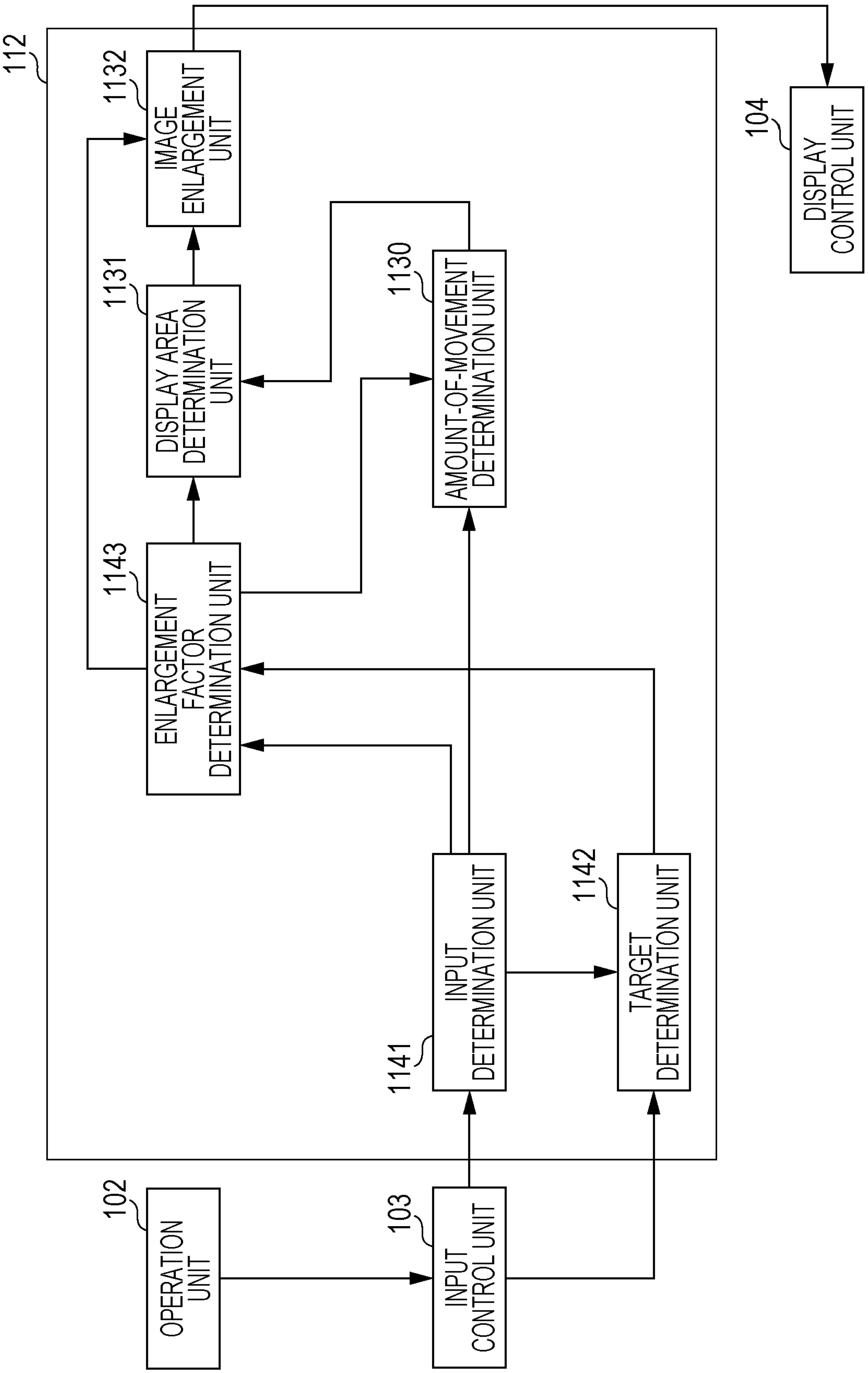
FIG. 82 is a block diagram illustrating another detailed configuration of the enlarged image generation unit, which is different from that illustrated in FIG. 80.

FIG. 82 is a block diagram illustrating a detailed configuration of the enlarged image generation unit 112, which is different from that illustrated in FIG. 80. The enlarged image generation unit 112 includes the input determination unit 1141, the target determination unit 1142, the enlargement factor determination unit 1143, an amount-of-movement determination unit 1130, a display area determination unit 1131, and an image enlargement unit 1132. In FIG. 82, substantially the same blocks as those in FIG. 65 and FIG. 80 are assigned the same numerals.

The amount-of-movement determination unit 1130 obtains the determined enlargement factors for the respective thumbnail images from the enlargement factor determination unit 1143. The amount-of-movement determination unit 1130 obtains the amount of operation from the input determination unit 1121. The amount-of-movement determination unit 1130 calculates the amount of movement in the thumbnail image before enlargement, by using the enlargement factors for the respective thumbnail images and the amount of operation. The amount-of-movement determination unit 1130 outputs the calculated amount of movement and the enlargement factors for the respective thumbnail images to the display area determination unit 1131.

Similarly to the first display area determination unit 1126, the display area determination unit 1131 determines a display area in the enlarged thumbnail image of the similar case that is a target of enlargement. That is, the display area determination unit 1131 obtains the similar case ID 4100 (FIG. 33) of the target of enlargement from the enlargement factor determination unit 1143. The display area determination unit 1131 extracts the region-of-interest information 4300 corresponding to the obtains similar case ID 4100 (FIG. 33) of the target of enlargement. The display area determination unit 1131 calculates the coordinates of the display area in the enlarged thumbnail image by using the enlargement factor input from the enlargement factor determination unit 1143 and the extracted region-of-interest information 4300 through the procedure described above with reference to S4520 and S4530 in FIG. 59.

The display area determination unit 1131 obtains the enlargement factors for the respective thumbnail images from the enlargement factor determination unit 1143. The display area determination unit 1131 obtains the amount of movement in the thumbnail image before enlargement from the amount-of-movement determination unit 1130. The display area determination unit 1131 calculates the coordinates of the display area in the thumbnail image before enlargement before the display area has moved, by using the calculated coordinates of the display area in the enlarged thumbnail image and the obtains enlargement factors.

The display area determination unit 1131 adds the obtained amount of movement in the thumbnail image before enlargement to the calculated coordinates of the display area in the thumbnail image before enlargement before the display area has moved to calculate the coordinates of the display area in the thumbnail image before enlargement after display area has moved. The display area determination unit 1131 outputs the calculated coordinates of the display area in the thumbnail image before enlargement after display area has moved to the image enlargement unit 1132.

The image enlargement unit 1132 obtains the enlargement factors for the respective thumbnail images from the enlargement factor determination unit 1143. The image enlargement unit 1132 enlarges thumbnail images in the display area, by using the coordinates of the display area in the thumbnail image before enlargement after display area has moved, which are input from the display area determination unit 1131, and the obtained enlargement factors for the respective thumbnail images. The image enlargement unit 1132 outputs the generated enlarged thumbnail images to the display control unit 104.

A description will be given here of the meaning of the modifications illustrated in FIG. 65 and FIG. 82. As described above with reference to FIG. 60, the enlarged thumbnail image illustrated in the right part of FIG. 60 is generated from the original thumbnail image illustrated in the left part of FIG. 60. For example, in a case where the entire enlarged thumbnail image illustrated in the right part of FIG. 60 is stored, as described above with reference to FIG. 63, it may be sufficient that the display area is changed (or caused to move) over the enlarged thumbnail image in accordance with the amount of operation performed by the user.

In some cases, only a portion of the enlarged thumbnail image illustrated in the right part of FIG. 60, which corresponds to the display area illustrated in FIG. 67A, may be stored. In particular, in the second embodiment, the enlargement factor changing process is performed in response to the selection of any distribution of lesions among the "diffuse" 751 to the "hematogenous" 757 (e.g., FIG. 20) or in response to the operation on any of the first to third instruction buttons 717 to 719 (e.g., FIG. 74). That is, in the second embodiment, an enlargement factor is determined in advance independently of the amount of operation performed by the user.

In the second embodiment, accordingly, it is conceivable that a thumbnail image produced by enlarging the original thumbnail image with a predetermined enlargement factor is created in advance and only a portion of the thumbnail image, which corresponds to the display area (FIG. 67A) to be displayed in the case display area 710, is stored. In this case, it will be difficult to use the technique illustrated in FIG. 63 in which a display area is caused to directly move over an enlarged thumbnail image. In this case, it may be effective that the display area be changed (or be caused to move) with the configuration according to the modifications illustrated in FIG. 65 and FIG. 82 through the procedure described above with reference to FIGS. 67A to 67C.

In the foregoing, an example has been provided in which the process for changing an enlargement factor for a thumbnail image is executed by the information terminal 100. In the case of a process for changing the enlargement factor by using the enlargement factor change button 716 according to the second embodiment, the enlargement factor changing process may be executed by the case search system 300. In this case, the case search system 300 may generate in advance a thumbnail image with a changed enlargement factor. When an enlargement factor change button is operated, the thumbnail image may be transmitted from the case search system 300 to the information terminal 100.

Figure 83:
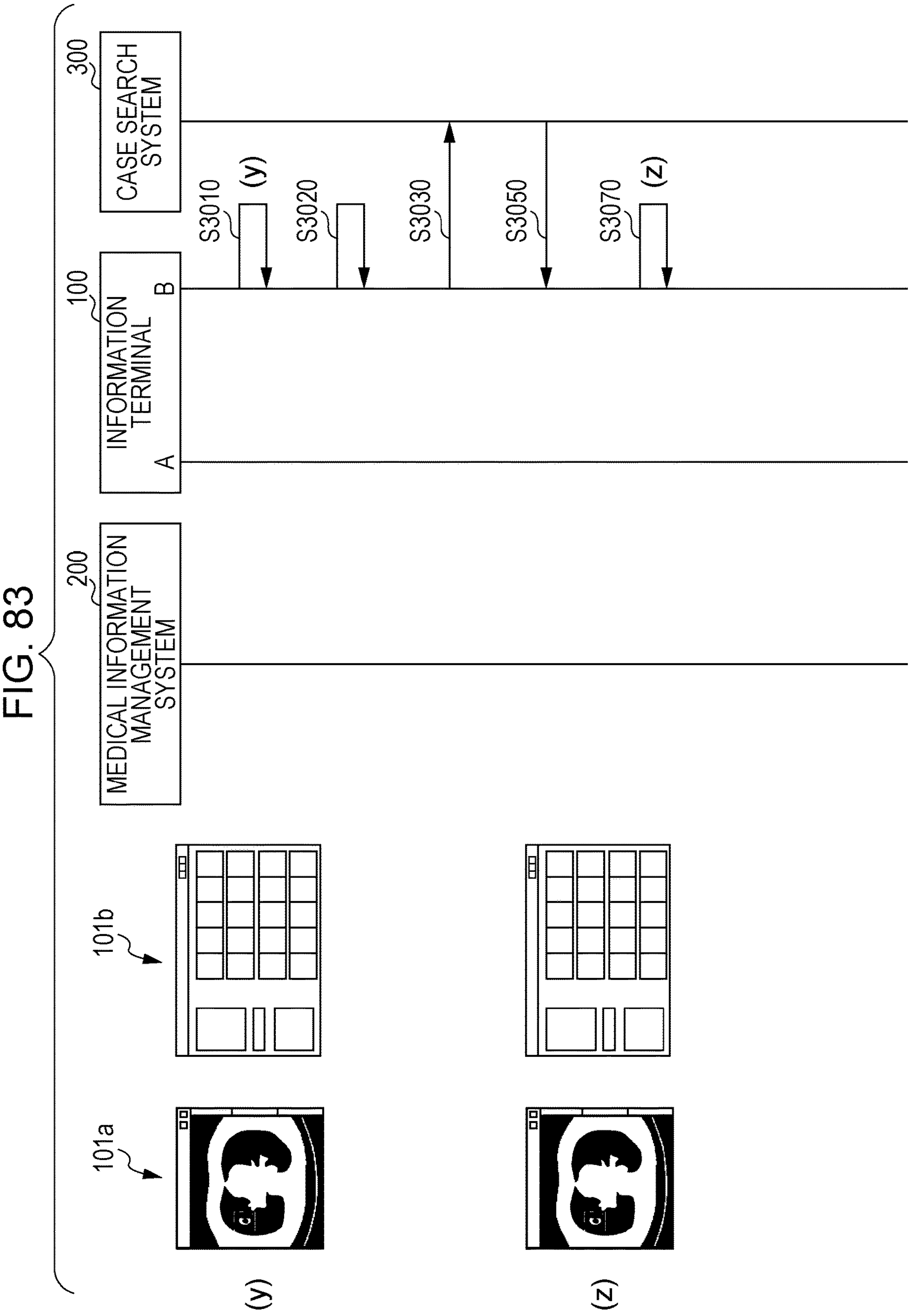
FIG. 83 is a sequence diagram illustrating a process performed during a period in which, after the case search system transmits similar case search results to the information terminal, the enlargement factor change button is selected on the information terminal and enlarged thumbnail images are displayed on the display of the information terminal.
Figure 84:
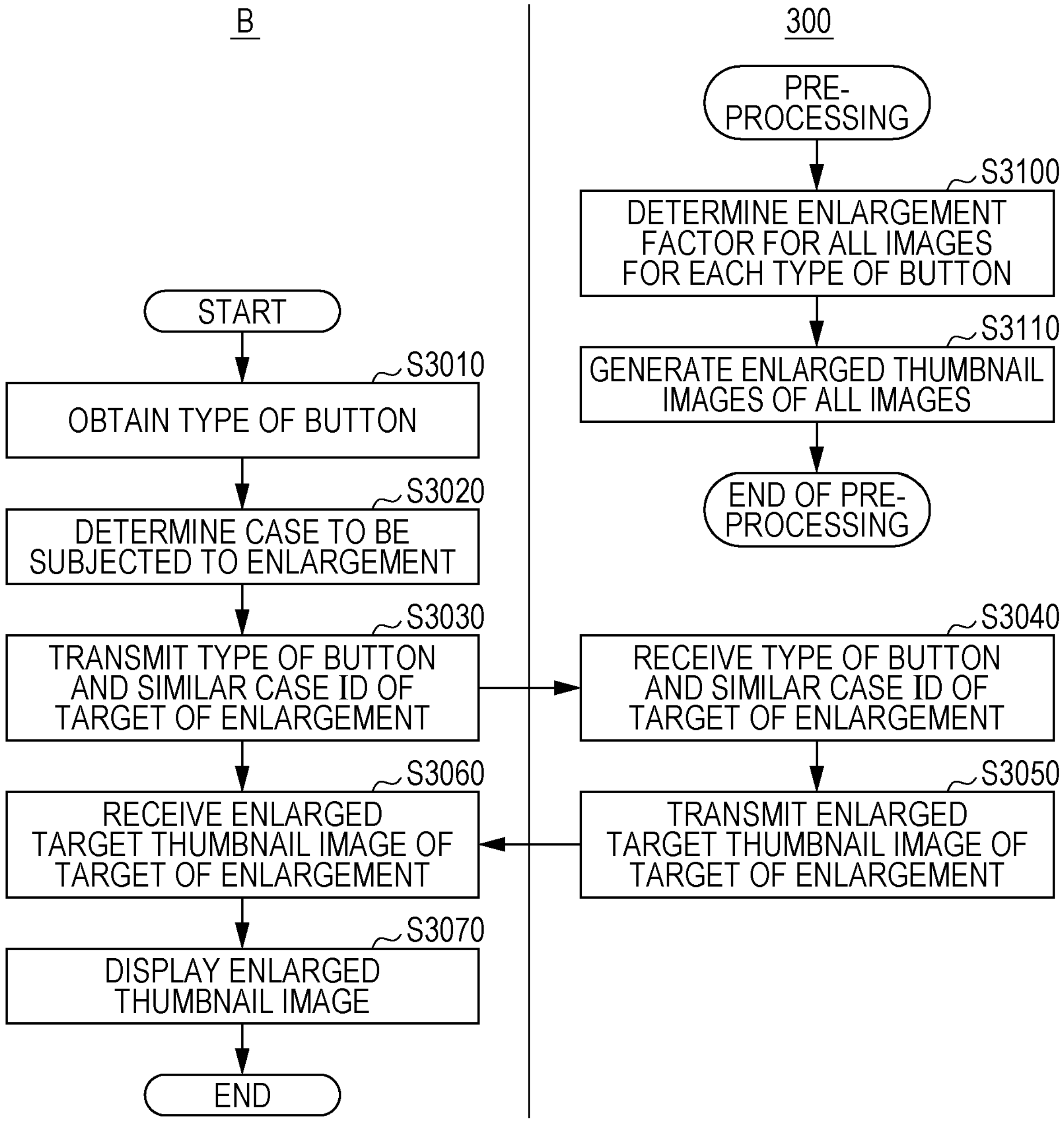
FIG. 84 is a flowchart illustrating pre-processing executed in the case search system and the process illustrated in FIG. 83.

FIG. 83 is a sequence diagram illustrating a process performed during a period in which, after the case search system 300 transmits similar case search results to the information terminal 100, the enlargement factor change button 716 is selected on the information terminal 100 and enlarged thumbnail images are displayed on the display 101*b* of the information terminal 100. FIG. 84 is a flowchart illustrating pre-processing executed in the case search system 300 and the process illustrated in FIG. 83. In FIG. 84, substantially the same processing steps as those illustrated in FIG. 83 are assigned the same numerals. The process will be described in detail with reference to FIG. 83 and FIG. 84.

First, pre-processing executed in the case search system 300 will be described. In S3100 in FIG. 84, the case search system 300 determines the enlargement factors for the respective thumbnail images for each of the first instruction button 717, the second instruction button 718, and the third instruction button 719 of the enlargement factor change button 716. The procedure for determining the enlargement factors may be the procedure described above with reference to S2500, S2600, and S2700 in FIG. 79.

In S3110, the case search system 300 generates enlarged thumbnail image data for each of the first instruction button 717, the second instruction button 718, and the third instruction button 719 in accordance with the enlargement factor determined in S3100 and the thumbnail image data 4500 of the similar case data 4000 (FIG. 33). As illustrated in FIG. 85, the case search system 300 stores the generated enlarged thumbnail image data in the similar case data accumulation unit 301 as enlarged thumbnail data 5000, separately from the similar case data 4000 (FIG. 33).

FIG. 85 is a diagram illustrating the data configuration of the enlarged thumbnail data 5000. The enlarged thumbnail data 5000 is data for storing enlarged thumbnail image data in the similar case data accumulation unit 301. As illustrated in FIG. 85, the enlarged thumbnail data 5000 includes, is association with similar case ID 5100, enlarged thumbnail image data 5200 corresponding to the first instruction button 717, enlarged thumbnail image data 5300 corresponding to the second instruction button 718, and enlarged thumbnail image data 5400 corresponding to the third instruction button 719.

Next, a process performed when the user selects an enlargement factor change button on the information terminal 100 will be described with reference to FIG. 83 and FIG. 84.

In S3010, the input control unit 103 detects the type of the instruction button selected by the user within the enlargement factor change button 716. That is, the input control unit 103 detects which of the first instruction button 717, the second instruction button 718, and the third instruction button 719 has been selected by the user.

In S3020, the display control unit 104 obtains, from the similar case data 4000 (FIG. 33), the similar case IDs of ND (in this embodiment, ND=20) similar cases that is being displayed in the case display area 710 when the enlargement factor change button 716 is selected by the user. Further, the display control unit 104 determines the obtained similar case IDs as similar cases to be subjected to enlargement.

In S3030, the communication control unit 110 transmits the type of the enlargement factor change button 716, which is detected by the input control unit 103 in S3010, and the similar case IDs of the targets of enlargement (the number of which is equal to ND), which are obtained by the display control unit 104 in S3020, to the case search system 300.

In S3040, the communication control unit 304 of the case search system 300 receives the type of the enlargement factor change button 716 and the similar case IDs of the targets of enlargement (the number of which is equal to ND), which are transmitted from the information terminal 100 in S3030.

In S3050, the case search system 300 designates image data to be used for display among the enlarged thumbnail image data 5200, 5300, and 5400 in the enlarged thumbnail data 5000, by using the received similar case IDs and the received type of the enlargement factor change button 716. The communication control unit 304 of the case search system 300 transmits the designated enlarged thumbnail image data to the information terminal 100.

In S3060, the communication control unit 110 of the information terminal 100 receives the enlarged thumbnail image data transmitted from the case search system 300.

In S3070, the display control unit 104 of the information terminal 100 displays enlarged thumbnail images of the similar cases in the case display area 710 of the display 101*b* of the information terminal 100, on the basis of the enlarged thumbnail image data received by the communication control unit 110 in S3060.

Supplementary Description of First Embodiment

Next, the process performed by the information terminal 100, the medical information management system 200, and the case search system 300 when the focus is on the sequence diagrams illustrated in FIG. 35 and FIG. 39 at the application level will be described.

Figure 86:
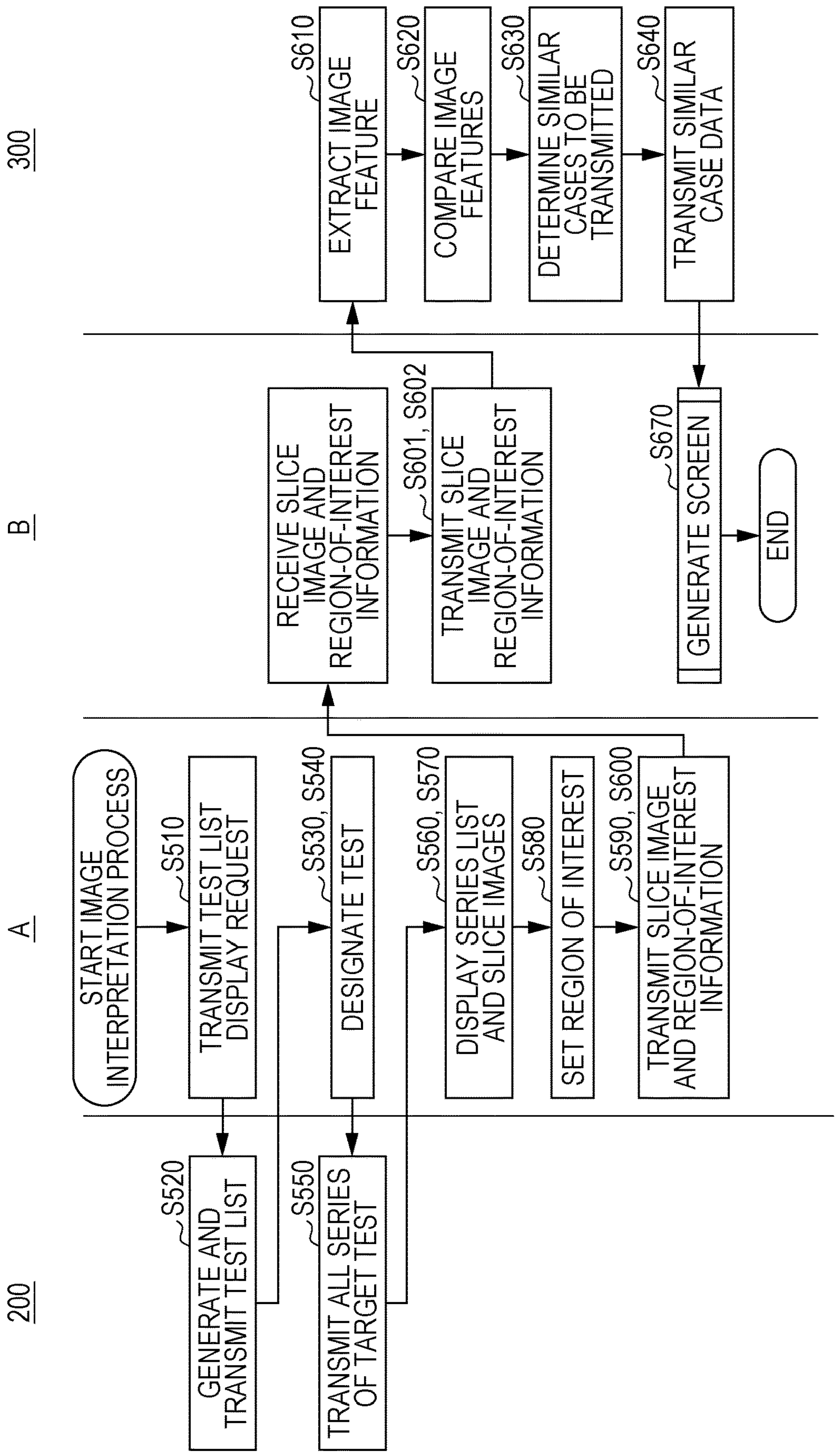
FIG. 86 is a sequence diagram focusing on the sequence diagrams illustrated in FIG. 35 and FIG. 39 at the application level.

FIG. 86 is a sequence diagram focusing on the sequence diagrams illustrated in FIG. 35 and FIG. 39 at the application level. In FIG. 86, substantially the same processing steps as those in FIG. 35 and FIG. 39 are assigned the same numerals.

Figure 87:
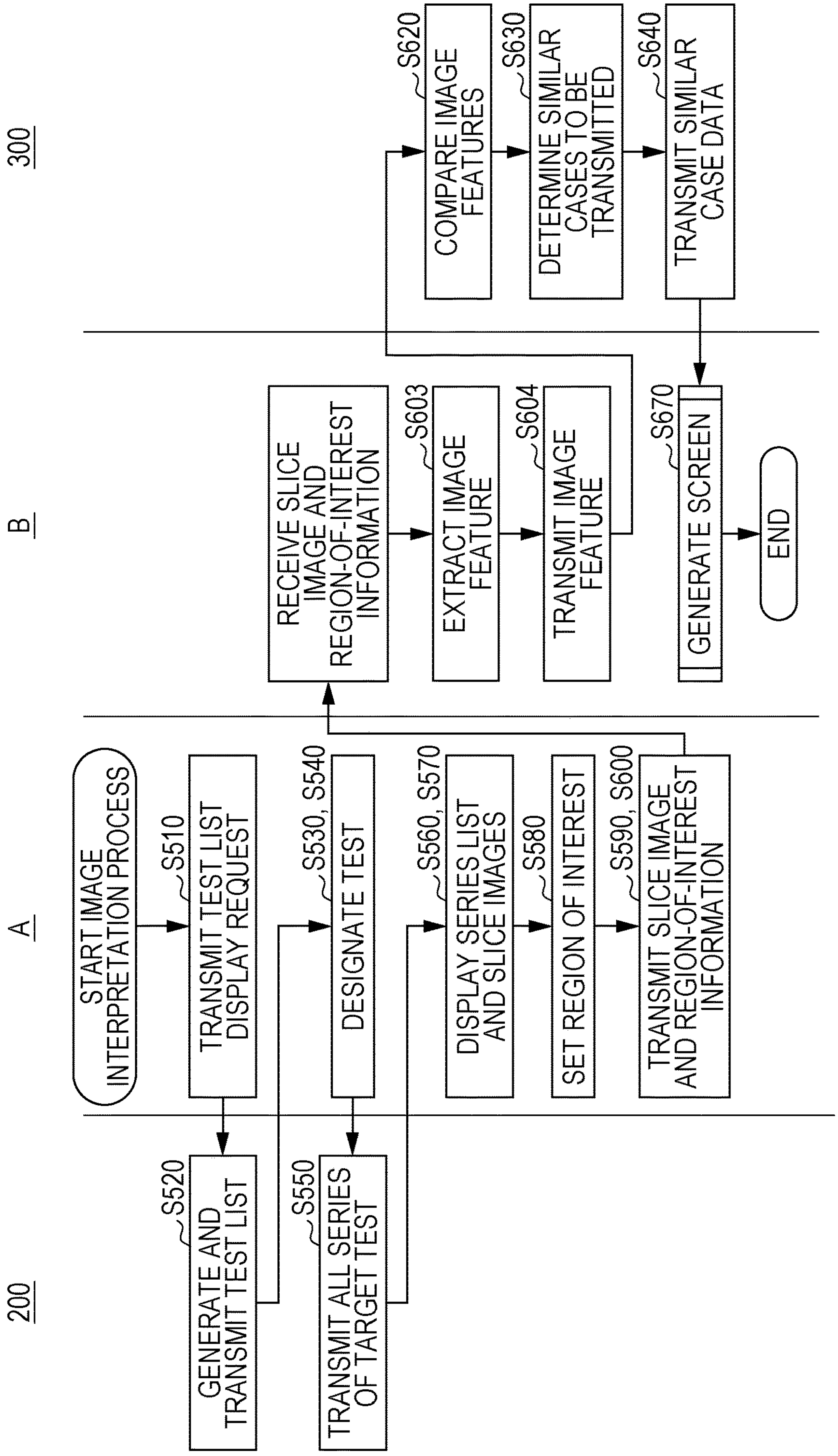
FIG. 87 is a sequence diagram focusing on the sequence diagrams illustrated in FIG. 54 and FIG. 55 at the application level.

In FIG. 86 and FIG. 87, part "A" illustrates the process of the medical information management application implemented by the information terminal 100, and part "B" illustrates the process of the similar case search application implemented by the information terminal 100. In the following, the medical information management application is represented by the "app A", and the similar case search application is represented by the "app B".

First, the app A accepts a request for displaying a test list for image interpretation from the user, and transmits the request to the medical information management system 200 (S510). Upon receipt of the request, the medical information management system 200 lists tests in which image interpretation is yet to be performed after the completion of an imaging test to generate a test list in which image interpretation is to be performed, and transmits the test list to the app A.

Upon receipt of the test list, the app A displays the test list as illustrated in FIG. 36 on the display 101. When the user selects a test from the test list (S530), the app A transmits a request for displaying the selected test to the medical information management system 200 (S540).

Upon receipt of the request for displaying the test, the medical information management system 200 transmits all the slice images in all the series included in the test ID specified in the request to the app A (S550).

Then, the app A displays a series list as illustrated in FIG. 37 in which pieces of information concerning all the series included in the specified test ID are displayed in list form (S560).

Then, when a series to be interpreted is selected by the user from the series list, the app A displays the slice image corresponding to the initial slice position in the selected series in the medical image viewer 610 (S570). In this case, the user inputs a slice-based forwarding operation to display the desired slice image in the medical image viewer 610.

Then, the app A accepts an operation of setting a region of interest in the slice image displayed in the medical image viewer 610 from the user (S580).

Then, the app A generates region-of-interest information indicating the region of interest set by the user, and transmits the region-of-interest information together with the slice image in which the region of interest has been set (i.e., the slice image of the case to be diagnosed) to the app B (S590, S600).

Upon receipt of the slice image of the case to be diagnosed and the region-of-interest information, the app B transmits the slice image and the region-of-interest information to the case search system 300 (S601, S602).

Upon receipt of the slice image and the region-of-interest information, as in FIG. 39, the case search system 300 executes the processing of S610 to S640.

Then, the app B generates an initial basic screen by using the similar case data transmitted in S640 and the display box management information 4410 (S670). Then, the app B executes the processing of S670, the details of which are illustrated in FIG. 44.

FIG. 87 is a sequence diagram focusing on the sequence diagrams illustrated in FIG. 54 and FIG. 55 at the application level. In FIG. 87, substantially the same processing steps as those in FIG. 54 and FIG. 55 are assigned the same numerals.

The difference from FIG. 86 is that S603 and S604 are provided. In FIG. 87, image features are extracted by the information terminal 100. To this end, the app B extracts an image feature from a region of interest set on a slice image of a case to be diagnosed (S603), and transmits the extracted image feature to the case search system 300 (S604).

Aspects of the present disclosure are applicable to a similar case search device that presents similar cases to be used as reference for diagnosis using medical images to be interpreted, an image interpretation training device for trainee radiologists, and the like.

What is claimed is:

1. A terminal, comprising:

a processor; and a non-transitory memory having stored thereon executable instructions, which when executed, cause the processor to perform:

generating information indicating a region of interest included in a medical image to be interpreted;

receiving first thumbnail images, the first thumbnail images including a first regions of interest, respectively, each of the first regions of interest having a predetermined similarity to the region of interest of the medical image to be interpreted;

displaying the first thumbnail images in a first display area on a screen of a display, the first thumbnail images displayed in the first display area on the screen of the display being first sizes, respectively;

receiving an enlargement instruction, and generating second thumbnail images corresponding to the first thumbnail images, respectively; and after receiving the enlargement instruction and generating the second thumbnail images, displaying the second thumbnail images in the first display area on the screen of the display by replacing the first thumbnail images displayed in the first display area on the screen of the display with the second thumbnail images, the second thumbnail images displayed in the first display area on the screen of the display being second sizes, respectively, each of the first sizes being same as the corresponding one of the second sizes, wherein in the displaying the second thumbnail images, each of the second thumbnail images is displayed at a same position in the first display area on the screen of the display as the corresponding one of the first thumbnail images in the displaying the first thumbnail images, wherein in the generating the second thumbnail images, each of the second thumbnail images is generated by enlarging the corresponding one of the first thumbnail images, and wherein the second thumbnail images displayed in the first display area on the screen of the display include second regions of interest, respectively, the first regions of interest corresponding to the second regions of interest, respectively, each of a size of the second regions of interest is bigger than the corresponding one of the first regions of interest.

2. The terminal according to claim 1, wherein each of the second regions of interest is centered in the corresponding one of the second thumbnail images.

3. A method, comprising:

generating information indicating a region of interest included in a medical image to be interpreted;

receiving first thumbnail images, the first thumbnail images including first regions of interest, respectively, each of the first regions of interest having a predetermined similarity to the region of interest of the medical image to be interpreted;

displaying the first thumbnail images in a display area on a screen of a display, the first thumbnail images displayed in the first display area on the screen of the display being first sizes, respectively;

receiving an enlargement instruction, and generating second thumbnail images corresponding to the first thumbnail images, respectively; and after receiving the enlargement instruction and generating the second thumbnail images, displaying the second thumbnail images in the display area on the screen of the display by replacing the first thumbnail images displayed in the display area on the screen of the display with the second thumbnail images, the second thumbnail images displayed in the first display area on the screen of the display being second sizes, respectively, each of the first sizes being same as the corresponding one of the second sizes, wherein in the displaying the second thumbnail images, each of the second thumbnail images is displayed at a same position in the display area on the screen of the display as the corresponding one of the first thumbnail images in the displaying the first thumbnail images, wherein in the generating the second thumbnail images, each of the second thumbnail images is generated by enlarging the corresponding one of the first thumbnail images, and wherein the second thumbnail images displayed in the first display area on the screen of the display include second regions of interest, respectively, the first regions of interest corresponding to the second regions of interest, respectively, each of a size of the second regions of interest is bigger than the corresponding one of the first regions of interest.

4. The method according to claim 3, wherein each of the second regions of interest is centered in the corresponding one of the second thumbnail images.

5. A nonvolatile medium storing a program, the program causing a terminal to perform:

generating information indicating a region of interest included in a medical image to be interpreted;

receiving first thumbnail images, the first thumbnail images including first regions of interest, respectively, each of the first regions of interest having a predetermined similarity to the region of interest of the medical image to be interpreted;

displaying the first thumbnail images in a display area on a screen of a display, the first thumbnail images displayed in the first display area on the screen of the display being first sizes, respectively;

receiving an enlargement instruction, and generating second thumbnail images corresponding to the first thumbnail images, respectively; and after receiving the enlargement instruction and generating the second thumbnail images, displaying the second thumbnail images in the display area on the screen of the display by replacing the first thumbnail images displayed in the display area on the screen of the display with the second thumbnail images, the second thumbnail images displayed in the first display area on the screen of the display being second sizes, respectively, each of the first sizes being same as the corresponding one of the second sizes, wherein in the displaying the second thumbnail images, each of the second thumbnail images is displayed at a same position in the display area on the screen of the display as the corresponding one of the first thumbnail images in the displaying the first thumbnail images, wherein in the generating the second thumbnail images, each of the second thumbnail images is generated by enlarging the corresponding one of the first thumbnail images, and wherein the second thumbnail images displayed in the first display area on the screen of the display include second regions of interest, respectively, the first regions of interest corresponding to the second regions of interest, respectively, each of a size of the second regions of interest is bigger than the corresponding one of the first regions of interest.

6. The nonvolatile medium according to claim 5, wherein each of the second regions of interest is centered in the corresponding one of the second thumbnail images.

* * * * *